US011497813B2

(12) United States Patent
Ebetino et al.

(10) Patent No.: US 11,497,813 B2
(45) Date of Patent: Nov. 15, 2022

(54) BORTEZOMIB CONJUGATES AND METHODS USING SAME

(71) Applicant: Frank EBETINO et al., Pasadena, CA (US)

(72) Inventors: Frank Ebetino, Pasadena, CA (US); Robert Boeckman, Honeoye Falls, NY (US); Lianping Xing, Webster, NY (US); Lifeng Xiao, Rochester, NY (US); Brendan Boyce, Woodbury, NY (US)

(73) Assignee: BIOVINC, LLC, Pasadena, CA (US)

( * ) Notice: Subject to any disclaimer, the term of this patent is extended or adjusted under 35 U.S.C. 154(b) by 0 days.

(21) Appl. No.: 15/772,910

(22) PCT Filed: Nov. 2, 2016

(86) PCT No.: PCT/US2016/060075
§ 371 (c)(1),
(2) Date: May 2, 2018

(87) PCT Pub. No.: WO2017/079262
PCT Pub. Date: May 11, 2017

(65) Prior Publication Data
US 2018/0318425 A1 Nov. 8, 2018

Related U.S. Application Data

(60) Provisional application No. 62/249,382, filed on Nov. 2, 2015.

(51) Int. Cl.
A61K 47/00 (2006.01)
A61K 47/54 (2017.01)
C07F 9/6561 (2006.01)
A61K 49/00 (2006.01)
C07K 5/078 (2006.01)
C07F 9/6558 (2006.01)
C07K 5/062 (2006.01)
A61P 19/00 (2006.01)
A61P 35/00 (2006.01)
A61K 31/69 (2006.01)
C07K 5/06 (2006.01)

(52) U.S. Cl.
CPC ............ A61K 47/548 (2017.08); A61K 31/69 (2013.01); A61K 49/0032 (2013.01); A61K 49/0052 (2013.01); A61P 19/00 (2018.01); A61P 35/00 (2018.01); C07F 9/6561 (2013.01); C07F 9/65583 (2013.01); C07F 9/65586 (2013.01); C07K 5/06043 (2013.01); C07K 5/06139 (2013.01); C07K 5/06191 (2013.01)

(58) Field of Classification Search
CPC .................................................. A61K 47/548
See application file for complete search history.

(56) References Cited

FOREIGN PATENT DOCUMENTS

CN            1780631 A      5/2006
WO     WO-2012119056 A1 *   9/2012  ............ A61K 31/69
WO     WO-2015117136 A1 *   8/2015  ............... C07F 5/04

OTHER PUBLICATIONS

Henry R. Henze and Charles M. Blair "The Number of Structurally Isomeric Alcohols of the Methanol Series" Journal of the American Chemical Society 1931, 3042.*
Smoum "Boron Containing Compounds as Protease Inhibitors" Chem. Rev. 2012, 112, 4156-4220.*
Russell "The Pharmacology of Bisphosphonates and New Insights Into Their Mechanisms of Action" Journal of Bone and Mineral Research vol. 14, Supplement 2, 1999 53-65.*
Agyin et al. "Design, synthesis, and biological evaluation of bone-targeted proteasome inhibitors for multiple myeloma" Bioorg. Medic. Chem. Lett., 2013, 23: 6455-6458.
Hideshima et al. "Mechanism of Action of Proteasome Inhibitors and Deacetylase Inhibitors and the Biological Basis of Synergy in Multiple Myeloma" 2011, Mol. Cancer Ther. 10:2034-2042.
Mukherjee et al. "Pharmacologic targeting of a stem/progenitor population in vivo is associated with enhanced bone regeneration in mice" 2008, J. Clin. Invest. 118:491-504.
Kaiser et al. "The proteasome inhibitor bortezomib stimulates osteoblastic differentiation of human osteoblast precursors via upregulation of vitamin D receptor signalling" 2013, Eur. J. Haematol. 90:263-272.
Hongming et al. "Bortezomib inhibits maturation and function of osteoclasts from PBMCs of patients with multiple myeloma by downregulating TRAF6" 2009, Leukemia Res. 33: 115-122.
Khedgikar et al. "Withaferin A: a proteasomal inhibitor promotes healing after injury and exerts anabolic effect on osteoporotic bone" 2013, Cell Death Dis. 4:e778.
Maseda et al. "Proteasome inhibition drastically but reversibly impairs murine lymphocyte development" 2008, Cell Death Differ. 15:600-612.
Weathington et al. "Emerging therapies targeting the ubiquitin proteasome system in cancer" 2014, J. Clin. Invest. 124:6-12.
Arns et al., "Design and synthesis of novel bone-targeting dual-action pro-drugs for the treatment and reversal of osteoporosis," 2012, Bioorg. Med. Chem. 20(6):2131-40.
Barten et al., "Gamma-secretase inhibitors for Alzheimer's disease: balancing efficacy and toxicity,". 2006, Drugs R D 7:87-97.
Chen et al., "The amplified WWP1 gene is a potential molecular target in breast cancer," 2007, Int. J. Cancer 121:80-87.
Gil et al., "Prostaglandin E2-bisphosphonate conjugates: potential agents for treatment of osteoporosis," 1999, Bioorg. Med. Chem. 7:901-919.
Hirabayashi and Fujisaki, "Bone-specific drug delivery systems: approaches via chemical modification of bone-seeking agents," 2003, Clin. Pharmacokinet. 42:1319-1330.

(Continued)

Primary Examiner — David K O'Dell
(74) Attorney, Agent, or Firm — Thomas|Horstemeyer, LLP

(57) ABSTRACT

The present invention provides compositions and methods for providing controllable local delivery of a conjugate of bortezomib (Btz) and a bisphosphonate to promote bone formation. In certain embodiments, the invention is used as a treatment for a subject with diseases and disorders characterized by bone loss.

36 Claims, 38 Drawing Sheets

(56) References Cited

OTHER PUBLICATIONS

Jones et al., "Upregulating CXCR4 in human fetal mesenchymal stem cells enhances engraftment and bone mechanics in a mouse model of osteogenesis imperfecta," 2012, Stem Cells Transl. Med. 1:70-78.

Liebergall et al., "Stem cell-based therapy for prevention of delayed fracture union: a randomized and prospective preliminary study," 2013, Mol. Ther. J. Am. Soc. Gene Ther. 21:1631-1638.

Lindsten et al., "A transgenic mouse model of the ubiquitin/proteasome system," 2003, Nat. Biotech. 21:897-902.

Mendez-Ferrer et al., "Mesenchymal and haematopoietic stem cells form a unique bone marrow niche," 2010, Nature 466:829-834.

Mignone et al., "Neural stem and progenitor cells in nestin-GFP transgenic mice," 2004, J. Comp. Neurol. 469:311-324.

Naik et al., "Reduced COX-2 expression in aged mice is associated with impaired fracture healing," 2009, J. Bone Min. Res 24:251-64.

Sapkota et al., "Balancing BMP signaling through integrated inputs into the Smad1 linker," 2007, Mol. Cell 25:441-454.

Satija et al., "Mesenchymal stem cells: molecular targets for tissue engineering," 2007, Stem Cells Dev. 16:7-23.

Shi et al., "Distribution and alteration of lymphatic vessels in knee joints of normal and osteoarthritic mice," 2014, Arthritis Rheumatol. 66:657-666.

Shu et al., "Ubiquitin E3 ligase Wwp1 negatively regulates osteoblast function by inhibiting osteoblast differentiation and migration," 2013, J. Bone Miner. Res. 28:1925-1935.

Tanaka et al., "Synthesis and in vitro evaluation of bisphosphonated glycopeptide prodrugs for the treatment of osteomyelitis," 2010, Bioorg. Med. Chem. Lett. 20:1355-1359.

Undale et al., "Induction of fracture repair by mesenchymal cells derived from human embryonic stem cells or bone marrow," 2011, J. Orthop. Res. 29:1804-1811.

Xing et al., "Smurf control in bone cells," 2010, J. Cell Biochem. 110:554-563.

Zhang et al., "NOTCH inhibits osteoblast formation in inflammatory arthritis via noncanonical NF-κB," 2014, J. Clin. Invest. 124:3200-14.

Zhao et al., "Smurf1 inhibits mesenchymal stem cell proliferation and differentiation into osteoblasts through JunB degradation," 2010, J. Bone Miner. Res. 25:1246-1256.

Zhao et al., "Tumor necrosis factor inhibits mesenchymal stem cell differentiation into osteoblasts via the ubiquitin E3 ligase Wwp1," 2011, Stem Cells 29:1601-1610.

Zhou et al., "Near-infrared lymphatic imaging demonstrates the dynamics of lymph flow and lymphangiogenesis during the acute versus chronic phases of arthritis in mice," 2010, Arthritis Rheum. 62:1881-1889.

Chinese Search Report for Application No. 2016800756976, dated Nov. 2, 2016, pp. 1-3 (partial translation).

\* cited by examiner

A

Treatment - 3/wk for 2 wks. Mice were sacrificed one wk later (3 wks post-cell inoculation)

- PBS + Saline
- MM + Saline
- MM + Btz
- MM + BP-Btz

B

| Type | PBS+Saline | MM+Saline | MM+Btz | MM+BP-Btz |
|---|---|---|---|---|
| Dead/Living | 0/6 | 3/5 | 3/5 | 2/6 |
| Weak | 0 | 5 | 4 | 0 |
| Megalosplenia | 0 | 5 | 5 | 3 |
| Disability | 0 | 5 | 4 | 0 |

Figures 25A-25B

BORTEZOMIB CONJUGATES AND METHODS USING SAME

CROSS-REFERENCE TO RELATED APPLICATIONS

This application is a U.S. national phase application filed under 35 U.S.C. § 371 claiming benefit to International Patent Application No. PCT/US16/60075, filed Nov. 2, 2016, which is entitled to priority under 35 U.S.C. § 119(e) to U.S. Provisional Patent Application No. 62/249,382, filed Nov. 2, 2015, each of which application is hereby incorporated herein by reference in its entirety.

STATEMENT REGARDING FEDERALLY SPONSORED RESEARCH OR DEVELOPMENT

This invention was made with government support under grant Nos. 1S10RR027340, AR069789, and AR063650 awarded by the National Institutes of Health. The government has certain rights in the invention.

BACKGROUND OF THE INVENTION

More than 5 million Americans suffer from fractures annually. Delayed fracture healing often occurs in the elderly, leading to decreased quality of life and increased health care cost. The development of new therapeutic approaches to promote fracture repair is a critical clinical need. Mesenchymal stem/Progenitor Cells (MPCs) have been tested in animal models and human of fracture with promising results (Mukherjee et al., 2008, J. Clin. Invest. 118:491-514). Three cellular processes which actively participate in fracture healing are MPC homing to the fracture site; expanding, and differentiating into osteogenic cells (Undale et al., 2011, J. Orthop. Res. 29:1804-1811; Satija et al., 2007, Stem Cells Dev. 16:7-23). A factor that regulates all three of these processes would be an ideal drug candidate or target. It was found that MPCs from mice deficient in several members of the Nedd4 sub-class of E3 ligases, have increased migration, growth and OB differentiation by increasing the stability of Runx2, JunB and CXCR4 proteins via the ubiquitin-proteasome system (UPS) (Xing et al., 2010, J. Cell Biochem. 110:554-563). MPCs from aged mice have increased UPS-mediated Runx2 and JunB degradation (Shu et al., 2013, Journal of Bone and Mineral Research 28 1925-1935).

The UPS is an important complex cellular machine for protein posttranslational modifications, which specifically adds or removes ubiquitin to the substrate, resulting in the degradation of ubiquitinated (Ub) substrate in proteasomes or lysosomes. The substrate ubiquitination is carried out via sequential enzymatic reactions involving ubiquitin activating enzyme E1, ubiquitin-conjugating enzyme E2, and ubiquitin ligase E3 that confer substrate specificity by linking ubiquitin to target molecules. A number of osteoblast (OB) positive regulators such as BMP (Sapkota et al., 2007, Mol. Cell 25:441-454) and TGFβ signaling proteins (Chen et al., 2007, Int. J. Cancer 121:80-87), Runx2 (Xing et al., 2010, J. Cell Biochem. 110:554-563), JunB (Jones et al., 2012, Stem Cells Transl. Med. 1:70-78), and CXCR4 (Gil et al., 1999, Bioorg. Med. Chem. 7:901-919; Hirabayashi and Fujisaki, 2003, Clin. Pharmacokinet. 42:1319-1330) are regulated via the UPS by the Nedd4 sub-class of E3 ligases, which is composed of 7 members, including Nedd4-1, Nedd4-2, Itch, WWP1&2, and Smad ubiquitination regulatory factor (Smurf) 1&2.

The role of E3 ligase Smurf1, Wwp1 and Itch has been investigated in bone using Smurf1$^{-/-}$, Wwp1$^{-/-}$, and Itch$^{-/-}$ mice. All of them have increased bone volumes, bone formation, and OB differentiation as a result of ubiquitination and degradation of JunB and Runx2 (Weathington and Mallampalli, 2014, J. Clin. Invest. 124:6-12; Morioka et al., 2010, Bioorg. Med. Chem. 18:1143-1148; Tanaka et al., 2010, Bioorg. Med. Chem. Lett. 20:1355-1359; Arns et al., 2012, Bioorg. Med. Chem. 20:2131-2140; Zhang et al., 2014, J. Clin. Invest.; Barten et al., 2006, Drugs R D 7:87-97; Zhou et al., 2010, Arthritis Rheum. 62:1881-1889). It has been discovered that bone fracture repair is composed of a series of events that involve inflammation, angiogenesis and osteogenesis, which are regulated by multiple mechanisms. However, the role of protein turnover by the UPS in fracture healing has not been explored.

In addition, a main challenge clinically is that an elderly individual often suffers from a non-union fracture, partially due to age-related decline of MPC-OB differentiation (Liebergall et al., 2013, Mol. Ther. J. Am. Soc. Gene Ther. 21:1631-1638). It has previously been reported that MPCs from aged mice have increased UPS-mediated proteasome degradation of Runx2 and JunB proteins (Shu et al., J. Bone Min. Res. 28:1925-1935).

Bortezimib (Btz, marketed as Velcade by Millennium Pharmaceuticals, originally named PS-341) is an FDA-approved proteasome inhibitor for patients with multiple myeloma. It acts by inhibiting the proteasome via reversible occupation of the active proteolytic site of the 20S proteasome (Jones et al., 2012, Stem Cells Transl. Med. 1:70-78). Its main cytotoxic effect on myeloma cells is through the induction of apoptosis after the accumulation of excessive protein (Hideshima et al., 2011, Mol. Cancer Ther. 10:2034-2042). It increases OB differentiation from mouse and human MPCs in vitro (Mukherjee et al., 2008, J. Clin. Invest. 118:491-504; Kaiser et al., 2013, Eur. J. Haematol. 90:263-272), promotes MPC-OB differentiation by inhibiting the turnover of OB positive regulators, and also inhibits osteoclast (OC) formation by inhibiting the NF-κB/TRAF6 signal pathway (Hongming and Jian, 2009, Leukemia Res. 33:115-122; Khedgikar et al., 2013, Cell Death Dis. 4:e778). Due to its positive effect on OBs and negative effect on OCs, Btz and other proteasome inhibitors have been considered as very attractive candidates for the development of bone anabolic agents. Several mouse studies reported that Btz increases bone volume in normal and OVX mice (Chen et al., 2007, Int. J. Cancer 121:80-87), and promotes fracture healing, all of which were performed in young or adult mice (Khedgikar et al., 2013, Cell Death Dis. 4:e778; Maseda et al., 2008, Cell Death Differ. 15:600-612). However, the utilization of Btz in the clinic is limited by its toxicities, such as peripheral neuropathy and thrombocytopenia (Weathington and Mallampalli, 2014, J. Clin. Invest. 124:6-12). There is an urgent need for new approaches to selectively target the delivery of Btz specifically to bone tissue to ameliorate and/or prevent the toxic side effects arising from systemic distribution and to make dose escalation possible in order to improve therapeutic outcomes.

Clinical information from myeloma therapy indicates that Btz and other proteasome inhibitors including Carfilzomib (marketed as Kyprolis by Onyx Pharmaceuticals) have significant toxicities, such as peripheral neuropathy and thrombocytopenia, which restrict their utilization. In mice, Btz significantly reduces the number of T cells in the thymus as early as 3 days after administration (Maseda et al., 2008, Cell Death Differ. 15:600-612). These adverse effects are considered due to the systemic distribution of the drug. The synthesis of a bone-targeted (BT) Btz by linking Btz to active bisphosphonates (BPs) has recently been attempted (Agyin et al., 2013, Bioorg. Med. Chem. Lett. 23:6455-6458). Despite the finding that these Btz-BP conjugates inhibit myeloma cell growth in vitro, their effect in vivo was not reported to be useful. Furthermore, these Btz-BP conjugates linked Btz to a BP using a chemically and biochemically stable linkage such that cleavage in vivo is unlikely, and even if a cleavage did occur, Btz would not be the released substrate. Further, a bioactive (antiresorptive) BP (alendronate) was also utilized in this conjugate preparation, which makes it difficult to determine the source of activity (Agyin et al., 2013, Bioorg. Med. Chem. Lett. 23:6455-6458).

Near-infrared (NIR) fluorescent BP derivatives have been developed and used in cells and in living mice, in which the NIR fluorophore IRDye78 was conjugated to the BP pamidronate that contains a single primary amine for conjugation (Shi et al., 2014, Arthritis Rheumatol. 66:657-666; Shu et al., 2013, J. Bone Miner. Res. 28:1925-1935). NIR imaging has also been used to study lymphatic draining function in mice (Zhao et al., 2010, J. Bone Miner. Res. 25:1246-1256; Zhao et al., 2011, Stem Cells 29:1601-1610).

There is a need in the art for new compounds and methods that selectively target the delivery of compounds such as Btz specifically to bone tissue in order to ameliorate and/or prevent the toxic side effects arising from systemic distribution and to make dose escalation possible in order to improve therapeutic outcomes. The present invention fulfills this need.

BRIEF SUMMARY OF THE INVENTION

The present invention includes a compound of formula (I):

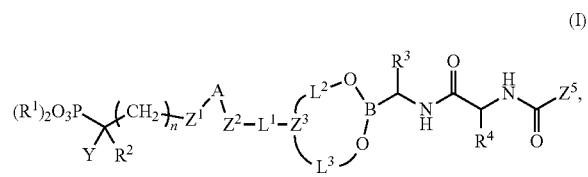

wherein in formula (I):

each occurrence of $R^1$ is independently selected from the group consisting of hydrogen and alkyl;

$R^2$ is selected from the group consisting of hydrogen, alkyl, —$OR^{13}$, —$N(R^{13})(R^{14})$, and halogen;

$R^3$ is selected from the group consisting of hydrogen and alkyl, wherein the alkyl group is optionally substituted with one to four substituents selected from the group consisting of hydroxyl, alkoxy, alkenyl, cycloalkyl, aryl, heteroaryl, halo, cyano and amino;

$R^4$ is selected from the group consisting of hydrogen, alkyl, aryl, and alkylaryl wherein the alkyl, aryl, or alkylaryl group is optionally substituted with one to four substituents selected from the group consisting of hydroxyl, alkoxy, alkenyl, cycloalkyl, aryl, heteroaryl, halo, cyano and amino;

$L^1$ is selected from the group consisting of alkyl, aryl, cycloalkyl, alkylaryl, alkylcycloalkyl, and alkyl-$Z^4$C(O)$NR^{10}$, wherein the alkyl, aryl, cycloalkyl, alkylaryl, or alkylcycloalkyl group is optionally substituted with one to four substituents selected from the group consisting of alkyl, hydroxyl, alkoxy, alkenyl, cycloalkyl, aryl, heteroaryl, halo, cyano and amino;

$L^2$ is aryl or an alkyl chain of $C_1$-$C_6$ alkyl, wherein any carbon atom in the alkyl chain is optionally substituted with one to two substituents selected from the group consisting of alkyl, cycloalkyl, and carbonyl;

$L^3$ is aryl or an alkyl chain of $C_1$-$C_6$ alkyl, wherein any carbon atom in the alkyl chain is optionally substituted with one to two substituents selected from the group consisting of alkyl, cycloalkyl, and carbonyl;

Y is selected from the group consisting of —PO(OR$^8$)(OR$^9$), —PO(R$^9$)(OR$^8$), —CO$_2$R$^8$, and —SO$_3$R$^8$;

$Z^1$ is selected from the group consisting of $CH_2$ and $NR^6$;

A is selected from the group consisting of $CH_2$, C(=O), C(=NR$^7$), and C(=S);

$Z^2$ is selected from the group consisting of $CH_2$, $NR^{11}$, S, and O;

$Z^3$ is selected from the group consisting of N, $CR^{12}$, and phenyl;

$Z^4$ is selected from the group consisting of $CH_2$ and O;

$Z^5$ is selected from the group consisting of aryl, alkyl, $OR^{18}$, and

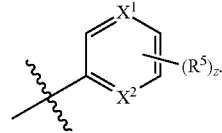

wherein the aryl or alkyl group is optionally substituted with one to four substituents selected from the group consisting of alkyl, hydroxyl, alkoxy, alkenyl, cycloalkyl, aryl, heteroaryl, halo, cyano and amino;

each occurrence of $R^5$ is independently selected from the group consisting of, alkyl, fluoroalkyl, heteroalkyl, aryl, F, Cl, Br, I, —CN, —NO$_2$, —OR$^{17}$, —SR$^{17}$, —S(=O)R$^{17}$, —S(=O)$_2$R$^{17}$, —NHS(=O)$_2$R$^{17}$, —C(=O)R$^{17}$, —OC(=O)R$^{17}$, —CO$_2$R$^{17}$, —OCO$_2$R$^{17}$, —CH(R$^{17}$)$_2$, —N(R$^{17}$)$_2$, —C(=O)N(R$^{17}$)$_2$, —OC(=O)N(R$^{17}$)$_2$, —NHC(=O)NH(R$^{17}$), —NHC(=O)R$^{17}$, —NHC(=O)OR$^{17}$, —C(OH)(R$^{17}$)$_2$, and —C(NH$_2$)(R$^{17}$)$_2$;

$X^1$ is selected from the group consisting of $CR^{15}$ and N;

$X^2$ is selected from the group consisting of $CR^{16}$ and N;

$R^6$ and $R^7$ are each independently selected from the group consisting of hydrogen and alkyl, wherein the alkyl group is optionally substituted with one to four substituents selected from the group consisting of hydroxyl, alkoxy, alkenyl, cycloalkyl, aryl, heteroaryl, halo, cyano and amino;

$R^8$, $R^9$, and $R^{10}$ are each independently selected from the group consisting of hydrogen and alkyl;

$R^{11}$, $R^{12}$, $R^{13}$, and $R^{14}$ are each independently selected from the group consisting of hydrogen and alkyl, wherein the alkyl group is optionally substituted with one to four substituents selected from the group consisting of hydroxyl, alkoxy, alkenyl, cycloalkyl, aryl, heteroaryl, halo, cyano and amino;

$R^{15}$ and $R^{16}$ are each independently selected form the group consisting of hydrogen, alkyl, fluoroalkyl, heteroalkyl, aryl, F, Cl, Br, I, —CN, —NO$_2$, —OR$^{17}$, —SR$^{17}$, —S(=O)R$^{17}$, —S(=O)$_2$R$^{17}$, —NHS(=O)$_2$R$^{17}$, —C(=O)R$^{17}$, —OC(=O)R$^{17}$, —CO$_2$R$^{17}$, —OCO$_2$R$^{17}$, —CH(R$^{17}$)$_2$, —N(R$^{17}$)$_2$, —C(=O)N(R$^{17}$)$_2$, —OC(=O)N(R$^{17}$)$_2$, —NHC(=O)NH(R$^{17}$), —NHC(=O)R$^{17}$, —NHC(=O)OR$^{17}$, —C(OH)(R$^{17}$)$_2$, and —C(NH$_2$)(R$^{17}$)$_2$;

each occurrence of $R^{17}$ is selected from the group consisting of hydrogen and alkyl;

$R^{18}$ is selected from the group consisting of alkyl, aryl, and arylalkyl;

n is an integer from 0 to 10; and z is an integer from 0 to 2; or a pharmaceutically acceptable salt thereof, an isomer thereof, or a mixture of isomers thereof.

In one embodiment, the compound of formula (I) is a compound of formula (II):

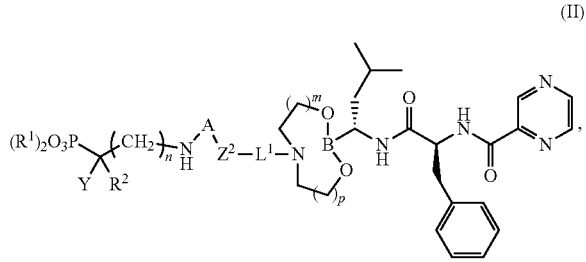

(II)

wherein in formula (II):

each occurrence of $R^1$ is independently selected from the group consisting of hydrogen and alkyl;

$R^2$ is selected from the group consisting of hydrogen, alkyl, $-OR^{13}$, $-N(R^{13})(R^{14})$, and halogen;

Y is selected from the group consisting of $-PO(OR^8)(OR^9)$, $-PO(R^9)(OR^8)$, $-CO_2R^8$, and $-SO_3R^8$;

$Z^1$ is selected from the group consisting of $CH_2$ and $NR^6$;

A is selected from the group consisting of $CH_2$, $C(=O)$, $C(=NR^7)$, and $C(=S)$;

$Z^2$ is selected from the group consisting of $CH_2$, $NR^{11}$, S, and O;

$R^6$ and $R^7$ are each independently selected from the group consisting of hydrogen and alkyl, wherein the alkyl group is optionally substituted with one to four substituents selected from the group consisting of hydroxyl, alkoxy, alkenyl, cycloalkyl, aryl, heteroaryl, halo, cyano and amino;

$R^8$ and $R^9$ are each independently selected from the group consisting of hydrogen and alkyl;

$R^{11}$, $R^{13}$, and $R^{14}$ are each independently selected from the group consisting of hydrogen and alkyl, wherein the alkyl group is optionally substituted with one to four substituents selected from the group consisting of hydroxyl, alkoxy, alkenyl, cycloalkyl, aryl, heteroaryl, halo, cyano and amino;

m is 1, or 2 or 3;

p is 1, or 2, or 3; and n is an integer from 0 to 10; or a pharmaceutically acceptable salt thereof, an isomer thereof, or a mixture of isomers thereof.

In one embodiment, the compound of formula (I) is a compound of formula (III):

wherein in formula (III):

each occurrence of $R^1$ is independently selected from the group consisting of hydrogen and alkyl;

$R^2$ is selected from the group consisting of hydrogen, alkyl, $-OR^{13}$, $-N(R^{13})(R^{14})$, and halogen;

Y is selected from the group consisting of $-PO(OR^8)(OR^9)$, $-PO(R^9)(OR^8)$, $-CO_2R^8$, and $-SO_3R^8$;

$Z^1$ is selected from the group consisting of $CH_2$ and $NR^6$;

A is selected from the group consisting of $CH_2$, $C(=O)$, $C(=NR^7)$, and $C(=S)$;

$Z^2$ is selected from the group consisting of $CH_2$, $NR^{11}$, S, and O;

$Z^4$ is selected from the group consisting of $CH_2$ and O;

$L^1$ is selected from the group consisting of alkyl, aryl, cycloalkyl, alkylaryl, alkylcycloalkyl, wherein the alkyl, aryl, cycloalkyl, alkylaryl, or alkylcycloalkyl group is optionally substituted with one to four substituents selected from the group consisting of hydroxyl, alkoxy, alkenyl, cycloalkyl, aryl, heteroaryl, halo, cyano and amino;

$R^6$ and $R^7$ are each independently selected from the group consisting of hydrogen and alkyl, wherein the alkyl group is optionally substituted with one to four substituents selected from the group consisting of hydroxyl, alkoxy, alkenyl, cycloalkyl, aryl, heteroaryl, halo, cyano and amino;

$R^8$, $R^9$, and $R^{14}$ are each independently selected from the group consisting of hydrogen and alkyl;

$R^{11}$, $R^{13}$, and $R^{14}$ are each independently selected from the group consisting of hydrogen and alkyl, wherein the alkyl group is optionally substituted with one to four substituents selected from the group consisting of hydroxyl, alkoxy, alkenyl, cycloalkyl, aryl, heteroaryl, halo, cyano and amino; and m is an integer from 1 to 5;

n is an integer from 0 to 10;

p is an integer from 1 to 5; and x is an integer from 0 to 10; or a pharmaceutically acceptable salt thereof, an isomer thereof, or a mixture of isomers thereof.

In one embodiment, Y is $-PO_3(R^1)_2$. In another embodiment, $L^1$ is selected from the group consisting of alkyl, aryl and alkylaryl. In another embodiment, $L^1$ is $-CH_2CHR^{19}-$, wherein $R^{19}$ is selected from the group consisting of:

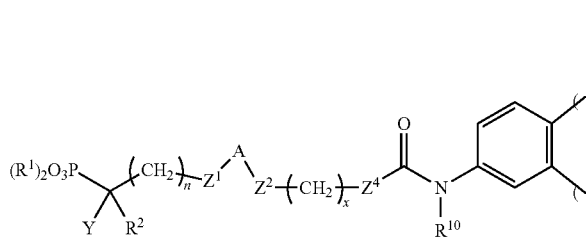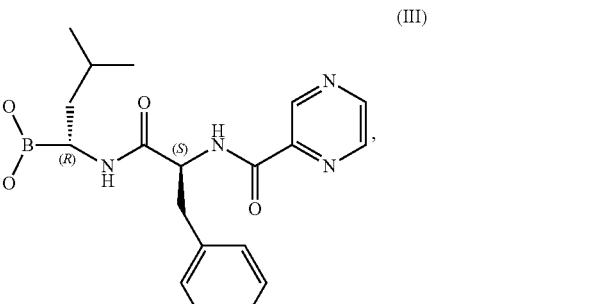

(III)

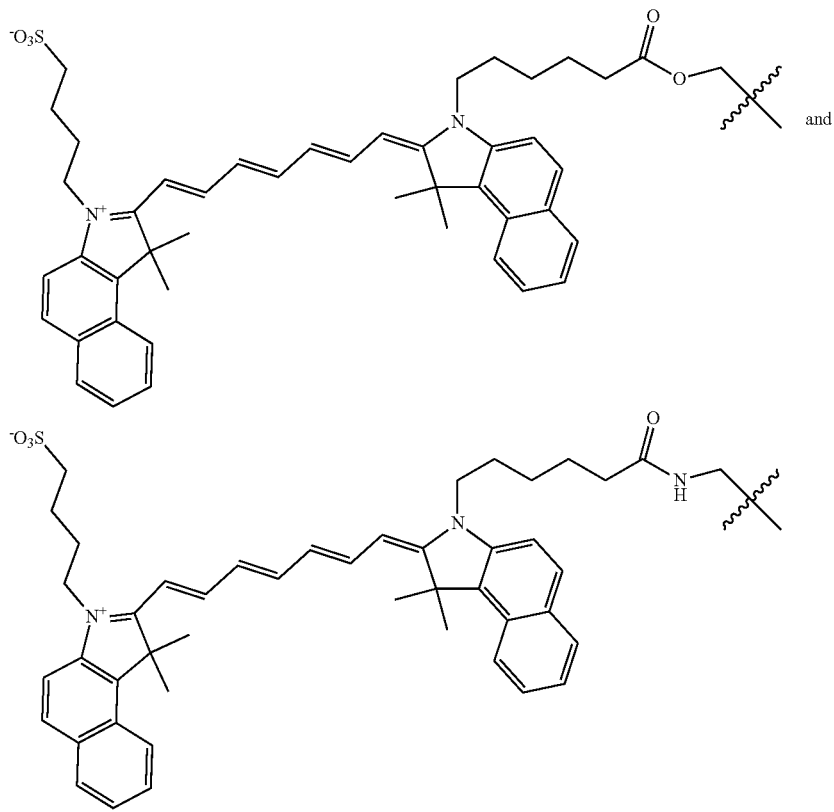

In another embodiment, $L^2$ is selected from the group consisting of phenyl and an alkyl chain of $C_1$-$C_6$ alkyl, wherein one carbon atom in the alkyl chain is optionally substituted with two alkyl groups, a carbonyl group, or a cycloalkyl group. In another embodiment, $L^3$ is selected from the group consisting of phenyl and an alkyl chain of $C_1$-$C_6$ alkyl, wherein one carbon atom in the alkyl chain is optionally substituted with two alkyl groups, a carbonyl group, or a cycloalkyl group. In another embodiment, A is C(=N) or C(=O). In another embodiment, $Z^2$ is O. In another embodiment, $Z^5$ is

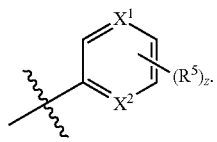

In another embodiment, $Z^5$ is

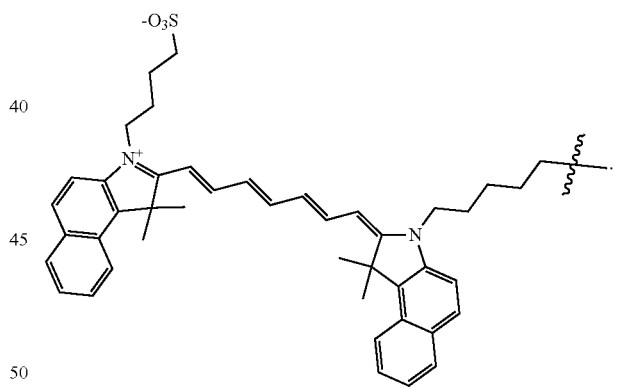

In another embodiment, the compound is

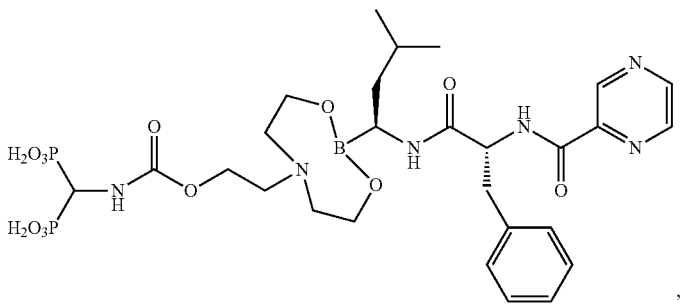

,

-continued
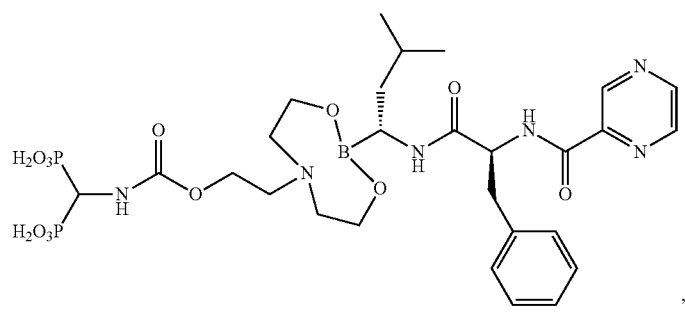
,
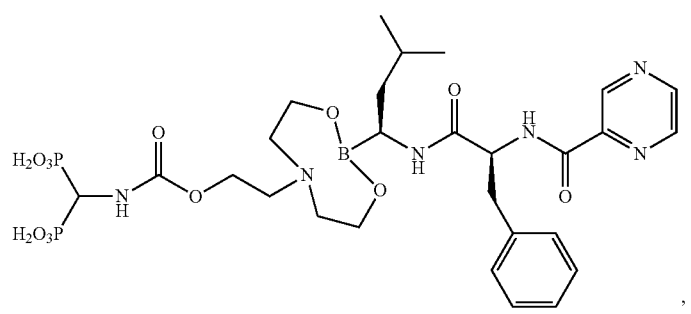
,
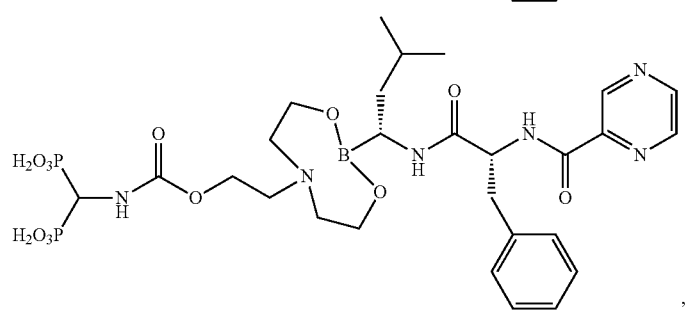
,
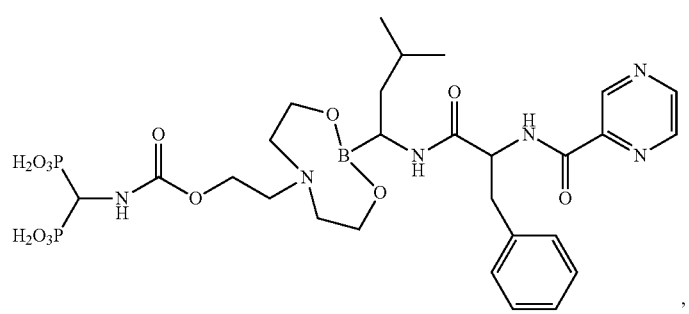
,
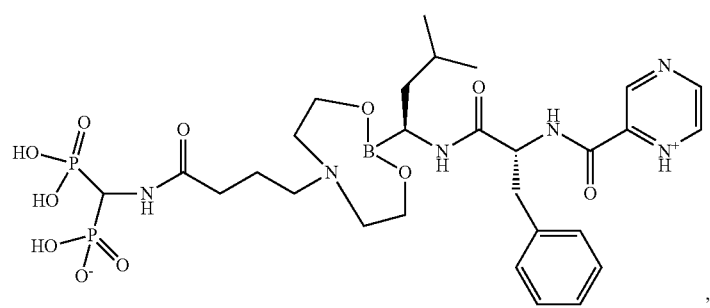
,

-continued
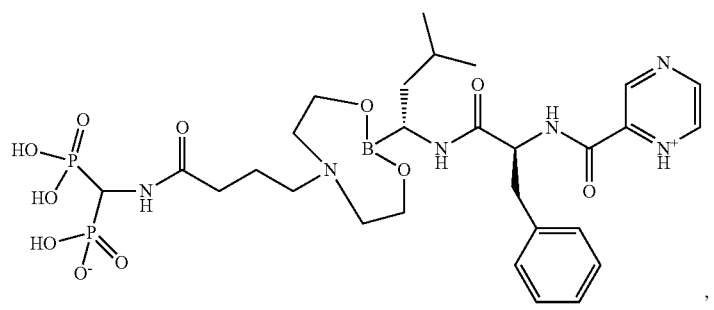
,
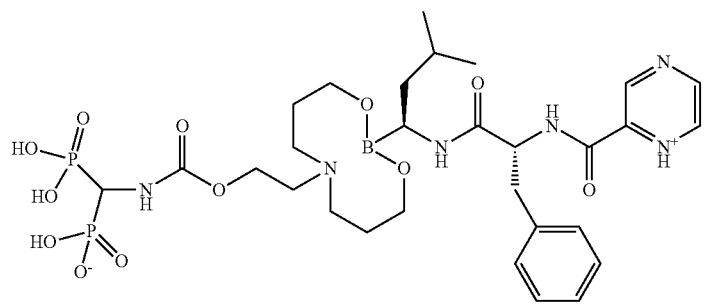
,
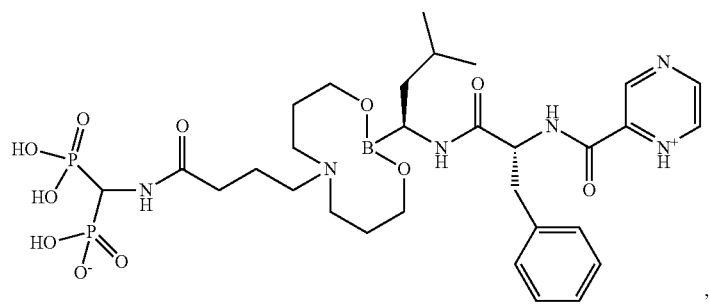
,
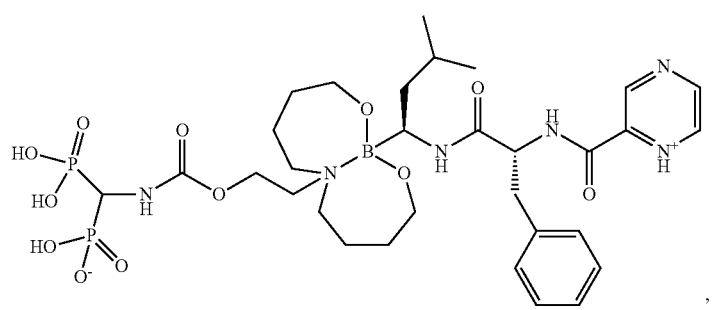
,
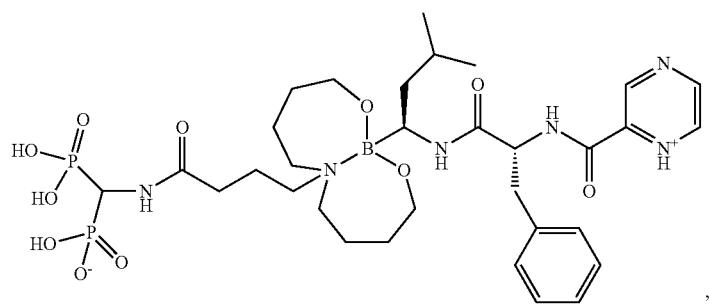
,

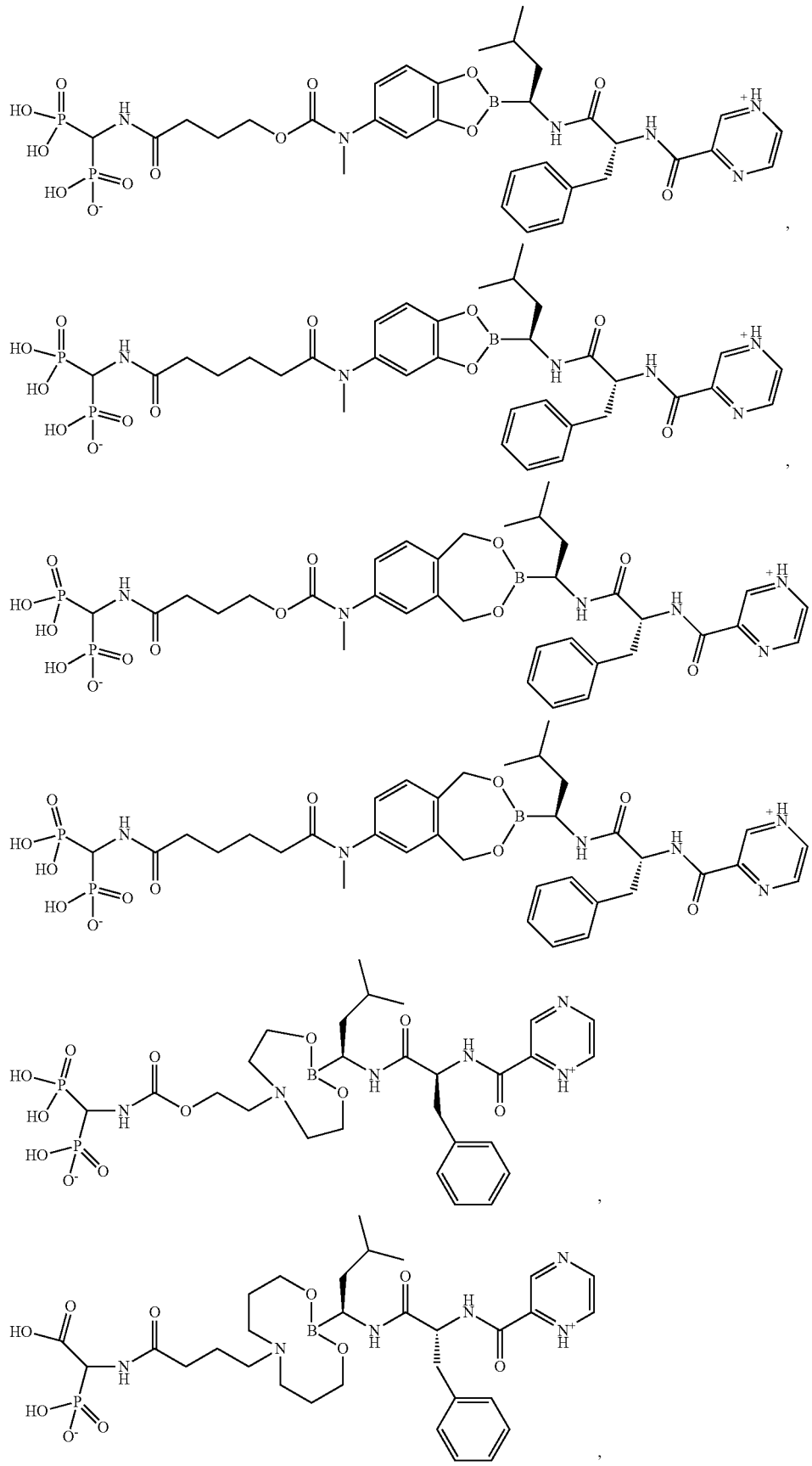

-continued
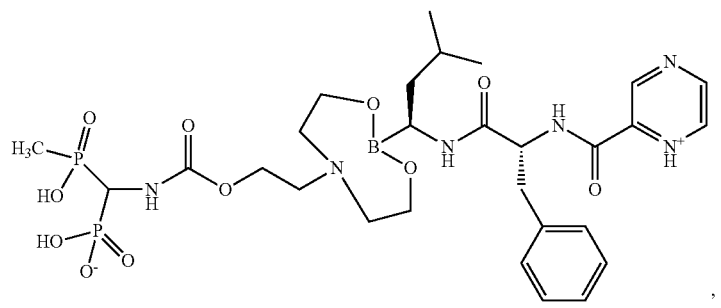
,
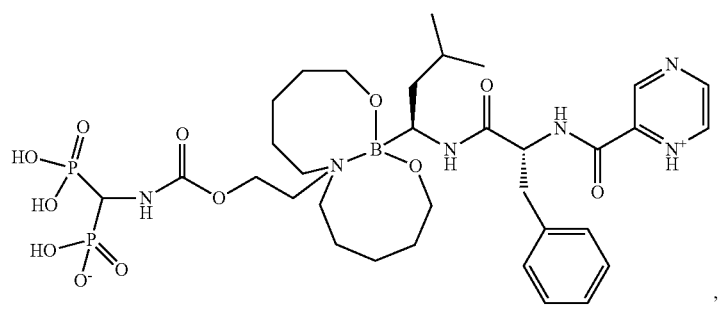
,
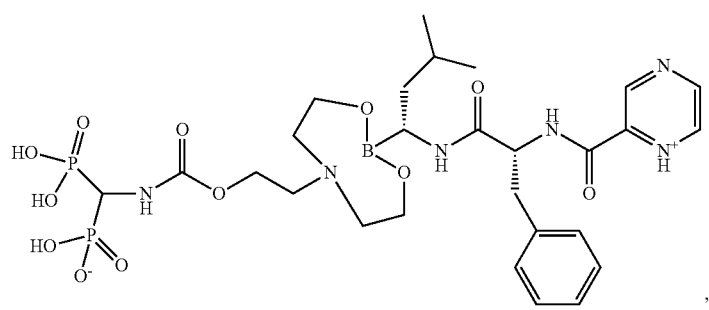
,
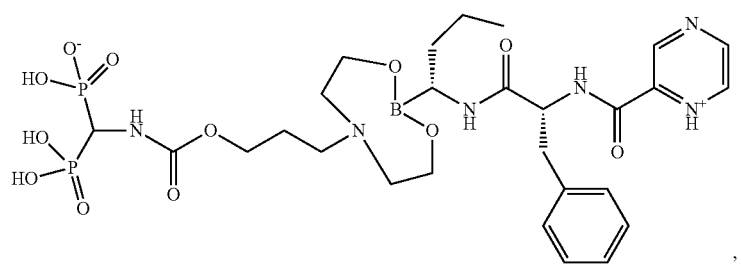
,
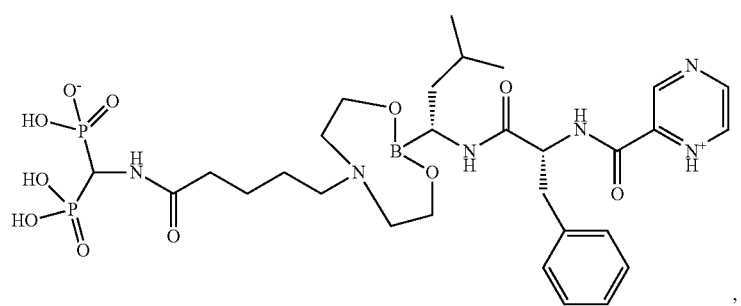
,

-continued
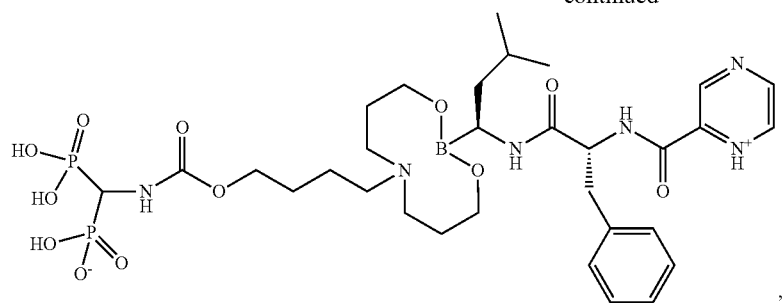
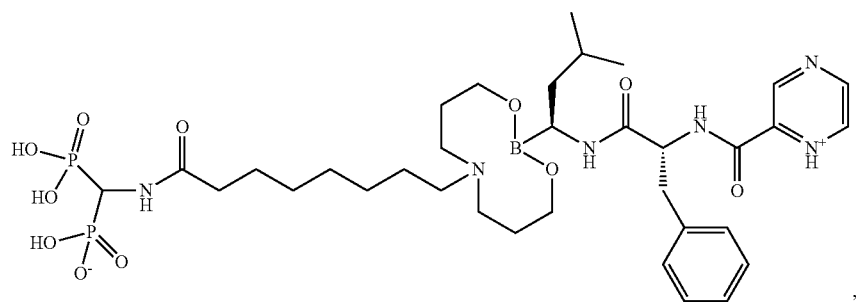
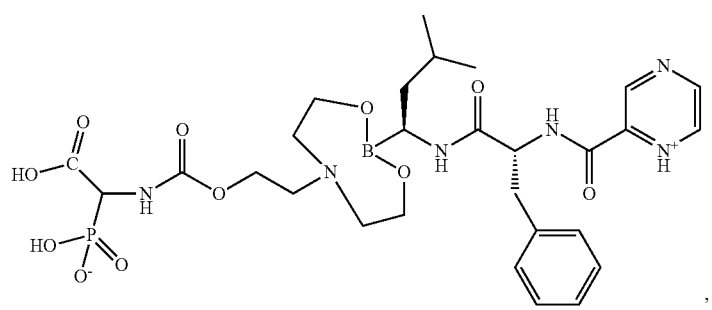
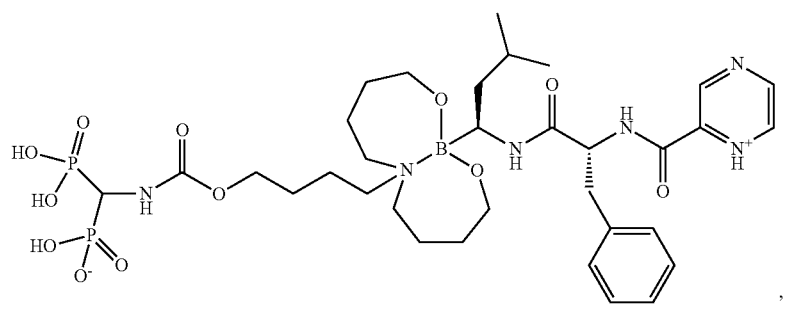
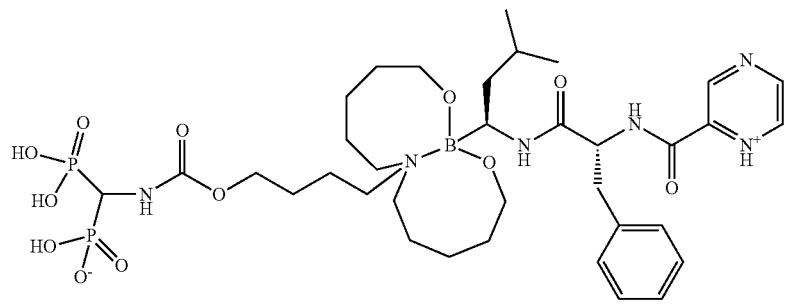

-continued
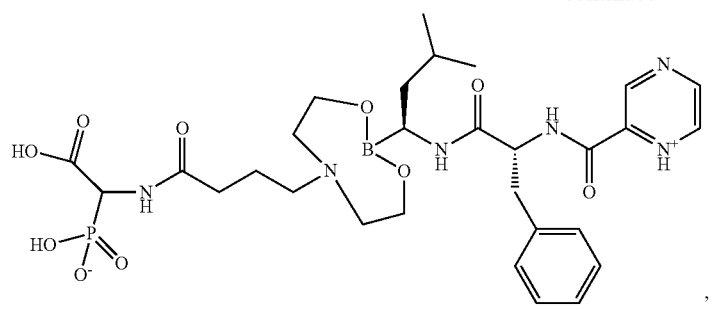,
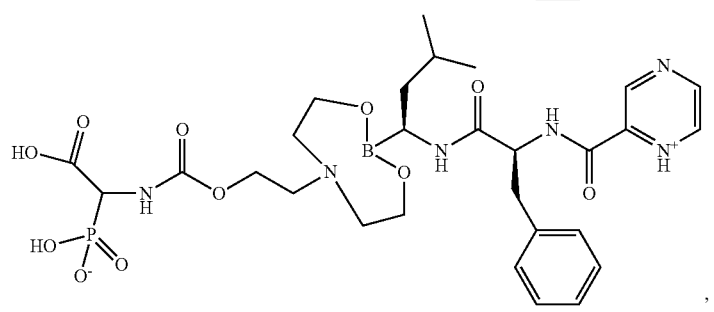,
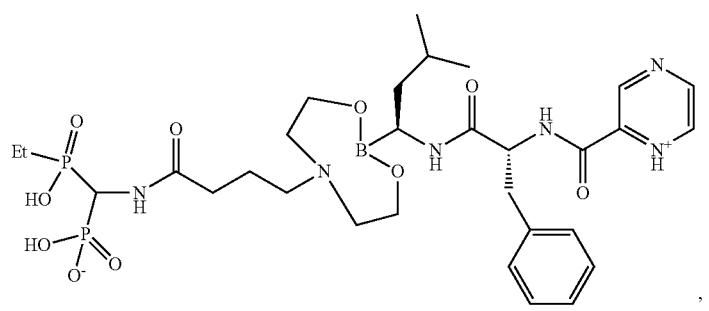,
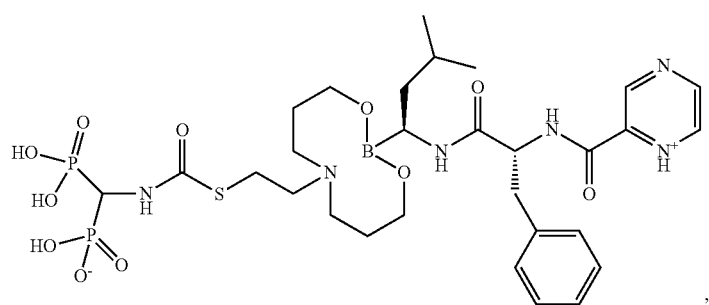,
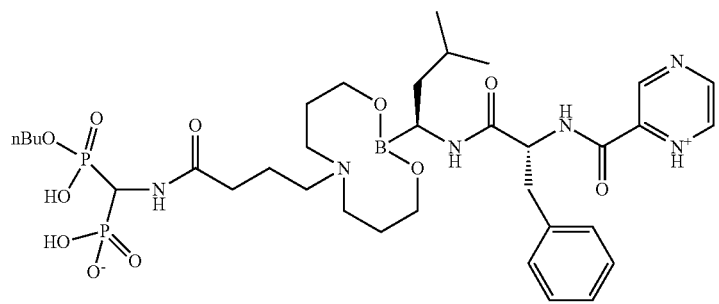,

-continued
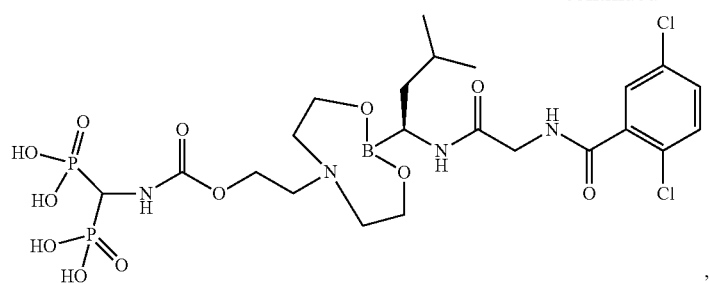
,
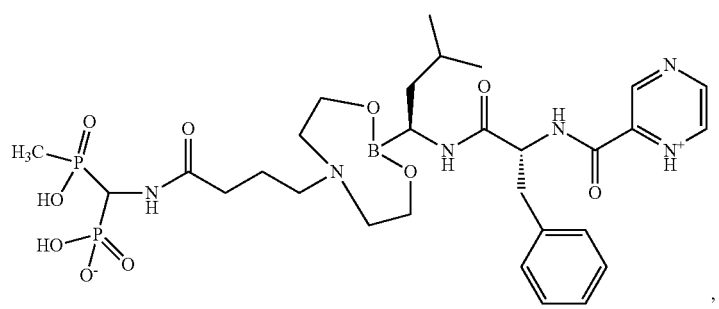
,
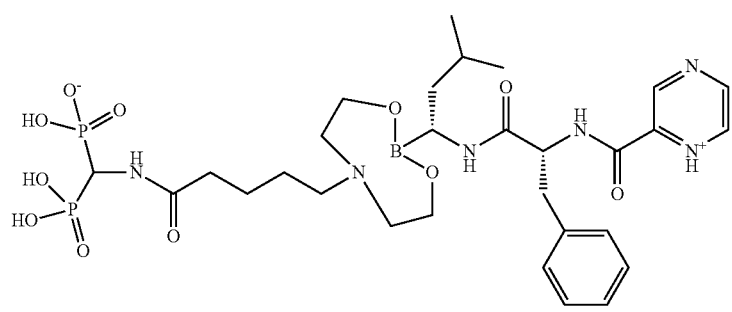
,
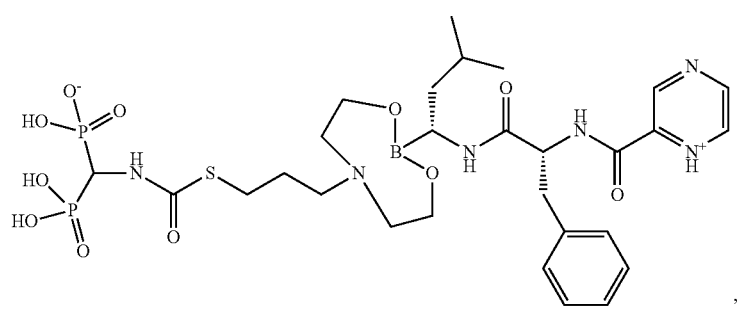
,
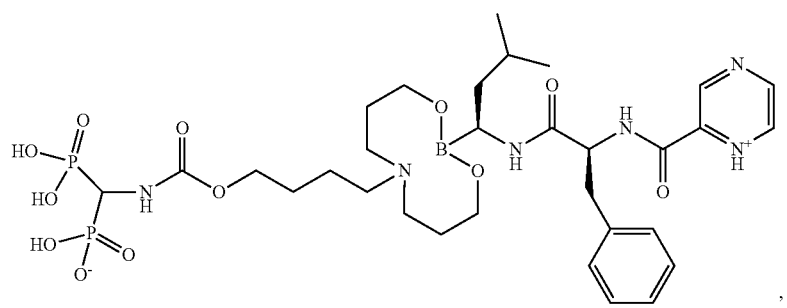
,

-continued
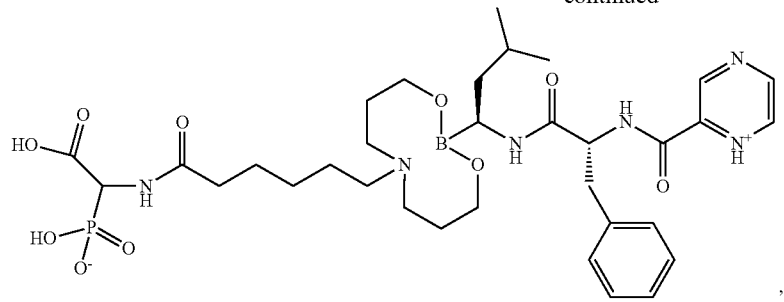,
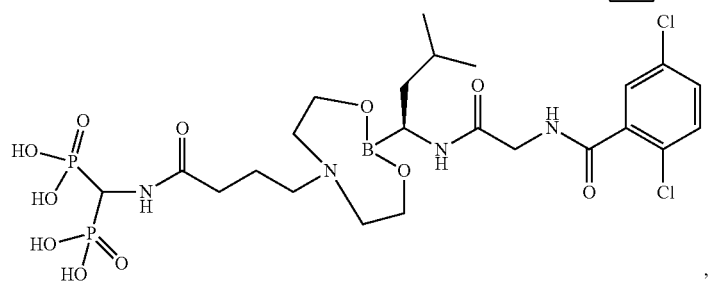,
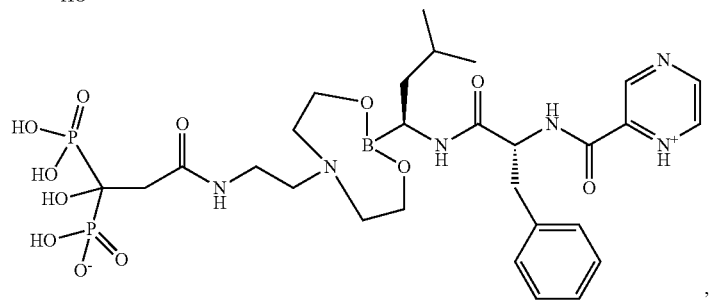,
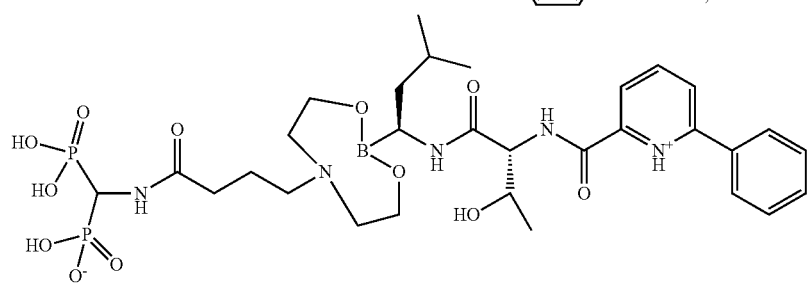,
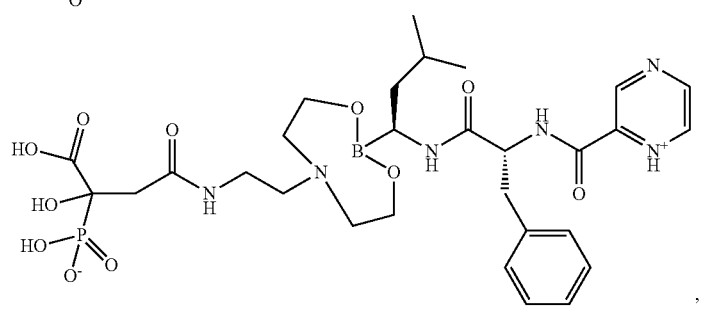,
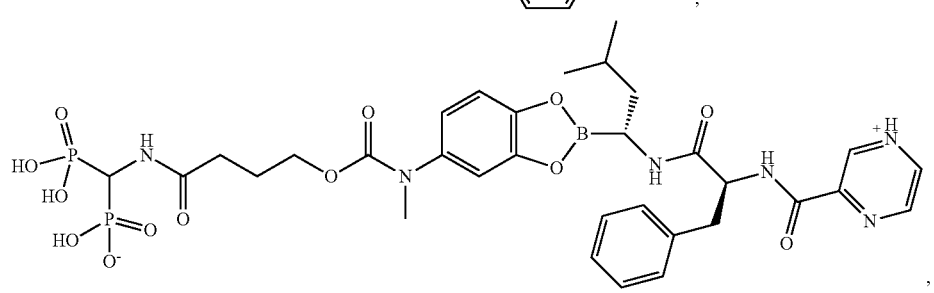, -continued
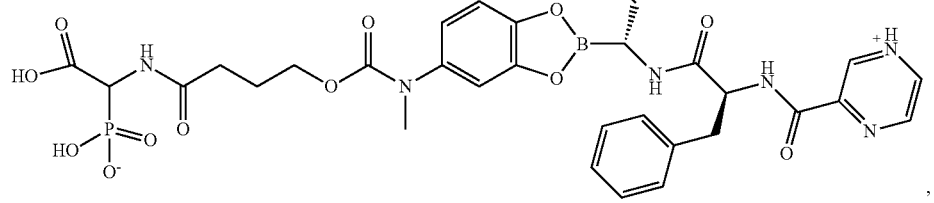
,
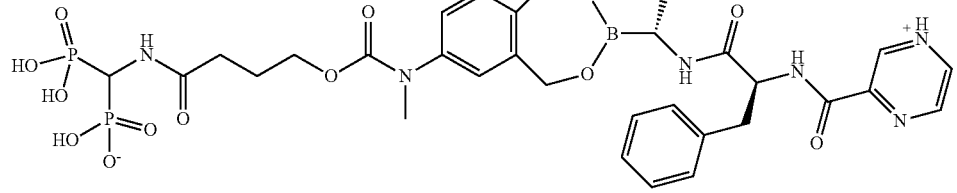
,
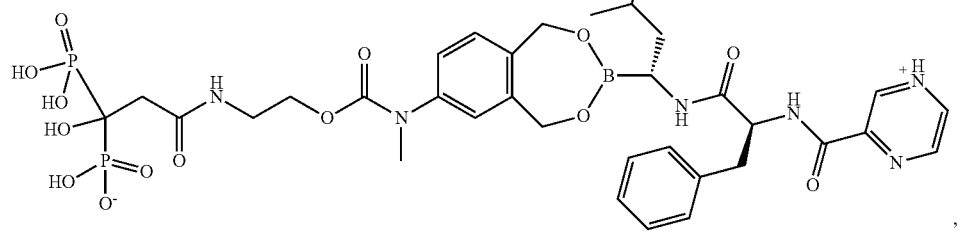
,
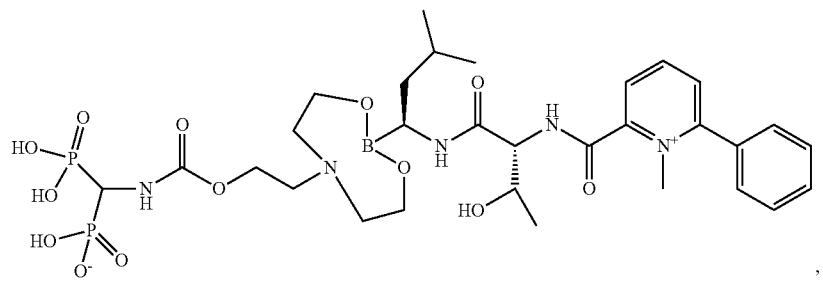
,
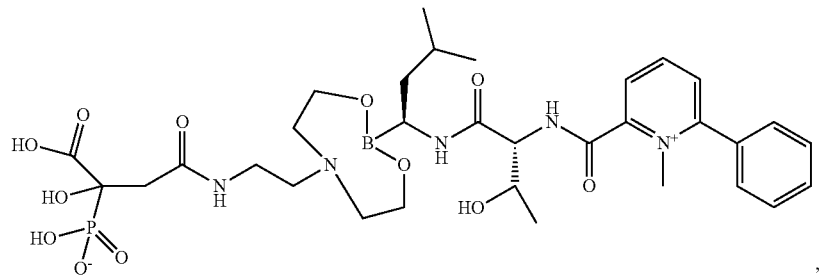
,
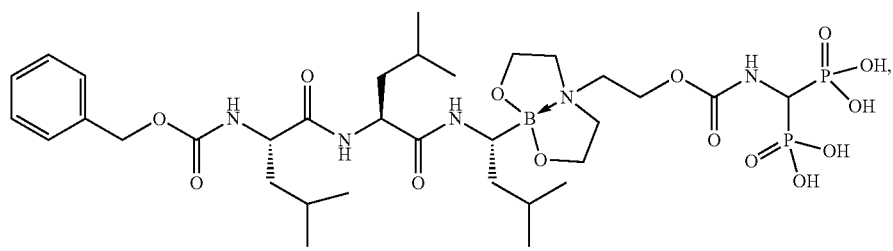

-continued
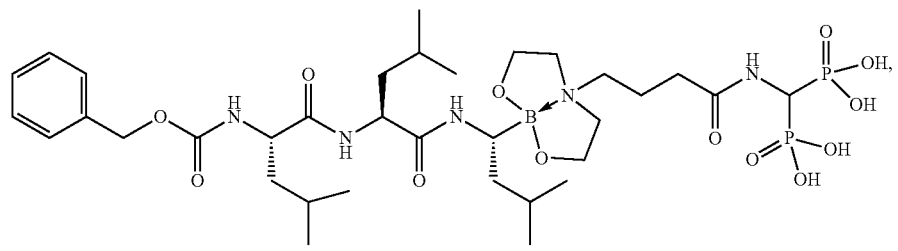
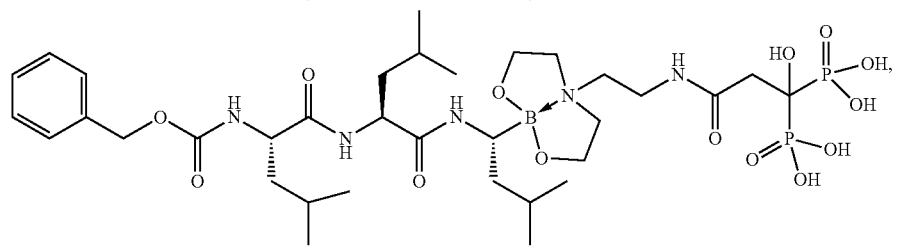
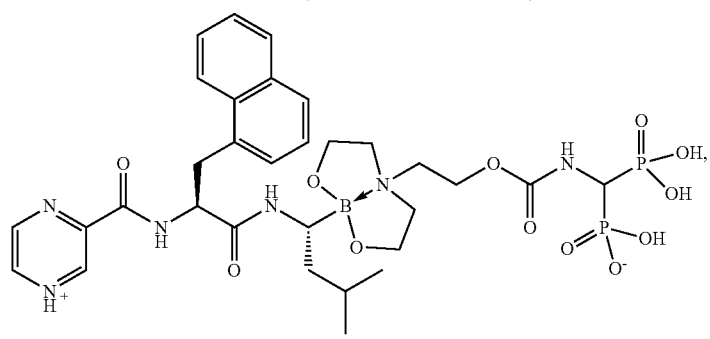
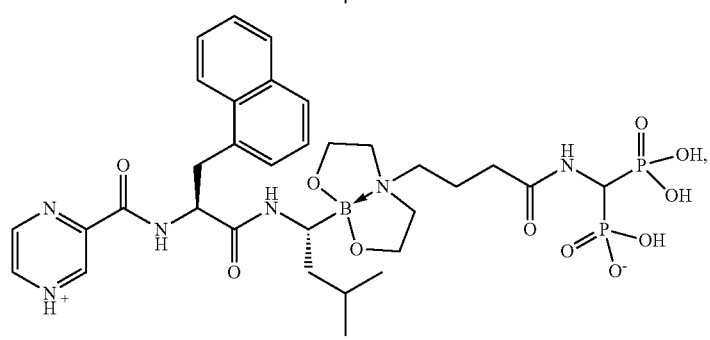
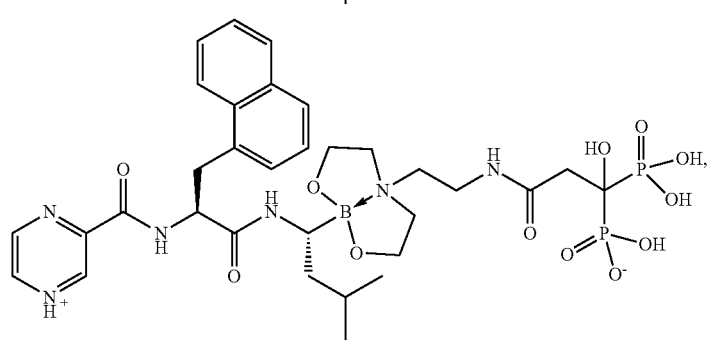
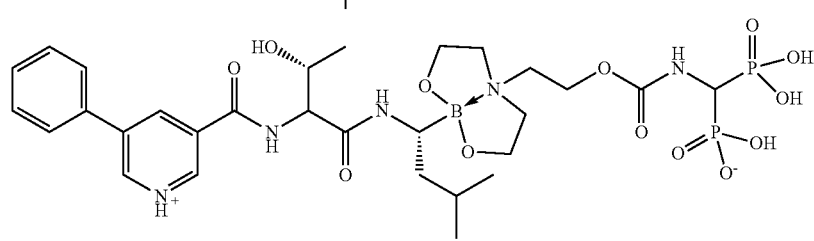

-continued
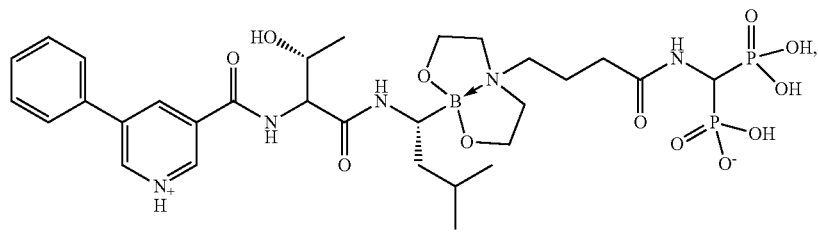
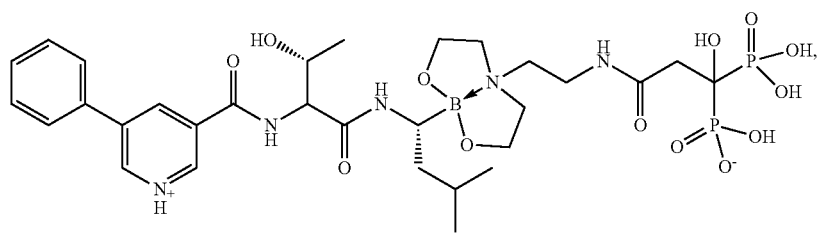
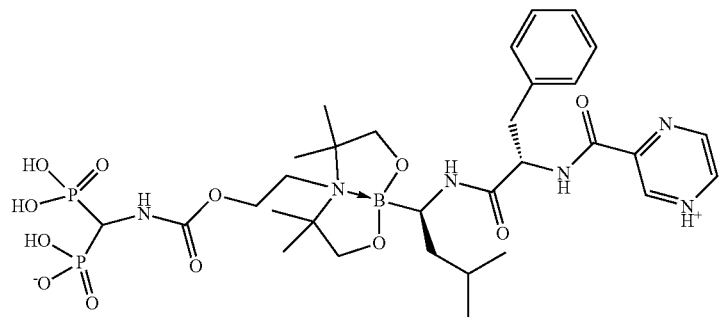
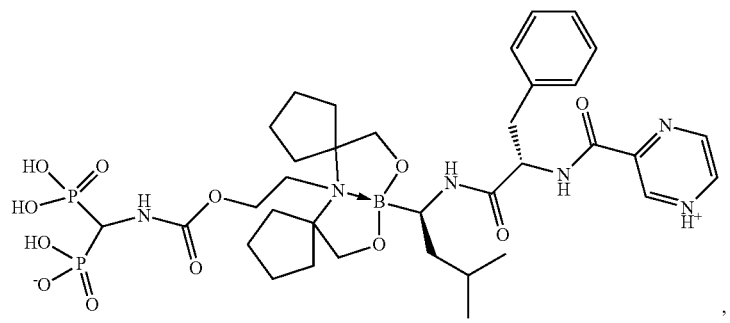
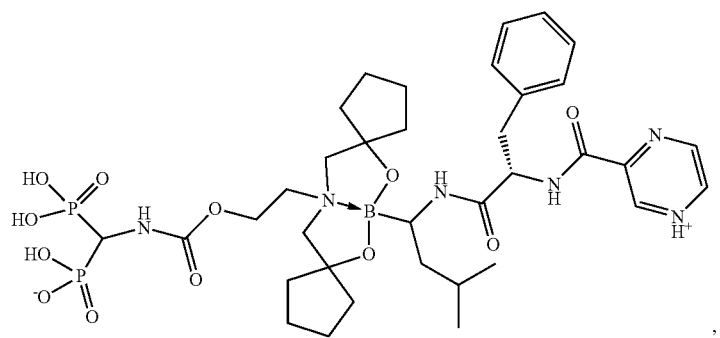

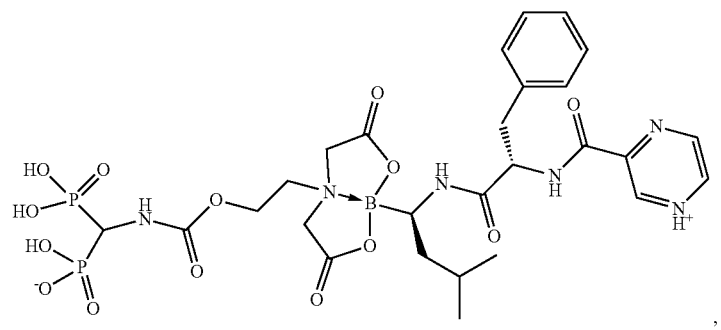,
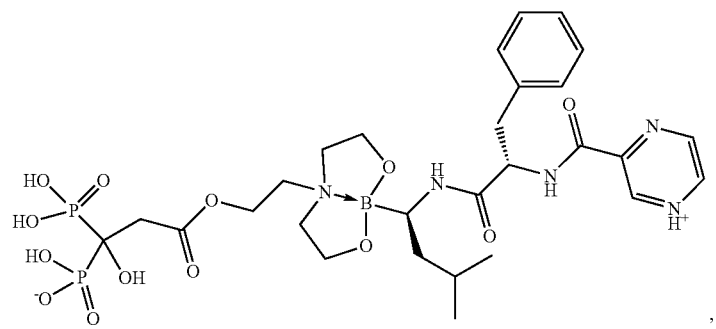,
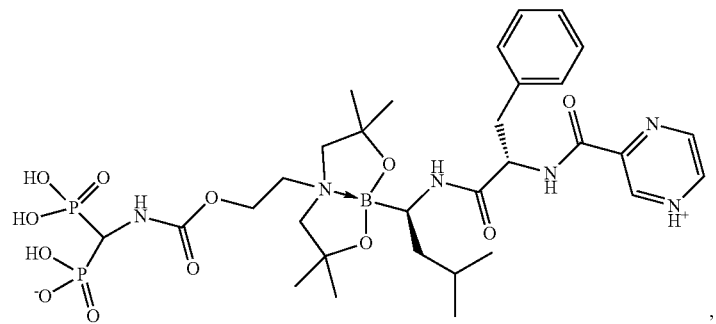,
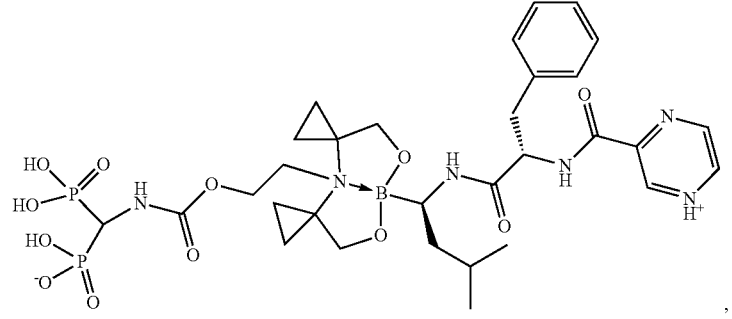,
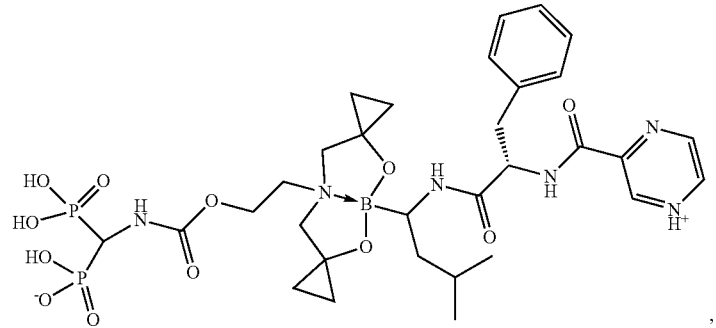,

-continued
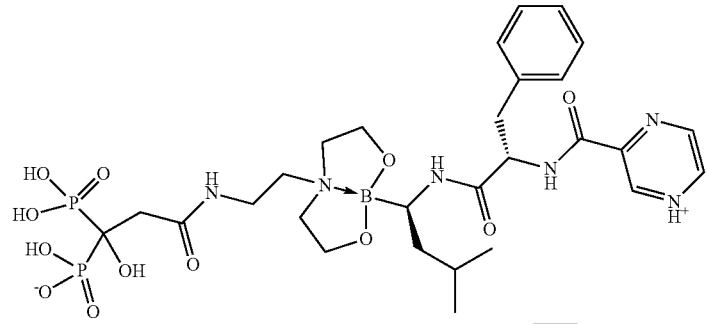
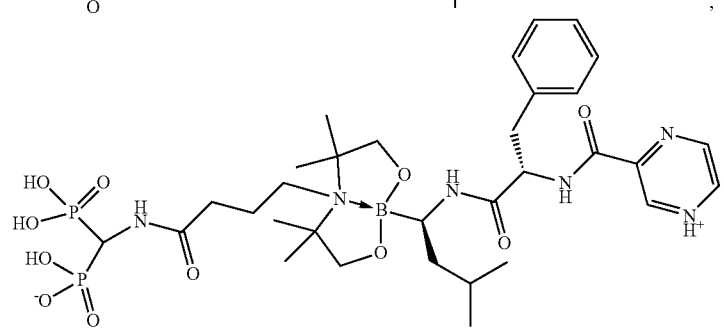
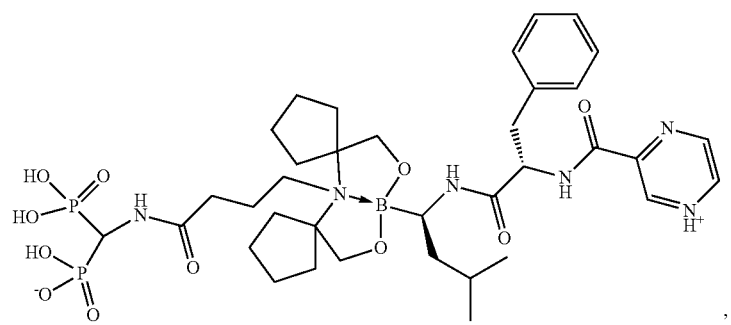
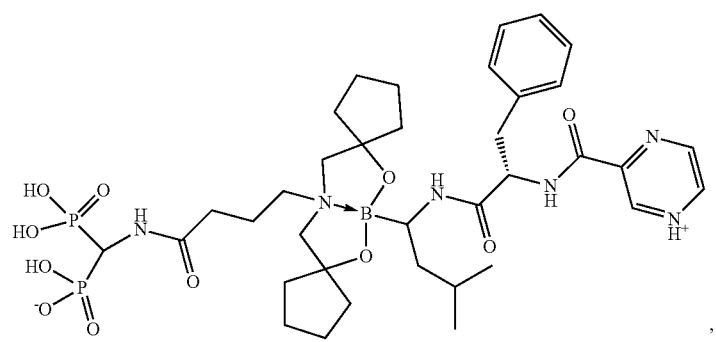

-continued
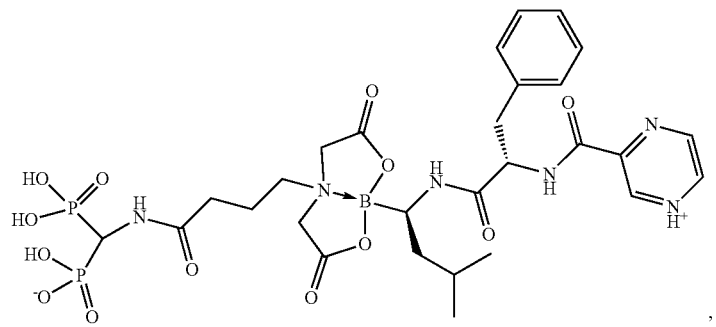
,
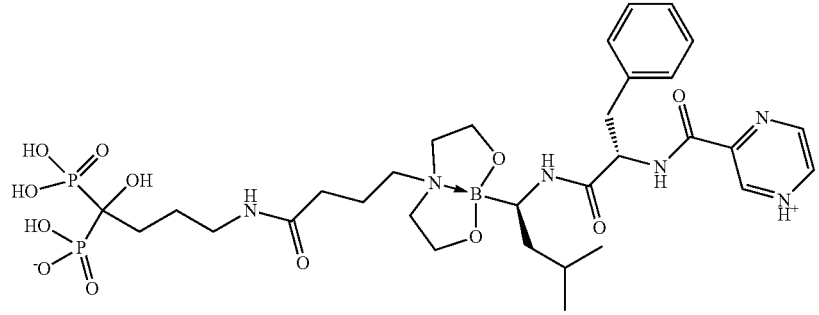
,
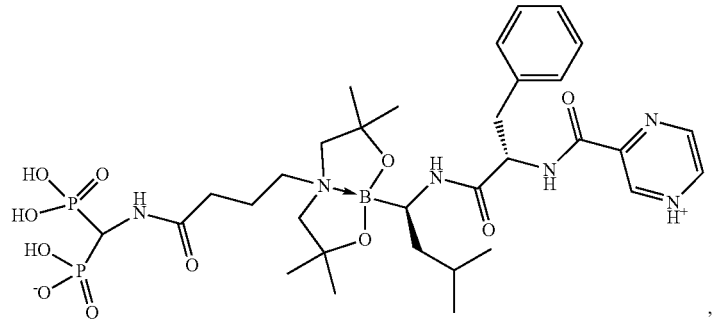
,
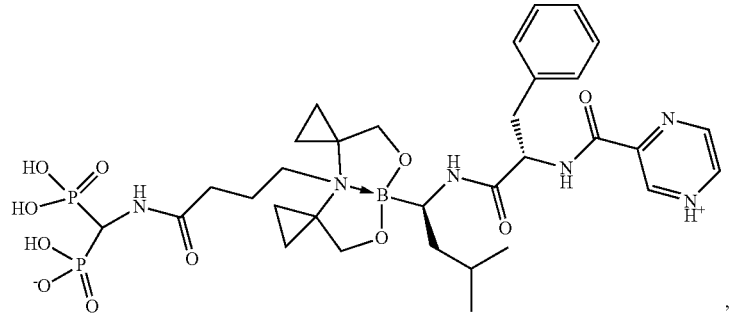
,
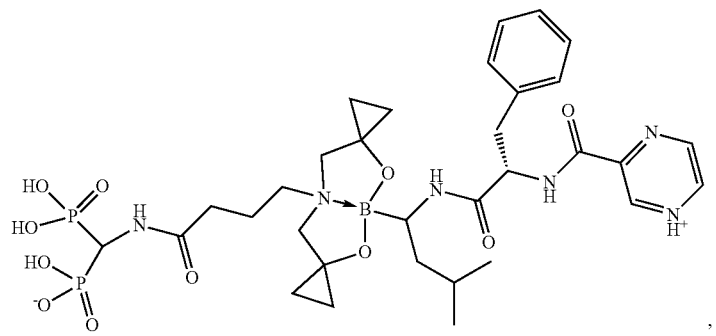
,

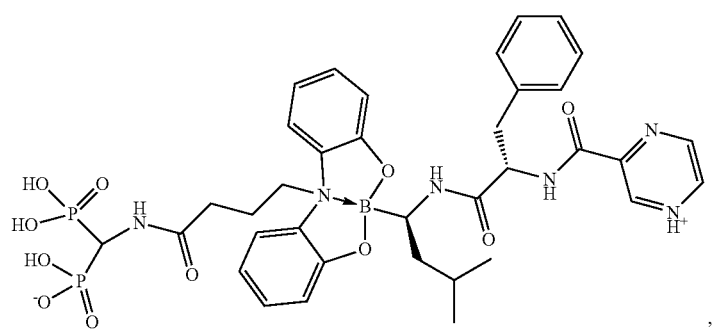
,
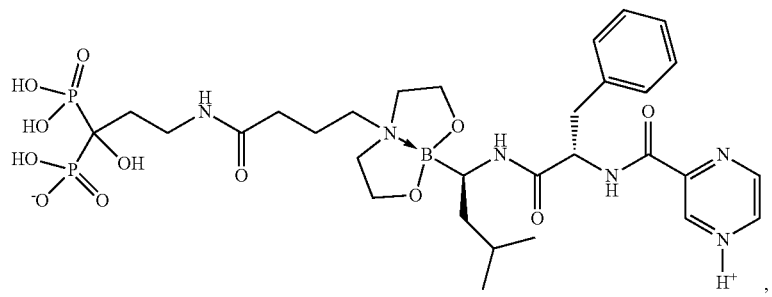
,
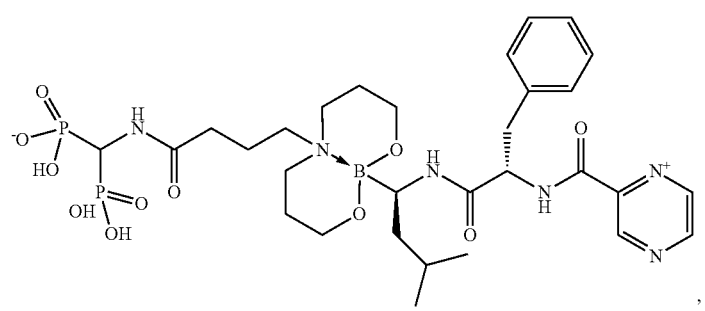
,
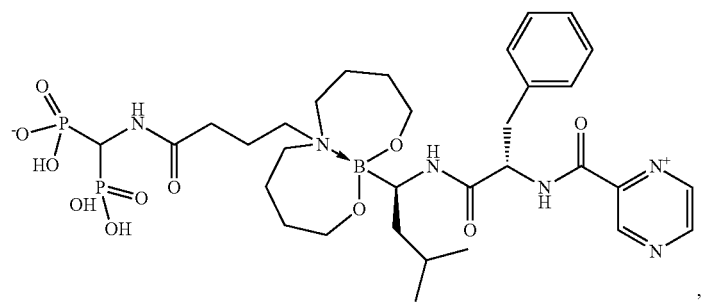
,
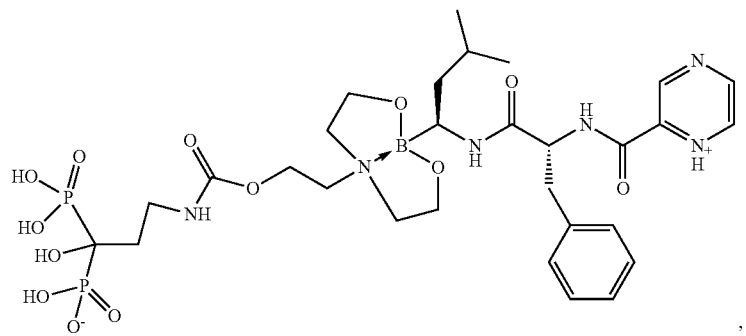
,

-continued
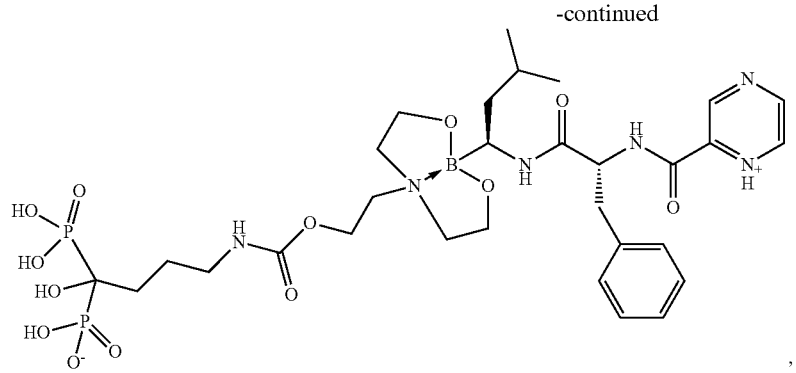
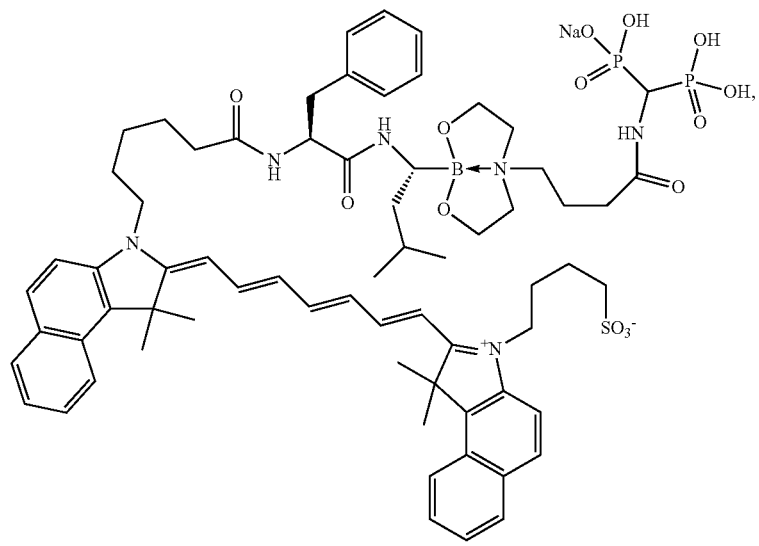
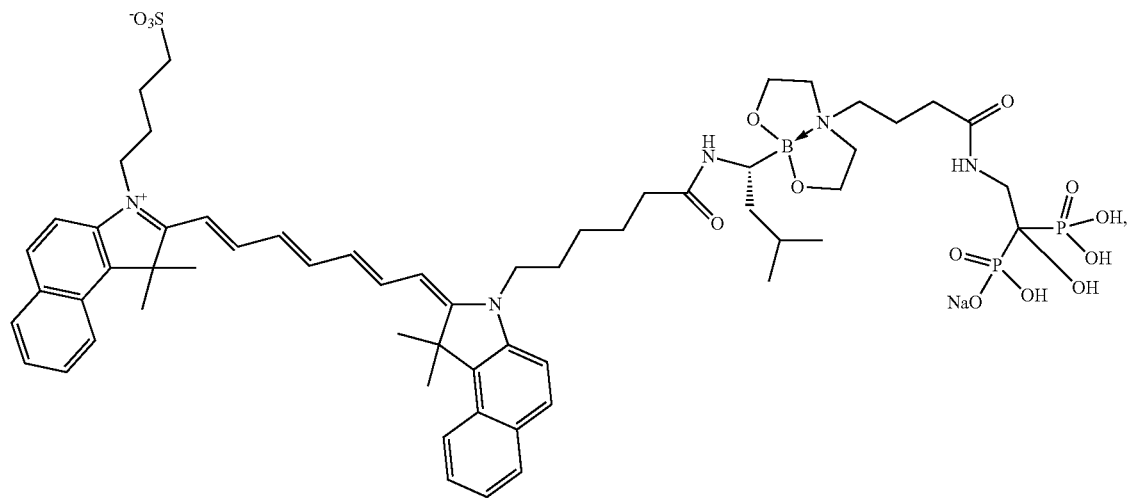

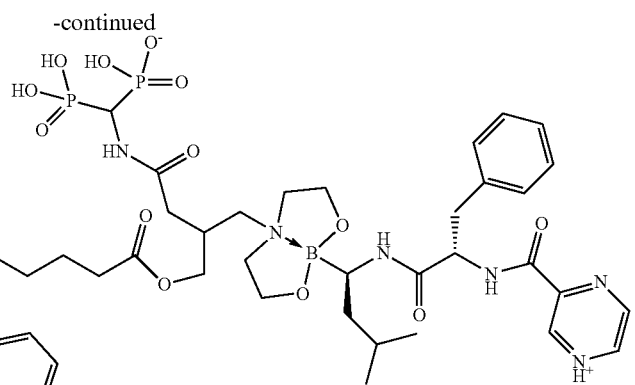
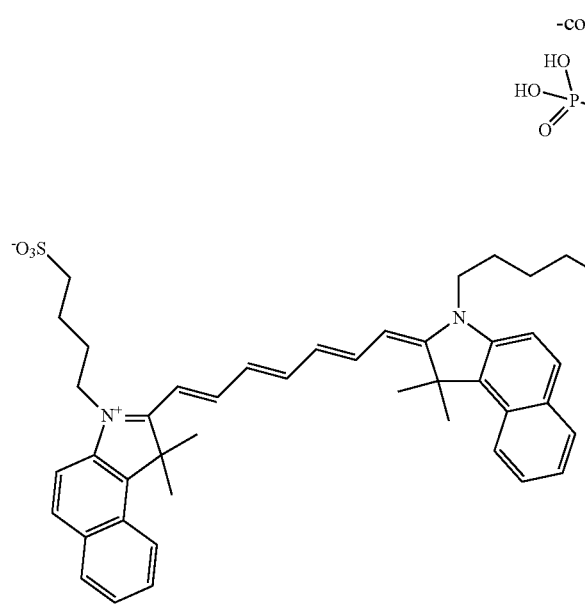
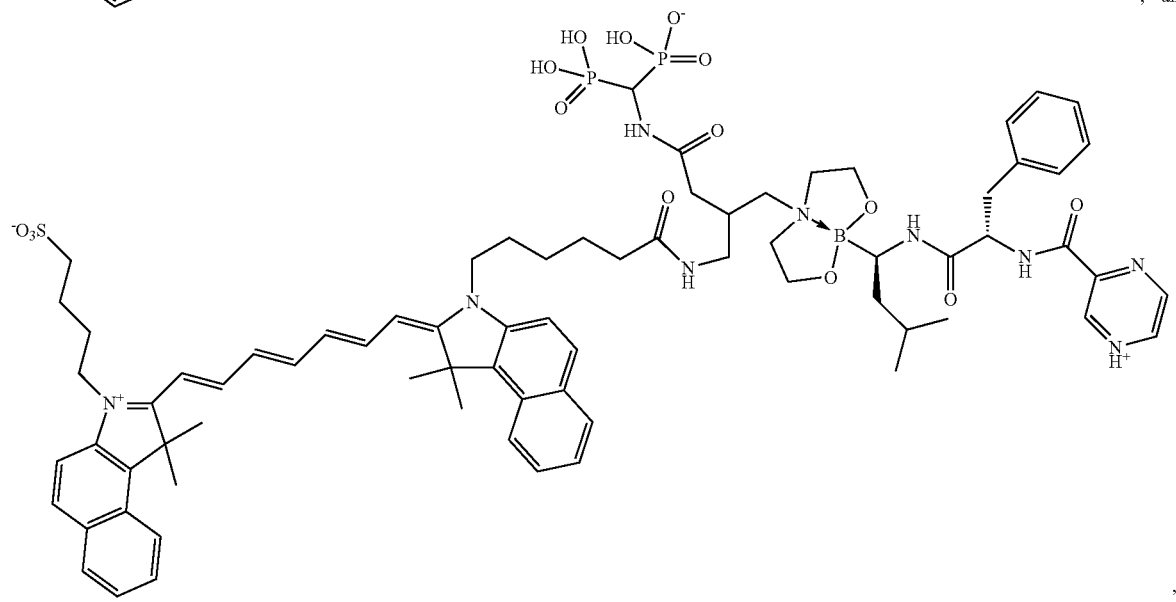

or a pharmaceutically acceptable salt thereof, an isomer thereof, or a mixture of isomers thereof.

In one embodiment, the compound is

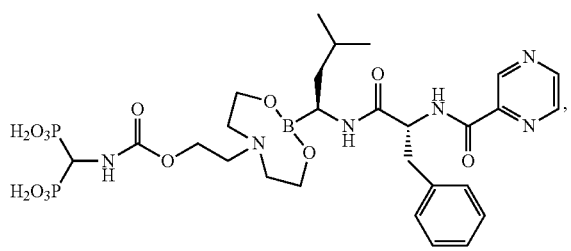

or a pharmaceutically acceptable salt thereof, an isomer thereof, or a mixture of isomers thereof.

The present invention also includes a composition for controlled local delivery of a therapeutic agent to bone, comprising at least one compound comprising or consisting of a therapeutic agent conjugated to a phosphonate moiety via a linker, wherein the therapeutic agent is bortezomib or an analogue thereof. In one embodiment, the at least one compound is a compound of formula (I), or a pharmaceutically acceptable salt thereof, an isomer thereof, or a mixture of isomers thereof. In another embodiment, the composition further comprises at least one pharmaceutically acceptable carrier. In another embodiment, the therapeutic agent is controllably released from the compound at a site in need of bone formation.

The present invention also includes a method of promoting bone formation at a site in need of bone formation in a subject or reducing bone resorption in a subject in need of less bone resorption, or both. In one embodiment, the method includes administering a therapeutically effective amount of a composition comprising at least one compound comprising a therapeutic agent conjugated to a phosphonate moiety via a linker, wherein the therapeutic agent is bortezomib (Btz) or an analogue thereof.

The present invention also includes a method of treating a disease selected from the group consisting of multiple myeloma and bone cancer in a subject in need thereof. In one embodiment, the method includes administering a therapeutically effective amount of a composition comprising at least one compound comprising a therapeutic agent conjugated to a phosphonate moiety via a linker, wherein the therapeutic agent is bortezomib (Btz) or an analogue thereof. In another embodiment, the at least one compound is a compound of formula (I), or a pharmaceutically acceptable salt thereof, an isomer thereof, or a mixture of isomers thereof. In another embodiment, the composition further comprises at least one pharmaceutically acceptable carrier.

In one embodiment, the subject has a disease or disorder selected from the group consisting of multiple myeloma, osteoporosis, osteonecrosis, osteoarthritis, rheumatoid arthritis, Paget's disease, bone fracture healing, prosthesis loosening, bone cancer, a myeloproliferative disease, radiotherapy-induced osteoporosis, leukemia, and cancers metastasized to bone. In another embodiment, the therapeutic agent is controllably released from the compound at the site in need of bone formation.

The present invention also includes a method of killing cancer cells of bone, bone marrow and bone surrounding tissues in a subject. The method includes administering a therapeutically effective amount of a composition comprising at least one compound of formula (I), or a pharmaceutically acceptable salt thereof, an isomer thereof, or a mixture of isomers thereof. In another embodiment, the subject has multiple myeloma.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1, comprising FIG. 1A is a graph of experimental data depicting the expression levels of E3 ligases in fracture callus measured by qPCR. The fold change was calculated by dividing the values at different time points by the value at 0 hr as 1. FIG. 1B is a series of images of immunoblots. Mice received MG132 24 hrs before they were sacrificed. Expression of total Ub-proteins was determined by blotting whole cell lysates with anti-ubiquitin Ab. Ub-JunB protein were detected by a Ub assay.

FIG. 2, comprising FIGS. 2A-2F, depicts experimental data demonstrating that Bortezomib (Btz) increases callus formation, bone strength, MSC numbers, and expression of osteoblast positive regulators. WT mice that received an open tibial fracture were treated with Btz (0.6 mg/kg body weight, ip) or vehicle at day 1, 3, 5, 7, and sacrificed at various days post-fracture. FIG. 2A is an image of the structure of Bortezomib. FIG. 2B is a graph depicting µCT data analyses of callus size from 10 days post-fracture. N+4 mice/group. FIG. 2C is a series of images of representative histology of fractured tibiae stained with alcian blue hematoxylin/orange G eosin showing cartilage (blue) and bone (pink) formation. Histomorphometric measurements were performed with a Visiopharm Imaging Analysis software system. N=3 mice/group. FIG. 2D is a series of graphs depicting data of biomechanical testing of tibiae from 28 days after fracture. N=5 mice/group. FIG. 2E is a series of images of spectra depicting data of immune-phenotyping of callus cells from 7 days post-fracture. FIG. 2F is a series of images of immunoblots depicting protein expression levels of total Ub-proteins and JunB and Runx2 levels in calluses from 10 days post-fracture. *p<0.05 vs. vehicle group.

FIG. 5, comprising FIG. 5A is a scheme of an exemplary synthesis of compound BP-Btz1. FIG. 5B is a series of images of bone slices pre-incubated with 1 µM BP-Btz1, Btz, or bisphosphonate (BP) overnight. Drug solutions were removed and bone slices were washed with PBS extensively. Bone matrix (BM) cells from $UB^{G76V}$-GFP mice were cultured on bone slices in the presence of M-CSF and RANKL for 9 days. Top images (a): GFP$^+$ cells were observed under a fluorescence microscope and GFP signal intensity was quantified. Middle images (b): bone slices were fixed and subjected to TRAP staining for osteoclasts (OCs). OC #/slice were counted. Bottom images (c): cells were removed from slices. Toluidine blue staining was performed and pit areas/slice were counted. FIG. 5C is a series of images of murine BM cells cultured and stained for ALP. FIG. 5D is a series of images of human MSCs cultured and stained for ALP. Murine BM cells and human MSCs were cultured in the OB-inducing medium plus different concentrations of BP-Btz1 or Btz for 4 or 6 days, respectively. Cells were stained for ALP. The ALP$^+$ areas were measured by Image J. *P<0.05 vs. Btz-treated cells.

FIG. 7, comprising FIGS. 7A-7C, depicts experimental data demonstrating increased Nestin-GFP$^+$ cells at an early phase of fracture callus. Nestin-GFP mice were used. FIG. 7A is a series of images of stained frozen sections of tibiae. Tibiae at 7 d post-fracture were subjected to frozen sections. Sections were stained by DAPI and converted to digital images after scanning with a whole slide imaging system. Numerous GFP$^+$ cells (green) were observed at newly formed woven bone adjacent to cartilage in the callus of a fractured bone. FIG. 7B is a graph of experimental data of cell populations 7 days post fracture. Cells were isolated from callus via enzyme digestion, stained with α-CD45, CD105, or Sca-1 Ab and subjected to flow cytometry to assess the percent of Nestin-GFP$^+$, CD45$^-$CD105$^+$, or CD45$^-$Sca-1$^+$ cells. FIG. 7C is a graph depicting the correlation between Nestin-GFP$^+$ cells and CD45$^-$CD105$^+$Sca-1$^+$ cells.

FIGS. 8A-8D, depicts experimental data demonstrating that Btz promotes fracture repair in aged mice. 20-m-old B6 mice had tibial fractures and were given Btz (0.6 mg/kg body weight, i.p.) or saline (Ctl) at day 1, 3, and 5 post-fracture 3 times. FIG. 8A is a graph depicting callus volumes for mice subjected to μCT at day 28. FIG. 8B is a graph depicting experimental data from mice subjected to bio-mechanical testing at day 28. FIG. 8C is a graph depicting experimental data of mice sacrificed for histological analyses at day 28. Values are the mean of 6 mice. *P<0.05 vs. saline-treated mice. FIG. 8D is a graph of data from 3-m-old (young) and 20-m-old (aged) mice after tibial fracture surgery and sacrificed at day 14 post-fracture. The % of CD45$^-$CD105$^+$Sca-1$^+$ cells in fracture callus were determined by flow cytometry as depicted in FIG. 7B. Values are the mean of 4 mice. *P<0.05 vs. saline-treated aged mice. #P<0.05 vs. young mice.

FIG. 20, comprising FIG. 20A depicts histomorphometric data. FIG. 20B depicts biomechanical data.

FIG. 25, comprising FIGS. 25A-25E, depicts experimental data demonstrating that BP-Btz1 reduces tumor burden and myeloma-induced bone loss more effectively than Btz. FIG. 25A depicts the groups and treatment used in the experimental examples. FIG. 25B depicts a table of clinical observations. FIG. 25C depicts images of GFP imaging showing the distribution of myeloma cells. FIG. 25D is a table of experimental data showing blood IgG2b levels. FIG. 25E is a table of experimental data showing osteoblast differentiation.

FIG. 29, comprising FIG. 29A depicts the groups and treatment used in the experimental examples. FIG. 29B depicts a table of experimental data of body weight before and after treatment. FIGS. 29C and 29D show experimental data demonstrating that BP-Btz reduces B cell numbers in bone marrow FIG. 29C depicts a table of experimental data of the thymus. FIG. 29D depicts experimental data of bone marrow. FIG. 29E depicts EM images of dorsal root ganglia-neuropathy demonstrating that BP-Btz1 prevents toxic effect on neurons.

DETAILED DESCRIPTION OF THE INVENTION

Figure 1A:
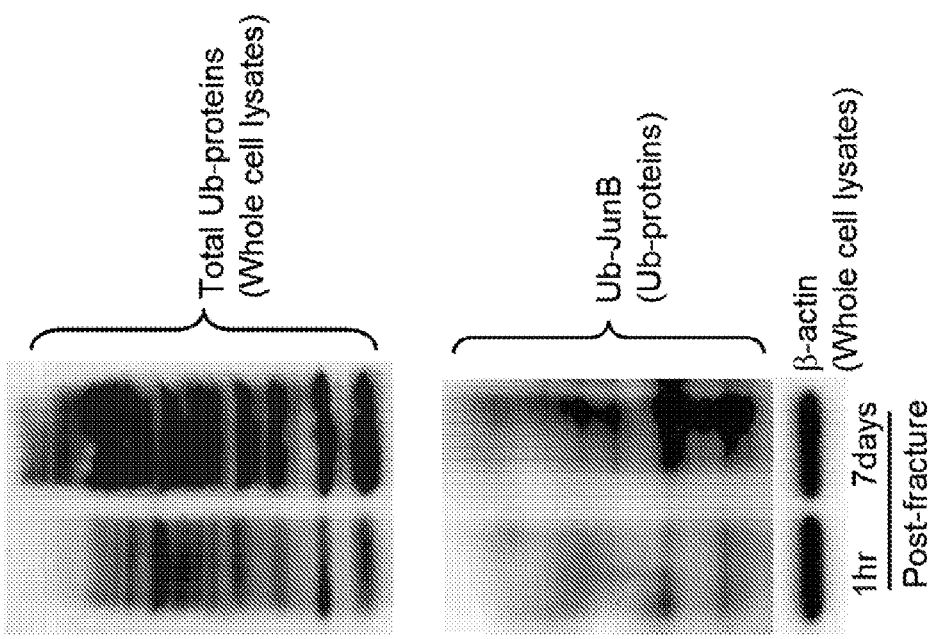
FIGS. 1A-1B, depicts experimental data demonstrating the increased levels of E3s and Ub-proteins in fracture callus. C57/B6 WT mice were sacrificed at different time points post-fracture.

This invention includes the unexpected identification of novel Bortezomib (Btz) conjugates that are useful for bone formation. In another aspect, the present invention includes the unexpected identification of novel Btz conjugates useful for the treatment of multiple myeloma. These bone-targeted compounds include a new chemical linker technology designed to conjugate Btz to a relatively biochemically inactive or active bisphosphonate (BP). As demonstrated herein, the compounds of the present invention have been shown to be effective in both reducing and preventing osteoclast formation and increasing osteoblast formation. The compounds of the invention have also been found to be effective directly as antitumor agents. The compounds of the invention have higher efficacy on bone fracture repair and as anti-myeloma cell agents and reduced systemic adverse effects, such as toxicity, than that of Btz (non-bone-targeted). The compounds of the invention are useful in treating patients with multiple myeloma, as well as patients with other bone disorders such as fracture, osteoporosis, cancer-bone metastasis, radiotherapy-induced osteoporosis, and arthritis. Thus, the present invention also includes compositions and methods useful for the treatment of bone disorders.

In part, the present invention provides a new chemical approach to link certain drugs to a bisphosphonate residue for a bone-targeting purpose, in which the drug is released from the conjugates on bone, allowing for a greater delivery of the drug to the bone compartment and a greater systemic safety of the conjugate than dosing the free drug component of the conjugate. Safety of the bisphosphonate component will generally be enhanced due to its inert bioactivity or short term use and low dose. The present invention also provides in part a new molecular pathway, the ubiquitin-proteasome system, to promote bone fracture healing in a large patient population, including the elderly which to date has not been studied.

The chemical attachment points and other chemical variants unique to the compounds of the invention may be modified in order to adjust the payload release rate, as would be understood by one of ordinary skill in the art. In some embodiments, the compound comprises a non-cleavable linker and the compound has a bioactivity at least the same as the inherent pharmacological activity of the parent Btz. As demonstrated herein, Btz was found to accelerate callus formation and increase bone strength in young and aged fractured mice, which is associated with increased Nestin$^+$ MPCs, Ub-proteins, and blood vessel formation.

The present invention also includes novel methods of promoting bone formation at a site in need of bone formation in a subject. The present invention also includes novel methods of promoting bone formation in a site at or near bone related cancers. In one embodiment, the subject has a disease or disorder selected from the group consisting of multiple myeloma, osteoporosis, osteonecrosis, osteomyelitis, osteoarthritis, rheumatoid arthritis, Paget's disease, bone fracture healing, prosthesis loosening, bone cancer, leukemia, a myeloproliferative disease, radiotherapy-induced osteoporosis, and a cancer metastasized to bone.

The present invention also includes a composition for controlled local delivery of a therapeutic agent to bone, comprising at least one compound comprising a therapeutic agent conjugated to a phosphonate moiety via a linker. In one embodiment, the therapeutic agent is bortezomib or an analogue thereof. The present invention also includes a composition comprising at least one compound of the invention, wherein the composition optionally further comprises at least one additional therapeutic agent. In one embodiment, the therapeutic agent is controllably released from the compound at the site in need of bone formation. In another embodiment, the therapeutic agent is controllably released from the compound at the site of bone related cancer therapy. In one embodiment, the cancer is multiple myeloma.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "abnormal," when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics that are normal or expected for one cell or tissue type might be abnormal for a different cell or tissue type.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a sign or symptom of the disease or disorder, the frequency with which such a sign or symptom is experienced by a patient, or both, is reduced.

The terms "patient," "subject," or "individual" are used interchangeably herein, and refer to any animal, or cells thereof whether in vitro or in situ, amenable to the methods described herein. In a non-limiting embodiment, the patient, subject or individual is a human.

As used herein, the term "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary and topical administration.

A "therapeutic" treatment is a treatment administered to a subject who exhibits signs of pathology, for the purpose of diminishing or eliminating those signs.

As used herein, the term "treatment" or "treating" is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has a condition contemplated herein, a sign or symptom of a condition contemplated herein or the potential to develop a condition contemplated herein, with the purpose to cure, heal, alleviate, relieve, alter, remedy, ameliorate, improve or affect a condition contemplated herein, the symptoms of a condition contemplated herein or the potential to develop a condition contemplated herein. Such treatments may be specifically tailored or modified, based on knowledge obtained from the field of pharmacogenomics.

As used herein, the terms "effective amount," "pharmaceutically effective amount" and "therapeutically effective amount" refer to a nontoxic but sufficient amount of an agent to provide the desired biological result. That result may be reduction and/or alleviation of a sign, a symptom, or a cause of a disease or disorder, or any other desired alteration of a biological system. An appropriate therapeutic amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively non-toxic, i.e., the material may be administered to an individual without causing an undesirable biological effect or interacting in a deleterious manner with any of the components of the composition in which it is contained.

As used herein, the language "pharmaceutically acceptable salt" refers to a salt of the administered compound prepared from pharmaceutically acceptable non-toxic acids, including inorganic acids, organic acids, solvates, hydrates, or clathrates thereof. Examples of such inorganic acids are hydrochloric, hydrobromic, hydroiodic, nitric, sulfuric, phosphoric, acetic, hexafluorophosphoric, citric, gluconic, benzoic, propionic, butyric, sulfosalicylic, maleic, lauric, malic, fumaric, succinic, tartaric, amsonic, pamoic, p-toluenesulfonic, and mesylic. Appropriate organic acids may be selected, for example, from aliphatic, aromatic, carboxylic and sulfonic classes of organic acids, examples of which are formic, acetic, propionic, succinic, camphorsulfonic, citric, fumaric, gluconic, isethionic, lactic, malic, mucic, tartaric, para-toluenesulfonic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic (besylate), stearic, sulfanilic, alginic, galacturonic, and the like. Furthermore, pharmaceutically acceptable salts include, by way of non-limiting example, alkaline earth metal salts (e.g., calcium or magnesium), alkali metal salts (e.g., sodium-dependent or potassium), and ammonium salts.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

An "effective amount" of a delivery vehicle is that amount sufficient to effectively bind or deliver a compound.

As used herein, the term "potency" refers to the dose needed to produce half the maximal response ($ED_{50}$).

As used herein, the term "efficacy" refers to the maximal effect ($E_{max}$) achieved within an assay.

As used herein, the term "alkyl," by itself or as part of another substituent means, unless otherwise stated, a straight or branched chain hydrocarbon having the number of carbon atoms designated (i.e. $C_{1-6}$ means one to six carbon atoms) and including straight, branched chain, or cyclic substituent groups. Examples include methyl, ethyl, propyl, isopropyl, butyl, isobutyl, tert-butyl, pentyl, neopentyl, hexyl, and cyclopropylmethyl.

As used herein, the term "substituted alkyl" means alkyl as defined above, substituted by one, two or three substituents selected from the group consisting of halogen, —OH, alkoxy, —$NH_2$, amino, azido, —$N(CH_3)_2$, —C(=O)OH, trifluoromethyl, C≡N, —C(=O)O($C_1$-$C_4$)alkyl, —C(=O)$NH_2$, —$SO_2NH_2$, —C(=NH)$NH_2$, and —$NO_2$. Examples of substituted alkyls include, but are not limited to, 2,2-difluoropropyl, 2-carboxycyclopentyl and 3-chloropropyl.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—$CH_2$—$CH_2$—$CH_3$, —$CH_2$—$CH_2$—$CH_2$—OH, —$CH_2$—$CH_2$—NH—$CH_3$, —$CH_2$—S—$CH_2$—$CH_3$, and —$CH_2CH_2$—S(=O)—$CH_3$. Up to two heteroatoms may be consecutive, such as, for example, —$CH_2$—NH—$OCH_3$, or —$CH_2$—$CH_2$—S—S—$CH_3$ As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers.

As used herein, the term "halo" or "halogen" alone or as part of another substituent means, unless otherwise stated, a fluorine, chlorine, bromine, or iodine atom.

As used herein, the term "cycloalkyl" refers to a mono cyclic or polycyclic non-aromatic radical, wherein each of the atoms forming the ring (i.e. skeletal atoms) is a carbon atom. In one embodiment, the cycloalkyl group is saturated or partially unsaturated. In another embodiment, the cycloalkyl group is fused with an aromatic ring. Cycloalkyl groups include groups having from 3 to 10 ring atoms. Illustrative examples of cycloalkyl groups include, but are not limited to, the following moieties:

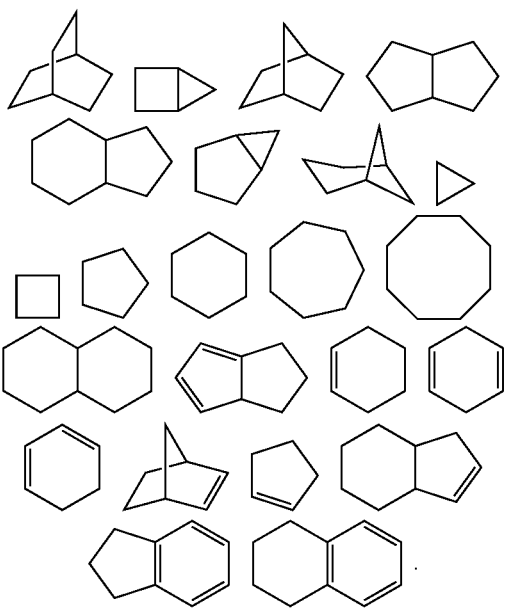

Monocyclic cycloalkyls include, but are not limited to, cyclopropyl, cyclobutyl, cyclopentyl, cyclohexyl, cycloheptyl, and cyclooctyl. Dicyclic cycloalkyls include, but are not limited to, tetrahydronaphthyl, indanyl, and tetrahydropentalene. Polycyclic cycloalkyls include adamantine and norbornane. The term cycloalkyl includes "unsaturated nonaromatic carbocyclyl" or "nonaromatic unsaturated carbocyclyl" groups, both of which refer to a nonaromatic carbocycle as defined herein, which contains at least one carbon carbon double bond or one carbon carbon triple bond.

As used herein, the term "heterocycloalkyl" or "heterocyclyl" refers to a heteroalicyclic group containing one to four ring heteroatoms each selected from O, S and N. In one embodiment, each heterocycloalkyl group has from 4 to 10 atoms in its ring system, with the proviso that the ring of said group does not contain two adjacent O or S atoms. In another embodiment, the heterocycloalkyl group is fused with an aromatic ring. In one embodiment, the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

An example of a 3-membered heterocycloalkyl group includes, and is not limited to, aziridine. Examples of 4-membered heterocycloalkyl groups include, and are not limited to, azetidine and a beta lactam. Examples of 5-membered heterocycloalkyl groups include, and are not limited to, pyrrolidine, oxazolidine and thiazolidinedione. Examples of 6-membered heterocycloalkyl groups include, and are not limited to, piperidine, morpholine and piperazine. Other non-limiting examples of heterocycloalkyl groups are:

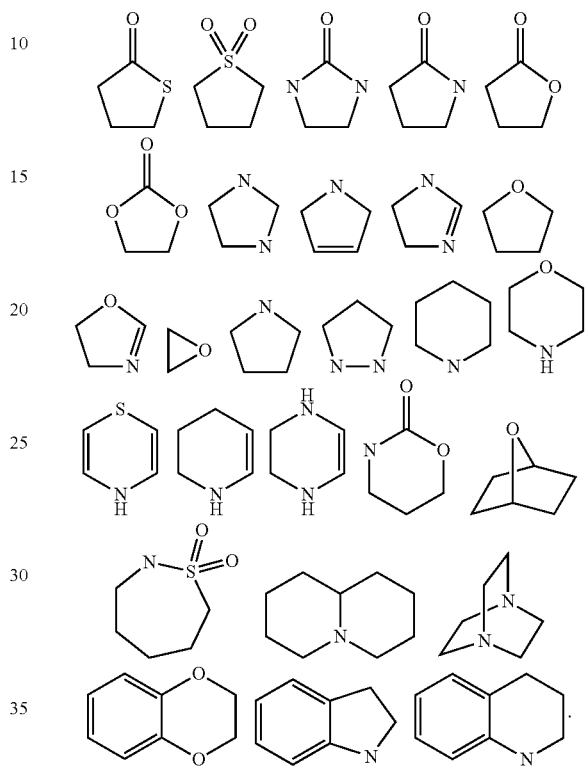

Examples of non-aromatic heterocycles include monocyclic groups such as aziridine, oxirane, thiirane, azetidine, oxetane, thietane, pyrrolidine, pyrroline, pyrazolidine, imidazoline, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin, and hexamethyleneoxide.

As used herein, the term "aromatic" refers to a carbocycle or heterocycle with one or more polyunsaturated rings and having aromatic character, i.e. having (4n+2) delocalized π (pi) electrons, where n is an integer.

As used herein, the term "aryl," employed alone or in combination with other terms, means, unless otherwise stated, a carbocyclic aromatic system containing one or more rings (typically one, two or three rings), wherein such rings may be attached together in a pendent manner, such as a biphenyl, or may be fused, such as naphthalene. Examples of aryl groups include phenyl, anthracyl, and naphthyl.

As used herein, the term "aryl-($C_1$-$C_3$)alkyl" means a functional group wherein a one- to three-carbon alkylene chain is attached to an aryl group, e.g., —$CH_2CH_2$-phenyl. Preferred is aryl-$CH_2$— and aryl-$CH(CH_3)$—. The term "substituted aryl-($C_1$-$C_3$)alkyl" means an aryl-($C_1$-$C_3$)alkyl functional group in which the aryl group is substituted. Similarly, the term "heteroaryl-($C_1$-$C_3$)alkyl" means a functional group wherein a one to three carbon alkylene chain is attached to a heteroaryl group, e.g., —CH₂CH₂-pyridyl. The term "substituted heteroaryl-(C₁-C₃)alkyl" means a heteroaryl-(C₁-C₃)alkyl functional group in which the heteroaryl group is substituted.

As used herein, the term "heteroaryl" or "heteroaromatic" refers to a heterocycle having aromatic character. A polycyclic heteroaryl may include one or more rings that are partially saturated. Examples include the following moieties:

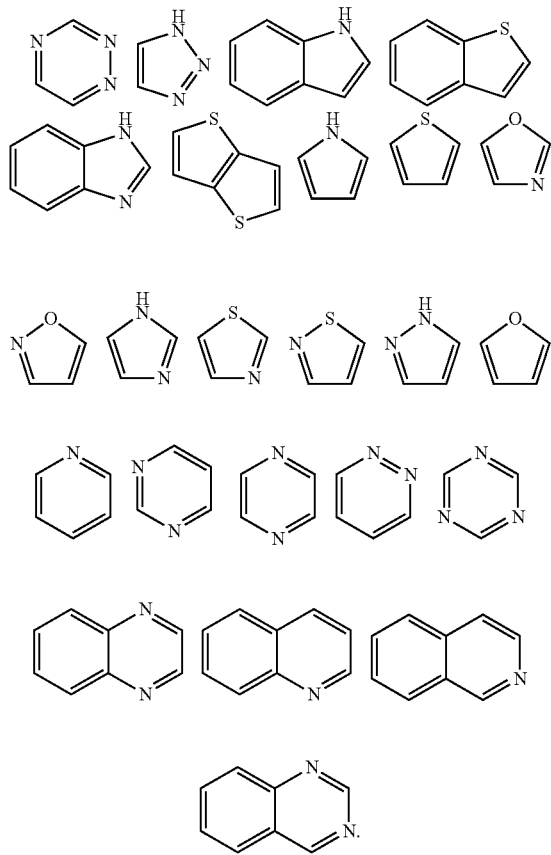

Examples of heteroaryl groups also include pyridyl, pyrazinyl, pyrimidinyl (particularly 2- and 4-pyrimidinyl), pyridazinyl, thienyl, furyl, pyrrolyl (particularly 2-pyrrolyl), imidazolyl, thiazolyl, oxazolyl, pyrazolyl (particularly 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl. Examples of polycyclic heterocycles and heteroaryls include indolyl (particularly 3-, 4-, 5-, 6- and 7-indolyl), indolinyl, quinolyl, tetrahydroquinolyl, isoquinolyl (particularly 1- and 5-isoquinolyl), 1,2,3,4-tetrahydroisoquinolyl, cinnolinyl, quinoxalinyl (particularly 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (particularly 3-, 4-, 5-, 6- and 7-benzofuryl), 2,3-dihydrobenzofuryl, 1,2-benzisoxazolyl, benzothienyl (particularly 3-, 4-, 5-, 6-, and 7-benzothienyl), benzoxazolyl, benzothiazolyl (particularly 2-benzothiazolyl and 5-benzothiazolyl), purinyl, benzimidazolyl (particularly 2-benzimidazolyl), benzotriazolyl, thioxanthinyl, carbazolyl, carbolinyl, acridinyl, pyrrolizidinyl, and quinolizidinyl.

As used herein, the term "substituted" means that an atom or group of atoms has replaced hydrogen as the substituent attached to another group. The term "substituted" further refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two.

As used herein, the term "optionally substituted" means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

In one embodiment, the substituents are independently selected from the group consisting of oxo, halogen, —CN, —NH₂, —OH, —NH(CH₃), —N(CH₃)₂, alkyl (including straight chain, branched and/or unsaturated alkyl), substituted or unsubstituted cycloalkyl, substituted or unsubstituted heterocycloalkyl, fluoro alkyl, substituted or unsubstituted heteroalkyl, substituted or unsubstituted alkoxy, fluoroalkoxy, —S-alkyl, S(=O)₂alkyl, —C(=O)NH[substituted or unsubstituted alkyl, or substituted or unsubstituted phenyl], —C(=O)N[H or alkyl]₂, —OC(=O)N[substituted or unsubstituted alkyl]₂, —NHC(=O)NH [substituted or unsubstituted alkyl, or substituted or unsubstituted phenyl], —NHC(=O)alkyl, —N[substituted or unsubstituted alkyl]C(=O)[substituted or unsubstituted alkyl], —NHC(=O)[substituted or unsubstituted alkyl], —C(OH)[substituted or unsubstituted alkyl]₂, and —C(NH₂)[substituted or unsubstituted alkyl]₂. In another embodiment, by way of example, an optional substituent is selected from oxo, fluorine, chlorine, bromine, iodine, —CN, —NH₂, —OH, —NH(CH₃), —N(CH₃)₂, —CH₃, —CH₂CH₃, —CH(CH₃)₂, —CF₃, —CH₂CF₃, —OCH₃, —OCH₂CH₃, —OCH(CH₃)₂, —OCF₃, —OCH₂CF₃, —S(=O)₂—CH₃, —C(=O)NH₂, —C(=O)—NHCH₃, —NHC(=O)NHCH₃, —C(=O)CH₃, —ON(O)₂, and —C(=O)OH. In yet one embodiment, the substituents are independently selected from the group consisting of C₁₋₆ alkyl, —OH, C₁₋₆ alkoxy, halo, amino, acetamido, oxo and nitro. In yet another embodiment, the substituents are independently selected from the group consisting of C₁₋₆ alkyl, C₁₋₆ alkoxy, halo, acetamido, and nitro. As used herein, where a substituent is an alkyl or alkoxy group, the carbon chain may be branched, straight or cyclic, with straight being preferred.

As used herein, the term "analogue" refers to a molecule that is not identical, but has analogous functional or structural features.

As used herein, the terms "bortezomib" and "Velcade," which may be used interchangeably, refer to [(1R)-3-methyl-1-[[(2S)-1-oxo-3-phenyl-2[(pyrazinylcarbonyl)amino]propyl]amino]butyl] boronic acid.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention is partly based on the discovery that the use of carbamate linkers resulted in the delivery of Btz to bone by utilizing the boronic ester functional group of Btz as a linking group. One advantage of the present invention is that the linker is labile in the presence of the low pH conditions that occur on the bone surface.

Compounds Useful within the Invention

In one aspect, the present invention includes a compound comprising a therapeutic agent conjugated to a phosphonate moiety via a linker, wherein the therapeutic agent is bortezomib (Btz) or an analogue thereof. As used herein, the term "conjugate" refers to a compound comprising a therapeutic agent conjugated or attached to a phosphonate moiety via a linker.

Any suitable linker may be used in the invention, as would be understood by one ordinary skill in the art. The linkers may comprise any of a variety of functional groups including an amide, ester, ether, thioether, carbamate, urea, amine or other linkage. In some embodiments, the linker comprises a cleavable bond, e.g. a bond that is unstable and/or is cleaved upon changes in certain intracellular parameters (e.g., pH or redox potential). In one embodiment, the linker is cleaved due to acidic hydrolysis. In another embodiment, the linker is cleaved enzymatically, such as by a protease. In another embodiment, the linker is cleaved due to both acidic hydrolysis and enzymatically. In some embodiments, the linker is non-cleavable. For example, it may be desirable to prevent or reduce the rate of release of Btz from the conjugate when the conjugate itself possesses desirable bioactivity. As would be understood by one of ordinary skill in the art, the stability of the bond between the linker and the bisphosphonate group and between the linker and the Btz molecule influences how slowly or rapidly each respective bond is cleaved in a particular environment, thereby influencing how slowly or rapidly Btz may be released from the conjugate. In one embodiment, Btz is released slowly from the conjugate. In another embodiment, Btz is released rapidly from the conjugate. In a non-limiting example, the linker is bonded to the Btz molecule and/or the bisphosphonate via a functional group on the linker that provides a more stable bond, and therefore reduces the rate at which Btz is released from the conjugate. In another non-limiting example, the linker may be bonded to the Btz molecule and/or the bisphosphonate via a functional group on the linker that provides a more labile or less stable bond, and therefore increases the rate at which Btz is released from the conjugate. Examples of functional groups that provide a more stable bond include an amide. Examples of functional groups that provide a more labile bond or a less stable or unstable bond include a carbonate group or a carbamate group.

In other embodiments, the electronics of the linker may contribute to the rate at which the Btz molecule is released from the conjugate. For example, in formula (I) when $Z^3$ is N or in formula (II), the Lewis basicity of the amine bonded to the Btz molecule can be modulated based on the electronics of the linker. In one embodiment, the incorporation of electron donor groups, such as additional methylene groups, in the linker increases the Lewis basicity of the amine, thereby increasing the stability of the bond between the linker and the Btz molecule. In another embodiment, the incorporation of electron withdrawing groups in the linker decreases the Lewis basicity of the amine, thereby decreasing the stability of the bond between the linker and the Btz molecule. In one aspect, the reactivity of compounds of the invention is designed to be tunable to allow for the preparation of sufficiently stable conjugates which will still release Btz efficiently once targeted to bone due to the lower pH in the bone matrix. The high kinetic affinity of bisphosphonates for bone allows for transport to bone to be accomplished without significant degradation of the conjugate and release of the Btz systemically.

Figure 13:
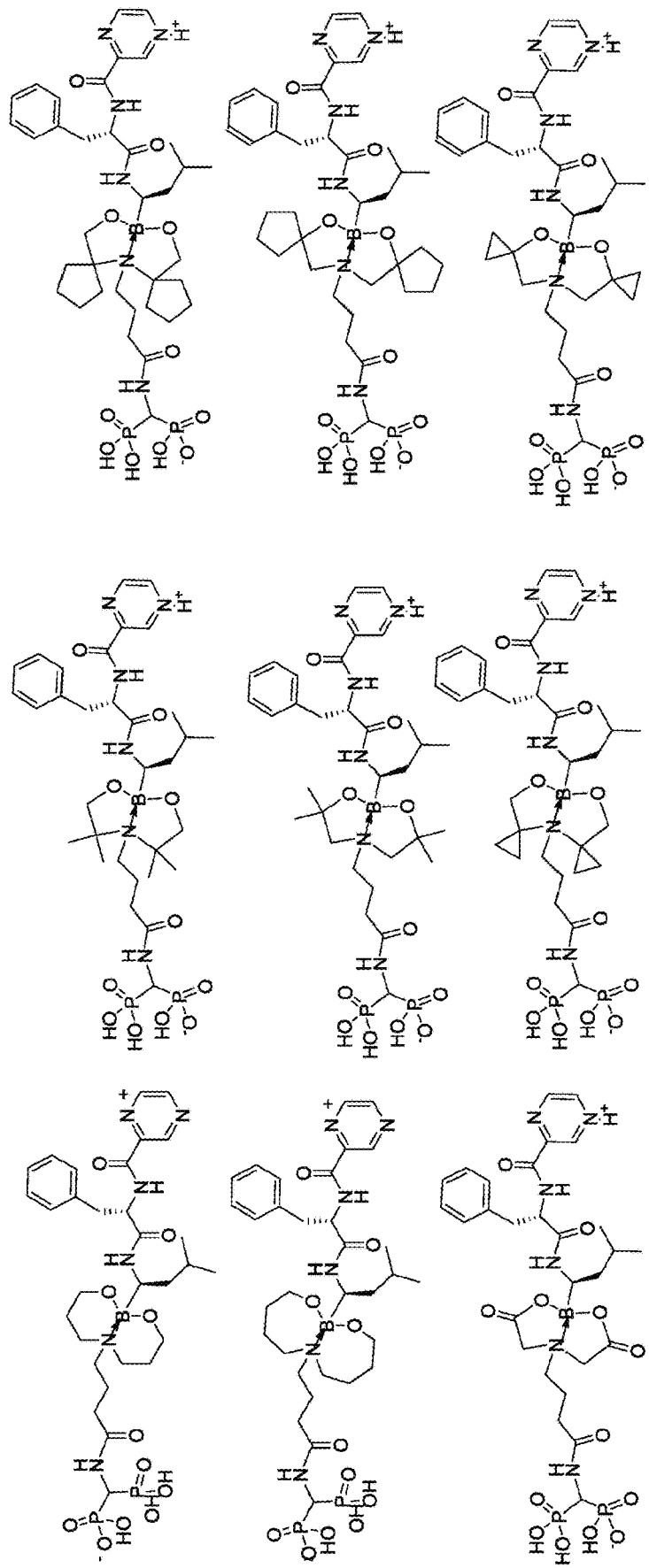
FIG. 13 depicts compounds of the invention with a variety of boronate linkages with different relative rates of cleavage and release of bortezomib (Btz) or other proteasome inhibitor in vivo.
Figure 14:
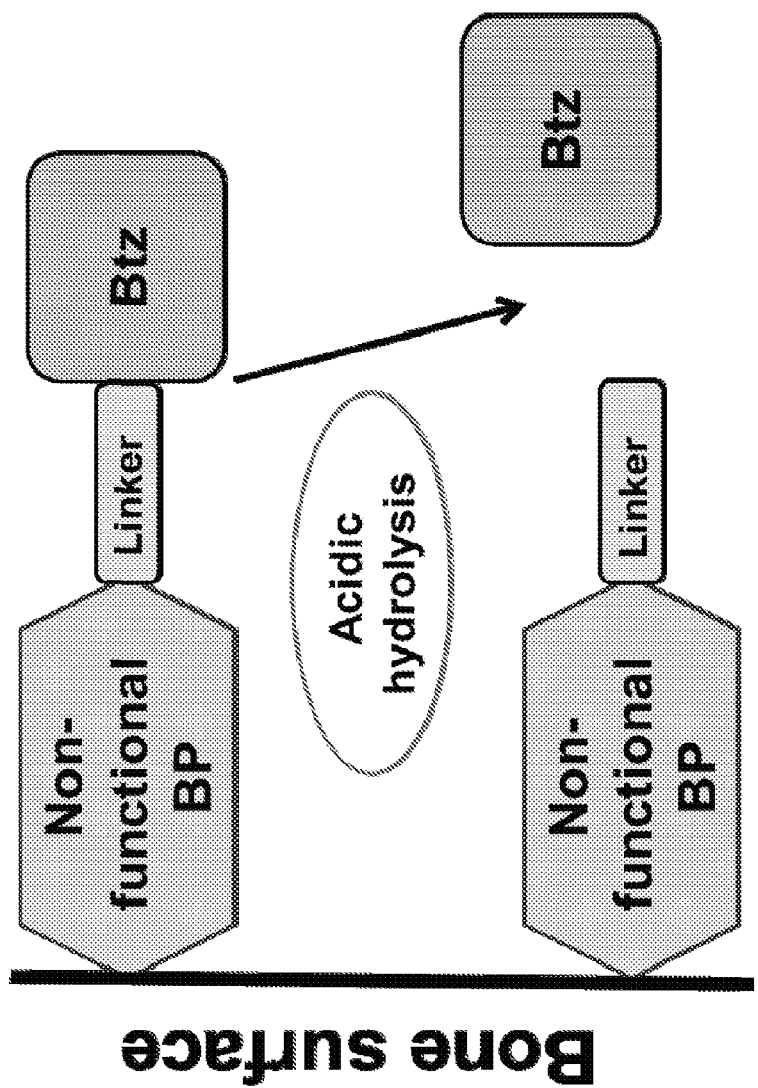
FIG. 14 depicts a schematic of cleavage of the Btz group from Bone-targeted Bortezomib analogues under acidic hydrolysis.

In one embodiment, the linker is aliphatic. In another embodiment, the linker comprises an aromatic ring. Non-limiting examples of aromatic rings include an aryl group or a heteroaryl group. In one embodiment, the aryl group is a phenyl group. In some embodiments, the aromatic ring is substituted. As would be understood by one of ordinary skill in the art, the substituents on the aromatic ring may be selected in order to modify the electronic character of the substituted aromatic ring. For example, electron withdrawing groups may be added to the aromatic ring in order to decrease the electron density of the ring, while electron donating groups may be added in order to increase the electron density of the ring. In some embodiments, altering the electronic character of the ring may be used to modulate the reactivity of the linker, thereby influencing the rate of cleavage between the linker and Btz and thus delivery of the Btz warhead to the desired site. FIG. 13 depicts examples of the boronate ester linkage with different relative rates of cleavage and release of bortezomib or other proteasome inhibitors. In another embodiment, a compound of the invention is conjugated to indocyanine green or any analogues thereof.

Figure 12:
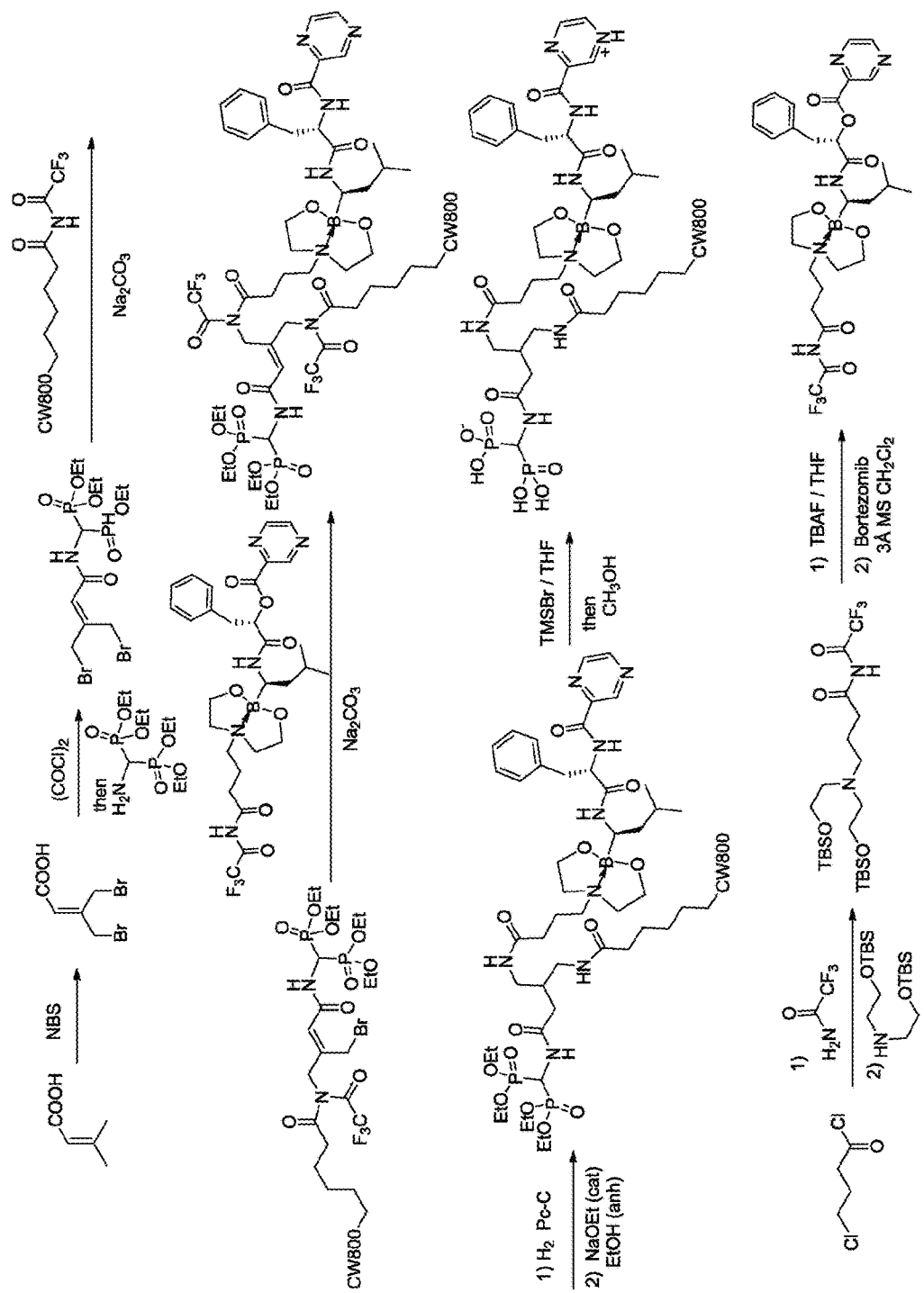
FIG. 12 is an exemplary synthesis of compounds of the invention conjugated to dye CW800.

In one aspect, the compounds of the invention may be conjugated to dyes or other fluorescent molecules. Compounds conjugated to dyes or other fluorescent molecules may be useful for studying their bone binding and release properties. For example, the compound may be conjugated to the dye or fluorescent molecule, injected into bloodstream of animals, and its radioactivity measured in blood and in bone at different time-points. Any dye or fluorescent molecule is contemplated by the present invention. In one embodiment, the dye is a cyanine fluorophore. In one embodiment, a compound of the invention is conjugated to CW800. FIG. 12 includes an exemplary synthesis of a compound of the invention conjugated to CW800.

The compounds of the present invention may be synthesized using techniques well-known in the art of organic synthesis. The starting materials and intermediates required for the synthesis may be obtained from commercial sources or synthesized according to methods known to those skilled in the art.

In one aspect, the compound of the invention is a compound of formula (I), a pharmaceutically acceptable salt thereof, an isomer thereof, or a mixture of isomers thereof:

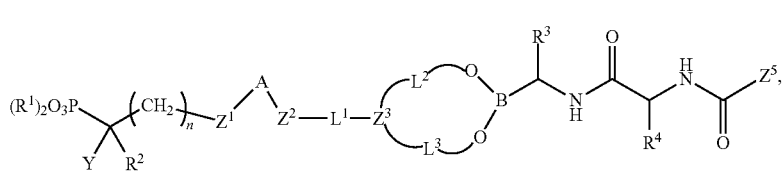

(I)

wherein in formula (I):

each occurrence of $R^1$ is independently selected from the group consisting of hydrogen and alkyl;

$R^2$ is selected from the group consisting of hydrogen, alkyl, —$OR^{13}$, —$N(R^{13})(R^{14})$, and halogen;

$R^3$ is selected from the group consisting of hydrogen and alkyl, wherein the alkyl group is optionally substituted with one to four substituents selected from the group consisting of hydroxyl, alkoxy, alkenyl, cycloalkyl, aryl, heteroaryl, halo, cyano and amino;

$R^4$ is selected from the group consisting of hydrogen, alkyl, aryl, and alkylaryl wherein the alkyl, aryl, or alkylaryl group is optionally substituted with one to four substituents selected from the group consisting of hydroxyl, alkoxy, alkenyl, cycloalkyl, aryl, heteroaryl, halo, cyano and amino;

$L^1$ is selected from the group consisting of alkyl, aryl, cycloalkyl, alkylaryl, alkylcycloalkyl, and alkyl-$Z^4C(O)NR^{10}$, wherein the alkyl, aryl, cycloalkyl, alkylaryl, or alkylcycloalkyl group is optionally substituted with one to four substituents selected from the group consisting of alkyl, hydroxyl, alkoxy, alkenyl, cycloalkyl, aryl, heteroaryl, halo, cyano and amino;

$L^2$ is aryl or an alkyl chain of $C_1$-$C_6$ alkyl, wherein any carbon atom in the alkyl chain is optionally substituted with one to two substituents selected from the group consisting of alkyl, cycloalkyl, and carbonyl;

$L^3$ is aryl or an alkyl chain of $C_1$-$C_6$ alkyl, wherein any carbon atom in the alkyl chain is optionally substituted with one to two substituents selected from the group consisting of alkyl, cycloalkyl, and carbonyl;

Y is selected from the group consisting of —$PO(OR^8)(OR^9)$, —$PO(R^9)(OR^8)$, —$CO_2R^8$, and —$SO_3R^8$;

$Z^1$ is selected from the group consisting of $CH_2$ and $NR^6$;

A is selected from the group consisting of $CH_2$, C(=O), C(=$NR^7$), and C(=S);

$Z^2$ is selected from the group consisting of $CH_2$, $NR^{11}$, S, and O;

$Z^3$ is selected from the group consisting of N, $CR^{12}$, and phenyl;

$Z^4$ is selected from the group consisting of $CH_2$ and O;

$Z^5$ is selected from the group consisting of aryl, alkyl, $OR^{18}$, and

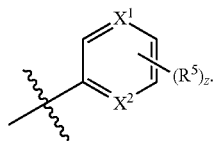

wherein the aryl or alkyl group is optionally substituted with one to four substituents selected from the group consisting of alkyl, hydroxyl, alkoxy, alkenyl, cycloalkyl, aryl, heteroaryl, halo, cyano and amino;

each occurrence of $R^5$ is independently selected from the group consisting of, alkyl, fluoroalkyl, heteroalkyl, aryl, F, Cl, Br, I, —CN, —$NO_2$, —$OR^{17}$, —$SR^{17}$, —S(=O)$R^{17}$, —S(=O)$_2R^{17}$, —NHS(=O)$_2R^{17}$, —C(=O)$R^{17}$, —OC(=O)$R^{17}$, —$CO_2R^{17}$, —$OCO_2R^{17}$, —CH($R^{17}$)$_2$, —N($R^{17}$)$_2$, —C(=O)N($R^{17}$)$_2$, —OC(=O)N($R^{17}$)$_2$, —NHC(=O)NH($R^{17}$), —NHC(=O)$R^{17}$, —NHC(=O)O$R^{17}$, —C(OH)($R^{17}$)$_2$, and —C($NH_2$)($R^{17}$)$_2$;

$X^1$ is selected from the group consisting of $CR^{15}$ and N;

$X^2$ is selected from the group consisting of $CR^{16}$ and N;

$R^6$ and $R^7$ are each independently selected from the group consisting of hydrogen and alkyl, wherein the alkyl group is optionally substituted with one to four substituents selected from the group consisting of hydroxyl, alkoxy, alkenyl, cycloalkyl, aryl, heteroaryl, halo, cyano and amino;

$R^8$, $R^9$, and $R^{10}$ are each independently selected from the group consisting of hydrogen and alkyl;

$R^{11}$, $R^{12}$, $R^{13}$, and $R^{14}$ are each independently selected from the group consisting of hydrogen and alkyl, wherein the alkyl group is optionally substituted with one to four substituents selected from the group consisting of hydroxyl, alkoxy, alkenyl, cycloalkyl, aryl, heteroaryl, halo, cyano and amino;

$R^{15}$ and $R^{16}$ are each independently selected form the group consisting of hydrogen, alkyl, fluoroalkyl, heteroalkyl, aryl, F, Cl, Br, I, —CN, —$NO_2$, —$OR^{17}$, —$SR^{17}$, —S(=O)$R^{17}$, —S(=O)$_2R^{17}$, —NHS(=O)$_2R^{17}$, —C(=O)$R^{17}$, —OC(=O)$R^{17}$, —$CO_2R^{17}$, —$OCO_2R^{17}$, —CH($R^{17}$)$_2$, —N($R^{17}$)$_2$, —C(=O)N($R^{17}$)$_2$, —OC(=O)N($R^{17}$)$_2$, —NHC(=O)NH($R^{17}$), —NHC(=O)$R^{17}$, —NHC(=O)O$R^{17}$, —C(OH)($R^{17}$)$_2$, and —C($NH_2$)($R^{17}$)$_2$;

each occurrence of $R^{17}$ is selected from the group consisting of hydrogen and alkyl;

$R^{18}$ is selected from the group consisting of alkyl, aryl, and arylalkyl;

n is an integer from 0 to 10; and z is an integer from 0 to 2.

In another aspect, the compound of the invention is a compound of formula (II), a pharmaceutically acceptable salt thereof, an isomer thereof, or a mixture of isomers thereof:

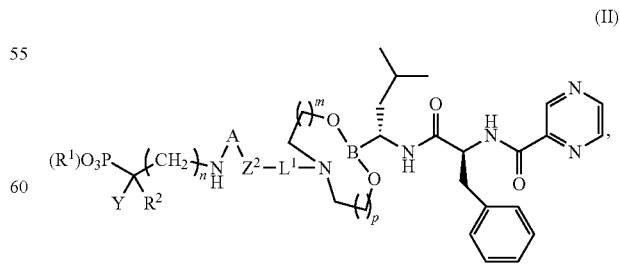

(II)

wherein in formula (II):

each occurrence of $R^1$ is independently selected from the group consisting of hydrogen and alkyl;

$R^2$ is selected from the group consisting of hydrogen, alkyl, —$OR^{13}$, —$N(R^{13})(R^{14})$, and halogen;

Y is selected from the group consisting of —$PO(OR^8)(OR^9)$, —$PO(R^9)(OR^8)$, —$CO_2R^8$, and —$SO_3R^8$;

$Z^1$ is selected from the group consisting of $CH_2$ and $NR^6$;

A is selected from the group consisting of $CH_2$, C(=O), C(=$NR^7$), and C(=S);

$Z^2$ is selected from the group consisting of $CH_2$, $NR^{11}$, S, and O;

$R^6$ and $R^7$ are each independently selected from the group consisting of hydrogen and alkyl, wherein the alkyl group is optionally substituted with one to four substituents selected from the group consisting of hydroxyl, alkoxy, alkenyl, cycloalkyl, aryl, heteroaryl, halo, cyano and amino;

$R^8$ and $R^9$ are each independently selected from the group consisting of hydrogen and alkyl;

$R^{11}$, $R^{13}$, and $R^{14}$ are each independently selected from the group consisting of hydrogen and alkyl, wherein the alkyl group is optionally substituted with one to four substituents selected from the group consisting of hydroxyl, alkoxy, alkenyl, cycloalkyl, aryl, heteroaryl, halo, cyano and amino;

m is 1, or 2 or 3;

p is 1, or 2, or 3; and n is an integer from 0 to 10.

In another aspect, the compound of the invention is a compound of formula (III), a pharmaceutically acceptable salt thereof, an isomer thereof, or a mixture of isomers thereof:

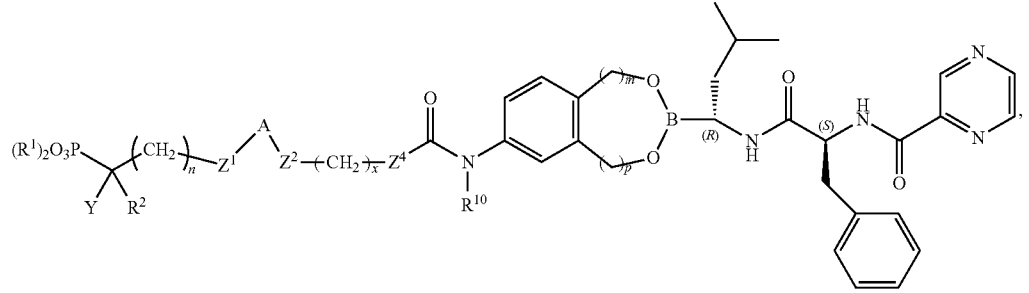

(III)

wherein in formula (III):

each occurrence of $R^1$ is independently selected from the group consisting of hydrogen and alkyl;

$R^2$ is selected from the group consisting of hydrogen, alkyl, —$OR^{13}$, —$N(R^{13})(R^{14})$, and halogen;

Y is selected from the group consisting of —$PO(OR^8)(OR^9)$, —$PO(R^9)(OR^8)$, —$CO_2R^8$, and —$SO_3R^8$;

$Z^1$ is selected from the group consisting of $CH_2$ and $NR^6$;

A is selected from the group consisting of $CH_2$, C(=O), C(=$NR^7$), and C(=S);

$Z^2$ is selected from the group consisting of $CH_2$, $NR^{11}$, S, and O;

$Z^4$ is selected from the group consisting of $CH_2$ and O;

$L^1$ is selected from the group consisting of alkyl, aryl, cycloalkyl, alkylaryl, alkylcycloalkyl, wherein the alkyl, aryl, cycloalkyl, alkylaryl, or alkylcycloalkyl group is optionally substituted with one to four substituents selected from the group consisting of hydroxyl, alkoxy, alkenyl, cycloalkyl, aryl, heteroaryl, halo, cyano and amino;

$R^6$ and $R^7$ are each independently selected from the group consisting of hydrogen and alkyl, wherein the alkyl group is optionally substituted with one to four substituents selected from the group consisting of hydroxyl, alkoxy, alkenyl, cycloalkyl, aryl, heteroaryl, halo, cyano and amino;

$R^8$, $R^9$, and $R^{10}$ are each independently selected from the group consisting of hydrogen and alkyl;

$R^{11}$, $R^{13}$, and $R^{14}$ are each independently selected from the group consisting of hydrogen and alkyl, wherein the alkyl group is optionally substituted with one to four substituents selected from the group consisting of hydroxyl, alkoxy, alkenyl, cycloalkyl, aryl, heteroaryl, halo, cyano and amino; and m is an integer from 1 to 5;

n is an integer from 0 to 10;

p is an integer from 1 to 5; and x is an integer from 0 to 10.

In one embodiment, each occurrence of $R^1$ is hydrogen. In another embodiment, each occurrence of $R^1$ is alkyl. In another embodiment, one $R^1$ is hydrogen and the other $R^1$ is alkyl.

In one embodiment, $R^2$ is hydrogen. In another embodiment, $R^2$ is $OR^{13}$.

In one embodiment, $R^3$ is $C_1$-$C_5$ alkyl. In another embodiment, $R^3$ is i-butyl.

In one embodiment, $R^4$ is ($C_1$-$C_3$ alkyl)aryl. In another embodiment, $R^4$ is benzyl. In one embodiment, $R^4$ is $C_1$-$C_5$ alkyl. In another embodiment, $R^4$ is $C_1$-$C_5$ alkyl substituted with one hydroxyl group.

In one embodiment, $Z^1$ is $CH_2$. In another embodiment, $Z^1$ is $NR^6$.

In one embodiment, $X^1$ is N. In another embodiment, $X^1$ is $CR^{15}$.

In one embodiment, $X^2$ is N. In another embodiment, $X^2$ is $CR^{16}$.

In one embodiment, at least one occurrence of $R^5$ is aryl. In another embodiment, at least one occurrence of $R^5$ is phenyl.

In one embodiment, $R^6$ is hydrogen.

In one embodiment, A is C(=O). In another embodiment, A is C(=$NR^7$). In another embodiment, A is C(=S). In another embodiment, A is $CH_2$. In one embodiment, A is C(=N) or C(=O).

In one embodiment, $Z^2$ is $CH_2$. In another embodiment, $Z^2$ is $NR^{11}$. In another embodiment, $Z^2$ is S. In another embodiment, $Z^2$ is O.

In one embodiment, Y is —$PO(OR^8)_2$. In another embodiment, Y is —$PO(R^9)(OR^8)$. In another embodiment, Y is —$CO_2R^8$. In another embodiment, Y is —$SO_3R^8$.

In one embodiment, $L^1$ is selected from the group consisting of alkyl, aryl and alkylaryl. In another embodiment, $L^1$ is $C_1$-$C_3$ alkyl-$Z^4$C(O)$NR^{10}$. In another embodiment, $L^1$ is $C_1$-$C_3$ alkyl-OC(O)$NR^{10}$. In another embodiment, $L^1$ is $C_1$-$C_3$ alkyl-$(CH_2)C(O)NR^{10}$. In one embodiment, $L^1$ is alkyl. In another embodiment, $L^1$ is a $C_1$-$C_3$ alkyl group. In another embodiment, $L^1$ is $C_2$-alkyl. In one embodiment, $L^1$ is aryl. In another embodiment, $L^1$ is phenyl. In one embodiment, $L^1$ is alkylaryl. In another embodiment, $L^1$ is —$CH_2CHR^{19}$—, wherein $R^{19}$ is selected from the group consisting of

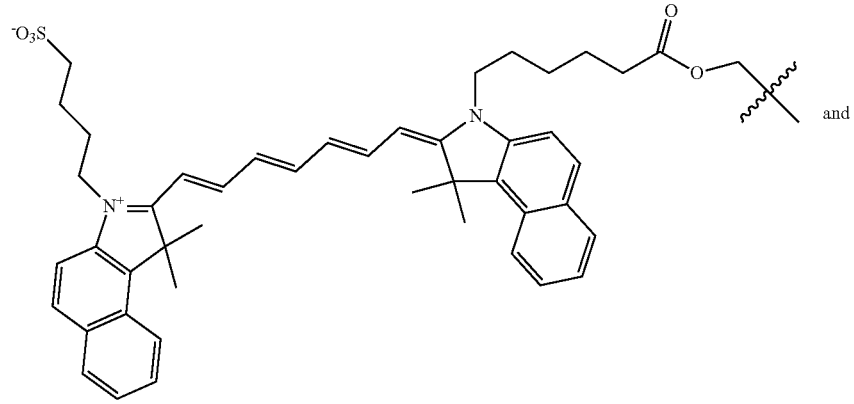

and

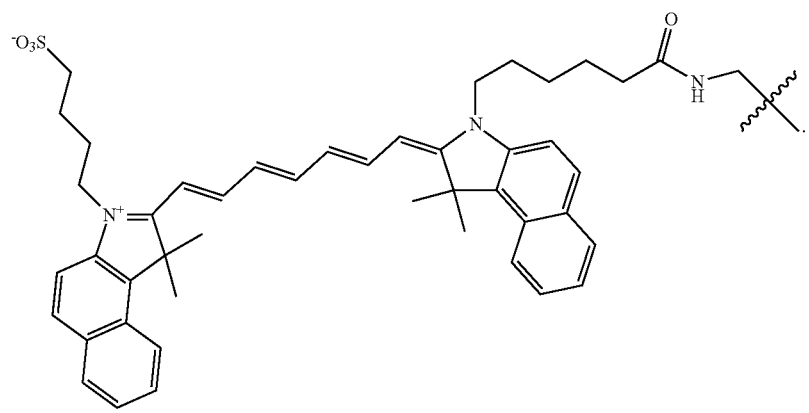

.

In another embodiment, $L^2$ is aryl. In one embodiment, $L^2$ is phenyl. In another embodiment, $L^2$ is an alkyl chain of $C_1$-$C_6$ alkyl. In another embodiment, $L^2$ is an alkyl chain of $C_1$-$C_6$ alkyl, wherein one carbon atom in the alkyl chain is substituted with two alkyl groups. In one embodiment, the alkyl group is a methyl group. In another embodiment, $L^2$ is an alkyl chain of $C_1$-$C_6$ alkyl, wherein one carbon atom in the alkyl chain is substituted with a cycloalkyl group. In one embodiment, the cycloalkyl group is selected from the group consisting of cyclopropane and cyclopentane. In another embodiment, $L^2$ is an alkyl chain of $C_1$-$C_6$ alkyl, wherein one carbon atom in the alkyl chain is substituted with a carbonyl group. In one embodiment, $L^2$ is selected from the group consisting of phenyl and an alkyl chain of $C_1$-$C_6$ alkyl, wherein one carbon atom in the alkyl chain is optionally substituted with two alkyl groups, a carbonyl group, or a cycloalkyl group.

In one embodiment, $L^3$ is aryl. In one embodiment, $L^3$ is phenyl. In another embodiment, $L^3$ is an alkyl chain of $C_1$-$C_6$ alkyl. In another embodiment, $L^3$ is an alkyl chain of $C_1$-$C_6$ alkyl, wherein one carbon atom in the alkyl chain is substituted with two alkyl groups. In one embodiment, the alkyl group is a methyl group. In another embodiment, $L^3$ is an alkyl chain of $C_1$-$C_6$ alkyl, wherein one carbon atom in the alkyl chain is substituted with a cycloalkyl group. In one embodiment, the cycloalkyl group is selected from the group consisting of cyclopropane and cyclopentane. In another embodiment, $L^3$ is an alkyl chain of $C_1$-$C_6$ alkyl, wherein one carbon atom in the alkyl chain is substituted with a carbonyl group. In one embodiment, $L^3$ is selected from the group consisting of phenyl and an alkyl chain of $C_1$-$C_6$ alkyl, wherein one carbon atom in the alkyl chain is optionally substituted with two alkyl groups, a carbonyl group, or a cycloalkyl group.

In one embodiment, $Z^3$ is N. In another embodiment, $Z^3$ is phenyl.

In one embodiment, $Z^4$ is $CH_2$. In another embodiment, $Z^4$ is O.

In one embodiment, $Z^5$ is $OR^{18}$. In another embodiment, $Z^5$ is

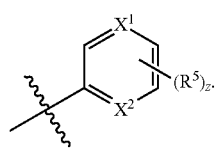

In another embodiment, $Z^5$ is substituted alkyl. In another embodiment, $Z^5$ is

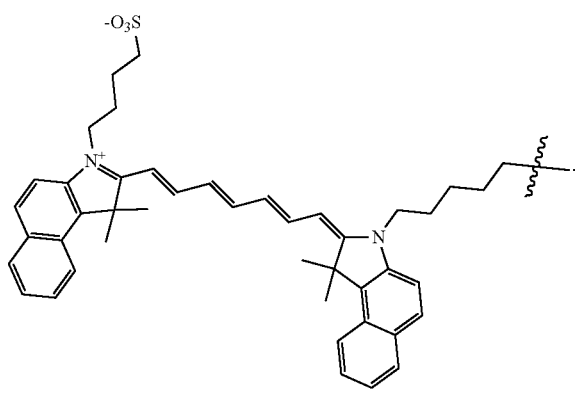

In one embodiment, $R^8$ is hydrogen.

In one embodiment, $R^9$ is hydrogen. In another embodiment, $R^9$ is $C_1$-$C_5$ alkyl. In another embodiment, $R^9$ is methyl. In another embodiment, $R^9$ is ethyl. In another embodiment, $R^9$ is n-butyl.

In one embodiment, $R^{10}$ is $C_1$-$C_3$ alkyl. In one embodiment, $R^{10}$ is methyl.

In one embodiment, $R^{11}$ is hydrogen.

In one embodiment, $R^{13}$ is hydrogen.

In one embodiment, $R^{15}$ is hydrogen. In another embodiment, $R^{15}$ is halo. In another embodiment, $R^{15}$ is Cl.

In one embodiment, $R^{16}$ is hydrogen. In another embodiment, $R^{16}$ is halo. In another embodiment, $R^{16}$ is Cl.

In one embodiment, $R^{18}$ is benzyl.

In one embodiment, m is 1. In another embodiment, m is 2. In another embodiment, m is 3. In another embodiment, m is 4. In another embodiment, m is 5.

In one embodiment, p is 1. In another embodiment, p is 2. In another embodiment, p is 3. In another embodiment, p is 4. In another embodiment, p is 5.

In one embodiment, n is 0. In another embodiment, n is 1.

In one embodiment, z is 0. In another embodiment, z is 1. In another embodiment, z is 2.

In one embodiment, the compound of the invention is selected from the group consisting of:

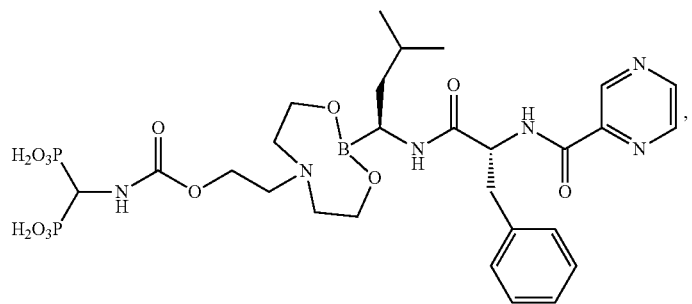

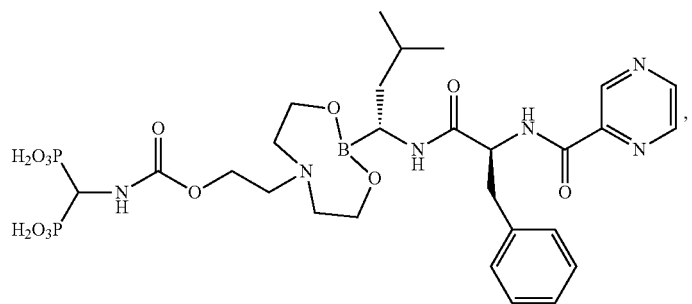

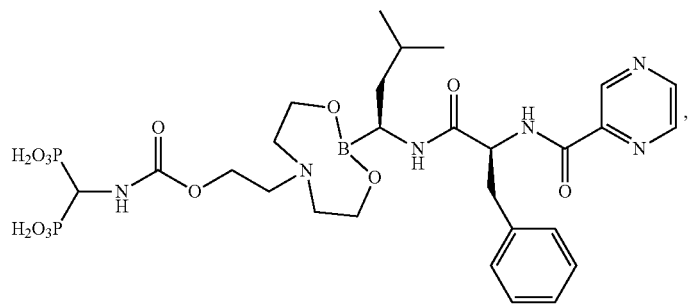

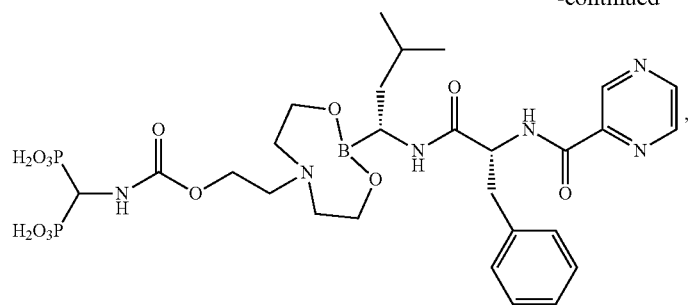
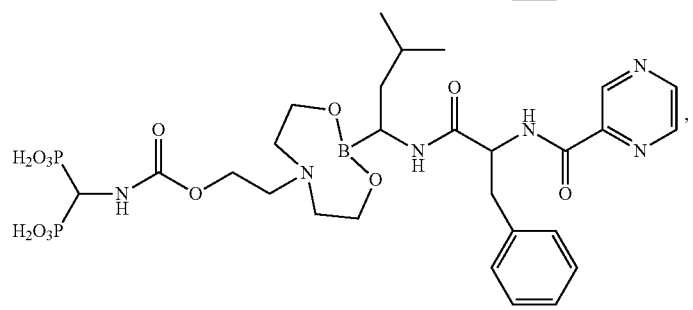
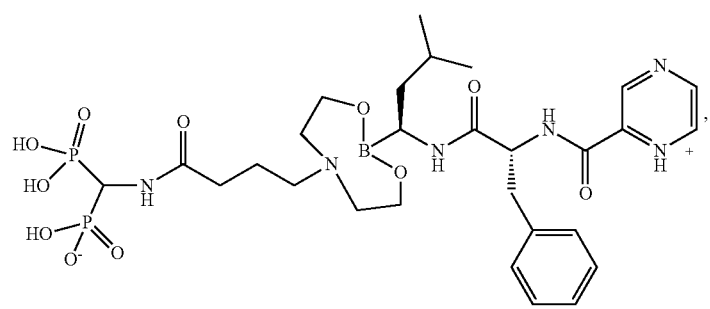
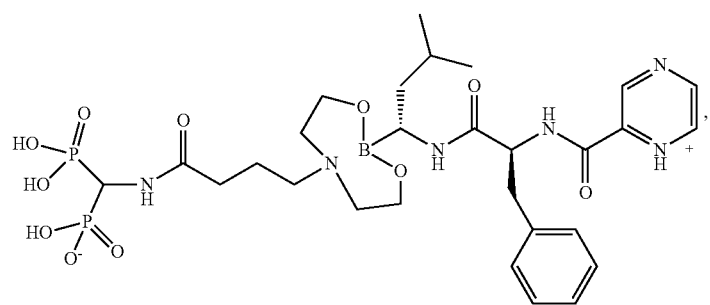
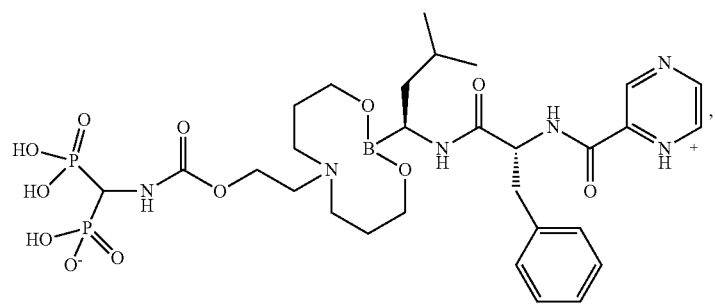

-continued
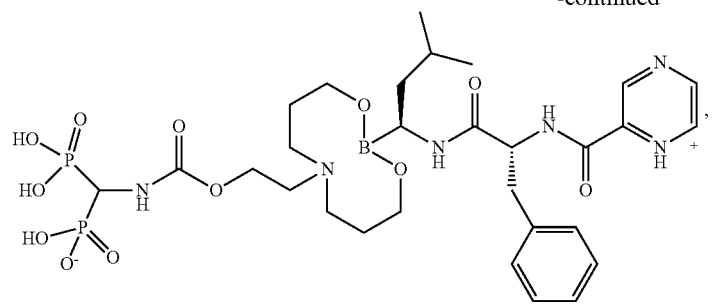
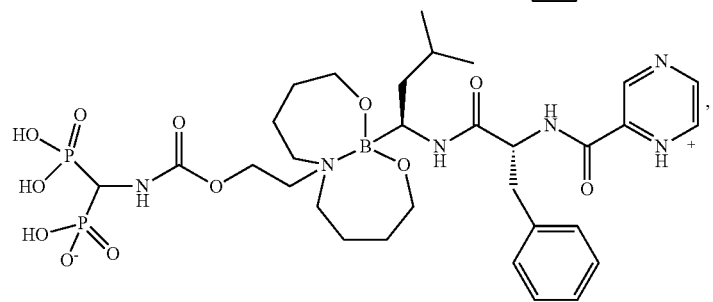
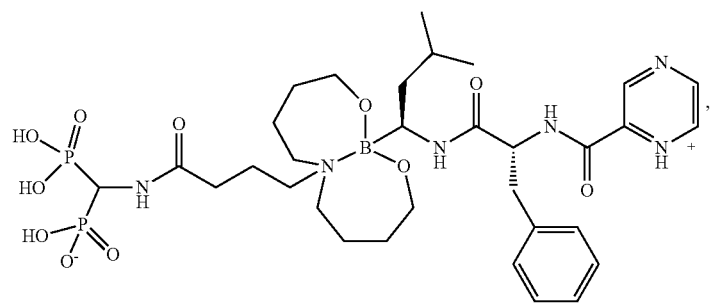
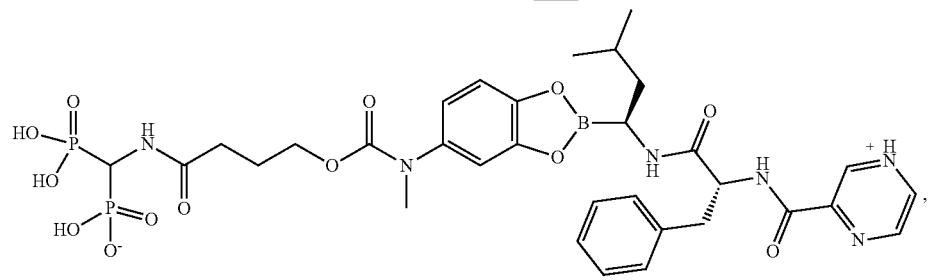
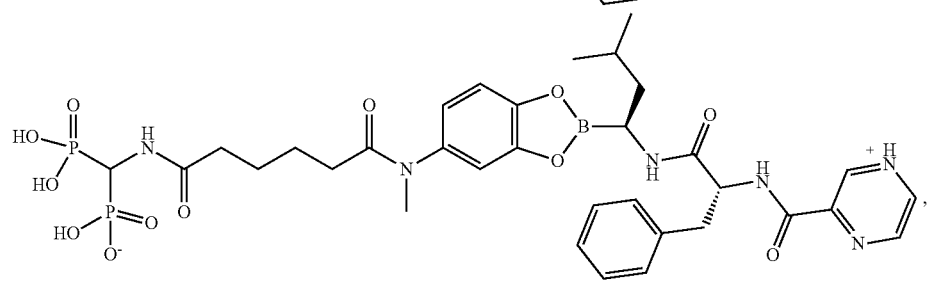
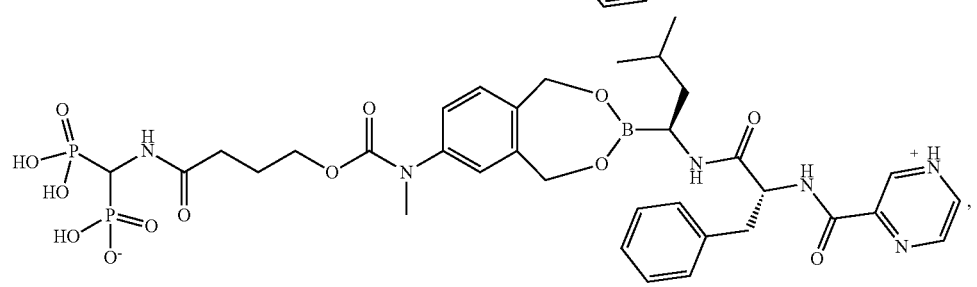

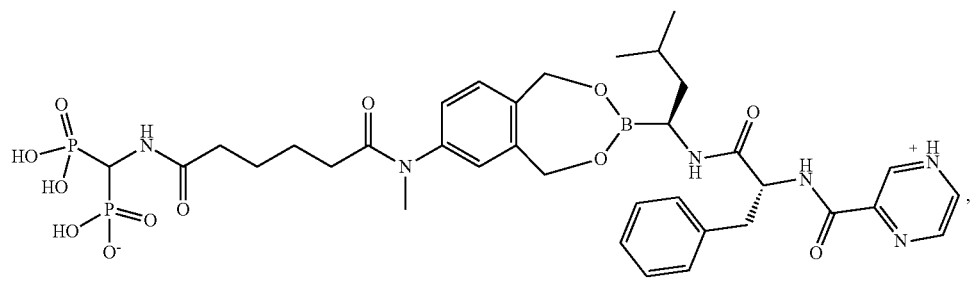
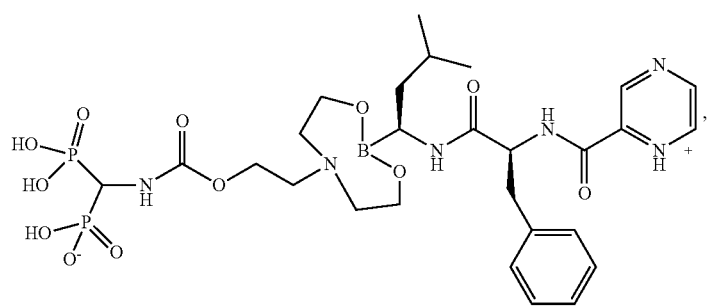
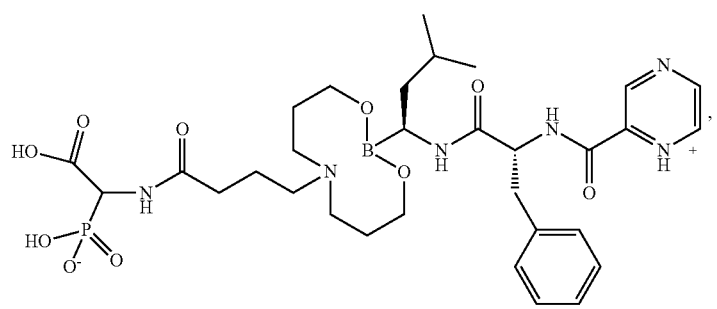
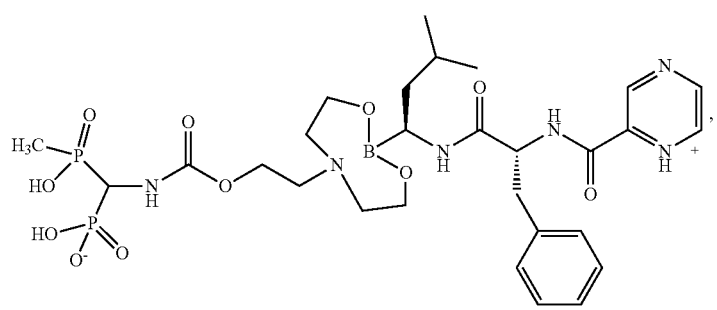
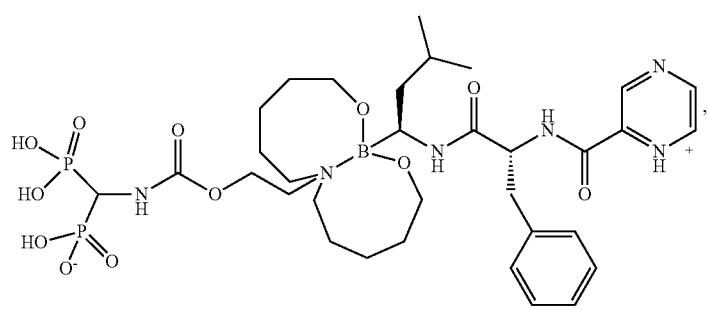

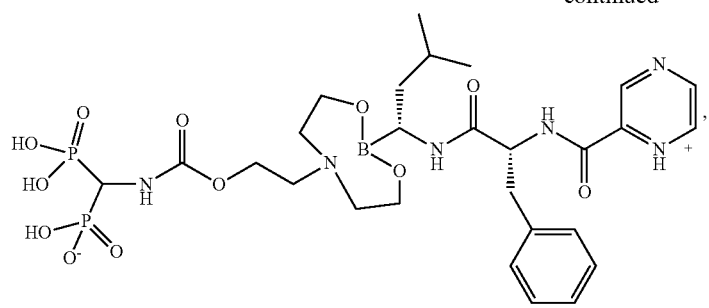
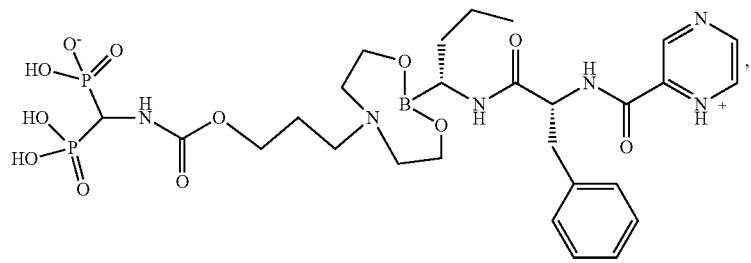
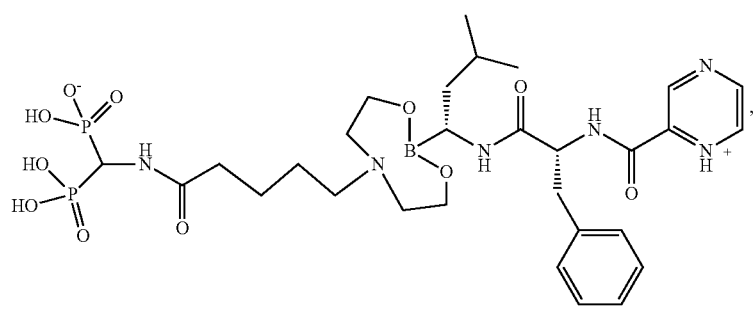
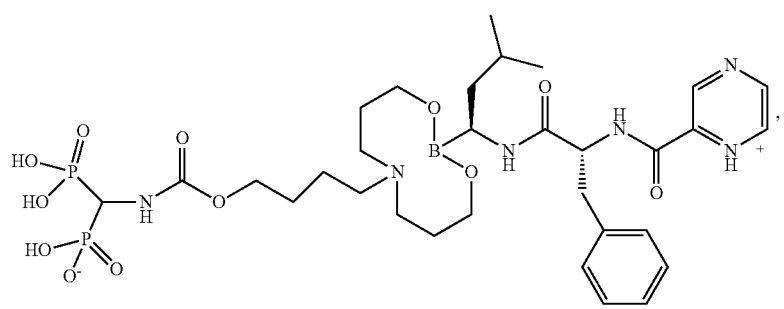
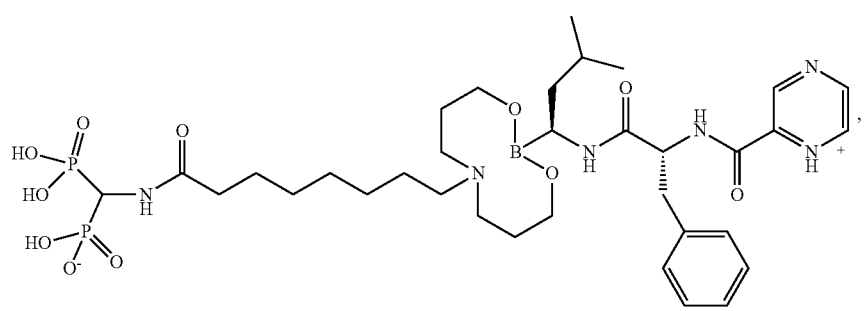

-continued
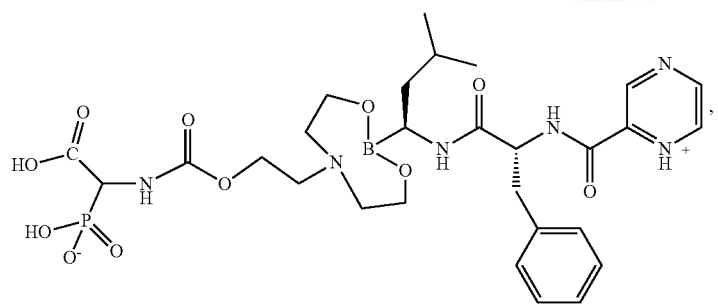
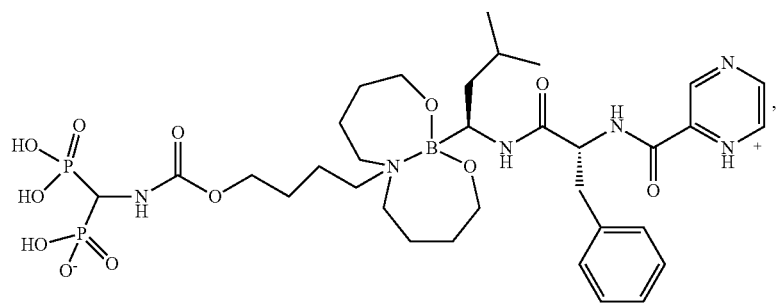
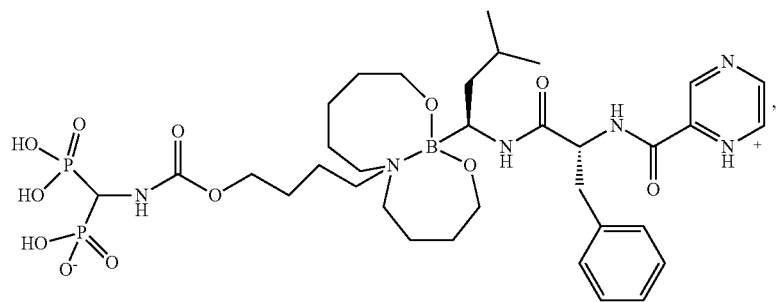
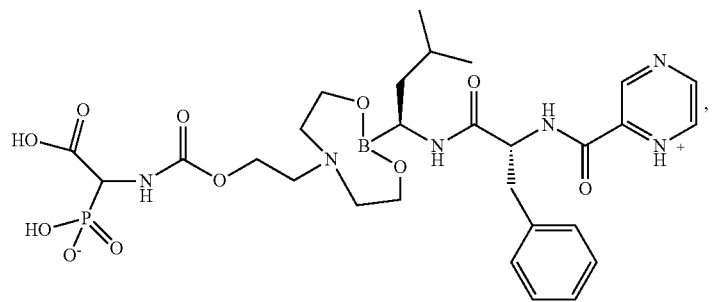
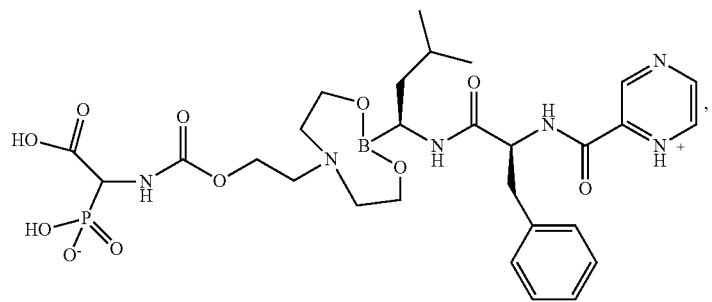

-continued
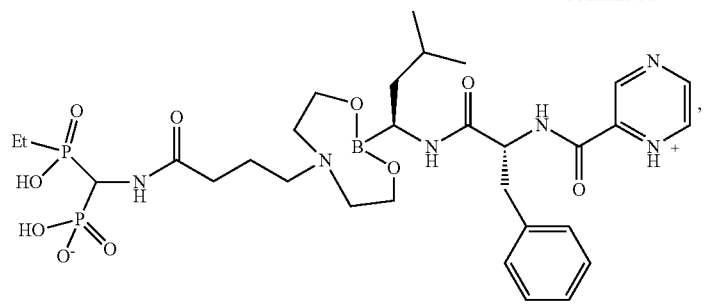
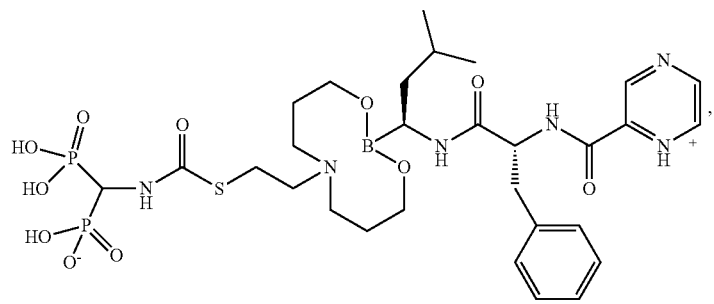
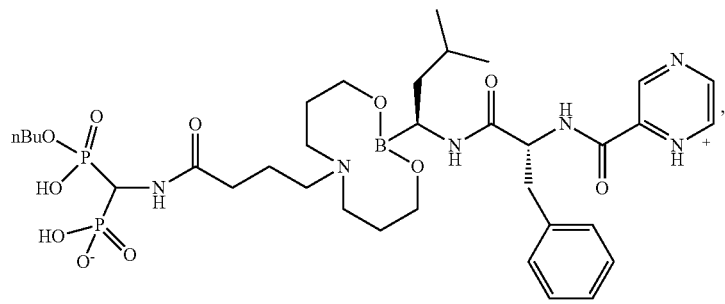
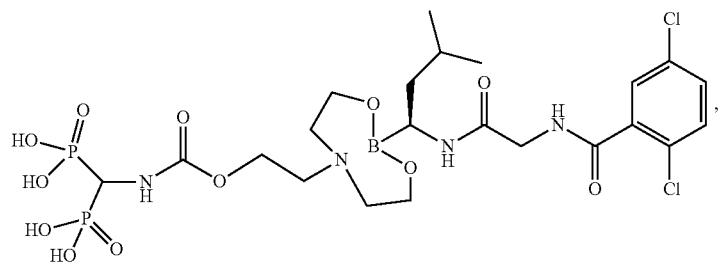
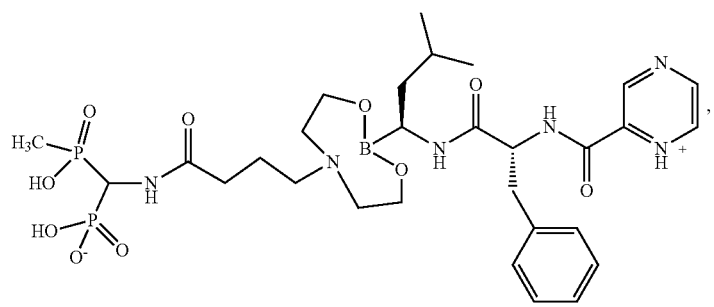

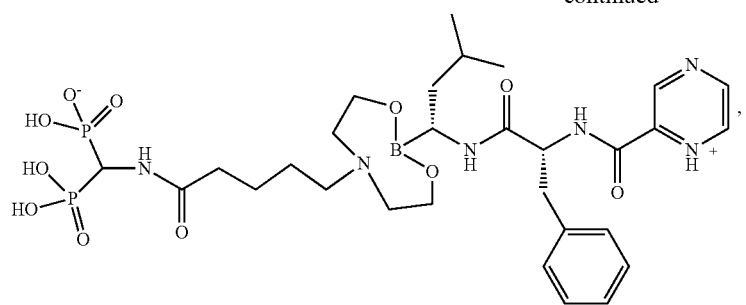
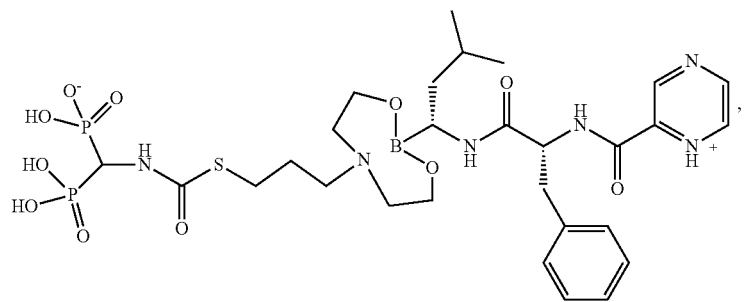
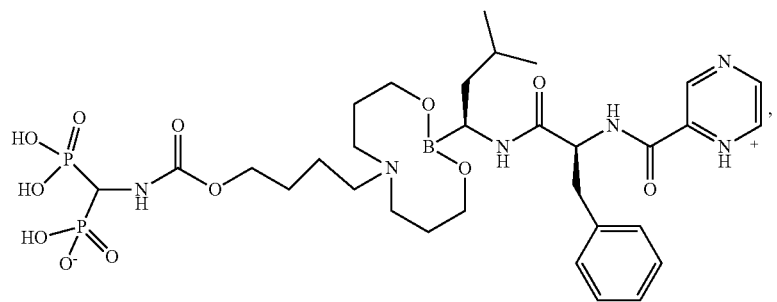
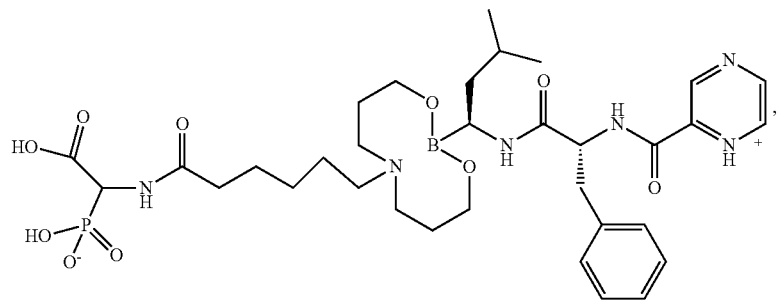
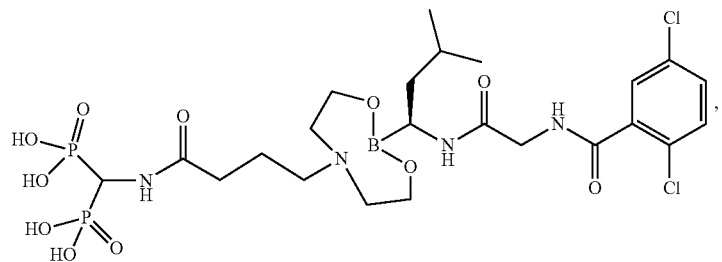

-continued
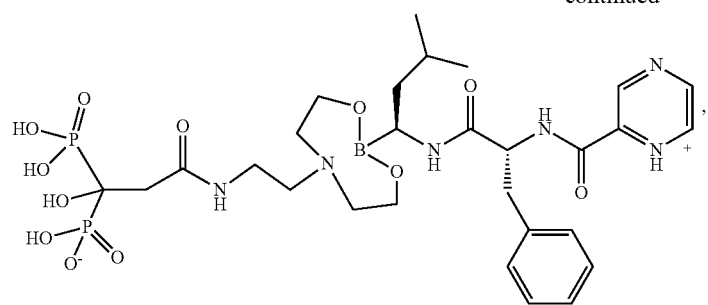
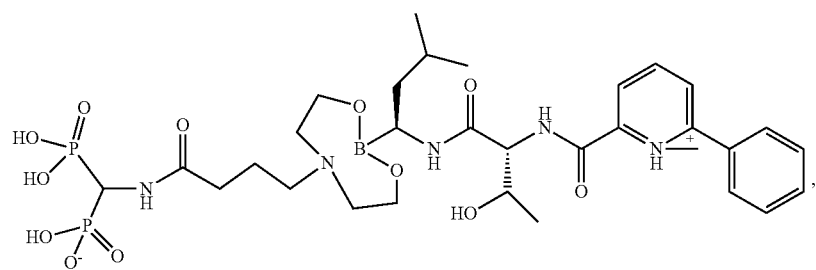
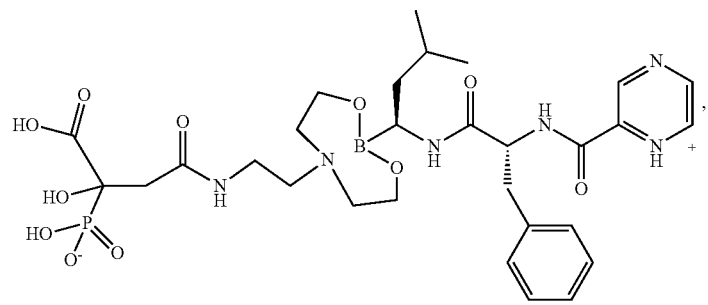
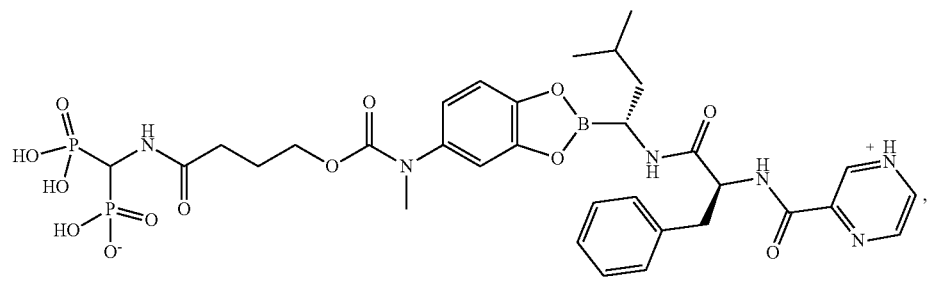
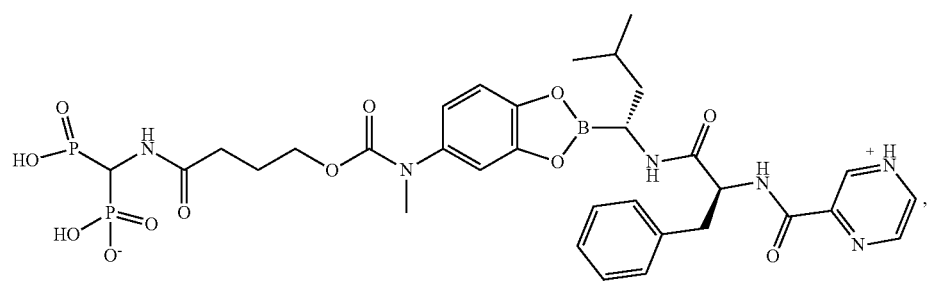
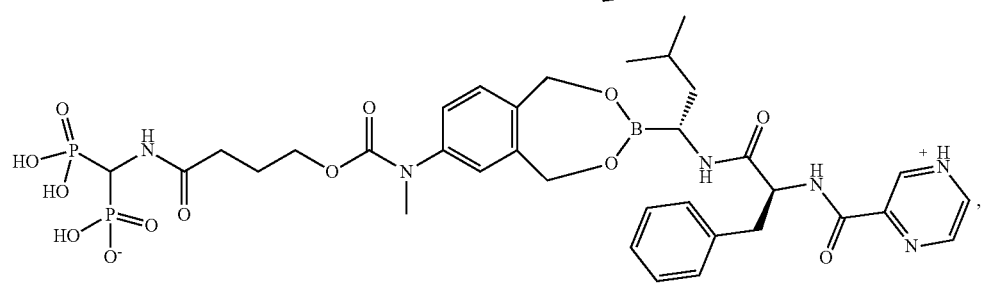

-continued
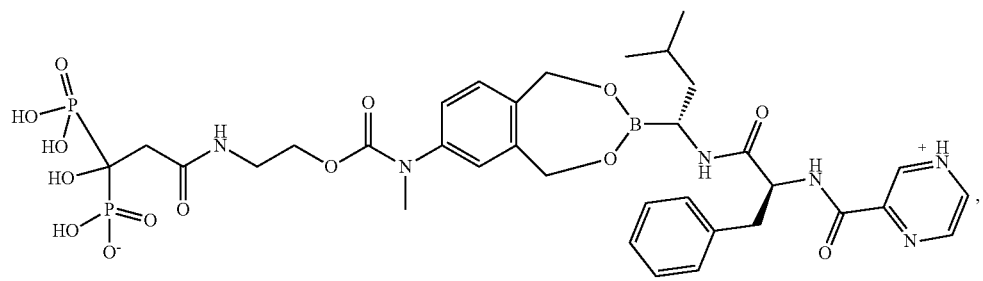
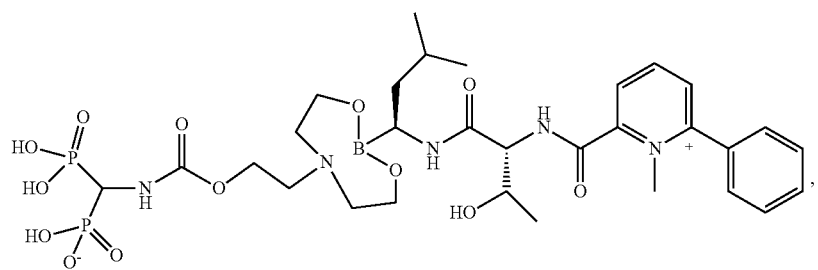
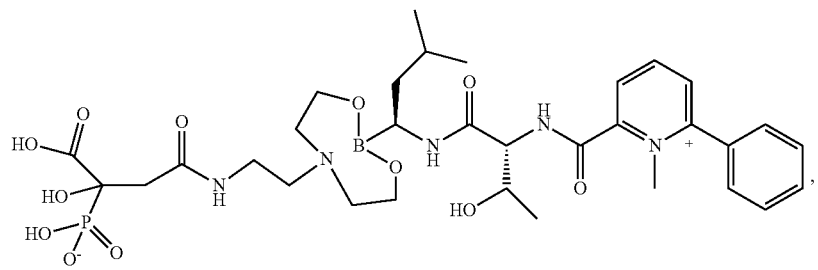
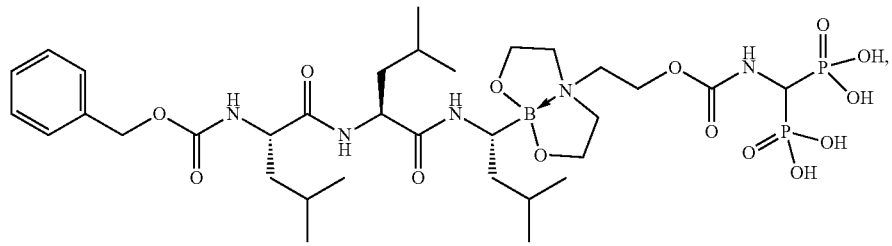
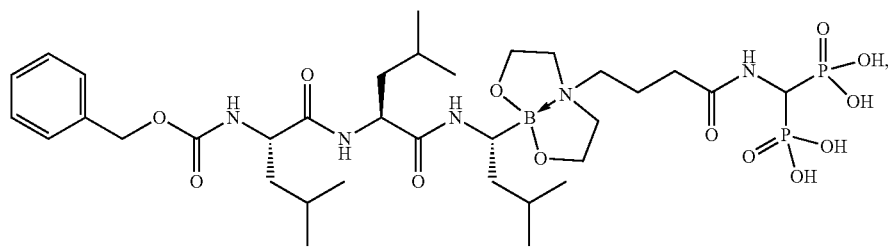
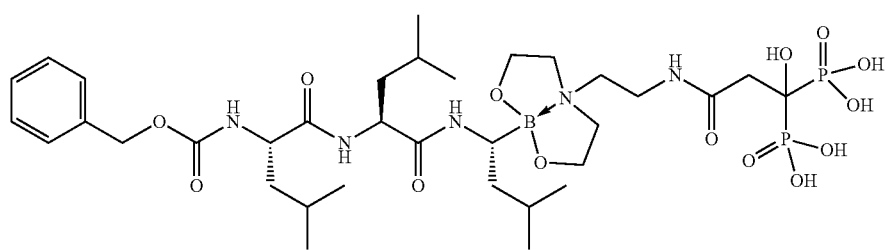

-continued
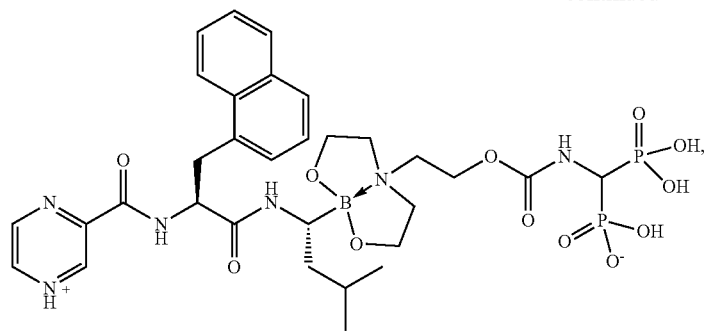
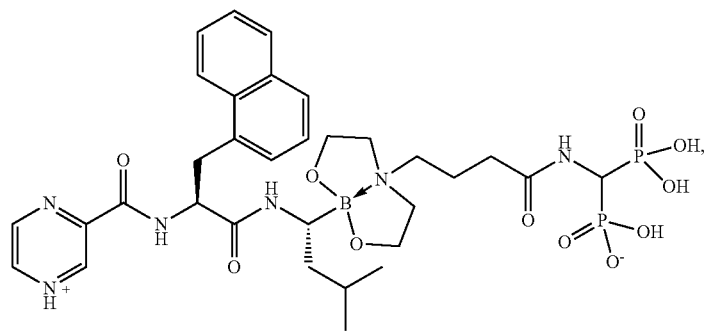
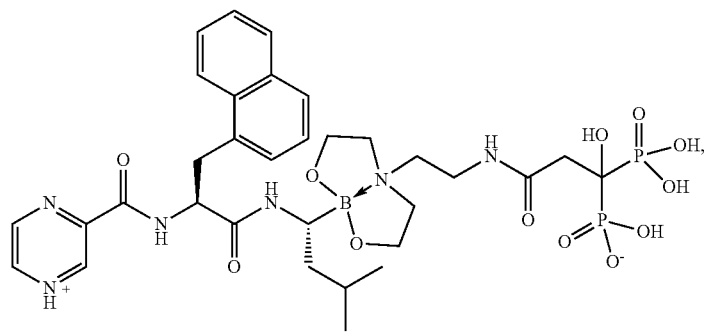
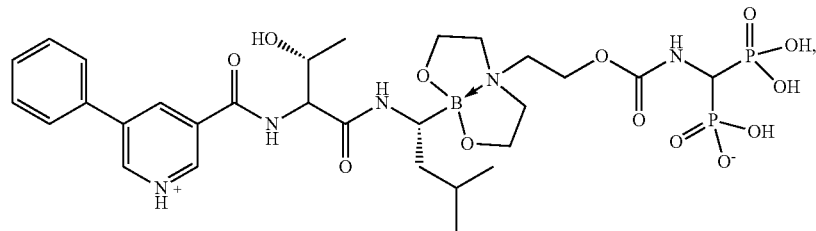
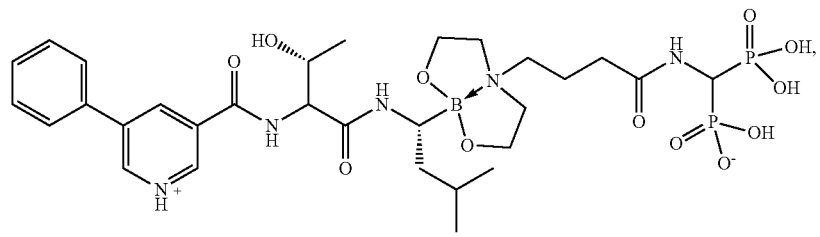
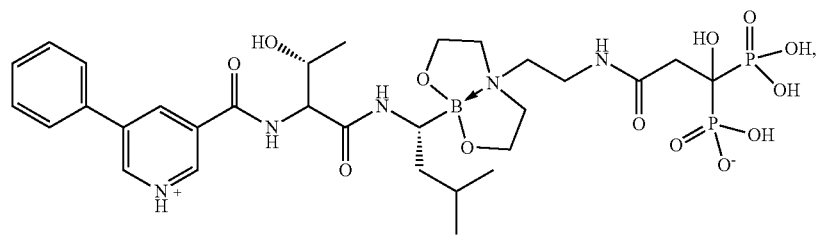

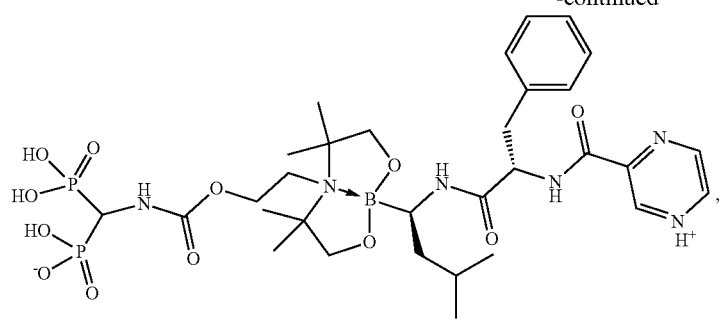
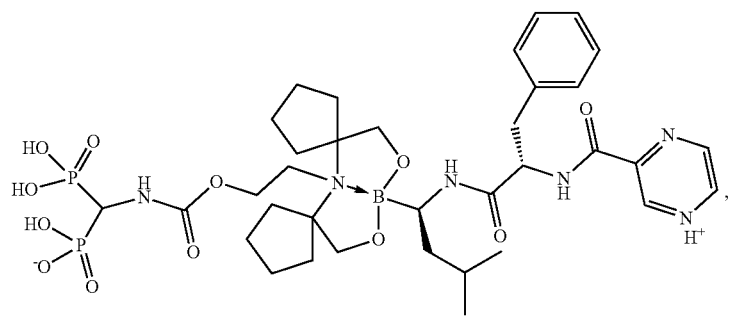
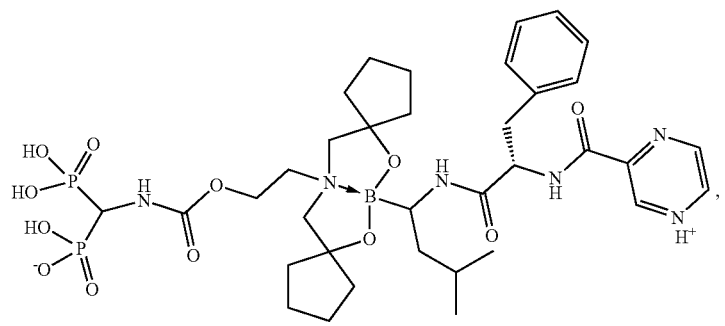
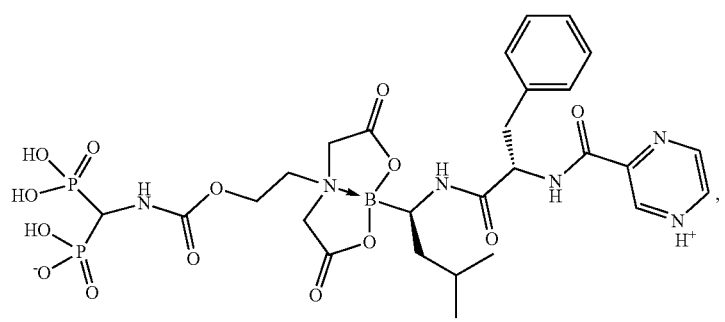
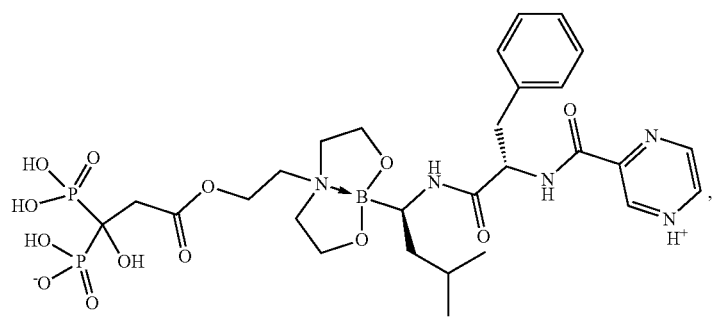

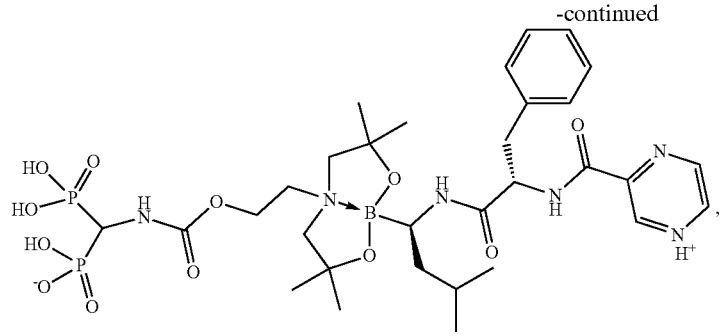
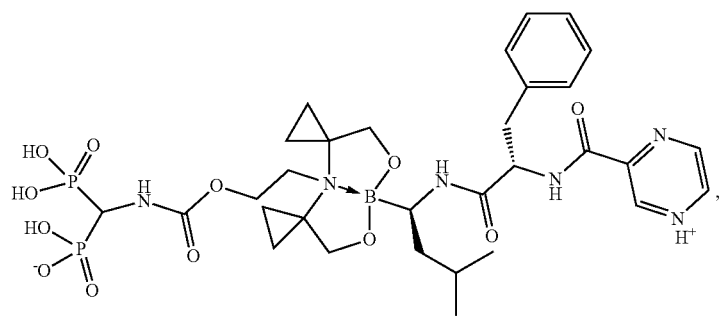
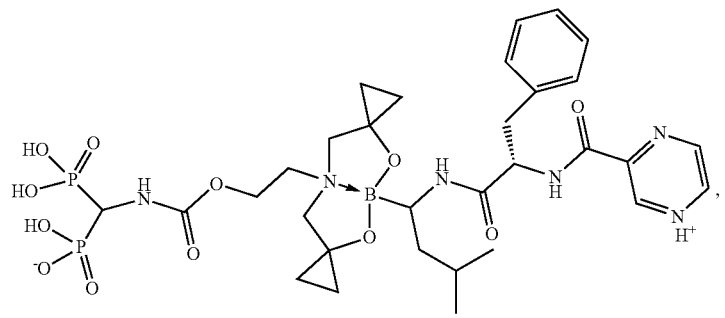
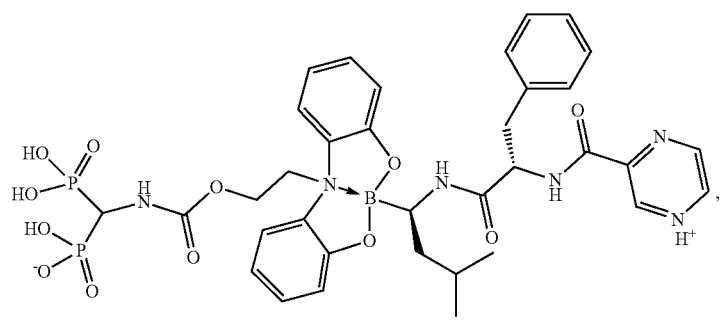
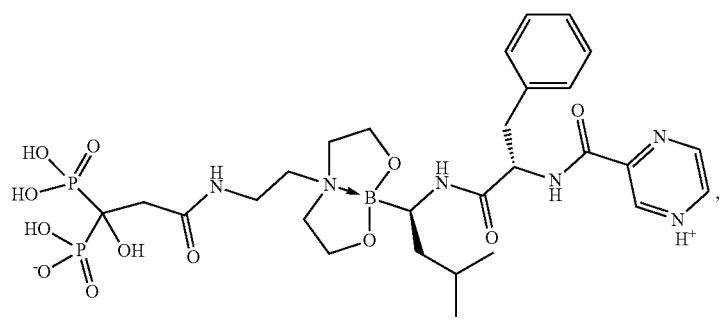

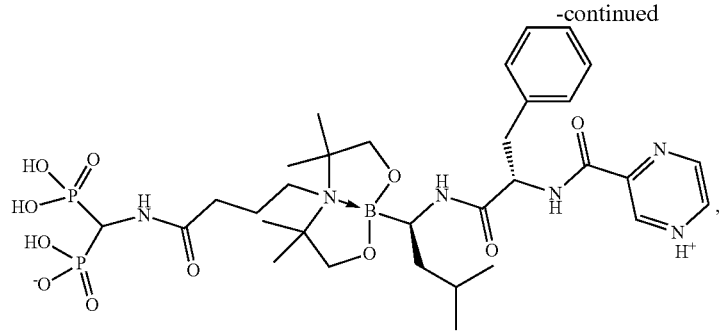
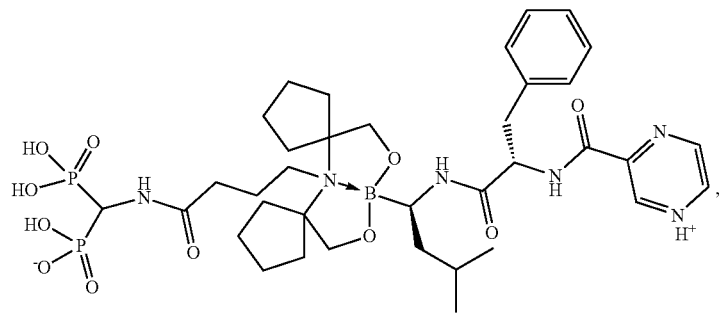
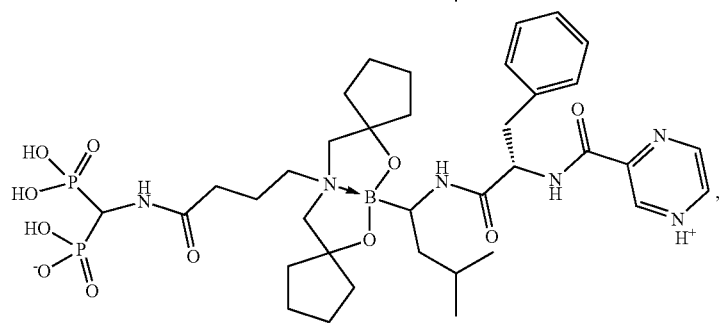
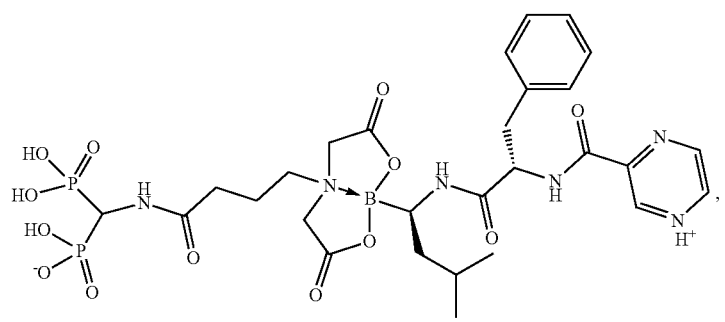
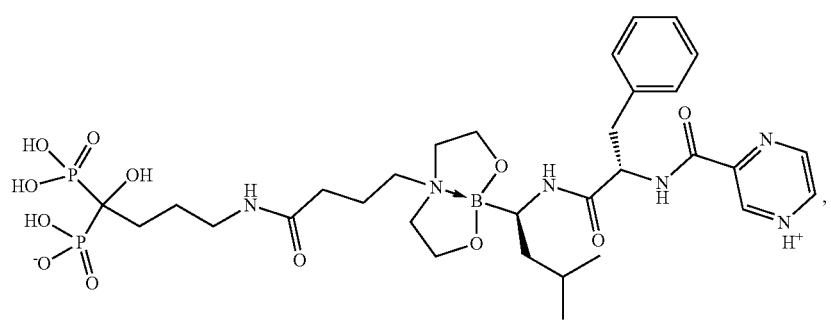

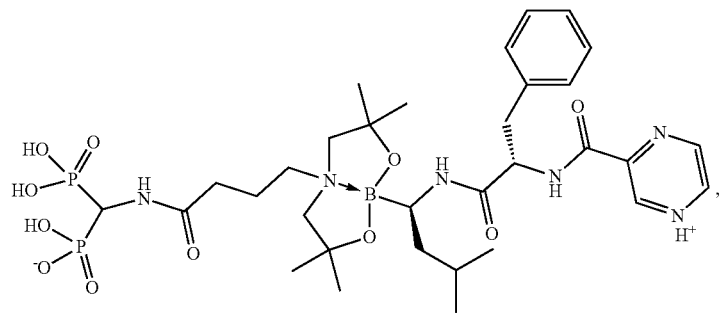
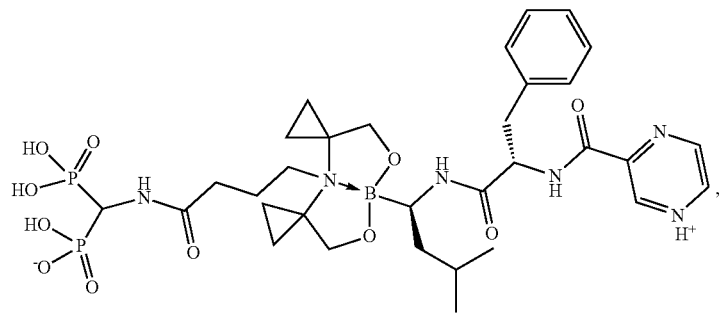
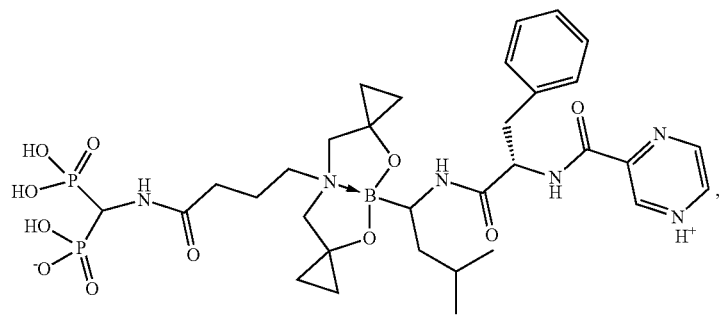
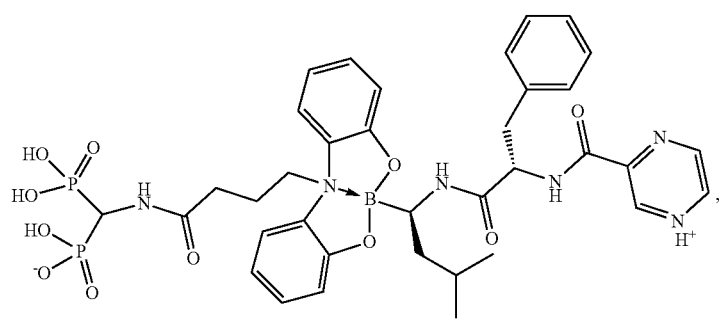
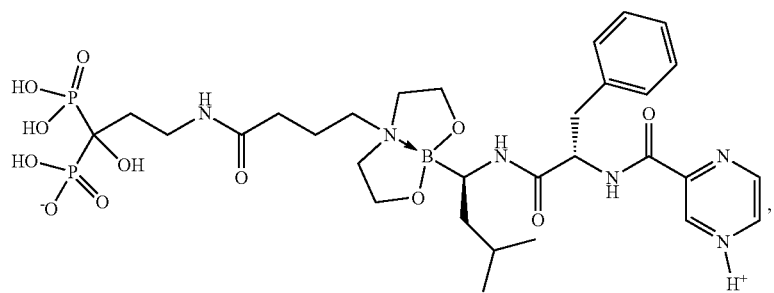

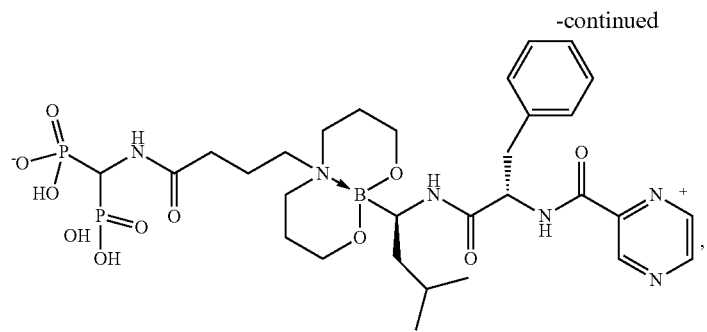
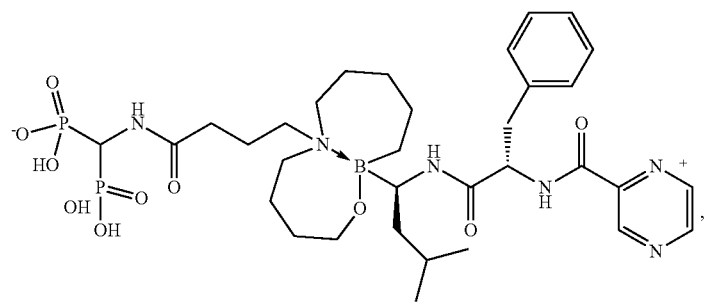
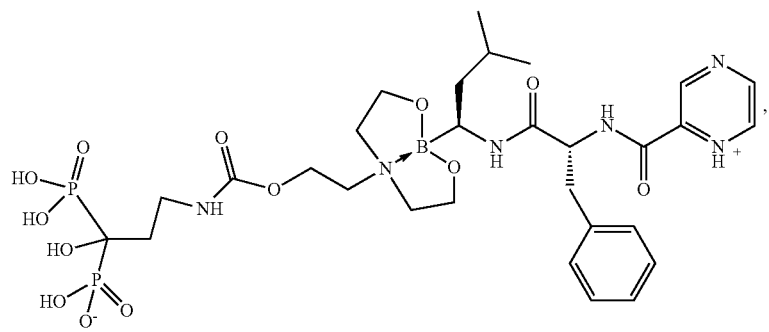
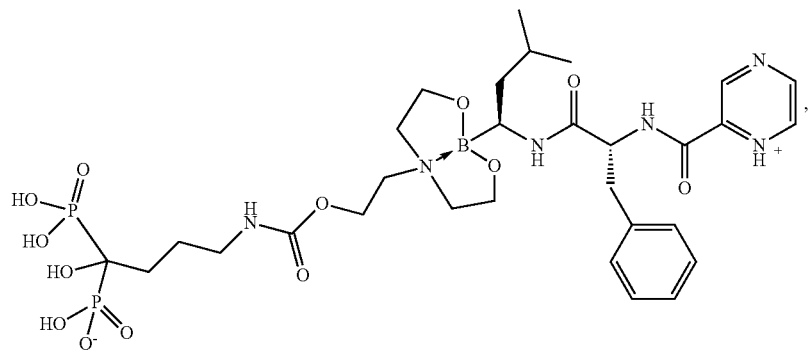

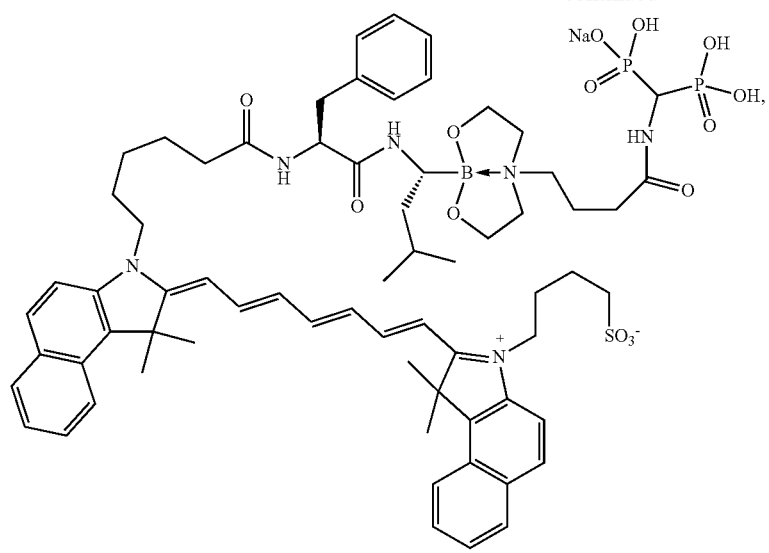
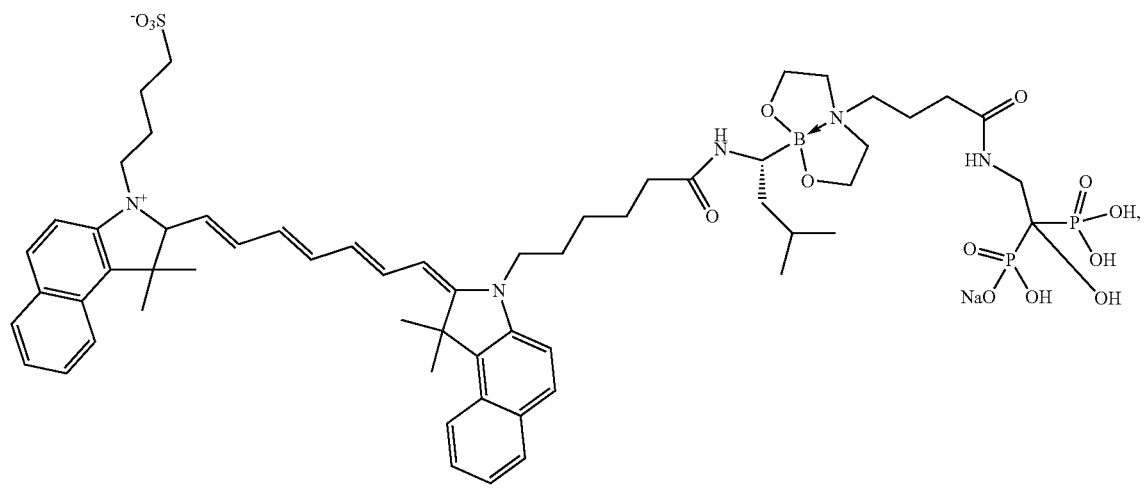
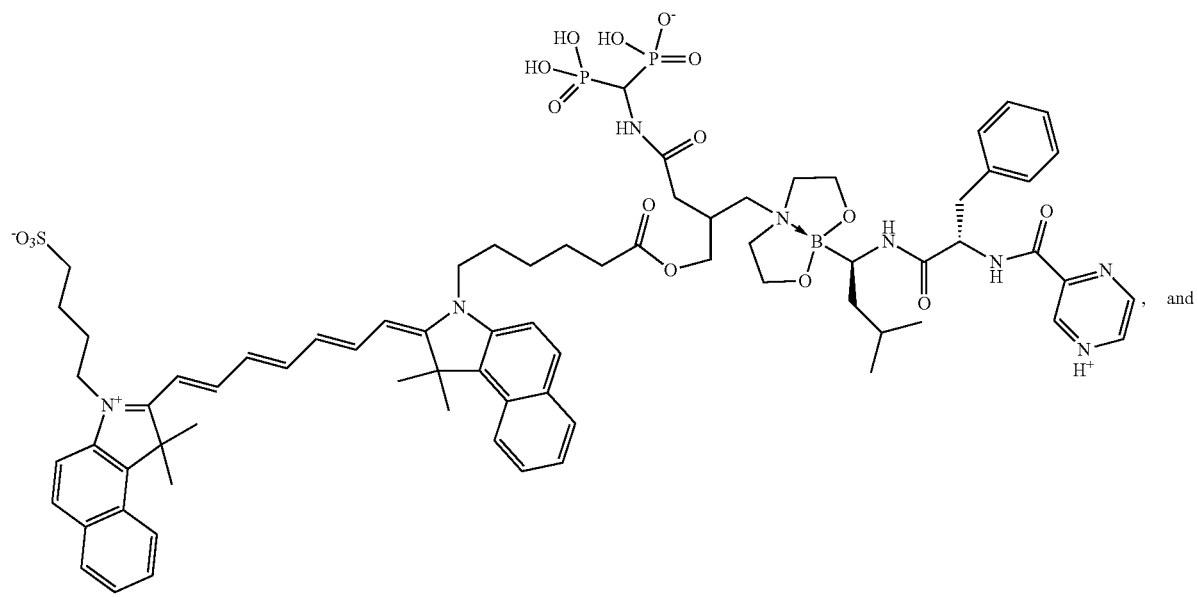

-continued

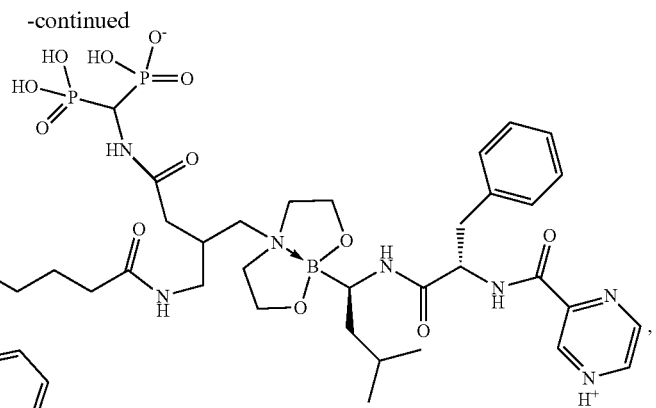

or a pharmaceutically acceptable salt thereof, an isomer thereof, or a mixture of isomers thereof.

In one embodiment, the compound is

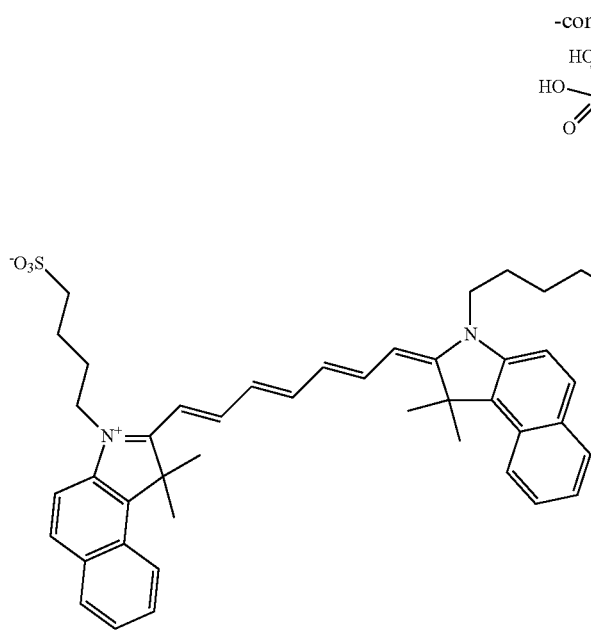

or a pharmaceutically acceptable salt thereof, an isomer thereof, or a mixture of isomers thereof.

In another aspect, the present invention includes a compound comprising a therapeutic agent conjugated to a phosphonate moiety via a linker, wherein the therapeutic agent is a Notch inhibitor. Notch signaling has been found to play a role in certain bone diseases and disorders, such as inflammatory osteoporosis.

It was found that persistent activation of Notch in MPCs limits their OB differentiation potential and causes bone loss, which can be prevented by treatment with Notch inhibitors (Zhang et al., 2014, J. Clin. Invest.). Non-limiting examples of Notch inhibitors include DAPT (N—[N-(3,5-difluorophenacetyl)-L-alanyl]-S-phenylglycine t-butyl ester) and Thapsigarin ((3S,3aR,4S,6S,6aR,7S,8S,9bS)-6-(acetyloxy)-4-(butyryloxy)-3,3a-dihydroxy-3,6,9-trimethyl-8-{[(2Z)-2-methylbut-2-enoyl]oxy}-2-oxo-2,3,3a,4,5,6,6a,7,8,9b-decahydroazuleno[4,5-b]furan-7-yl octanoate). Although not wishing to be bound by any particular theory, these results suggest that Notch inhibitors could be used as bone anabolic agents. However, like bortezomib, Notch inhibitors also have severe adverse effects due to systemic distribution (Barten et al., 2006, Drugs R D 7:87-97), limiting their use in common diseases such as osteoporosis. Therefore, the present invention also provides compounds comprising Notch inhibitors with reduced or no systemic toxic side effects.

Preparation of the Compounds of the Invention

Compounds of formulae (I)-(III) may be prepared by the general schemes described herein, using the synthetic method known by those skilled in the art. The following examples illustrate non-limiting embodiments of the invention.

In a non-limiting embodiment, compounds of the invention may be synthesized by conjugating a phosphonate with a diol, followed by joining the diol to a boronic acid moiety using any methods known in the art.

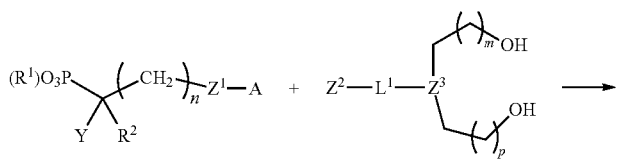

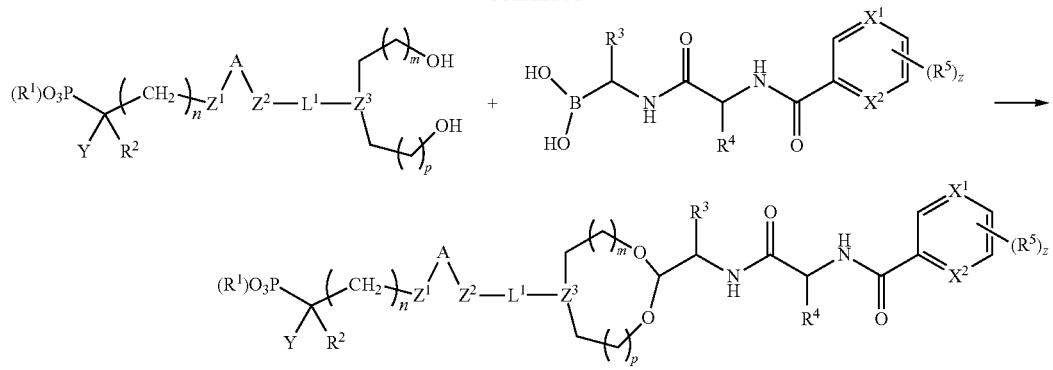

For example, compounds of the invention may be synthesized by conjugating an aminophosphonate to a triol linker region in order to form a carbamate using any methods known in the art. The aminophosphonate can be treated first with triphosgene, followed by treatment with the triol moiety in the presence of dibutyltin dilaurate to produce a carbamate diol.

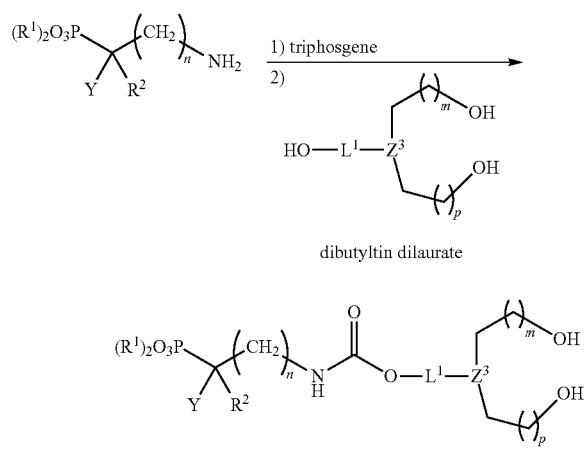

The compounds of the invention may then be produced by treatment of the diol with a boronic acid, followed by trimethylsilyl bromide (TMSBr), to form the boronate ester.

Compounds of the invention may possess one or more stereocenters, and each stereocenter may exist independently in either the R or S configuration. In one embodiment, compounds described herein are present in optically active or racemic forms. It is to be understood that the compounds described herein encompass racemic, optically-active, regioisomeric and stereoisomeric forms, or combinations thereof that possess the therapeutically useful properties described herein. In one embodiment, the compounds of the invention include stereoisomers and mixtures of stereoisomers. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In one embodiment, a mixture of one or more isomer is utilized as the therapeutic compound described herein. In another embodiment, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or

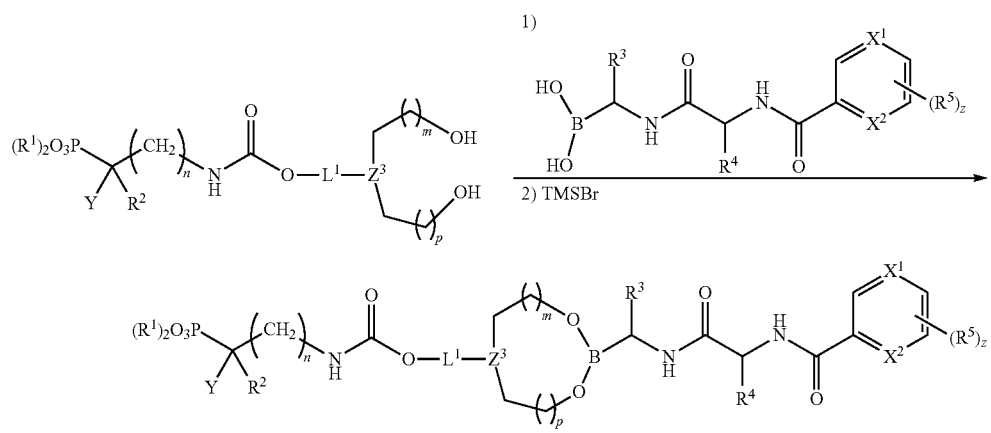

pharmaceutically acceptable salts of compounds having the structure of any compound of the invention, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In one embodiment, the compounds described herein exist in solvated forms with pharmaceutically acceptable solvents such as water, and ethanol. In one embodiment, the compound of the invention is a solvate comprising methanol and water. In another embodiment, the compounds described herein exist in unsolvated form.

In one embodiment, the compounds of the invention may exist as tautomers. All tautomers are included within the scope of the compounds presented herein.

In one embodiment, compounds described herein are prepared as prodrugs. A "prodrug" refers to an agent that is converted into the parent drug in vivo. In one embodiment, upon in vivo administration, a prodrug is chemically converted to the biologically, pharmaceutically or therapeutically active form of the compound. In another embodiment, a prodrug is enzymatically metabolized by one or more steps or processes to the biologically, pharmaceutically or therapeutically active form of the compound.

In one embodiment, sites on, for example, the aromatic ring portion of compounds of the invention are susceptible to various metabolic reactions. Incorporation of appropriate substituents on the aromatic ring structures may reduce, minimize or eliminate this metabolic pathway. In one embodiment, the appropriate substituent to decrease or eliminate the susceptibility of the aromatic ring to metabolic reactions is, by way of example only, a deuterium, a halogen, or an alkyl group.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In one embodiment, isotopically-labeled compounds are useful in drug and/or substrate tissue distribution studies. In another embodiment, substitution with heavier isotopes such as deuterium affords greater metabolic stability (for example, increased in vivo half-life or reduced dosage requirements). In yet another embodiment, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In one embodiment, the compounds described herein are labeled by other means, including, but not limited to, the use of chromophores or fluorescent moieties, bioluminescent labels, or chemiluminescent labels.

The compounds described herein, and other related compounds having different substituents are synthesized using techniques and materials described herein and as described, for example, in Fieser & Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey & Sundberg, Advanced Organic Chemistry 4th Ed., Vols. A and B (Plenum 2000, 2001), and Green & Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources, or are prepared using procedures described herein.

In one embodiment, reactive functional groups, such as hydroxyl, amino, imino, thio or carboxy groups, are protected in order to avoid their unwanted participation in reactions. Protecting groups are used to block some or all of the reactive moieties and prevent such groups from participating in chemical reactions until the protective group is removed. In another embodiment, each protective group is removable by a different means. Protective groups that are cleaved under totally disparate reaction conditions fulfill the requirement of differential removal.

In one embodiment, protective groups are removed by acid, base, reducing conditions (such as, for example, hydrogenolysis), and/or oxidative conditions. Groups such as trityl, dimethoxytrityl, acetal and t-butyldimethylsilyl are acid labile and are used to protect carboxy and hydroxy reactive moieties in the presence of amino groups protected with Cbz groups, which are removable by hydrogenolysis, and Fmoc groups, which are base labile. Carboxylic acid and hydroxy reactive moieties are blocked with base labile groups such as, but not limited to, methyl, ethyl, and acetyl, in the presence of amines that are blocked with acid labile groups, such as t-butyl carbamate, or with carbamates that are both acid and base stable but hydrolytically removable.

In one embodiment, carboxylic acid and hydroxy reactive moieties are blocked with hydrolytically removable protective groups such as the benzyl group, while amine groups capable of hydrogen bonding with acids are blocked with base labile groups such as Fmoc. Carboxylic acid reactive moieties are protected by conversion to simple ester compounds as exemplified herein, which include conversion to alkyl esters, or are blocked with oxidatively-removable protective groups such as 2,4-dimethoxybenzyl, while co-existing amino groups are blocked with fluoride labile silyl carbamates.

Allyl blocking groups are useful in the presence of acid- and base-protecting groups since the former are stable and are subsequently removed by metal or pi-acid catalysts. For example, an allyl-blocked carboxylic acid is deprotected with a palladium-catalyzed reaction in the presence of acid labile t-butyl carbamate or base-labile acetate amine protecting groups. Yet another form of protecting group is a resin to which a compound or intermediate is attached. As long as the residue is attached to the resin, that functional group is blocked and does not react. Once released from the resin, the functional group is available to react.

Typically blocking/protecting groups may be selected from:

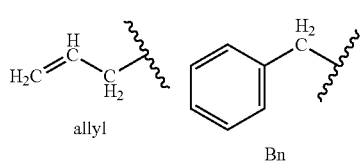

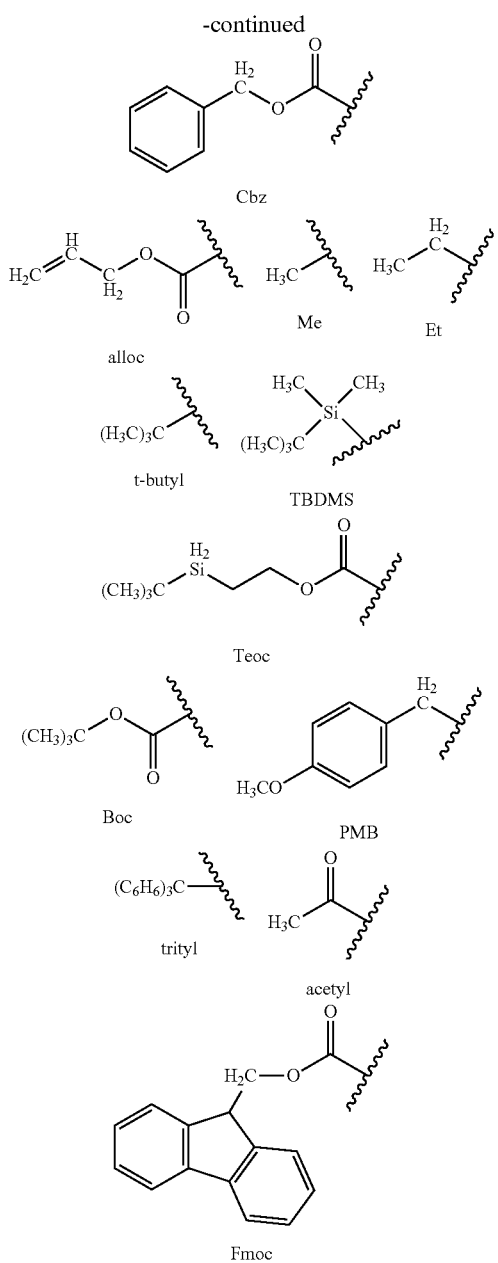

Other protecting groups, plus a detailed description of techniques applicable to the creation of protecting groups and their removal are described in Greene & Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

Therapeutic Methods

The present invention provides a method for promoting or inducing bone formation. The method may be used, for example, as a therapy in treating diseases and disorders characterized by bone loss. In one embodiment, the method is used to treat a subject having osteoporosis. In another embodiment, the method is used to treat a subject at risk for having osteoporosis. In another embodiment, the method is used to treat a subject with bone cancer. In yet another embodiment, the method is used to treat a subject with a fractured bone. The method of the invention provides local delivery of a compound of the invention to a site in need of bone formation. Thus, the method of the invention should not be construed to be limited solely to treat osteoporosis, but rather should be construed to include any disease or disorder where bone formation is desired and beneficial for the subject, including for example, multiple myeloma, osteoporosis, osteonecrosis, osteomyelitis, osteoarthritis, rheumatoid arthritis, Paget's disease, bone fracture healing, prosthesis loosening, bone cancer, leukemia, a myeloproliferative disease, radiotherapy-induced osteoporosis, and a cancer metastasized to bone.

In one aspect, the present invention includes a method of treating a disease selected from the group consisting of multiple myeloma and bone cancer in a subject in need thereof. In one embodiment, the method includes administering a therapeutically effective amount of a composition comprising at least one compound comprising a therapeutic agent conjugated to a phosphonate moiety via a linker, wherein the therapeutic agent is bortezomib (Btz) or an analogue thereof.

In one aspect, the present invention includes a method of promoting bone formation at a site in need of bone formation in a subject. In one embodiment, the method includes administering a therapeutically effective amount of a composition comprising a compound comprising a therapeutic agent conjugated to a phosphonate moiety via a linker. In one embodiment, the therapeutic agent is bortezomib (Btz) or an analogue thereof.

In one aspect, the present invention includes a method of promoting bone formation in a site at or near bone related cancers in a subject. In one embodiment, the method includes administering a therapeutically effective amount of a composition comprising a compound comprising a therapeutic agent conjugated to a phosphonate moiety via a linker. In one embodiment, the therapeutic agent is bortezomib (Btz) or an analogue thereof.

In another aspect, the present invention includes a method of reducing bone resorption at a site in need of a reduction in bone resorption in a subject. In one embodiment, the method includes administering a therapeutically effective amount of a composition comprising at least one compound comprising a therapeutic agent conjugated to a phosphonate moiety via a linker. In one embodiment, the therapeutic agent is bortezomib (Btz) or an analogue thereof.

In another aspect, the present invention includes a method of inhibiting inflammation of bone, bone marrow, or surrounding tissues. In one embodiment, the method includes administering a therapeutically effective amount of a composition comprising at least one compound comprising a therapeutic agent conjugated to a phosphonate moiety via a linker. In one embodiment, the therapeutic agent is bortezomib (Btz) or an analogue thereof.

In another aspect, the present invention includes a method of killing cancer cells of bone, bone marrow and bone surrounding tissues in a subject. In one embodiment, the method includes administering a therapeutically effective amount of a composition comprising at least one compound comprising a therapeutic agent conjugated to a phosphonate moiety via a linker. In one embodiment, the therapeutic agent is bortezomib (Btz) or an analogue thereof. In one embodiment, the subject has multiple myeloma.

In one embodiment, the composition further comprises at least one pharmaceutically acceptable carrier. In one embodiment, the therapeutic agent is controllably released from the compound at the site in need of bone formation. In another embodiment, the therapeutic agent is controllably released from the compound at the site in need of a reduction in bone resorption.

In certain embodiments, the method comprises administering a pharmaceutical composition comprising a compound of the invention. The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

In some embodiments, the compositions of the present invention are useful in combination with one or more additional compounds. In one embodiment, the additional compound is also a compound of the invention. In non-limiting examples, the compositions of the invention may be used in combination with one or more therapeutic agents (or a salt, solvate or prodrug thereof). In another embodiment, the therapeutic agent is a drug useful for treating multiple myeloma. In another embodiment, the therapeutic agent is a bone-targeted drug.

Although the description of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as non-human primates, cattle, pigs, horses, sheep, cats, and dogs.

Pharmaceutical Compositions and Administration

Pharmaceutical compositions that are useful in the methods of the invention may be prepared, packaged, or sold in formulations suitable for ophthalmic, oral, rectal, vaginal, parenteral, topical, pulmonary, intranasal, buccal, or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Other active agents include growth factors, hormones, anti-inflammatories, including corticosteroids, and immunosuppressants, proteins (eg. BMPs), and the like.

Controlled- or sustained-release formulations of a pharmaceutical composition of the invention may be made using conventional technology.

For oral application, particularly suitable are tablets, dragees, liquids, drops, suppositories, or capsules, caplets and gelcaps. Other formulations suitable for oral administration include, but are not limited to, a powdered or granular formulation, an aqueous or oily suspension, an aqueous or oily solution, a paste, a gel, toothpaste, a mouthwash, a coating, an oral rinse, or an emulsion. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically controlled release tablets. Tablets may further comprise a sweetening agent, a flavoring agent, a coloring agent, a preservative, or some combination of these in order to provide for pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

For oral administration, the compositions of the invention may be in the form of tablets or capsules prepared by conventional means with pharmaceutically acceptable excipients such as binding agents; fillers; lubricants; disintegrates; or wetting agents. If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400).

Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid). Liquid formulations of a pharmaceutical composition of the invention which are suitable for oral administration may be prepared, packaged, and sold either in liquid form or in the form of a dry product intended for reconstitution with water or another suitable vehicle prior to use.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface-active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) will melt.

The present invention also includes a multi-layer tablet comprising a layer providing for the delayed release of one or more compounds of the invention, and a further layer providing for the immediate release of a medication for treatment of a disease. Using a wax/pH-sensitive polymer mix, a gastric insoluble composition may be obtained in which the active ingredient is entrapped, ensuring its delayed release.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations that are useful include those that comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Remington's Pharmaceutical Sciences (1985, Genaro, ed., Mack Publishing Co., Easton, Pa.), which is incorporated herein by reference.

It will be appreciated that a composition of the invention may be administered to a subject either alone, or in conjunction with another therapeutic agent.

The therapeutic and prophylactic methods of the invention thus encompass the use of pharmaceutical compositions comprising a therapeutic agent that induces or promotes bone formation to practice the methods of the invention. The pharmaceutical compositions useful for practicing the invention may be administered to deliver a dose of from ng/kg/day and 100 mg/kg/day. In one embodiment, the invention envisions administration of a dose which results in a concentration of the compound of the present invention from 1 µM and 10 µM in a mammal.

Typically, dosages which may be administered in a method of the invention to a mammal, preferably a human, range in amount from 0.5 µg to about 50 mg per kilogram of body weight of the mammal, while the precise dosage administered will vary depending upon any number of factors, including but not limited to, the type of mammal and type of disease state being treated, the age of the mammal and the route of administration. Preferably, the dosage of the compound will vary from about 1 µg to about 10 mg per kilogram of body weight of the mammal. More preferably, the dosage will vary from about 3 µg to about 1 mg per kilogram of body weight of the mammal.

The composition may be administered to a mammal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the mammal, etc.

Controlled Release Formulations and Drug Delivery Systems

In one embodiment, the formulations of the present invention may be, but are not limited to, short-term, rapid-offset, as well as controlled, for example, sustained release, delayed release and pulsatile release formulations.

The term sustained release refers to a drug formulation that provides for gradual release of a drug over an extended period of time, and that may, although not necessarily, result in substantially constant blood levels of a drug over an extended time period. The period of time may be as long as a day, a week, or a month or more and should be a release which is longer that the same amount of agent administered in bolus form. The term delayed release is used herein in its conventional sense to refer to a drug formulation that provides for an initial release of the drug after some delay following drug administration and that mat, although not necessarily, includes a delay of from about 10 minutes up to about 12 hours.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In one embodiment of the invention, the compounds of the invention are administered to a patient, alone or in combination with another pharmaceutical agent, using a sustained release formulation.

The term pulsatile release refers to a drug formulation that provides release of the drug in such a way as to produce pulsed plasma profiles of the drug after drug administration.

The term immediate release refers to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Those skilled in the art recognize, or are able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

The materials and methods employed in the experiments and the results of the experiments presented in this Example are now described.

The following Table A includes compounds referred to in the working examples.

TABLE A

| COMPOUND NUMBER | STRUCTURE |
| --- | --- |
| BP-Btz1 | 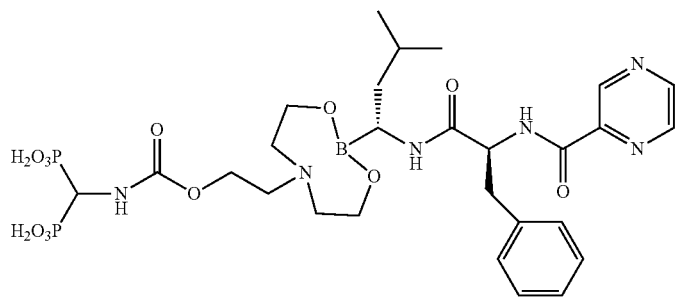 |
| BP-Btz2 | 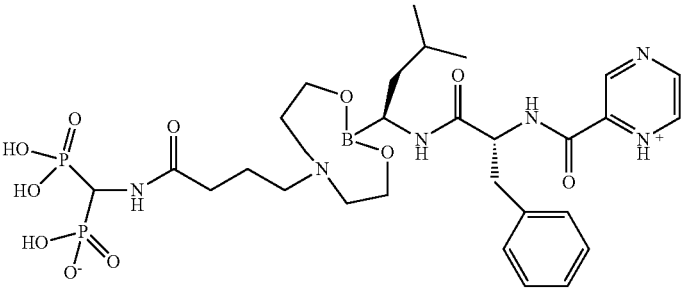 [SMILES: CC(C)C[C@@H](NC(=O)[C@@H](Cc1ccccc1)NC(=O)c1cnccn1)B1OCCCN(CCCC(=O)NC(P(=O)([O-])O)P(=O)(O)O)CCO1] |

TABLE A-continued

| COMPOUND NUMBER | STRUCTURE |
| --- | --- |
| BP-Btz3 | 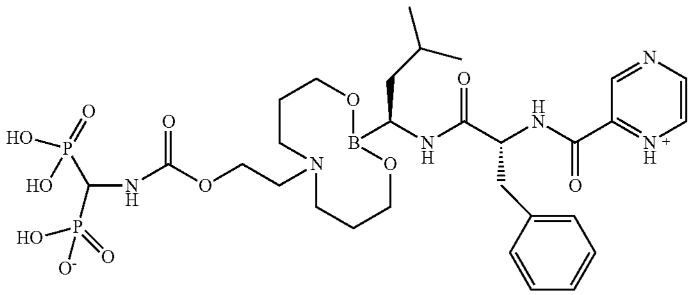 |
| BP-Btz4 | 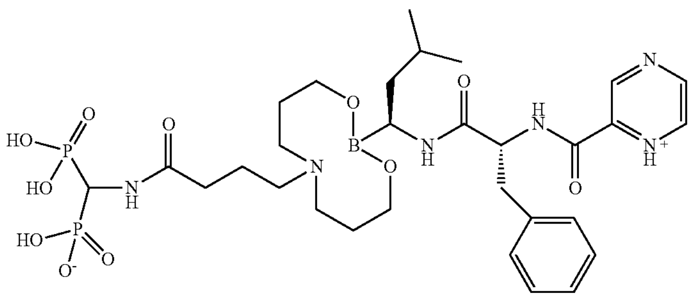 [SMILES: CC(C)C[C@@H](NC(=O)[C@@H](Cc1ccccc1)NC(=O)c1cnccn1)B1OCCCN(CCCC(=O)NC(P(=O)([O-])O)P(=O)(O)O)CCCO1] |
| BP-Btz5 | 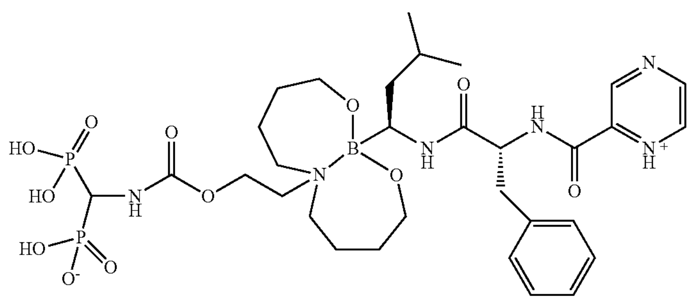 |
| BP-Btz6 | 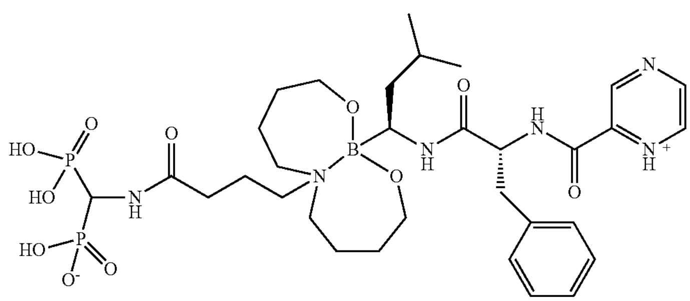 |
| BP-Btz7 | 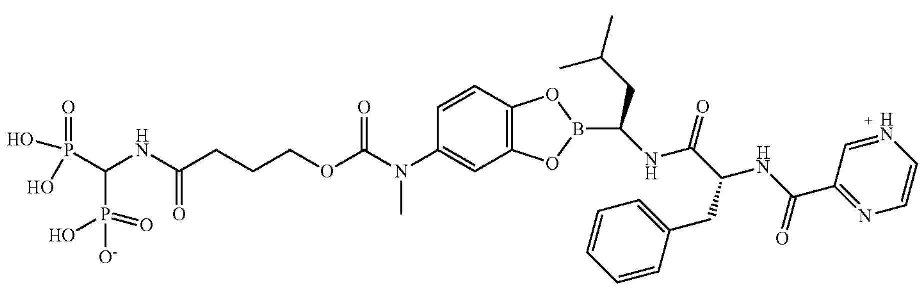 |

TABLE A-continued

| COMPOUND NUMBER | STRUCTURE |
|---|---|
| BP-Btz8 | 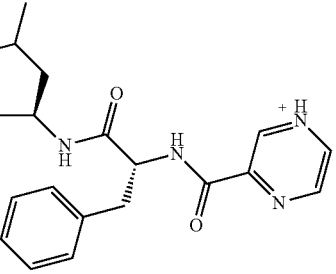 |
| BP-Btz9 | 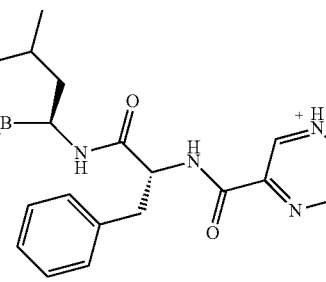 |
| BP-Btz10 | 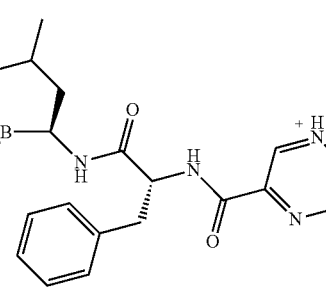 |

Example 1: Synthesis of BP-Btz1

Synthesis of Urethane Diol 2

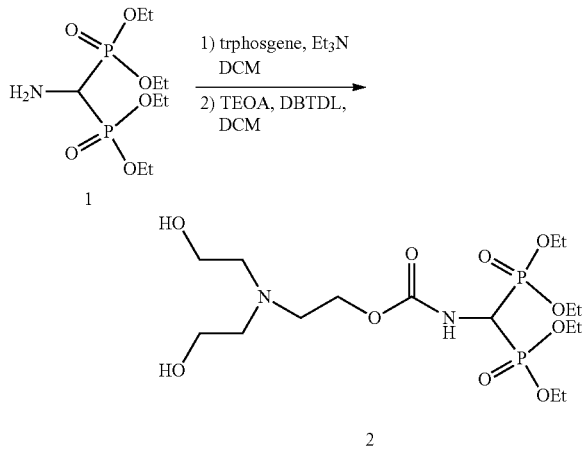

A dry 10 mL round bottom flask at 0° C. under Ar was charged with tetraethyl aminomethylenediphosphonate 1 (200 mg, 0.66 mmol), and triphosgene (78 mg, 0.264 mmol, 0.4 equiv) in dry $CH_2Cl_2$ (3 mL). Neat triethylamine, (67 mg, 0.66 mmol, 1 equiv) was added to the reaction mixture. The resulting reaction mixture was allowed to warm to rt and stir overnight. The reaction mixture was the quenched by addition of 25 mL of 1M aq HCl. After separation of the phases, the aqueous phases was extracted with $CH_2Cl_2$ (3×30 mL). The combined organic layers were washed with sat brine (15 mL), dried over $Na_2SO_4$, filtered, and concentrated in vacuo to afford 190 mg of the derived isocyanate as a yellow oil.

A dry 5 mL round bottom flask charged with the preceding crude product mixture (190 mg), followed by addition of a solution of dibuthyltin dilaurate (DBTDL) (36.6 mg, 0.058 mmol, 0.1 equiv), and 77.5 mg (0.52 mmol, 0.9 equiv) of triethanolamine (TEOA) in 1.2 mL of dry $CH_2Cl_2$. The resulting reaction mixture was allowed to stir at rt for 2 da. The reaction mixture was then filtered through celite pad and the pad washed with additional $CH_2Cl_2$ (15 mL). The filtrate was concentrated in vacuo and the residue was purified by column chromatography ($CH_3OH$—$CH_2Cl_2$ gradient, 5:95 to 2:8) to afford 126 mg (40%) of the urethane diol 2 ($R_f$=0.45 ($CH_3OH$—$CH_2Cl_2$, 2:8, visualized with $KMnO_4$) as light yellow oil having $^1H$ NMR (500 MHz, DMSO) δ 8.21 (d, J=10 Hz, 1H), 5.27 (s, 2H), 4.43-4.32 (m, 3H), 4.07 (s, 8H), 3.48 (s, 2H), 3.28 (s, 4H), 1.23 (m, 12H); $^{13}C$ NMR (400 MHz, $CDCl_3$) δ 115.36, 63.98, 59.63, 56.64, 56.03, 53.68, 46.17 (t), 16.37; $^{31}P$ NMR (400 MHz, $CDCl_3$) δ 13.09; MS (ESI) m/z 501.2 (M+Na$^+$), 479.5 (M+H$^+$).

Synthesis of BP-Btz1

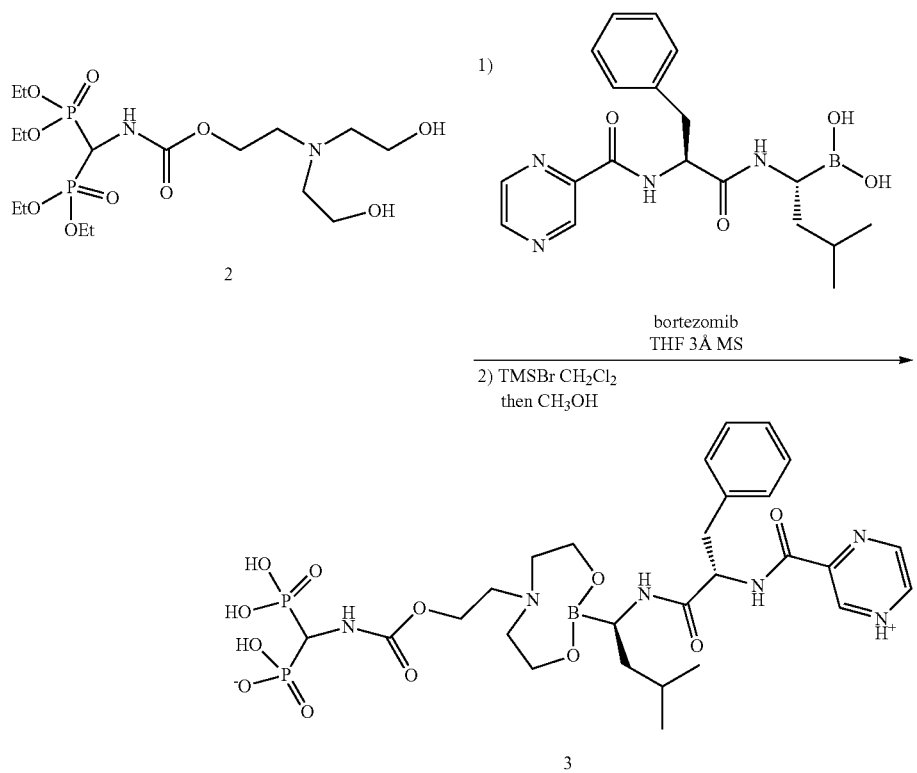

A dry 10 mL round bottom flask was charged with 1 g of powdered 3 Å molecular sieves (activated by drying in a vacuum oven at 120° C. overnight) and a solution of 2 (125 mg, 0.26 mmol) and bortezomib (120.5 mg, 0.31 mmol, 1.2 equiv) in dry THF (5 mL). The reaction mixture was stirred at rt for 3 da. After filtration of the reaction mixture was though glass wood followed by a celite pad, the filtrate was concentrated in vacuo. The crude product was washed with Et$_2$O (10 mL×2) to remove any unreacted bortezomib affording 215 mg of crude product as brown solid. Crude material characterized by mass spectroscopy: MS (ESI) m/z 827.4 (M+H$^+$), 849.4 (M+Na$^+$), 865.3 (M+K$^+$). No ion of m/z 385.2 corresponding to bortezomib was observed.

A dry 10 mL round bottom flask was charged with a solution of the crude product above (215 mg-0.26 mmol) in dry DCM (8 mL) under Ar at 0° C. Trimethylsilyl bromide (TMSBr) (239.7 mg, 0.156 mmol, 6 equiv) was added dropwise with magnetic stirring. After addition was complete, the reaction mixture was allowed to stir and warm to rt overnight. The reaction mixture was then concentrated in vacuo and kept under high vacuum for 10 min to afford a brown solid. Methanol (5 mL) was added to dissolve the solid, and the resulting solution was concentrated in vacuo. This procedure was repeated 3 additional times. The resulting solid was dissolved in EtOH (0.5 mL) followed by addition to 10 mL of Et$_2$O resulting in formation of a brownish-white precipitate. The solid was isolated by filtration and dried under high vacuum at 90° C. affording 170 mg of 3 (BP-Btz1) (91%) as a light brown solid having $^1$H NMR (500 MHz, CDCl$_3$) δ 8.95 (s, 1H), 8.68 (s, 1H), 8.62 (s, 1H), 7.37 (s, 4H), 7.16 (s, 1H), 4.71 (t, J=10 Hz, 1H), 4.30 (s, 2H), 3.94 (t, J=20 Hz, 1H), 3.74 (s, 4H), 3.47 (s, 2H), 3.28 (s, 4H), 3.08 (m, 1H), 2.97 (m, 1H), 2.78 (m, 1H), 1.32-1.24 (m, 2H), 1.16 (m, 1H), 0.72 (m, 6H); $^{13}$C NMR (400 MHz, CDCl$_3$) δ 177.38, 163.85, 155.7, 148.34, 144.34, 144.14, 143.88, 135.23, 129.72, 128.77, 127.31, 59.59, 55.81, 55.68, 52.67, 50.67, 48.74, 47.88, 36.39, 24.83, 23.85, 21.99; $^{31}$P NMR (400 MHz, CDCl$_3$) δ −1.43, −4.81.

Example 2: Study of Osteoblast Regulation in TNF-Mediated Bone Loss

There had previously not been any study of the role of UPS-mediated protein modification in bone repair. However, during the course of studying ubiquitin E3 ligases and osteoblast regulation, it was found that MSCs from mice deficient Smurf1, Wwp1 and Itch (members of the Nedd4 sub-class of E3 ligases) have increased migration, growth and osteoblast (OB) differentiation by increasing the stability of Runx2, JunB and CXCR4 proteins via the ubiquitin-proteasome system (UPS) (Jones et al., 2012, Stem Cells Transl. Med. 1:70-78). Runx2 and JunB are key positive regulators of OB differentiation and CXCR4 is essential for cell migration. Thus, targeting the UPS may represent a new strategy to promote fracture healing by improving MPC function.

Delivering a drug to bone is a significant challenge in the field of bone research. Many clinically used drugs or compounds have positive effects on OBs in cell cultures, including Bortezomib. However, they cannot be used in the treatment of common bone diseases such as osteoporosis and bone fractures due to severe adverse effects on other cell types via systemic distribution. Furthermore, difficulties in chemistry make it hard to achieve.

Initial approaches to target drugs to bone with bisphosphonates (BPs) have previously had limited efficacy (Gil et al., 1999, Bioorg. Med. Chem. 7:901-919; Hirabayashi and Fujisaki, 2003, Clin. Pharmacokinet. 42:1319-1330). However, recent attempts to target estrogen analogues (Morioka et al., 2010, Bioorg. Med. Chem. Lett. 18:1143-1148), antibiotic agents (Tanaka et al., 2010, Bioorg. Med. Chem. Lett. 20:1355-1359), and prostaglandins (Ams et al., 2012, Bioorg. Med. Chem. 20:2131-2140) to bone through a carbamate linker conjugation have been more successful specifically through chemical linkages that allow the subsequent release of an active agent at the bone surface. This approach improved the efficacy of estradiol to inhibit bone resorption, while limiting side-effects, such as endometrial hyperplasia (Morioka et al., 2010, Bioorg. Med. Chem. Lett. 18:1143-1148). In a related effort, this BP-drug conjugation technology facilitated adequate delivery to bone and the slow release of prostaglandin 'warheads' in radiolabelled PK studies to estimate concentrations of delivered drug (Ams et al., 2012, Bioorg. Med. Chem. 20:2131-2140; Liu et al., 2015, J. Bone Min. Res. 30:670-680). Carbamate linkers are cleaved by enzymatic or hydrolytic means in the acidic microenvironment under the osteoclast ruffled border in bone resorption sites, thus releasing the active drug ('warhead/payload') (Arns et al., 2012, Bioorg. Med. Chem. 20:2131-2140). As demonstrated herein, the use of carbamate linkers has resulted in the delivery of Btz to bone by utilizing the boronic ester functional group of Btz as a linker, which is labile in the presence of the low pH conditions that occur on the bone surface.

Figure 1B:
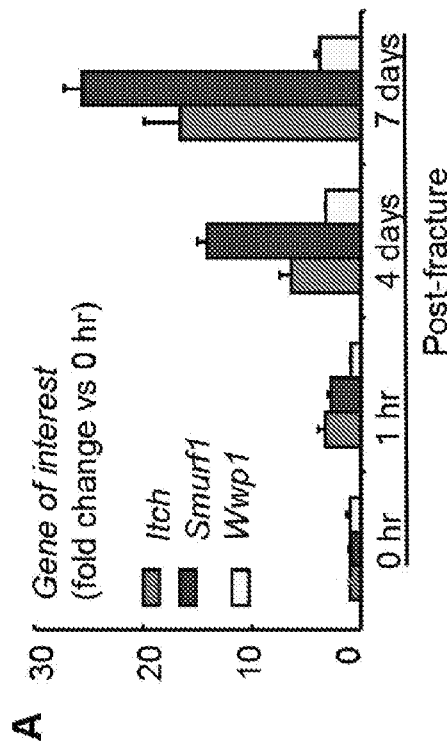

The results described herein demonstrate a bone-targeted conjugate compound comprising Bortezomib, BP-Btz1, used to determine if the Btz released in bone would have anti-osteoclast efficacy at least equivalent to Btz in standard in vitro osteoclast formation assays. As a control, the effects of the non-bioactive bisphosphonate (BP) that would be released in the bone compartment were also studied. In in vitro studies on bone slices, it was demonstrated that the Btz conjugate bearing this boronic ester degradable linker has anti-osteoclast activity equivalent to than Btz itself. In a pivotal in vitro study, this BP-Btz1 and Btz were independently incubated with bone slices for 24 hours, after which the bone slices were removed and placed in culture wells with fresh media along with osteoclast precursors. Formation and activity of osteoclasts derived from these precursors were significantly reduced on the bone slices pre-incubated with the conjugate (1 μM), but not on those slices pre-incubated with Btz only. These results are consistent with the bisphosphonate component binding to the bone slices during the 24 hour exposure and the Btz being released and taken up subsequently by osteoclast precursors to inhibit their differentiation into osteoclasts. Osteoblast assays were also to demonstrate that similar to Btz, BP-Btz1 stimulates osteoblast differentiation of mouse and human MPCs, indicating that this chemical approach does not affect bone anabolic property of Btz (FIG. 1).

In vivo studies demonstrate in dose-response experiments that the conjugate BP-Btz1 inhibits bone resorption and stimulates formation at doses lower than effective doses of Btz alone. In vitro testing is also used to examine analogues of BP-Btz1.

Example 3: Study of Osteoblast Regulation in TNF-Mediated Bone Loss

The role of E3 ligase Smurf1, Wwp1 and Itch in bone using Smurf1$^{-/-}$, Wwp1$^{-/-}$, and Itch$^{-/-}$ mice has been investigated. All of these knockout mice have increased bone volumes, bone formation, and OB differentiation by causing ubiquitination and degradation of JunB and Runx2 (Weathington and Mallampalli, 2014, J. Clin. Invest. 124:6-12; Morioka et al., 2010, Bioorg. Med. Chem. 18:1143-1148; Tanaka et al., 2010, Bioorg. Med. Chem. Lett. 20:1355-1359; Arns et al., 2012, Bioorg. Med. Chem. Lett. 20:2131-2140; Zhang et al., 2014, J. Clin. Invest.; Barten et al., 2006, Drugs R D 7:87-97; Zhou et al., 2010, Arthritis Rheum. 62:1881-1889). Bone fracture repair is composed of a series of events that involve inflammation, angiogenesis and osteogenesis, which are regulated by multiple mechanisms. However, the role of protein turnover by the UPS in fracture healing has not been explored previously. High expression levels of E3 ligases and Ub-proteins in bone fracture calluses were detected (FIG. 1), indicating that a UPS-mediated cellular event may be involved in the bone repair process, which forms a basis for this application. Nestin-GFP mice were used to label Mesenchymal stem/Progenitor Cells (MPCs) (Mignone et al., 2004, J. Comp. Neurol. 469:311-324; Mendez-Ferrer et al., 2010, Nature 466:829-834) and showed remarkably increased Nestin$^+$ MPCs at early phases of fracture callus.

Figures 2A, 2B, 2C, 2D:
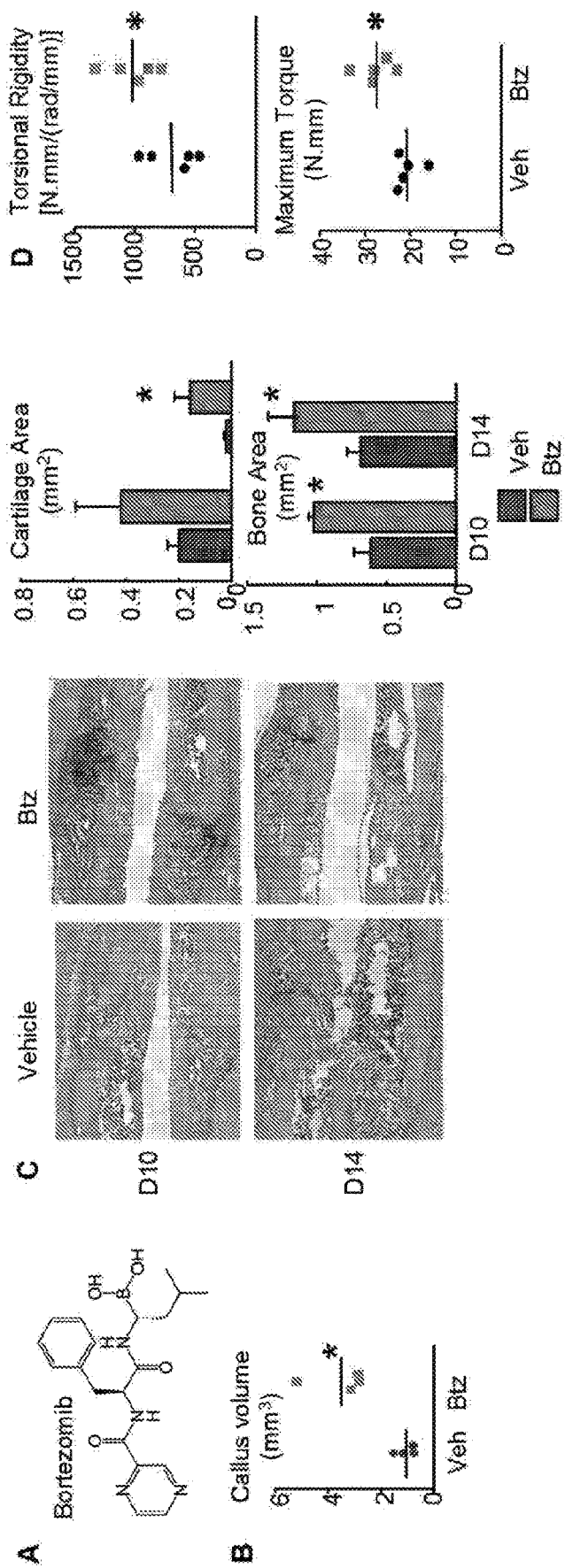
Figures 2F, 2G:
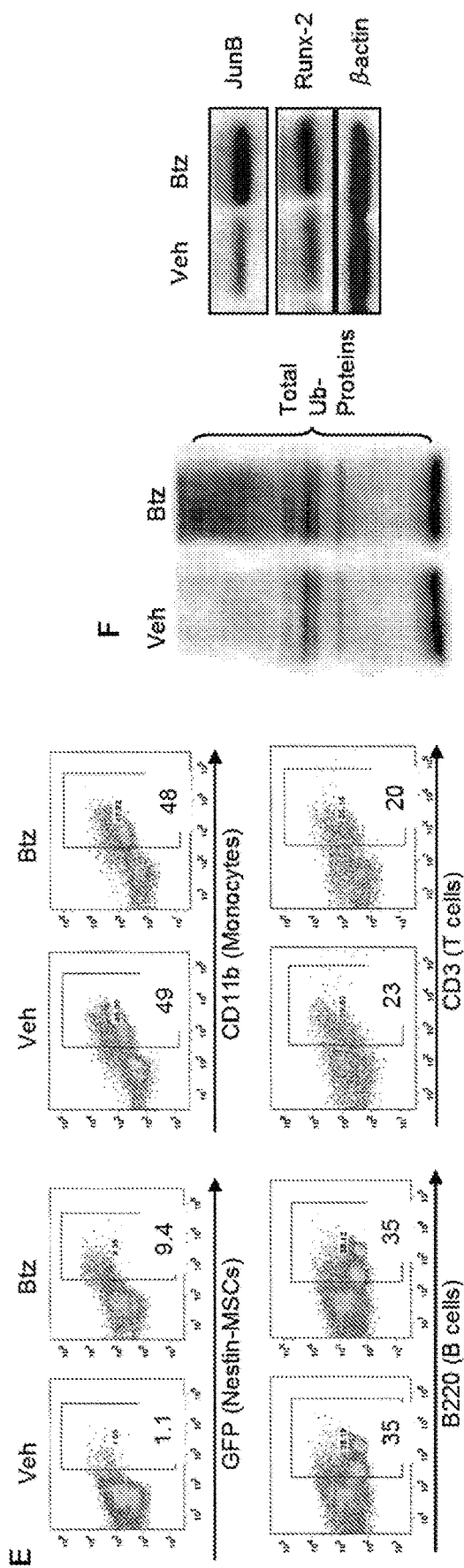

It was further demonstrated that the proteasome inhibitor Bortezomib (Btz) accelerates callus formation and increases bone strength in fractured mice, which is associated with increased Nestin$^+$MPCs and Ub-proteins (FIG. 2). It was found that short-term Btz treatment increases fracture healing in mice, accompanying the accumulation of Ub-proteins in facture calluses (FIG. 2), suggesting that Btz may promote bone regeneration. However, clinical information from myeloma therapy indicates that Btz and other proteasome inhibitors including Carfilzomib (marketed as Kyprolis by Onyx Pharmaceuticals) have significant toxicities, such as peripheral neuropathy and thrombocytopenia, which restrict their utilization. As described herein, conjugates of Btz and bisphosphonates (BPs) are synthesized using a carbamate linker (FIG. 3), thereby avoid any confounding effects associated with direct actions of BPs on osteoclasts and bone destruction.

Design and Synthesis of Bone-Targeted Bortezomib Conjugates

Figure 3:
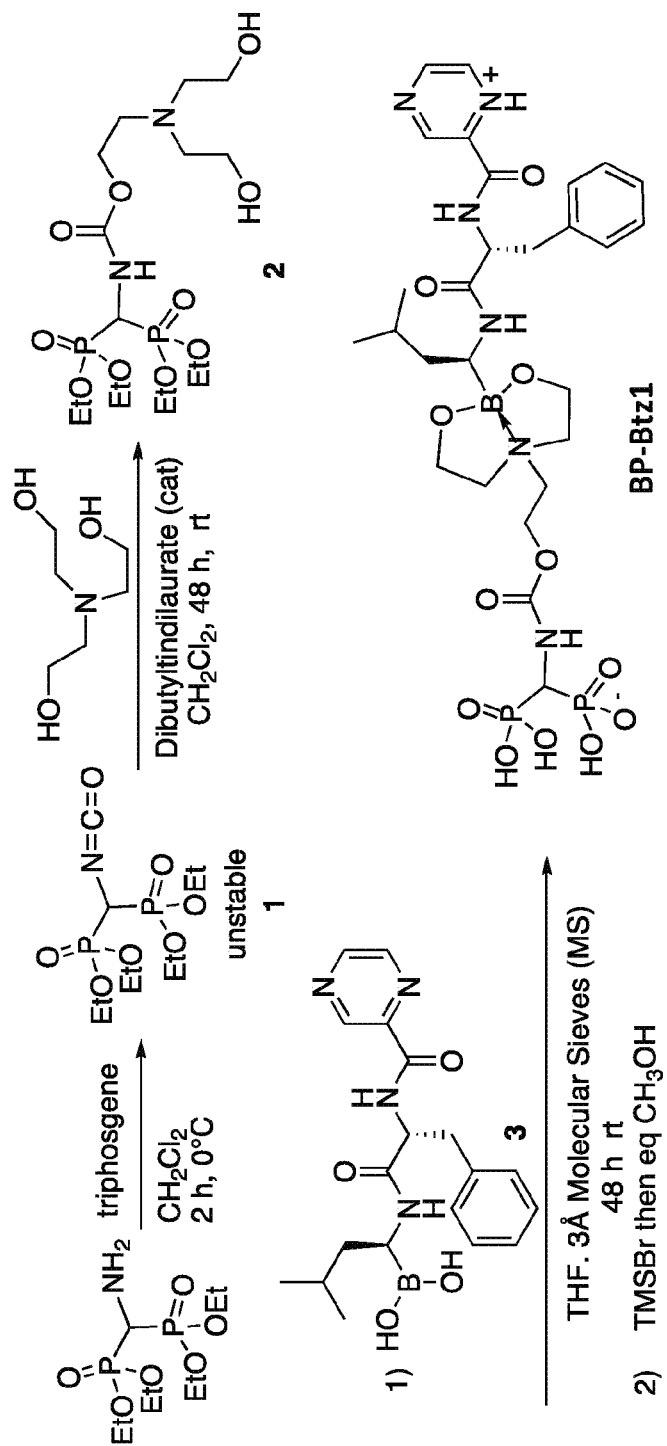
FIG. 3 is a scheme of an exemplary synthesis of BP-Btz1. In one embodiment, Btz may be released via the cleavage of the carbamate linker and/or hydrolysis of the boronate ester. Reagents and conditions: 1: triphosgene (0.5) equiv), $Et_3N$, $CH_2Cl_2$; 2: triethanolamine, toluene; 4: Btz (3), toluene-DMSO, heat (—$H_2O$), then trimethylsilyl bromide followed by $H_2O$.
Figure 4:
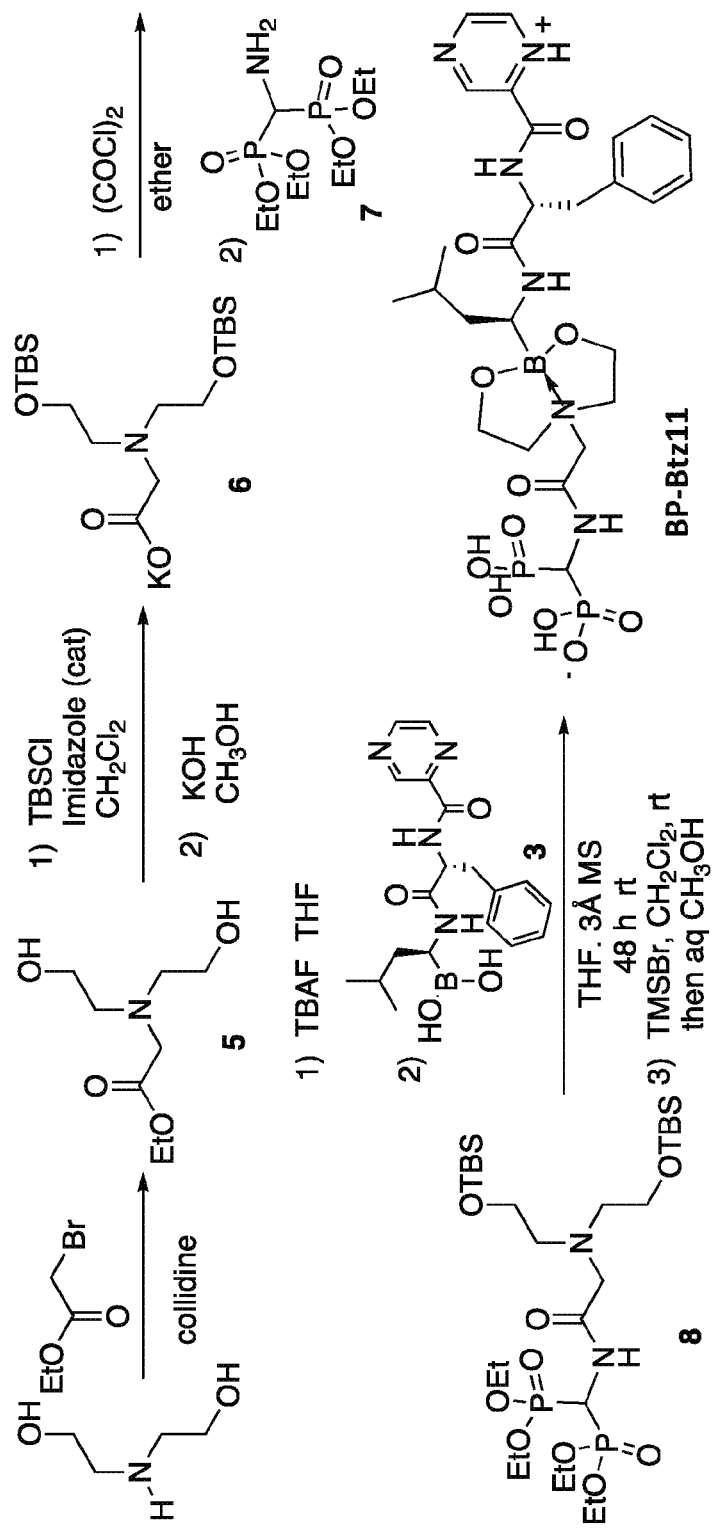
FIG. 4 is a scheme of an exemplary synthesis of BP-Btz11 which may be released via the amine-stabilized boronate ester complex. Reagents and conditions: 5: diethanolamine, ethyl bromoacetate collidine, $CH_2Cl_2$, rt; 6: t-butyl dimethylsilyl chloride, imidazole (cat.), $CH_2Cl_2$, rt, then potassium hydroxide, methanol; 8: oxalyl chloride, ether, 0° C. then amino BP 7; 9: tetrabutylammonium fluoride, tetrahydrofuran, rt; then Btz (3), toluene-DMSO, heat (—$H_2O$), then trimethylsilyl bromide, $CH_2Cl_2$, rt, followed by NaOH, water, lyophilize. BP-Btz2 may be prepared similarly by increasing the chain length of amino acid analog 6.

The synthesis of two structural classes of BT-Btz conjugates is performed. In the first class, BT-Btz1, the Btz will be conjugated to BP via a carbamate linkage (FIG. 3). The release of Btz can be achieved by one or both of two possible mechanisms. For example, Btz can be released due to carbamate cleavage and hydrolysis or by simple hydrolysis of the amine-stabilized borate complex of Btz. In the second class, BT-Btz2, Btz is conjugated to BP via an amine stabilized boronate ester complex.

Chemical Design and Synthesis

BT-Btz1 (with a Carbamate Linkage)

Carbamate linkers are cleaved by enzymatic reaction in an acidic microenvironment, releasing the active drug. This approach has been recently used in several BT-agents (Morioka et al., 2010, Bioorg. Med. Chem. 18:1143-1148; Tanaka et al., 2010, Bioorg. Med. Chem. Lett. 20:1355-1359; Arns et al., 2012, Bioorg. Med. Chem. Lett. 20:2131-2140). Thus, Btz is released when BT-Btz1 resides in an environment where the activity of proteoases, such as MMPs, is high, or under the osteoclast ruffled border in bone resorption sites.

1. Design

2-Aminomethane-1,1-bisphosphonic acid is used as the targeting BP module since it has limited cellular and antiresorptive activity, thus permitting determination of the activity delivered by the warhead Btz. The chemical attachment points and other chemical variants unique may be modified in order to adjust the payload release rate, as would be understood by one of ordinary skill in the art. A representative example of such targets using Btz is shown in FIG. 3, and exemplifies one of the types of linkers and release mechanisms in addition to hydrolysis of the amine stabilized boronate complex of Btz.

2. Synthesis.

The known BP isocyanate 1 is prepared using a previously reported method and condensed with triethanolamine to afford the BP carbamolyl diol 2. The target amine stabilized borate conjugate BP-Btz1 is prepared by dehydrative formation of the borate using standard procedures, and cleavage of the BP esters to the mono (or di) sodium salt of the target BP-Btz1 (compound 4; FIG. 3).

3. Purification

BT-Btz conjugates are purified using standard techniques such as precipitation, chromatography, including HPLC with super-critical $CO_2$, to >99% purity prior to use in biological studies. The structures and purity of the conjugates is verified by standard spectroscopic and analytical techniques including $^1H$, $^{13}C$, and $^{31}P$ NMR, IR, Mass Spectroscopy, Combustion Elemental Analysis, and analytical TLC and HPLC.

BT-Btz2 (with an Amine Stabilized Boronate Ester Complex)

Unlike in BT-Btz1, Btz can only be released from BT-Btz2 by the hydrolysis of the amine stabilized borate complex of Btz in the acidic microenvironment of the bone matrix. Because 2-aminomethane-1,1-bisphosphonic acid, which has a weak anti-osteoclast effect, is used as the BP module (carrier), it is hypothesized that the bioactivity of the BT-Btz2 should be mainly from Btz.

1. Design

As in BT-Btz1, 2-aminomethane-1,1-bisphosphonic acid is used to reduce the potential effect of BP. A robust but simple amide linker and the same amine stabilized boronate group are used to serve as both stabilizing element for the boronic acid moiety of Btz but also a suitable release mechanism in an acidic environment such as the bone matrix.

2. Synthesis

The use of the mono (or di) sodium salt is used to assure the stability of the amine stabilized borate complex. The preparation of BP-Btz2 includes conjugation of Btz to BP using the amine stabilized boronate ester complex (FIG. 4). Synthesis of the silyl protected carboxylate salt 6 is accomplished by standard literature procedures. The BP amine 7 is linked to 6 via the intermediate acid chloride using standard methods. Cleavage of the silyl protecting groups and formation of the amine stabilized borate complex with Btz are accomplished by the same dehydrative process as depicted in FIG. 3, followed by cleavage of the phosphate esters and basification by aqueous NaOH to afford the target conjugate BP-Btz2 as the mono or disodium salt.

3. Purification

Purification of BP-Btz2 is accomplished using the same procedure as described for BT-Btz1.

Test Bone-Targeted Bortezomib in Regulating Osteoblasts and Osteoclasts Vitro

The critical difference of bone-targeted-Btz (BT-Btz) from Btz (non-bone-targeted) is that in vivo BT-Btz releases Btz on bone, thereby exerting its bioactivity locally, while Btz exerts its bioactivity systemically. Prior to testing this hypothesis in vivo, in vitro cell culture is used to confirm that BP-Btz conjugates have a similar biological effect on OB and OC function as Btz when cells are cultured on plastic, but have a stronger effect when cells are cultured on bone slices. BP-Btz conjugates are examined to study whether they increase OB and inhibit OC function using various culture conditions. MPCs and OCPs derived from WT mouse bone marrow cells are treated with BP-Btz conjugates or Btz in OB differentiation and OC formation assays, respectively. OB differentiation potential (alkaline phosphatase+staining and nodule formation) is examined. OC formation and function are assessed by TRAP staining and bone resorption. The bone targeting property of BP-Btz is tested by culturing OCPs on bone slides that have been incubated with BP-Btz conjugates or Btz in bone resorption assays.

Experimental Design and Methods

Determination of the Effect of BT-Btz Conjugates on OB Differentiation and Protein Degradation In Vitro Full dose-response and time-course studies are performed in order to select BT-Btz1 and BT-Btz2 conjugates for in vivo study (see below). BM cells ($1\times10^6$/ml) from WT C57/B6 mice (Stock #000664, Jax lab) are cultured in α-MEM with 10% fetal bovine serum for 3 passages to generate BMSCs, which have previously been characterized as MPCs (Shu et al., 2013, J. Bone Miner. Res. 28:1925-1935). Cells are subjected to the following assays.

1. OB Differentiation

MPCs are cultured in the OB differentiation medium plus or minus Btz, BT-Btz1 or BT-Btz2 (0.1, 0.5, 1, 5, 10 μM) for 1 to 3 weeks. Plates are subjected for alkaline phosphatase (ALP) and alizarin red staining, and qPCR analyses. The area of ALP+ and mineralized bone nodule is assessed. The expression levels of OB marker genes (ALP, osteocalcin, Runx2) is measured.

2. Ub-Proteins

MPCs are treated with an effective dose of Btz, BT-Btz1 or BT-Btz2 for 4 or 8 hrs. Whole-cell lysate is lysed with RIPA Lysis Buffer containing a protease inhibitor cocktail. a) Western blot: Lysates (40 μg) are loaded in 10% SDS-PAGE gels and blotted with anti-ubiquitin, Runx2, or JunB antibodies to determine the expression levels of total Ub-proteins, Runx2 and JunB. b) Ub assay: Lysates (200 g) are incubated with UbiQapture matrix (Biomol) to pull down Ub-proteins and then blotted with anti-Runx2 and JunB antibodies to measure the expression levels of Ub-Runx2 and Ub-JunB, as shown in FIG. 2 and as previously described (Zhao et al., 2010, J. Bone Miner. Res. 25:1246-1256; Zhao et al., 2011, Stem Cells 29:1601-1610).

Examination of the Effect of BT-Btz Conjugates on OC Formation and Bone Resorption In Vitro Two culture conditions are used: 1) addition of BT-Btz conjugates in culture media; 2) pre-incubation of BT-Btz conjugates with bone slices.

1. BT-Btz Conjugates in Culture Media

Bone marrow cells are cultured with M-CSF for 3 days to generate OC precursors (OCPs). OCPs are cultured on plastic dishes or bone slices with M-CSF and RANKL plus or minus BT-Btz1 or BT-Btz2 (0.1, 0.5, 1, 5, 10 μM) for 5-10 days. Cells are stained for tartrate-resistant acid phosphatase (TRAP) for OC evaluation and bone slices are stained with Toludine blue for resorption pit evaluation. The same doses of Btz are included in all experiments as controls.

2. Pre-Incubation of BT-Btz Conjugates with Bone Slices

Bone slices are incubated for 12 hrs with BT-Btz1 or BT-Btz2 (0.1, 0.5, 1, 5, 10 μM). The compounds are removed and the bone slices are washed with culture medium twice. Bone marrow cells are seeded in the wells with the bone slices and cultured with M-CSF and RANKL for 10 days to generate OCs. Toluidine blue staining is performed to evaluate resorption pits. The same doses of Btz re included in all experiments as controls.

These experiments examine whether BT-Btz conjugates have 1) a similar stimulatory effect in MPC-OB differentiation and Ub-protein expression, Runx2 and JunB degradation, and a similar inhibitory effect in OC formation and bone resorption compared to Btz, and 2) a stronger inhibitory effect on OCs when they are cultured on bone slices that have been pre-incubated with BT-Btz.

Although not wishing to be bound by any particular theory, BT-Btz1 and BT-Btz2 may have similar increased ALP staining and nodule formation, and Runx2&JunB levels, or similar decreased TRAP+ OC numbers and resorption pits as Btz because in these in vitro experiments, cells are cultured in large plastic dishes and BT-Btz conjugate and Btz are directly added to culture medium.

Bone slices that have been pre-incubated with BT-Btz have an inhibitory effect on OC formation and resorption while bone slices that have been pre-incubated with Btz have no such effect. Although not wishing to be bound by any particular theory, this result suggests that the BP-Btz1 and BP-Btz2 remain attached to the bone matrix, despite washing, whereas Btz does not.

As described herein, in vitro cell cultures are used to examine the effect of bone-targeted Bortezomib in regulating osteoblasts and osteoclasts. These compounds may also be tested in vivo using the bone fracture model described above. First, it is examined whether BP-Btz conjugates increase bone fracture healing in vivo using a combination of cellular and morphologic approaches (FIGS. 1 and 2). The effect of BT-Btz conjugates and Btz (non-bone-targeted) on tibial fracture healing is examined by µCT, histology and biomechanical testing, and expression of Ub-proteins (total, Runx2 and JunB) in the fracture callus is also examined. Their systemic effects on immune cells in thymus, bone marrow and spleen are examined by FACS. Fracture healing in adult mice was selected to test the bioactivity of BT-Btz conjugates in vivo because high MMP activity and osteoclast or chondroclast-mediated cartilage and bone remodeling create a local environment that favours the release of Btz from BT-Btz conjugates. Other models of bone diseases, including osteoporosis, multiple myeloma, and fracture non-union, in young and aged mice may also be examined.

Statistical Plan and Data Analysis

All in vitro experiments are repeated at least 3 times. An unpaired t-test is used for comparisons between two groups. ANOVA followed by Bonferroni/Dunnet test is used for comparisons among more than two groups. Mean values and the standard error of the mean is calculated for each variable. A value of $p<0.05$ is designated as statistically significant.

Example 4: Protein Modification in Bone Cell Regulation

Figure 6:
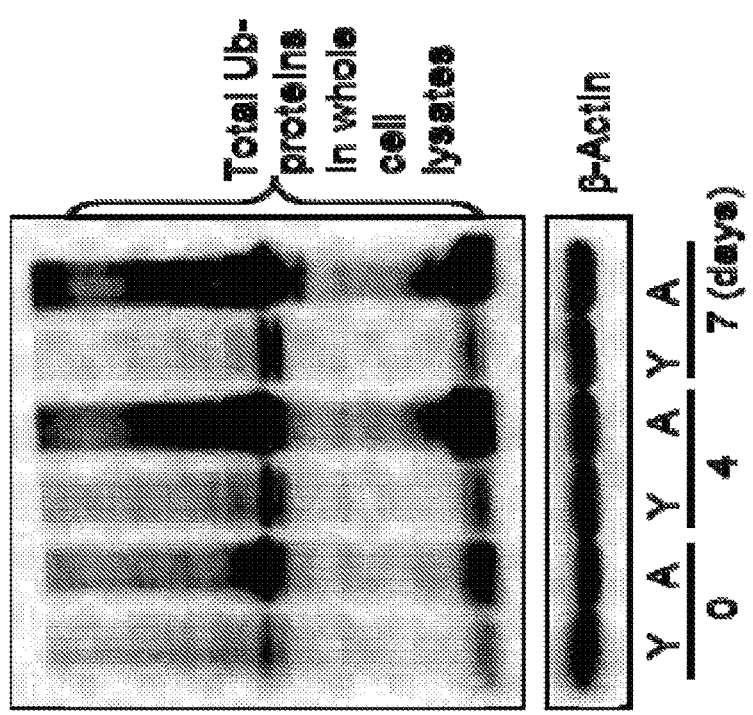
FIG. 6 is an image of an immunoblot depicting experimental data demonstrating increased Ub-proteins in fracture callus of aged mice. Y=young; A=aged mice.
Figures 7A, 7B:
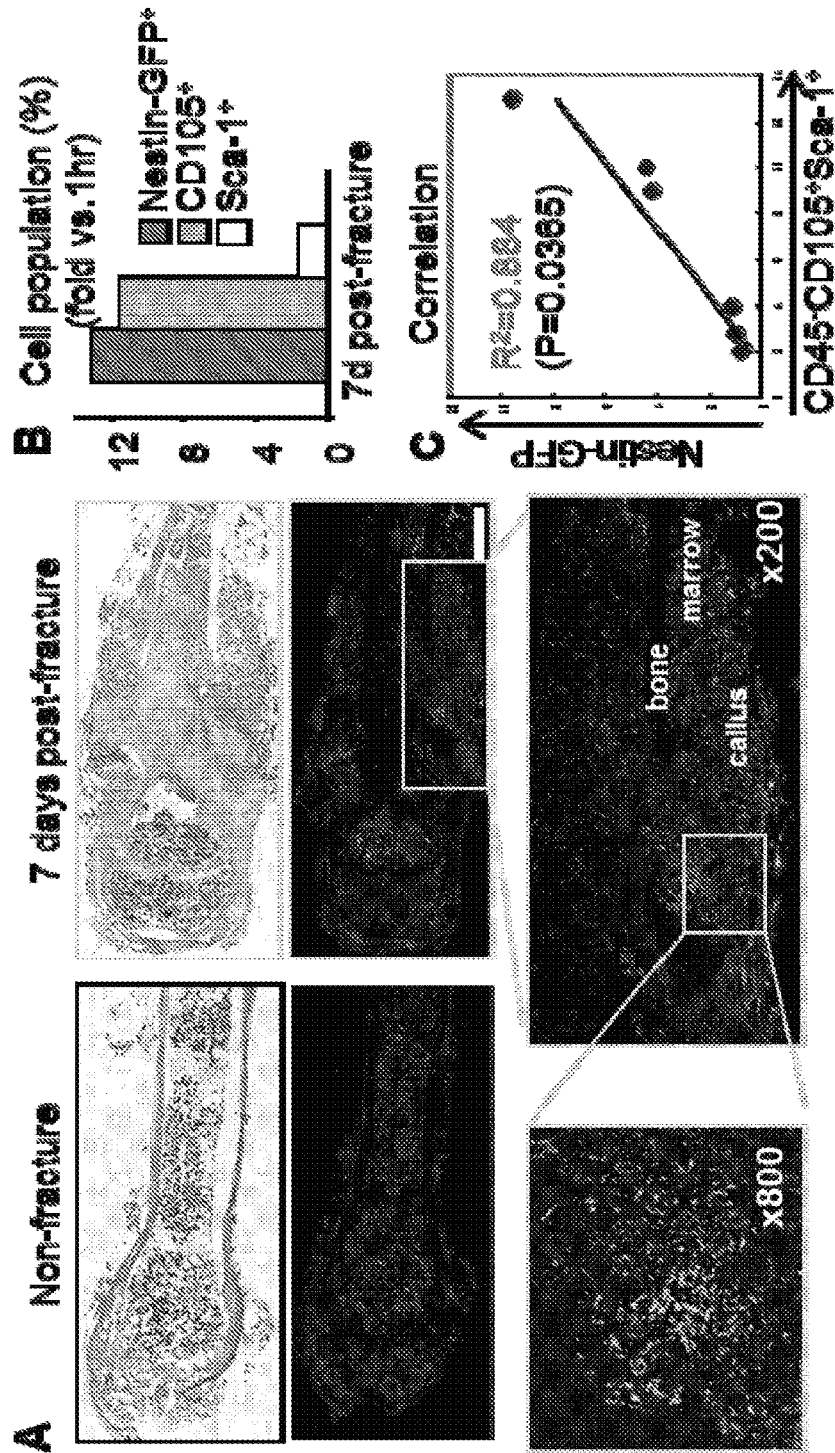
Figure 8:
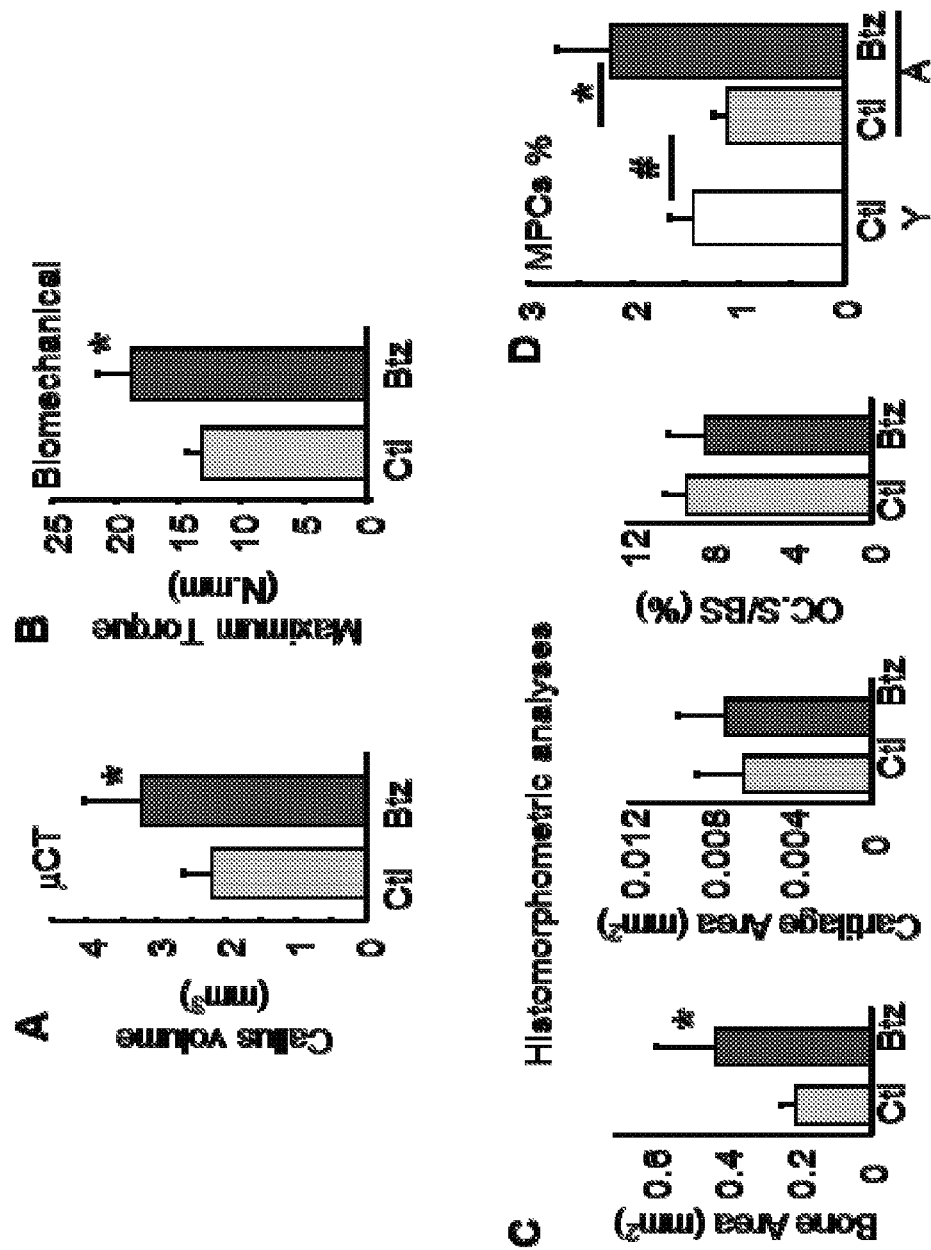
FIG. 8, comprising

It is hypothesized that the inhibition of UPS will promote fracture healing by improving MPC function in the elderly. In support of this hypothesis, higher amounts of ubiquitinated (Ub)-proteins were observed in fracture calluses from aged (20-m-old) mice than those from young (3-m-old) mice (FIG. 6). Using Nestin-GFP mice to label MPCs (Mignone et al., 2004, J. Comp. Neurol. 469:311-324; Mendez-Ferrer et al., 2010, Nature 466:829-834), markedly increased Nestin+ MPCs were observed at the early phases of fracture callus (FIG. 7). More importantly, Bortezomib (Btz), increased callus formation and bone strength in fractured aged mice, which is associated with increased MPCs (FIG. 8).

Design, Synthesis, and Testing of Bone-Targeted Bortezomib Conjugates In Vitro

Btz is linked to an inactive BP chemically, resulting in BP-Btz conjugates, and BP-Btz will bind to bone slices and inhibit OCs and increase OBs. Two types of bone-targeted BP-Btz conjugates are synthesized using two chemical synthesis approaches. Both conjugate classes bind to bone matrix and release Btz by acidic hydrolysis and/or proteases or a combination. These BP-Btz conjugates are tested to examine whether they bind to bone slices and inhibit OC function by culturing OC precursors on bone slices that have been pre-incubated with BP-Btz or Btz. Their effects on OB differentiation are also examined. Bone marrow cells from $Ub^{G76V}$-GFP mice, a reporter mouse line for monitoring UPS activation status, are used. The leading BP-Btz conjugates are selected and used for in vivo studies.

Experimental Design and Methods

Design and Synthesis of New Bone-Targeted Bortezomib Conjugates

Figure 5A:
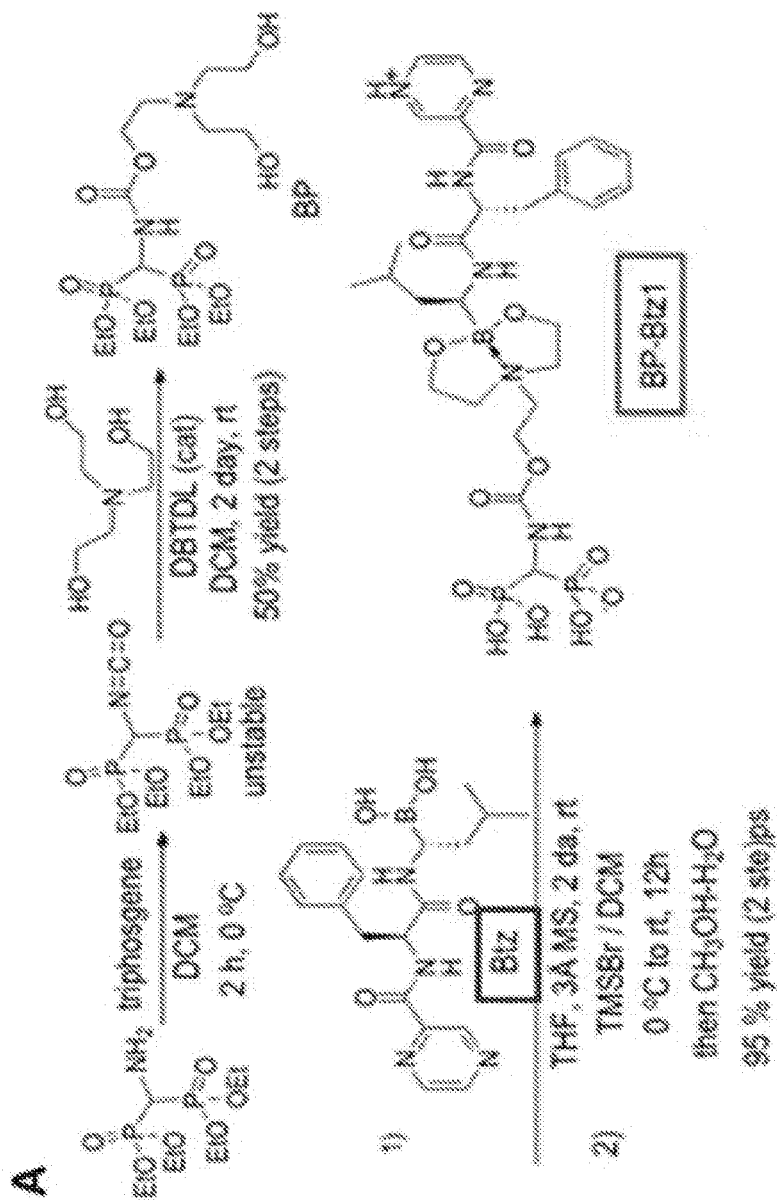
FIGS. 5A-5D, depicts experimental data demonstrating that bone-targeted Bortezimib (BP-Btz) binds to bone matrix, inhibits osteoclasts, and stimulates osteoblasts, which is associated with proteasome inhibition.
Figure 5B:
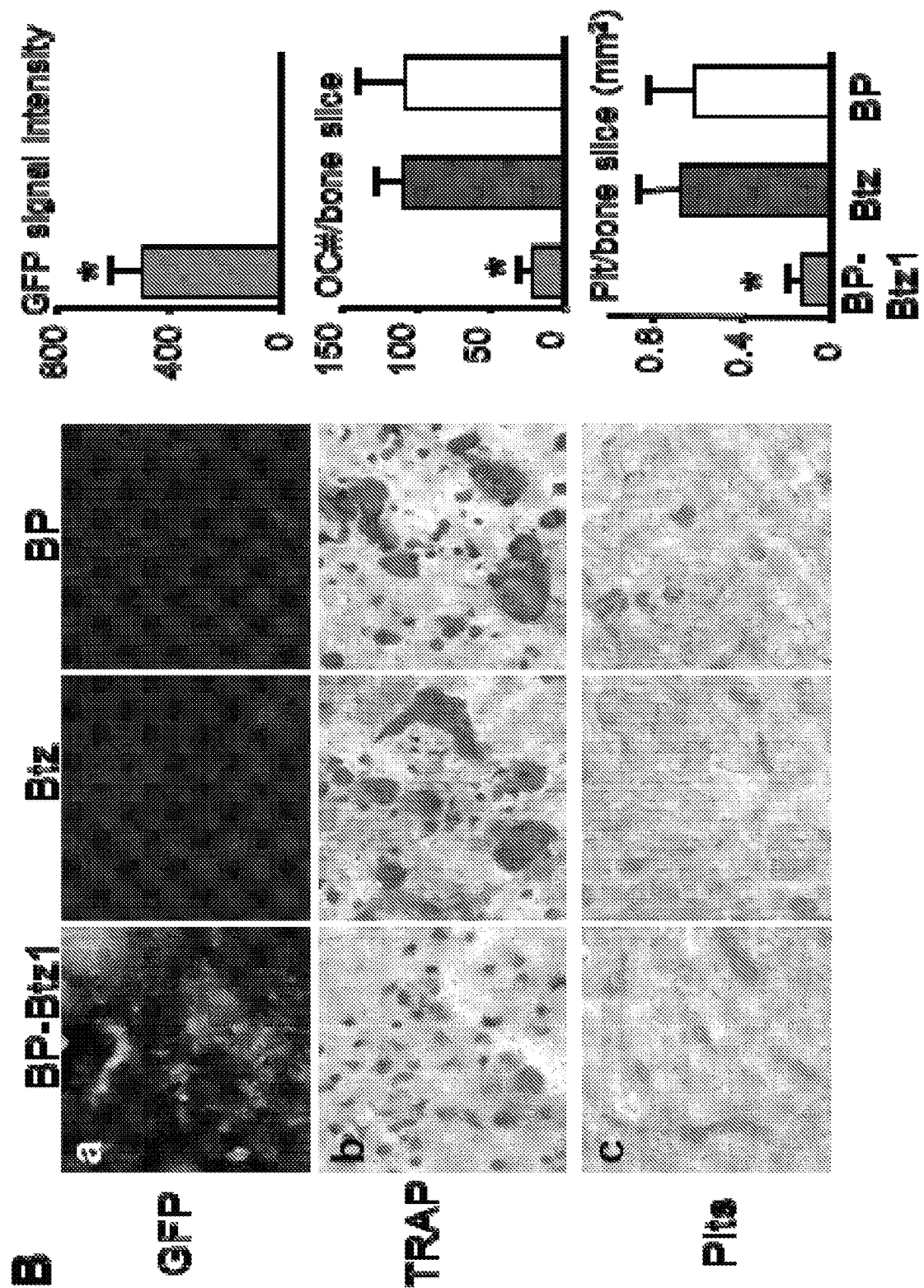
Figures 5C, 5D:
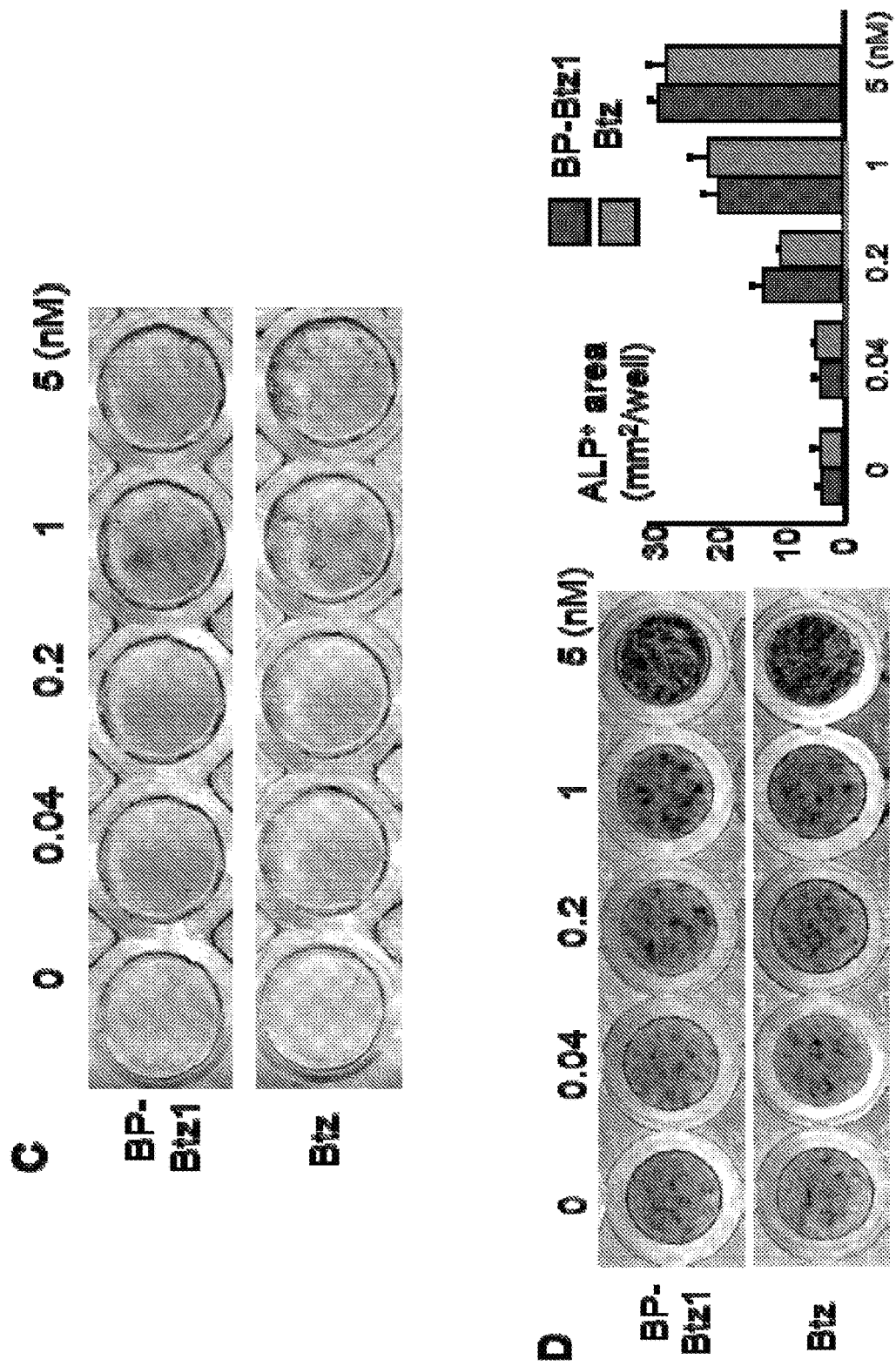
Figure 9:
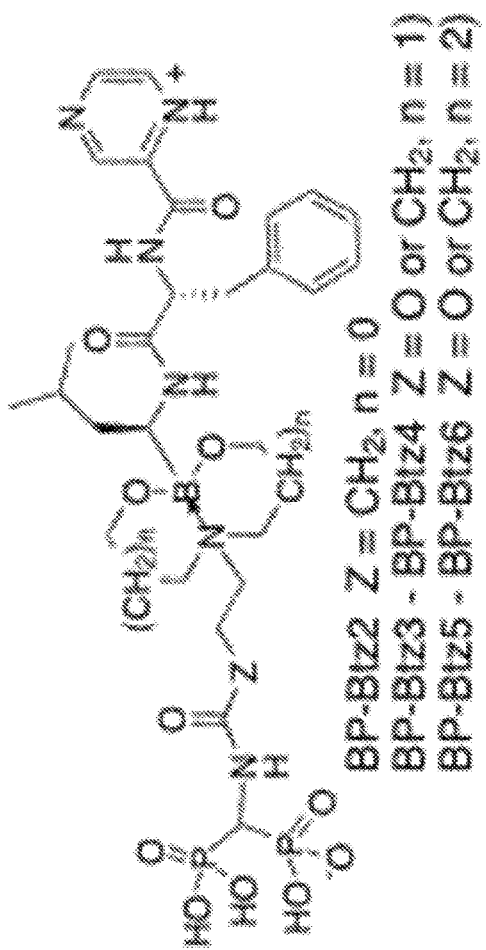
FIG. 9 depicts the structures of compounds BP-Btz2-BP-Btz6.
Figure 10:
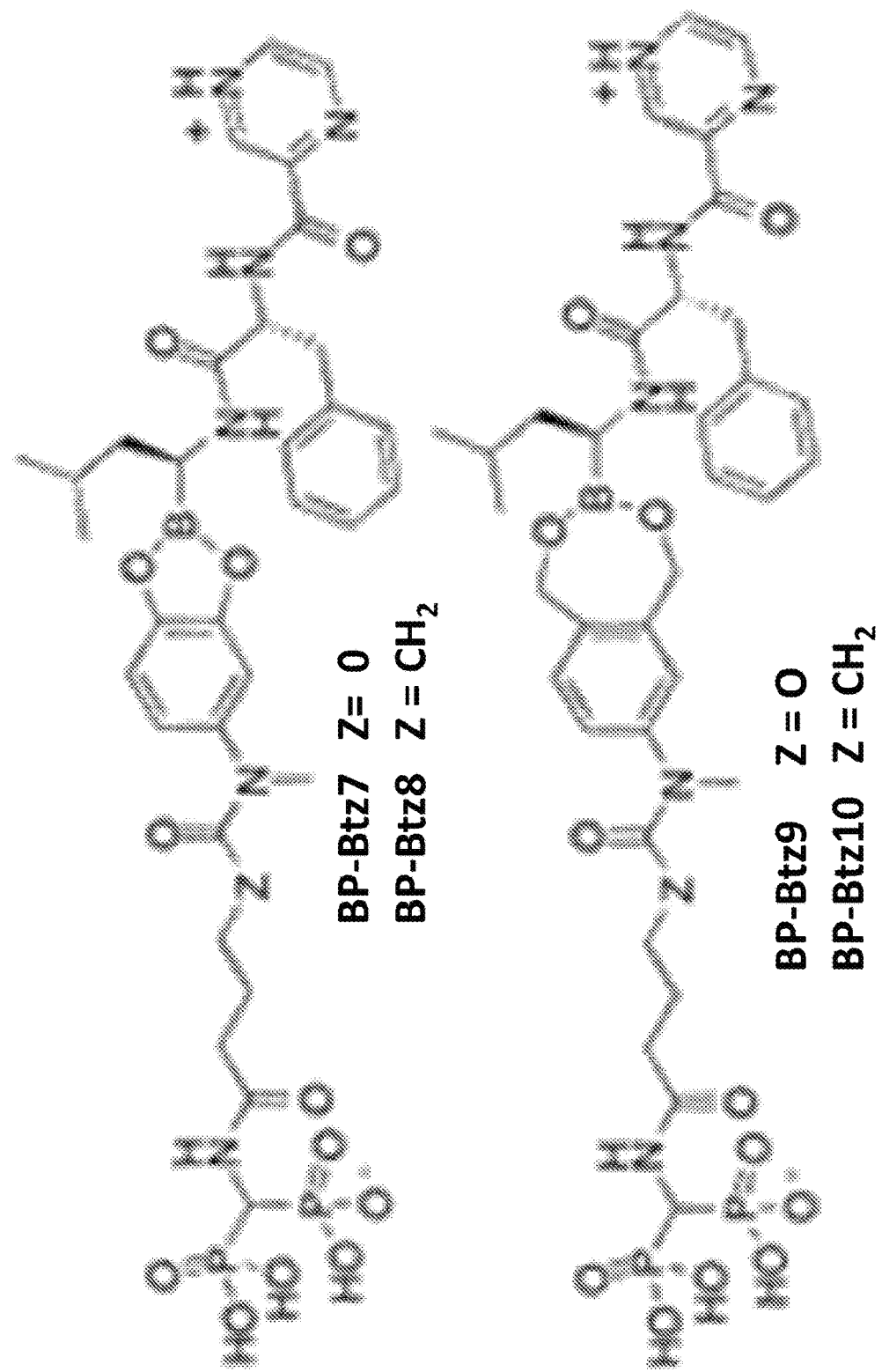
FIG. 10 depicts the structures of compounds BP-Btz7-BP-Btz10.

With an improved preparation of BP-Btz1 (FIG. 5A) and the observation of its excellent in vitro activity, sufficient quantities of BP-Btz1 are prepared to allow demonstration of in vivo activity by the existing route. The release of the Btz from the BP-Btz conjugate will be enhanced while maintaining sufficient stability of the conjugate to allow transport to bone. The BP-Btz conjugates are of two structural classes: 1) amine-stabilized boronate ester complexes BP-Btz2-BP-Btz6 (analogues of BP-Btz1; FIG. 9) and 2) non-amine-stabilized boronate esters BP-Btz7-BP-Btz10 where the linker bears carbamate or amide linkages (FIG. 10).

The linkers are of two types, enzymatically non-cleavable (amide) and enzymatically cleavable (carbamate) coupled with the amine boronate ester complexes, the latter allowing for release via multiple mechanisms (hydrolytic, or enzymatic/hydrolytic). Both however, exhibit equal lability at the boronate ester site and thus show similar efficacy overall. Compounds BP-Btz2-BP-Btz6 are linked to BP via a carbamate or amide linkage; the former are cleaved by either enzymatic reaction and/or hydrolysis in an acidic microenvironment, releasing the active drug. Btz is therefore released when BP-Btz2-BP-Btz6 are present in an environment where protease activity and/or acidity is high, such as under the OC ruffled border in bone resorption sites. The analogues bearing the amide linkage are not readily susceptible to proteases, but retain the ability to release Btz via acid catalysed hydrolysis in the acidic environment. These compounds will allow for the determination as to whether one or both of the possible release mechanisms are operating, initially in vitro, and ultimately in vivo.

Figure 11:
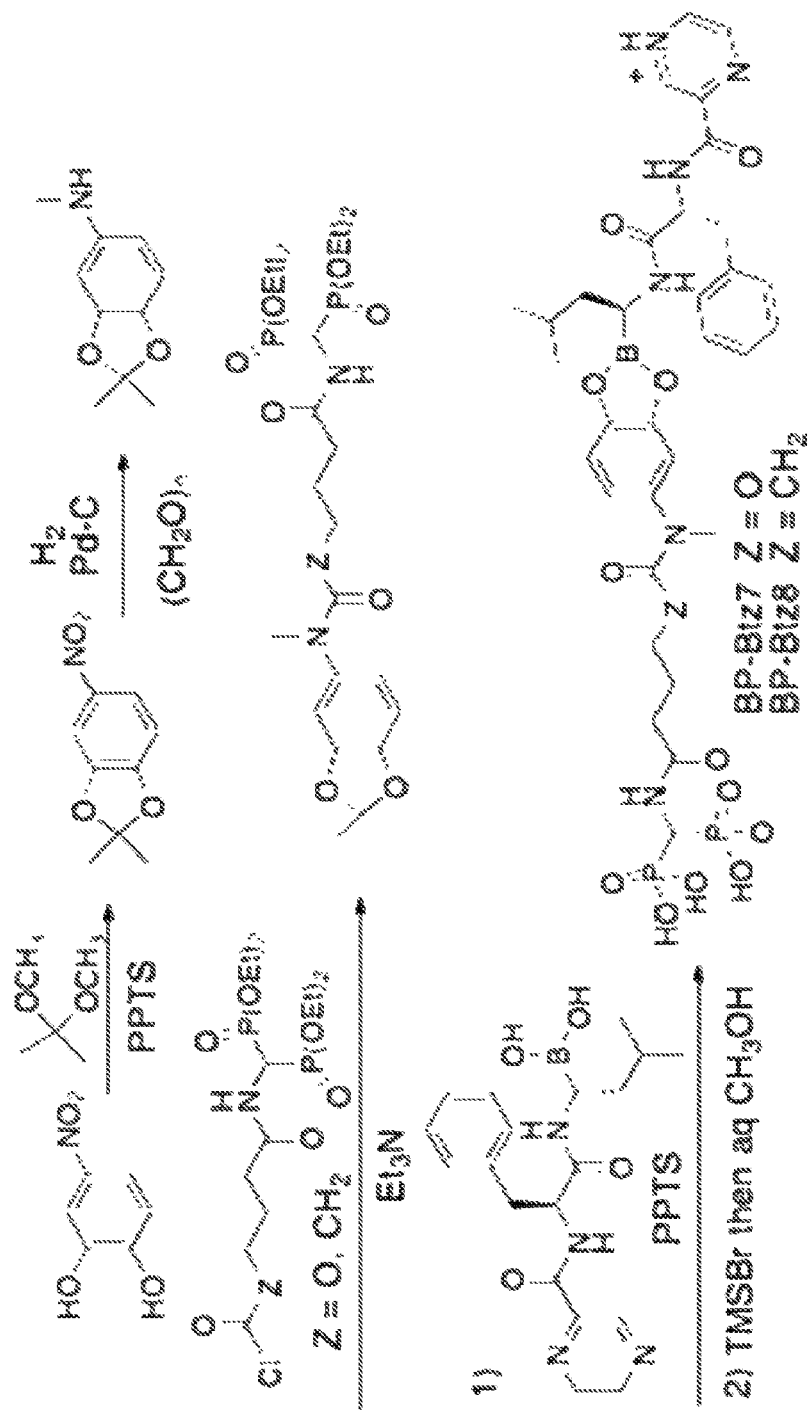
FIG. 11 is scheme of an exemplary synthesis of compounds BP-Btz7 and BP-Btz8.

The second structural class of compounds BP-Btz7-BP-Btz10, bearing either carbamate or amide linkages, provide increased reactivity of the boronate ester complex and are expected to undergo more rapid hydrolysis releasing the Btz than compounds BP-Btz2-BP-Btz6. The structure of the diol in the linker may be modified in order to further modulate the hydrolytic release of Btz. Compounds BP-Btz7-BP-Btz10 may be prepared by a synthetic route analogous to that shown for BP-Btz7 (FIG. 11)

BP-Btz3, BP-Btz 5 (a Carbamate Linkage and an Amine Stabilized Boronate Ester Complex)

1. Design

The structure of compounds BP-Btz3 and BP-Btz5 (FIG. 9) is related to the structure of BP-Btz1 in which variation in the ring size of the amine stabilized boronate ester complexes will modulate the payload (Btz) release rate.

2. Synthesis

Compounds BP-Btz3 and BP-Btz5 are prepared using a synthetic route analogous to that shown for BP-Btz1 (FIG. 5A).

3. Purification

Compounds BP-Btz3 and BP-Btz5 are purified using standard techniques such as selective precipitation before use in biological studies. The structures and purity of the conjugates re verified by standard spectroscopic and analytical techniques including $^{1}H$, $^{13}C$, and $^{31}P$ NMR, IR, Mass Spectroscopy, Combustion Elemental Analysis, and analytical TLC and HPLC.

BP-Btz2, BP-Btz4, and BP-Btz6, (Bearing a Linker Having Both Amide and Amine Stabilized Boronate Ester Moieties)

1. Design

The structures of compounds BP-Btz2, BP-Btz4, and BP-Btz6 are designed to be closely analogous to BP-Btz1, but bearing an amide and the same set of amine stabilized boronate ester moieties bearing two 2, 3, and 4 carbon alcohol side chains, respectively, in the linker. It is hypothesized that the use of amide/aminodiol linkers, such as in compounds BP-Btz2, BP-Btz4, and BP-Btz6, should permit preparation of a cleavable conjugate that will retain pharmacological activity by cleaving only at the boronate ester site.

2. Synthesis

Construction of the amide linked BP follows the general route outlined in FIG. 5A, except that an amide will replace the carbamate moiety in the linker.

3. Purification

Compounds BP-Btz2, BP-Btz4, and BP-Btz6 are purified using methods described elsewhereherein for BP-Btz1.

BP-Btz 7-BP-Btz10

Design

The structure of compounds BP-Btz 7-BP-Btz10, which are BP-Btz conjugates lacking the amine stabilizing group for the boronate ester (FIG. 10), ware designed to permit further modulation of the rate of release of Btz. It is hypothesized that the unstabilized boronate esters should release Btz even faster than other BP-Btz compounds in order to potentially increase efficacy. In one embodiment, the rate of release of Btz can be further modulated by the modification of the diol component. Both carbamate and amide linked analogues re prepared to determine whether enzymatic cleavage plays a role in the release mechanism. The pKa of the diol, its degree of substitution, and the ring size of the resulting boronaste ester are all variables which may modulate the rate of hydrolytic release of Btz.

2. Synthesis

Compounds BP-Btz 7-BP-Btz10 are prepared using a synthetic route analogous to that shown for compounds BP-Btz1-BP-Btz6 as shown in FIG. 11.

3. Purification

Compounds BP-Btz 7-BP-Btz10 are purified using methods described elsewhere herein for BP-Btz1.

Examine the Bioactivity of BP-Btz Conjugates on OB Differentiation and OC Formation In Vitro BM cells from $Ub^{G76V}$-GFP mice, a reporter mouse line for UPS activation, are used. Three set of assays are used: 1) OC and OB assays to examine the effect of BP-Btz on OC and OB function; 2) Western blot/Ub assays to determine the role of BP-Btz in the Ub and degradation of target proteins; 3) $GFP^{+}$ cells to minor the effect on BP-Btz on UPS activation status.

1. $Ub^{G76V}$-GFP mice in B6 background (Stock #008111, Jax lab) are generated using previously described methods (Lindsten et al., 2003, Nat. Biotech. 21:897-902). The $Ub^{G76V}$-GFP transgene was designed with a chicken beta-actin promoter and CMV immediate early enhancer upstream of a GFP fused to a mutant ubiquitin moiety ($Ub^{G76V}$), a constitutively active proteasome degradation signal. Following proteasome inhibitor administration, $Ub^{G76V}$ accumulates and GFP fluorescence is readily apparent. $GFP^{+}$ OCs were detected at 4 and 8 hrs after adding Btz to OC cultures, which disappeared at 24 hrs. More importantly, it was demonstrated that $GFP^{+}$ cells were present on bone slices that have been pre-incubated with BP-Btz1, but not Btz or BP (FIG. 5B), indicating the bioactivity of Btz within BP-Btz1.

2. OC formation and resorption assays and data analyses are performed as described herein (FIG. 4) and using previously described methods (Zhang et al., 2014, J. Clin. Invest. 124:3200-3214; Xiu et al., 2014, J. Clin. Invest. 124:297-310). BM cells are cultured with M-CSF to generate OC precursors (OCPs) that are cultured under 3 conditions±BP-Btz conjugates, Btz or BP (0.1-100 nM): i) on plastic plates to test if BP-Btz conjugation alters its bioactivity; ii) on bone slices to test if the effect of BP-Btz needs Btz release by activated OCs; and iii) on pre-incubated bone slides to test if BP-Btz binds to bone matrix. The number and area of OCs and resorption pits are assessed. The appearance, intensity and distribution of $GFP^{+}$ cells on bone slices and plastic surrounding bone slices during OC formation is observed and recorded.

3. OB differentiation. Third passages of BM stromal cells are used as MPCs, as previously described (Shu et al., 2013, J. Bone Min. Res. 28:1925-1935; Zhang et al., 2014, J. Clin. Invest. 124:3200-3214). MPCs are cultured on plastic plates in OB-inducing medium±BP-Btz conjugates, Btz or BP (0.1-100 nM) for 1-3 wks. Plates are subjected to alkaline phosphatase (ALP) and alizarin red staining, and qPCR analyses. Area of $ALP^{+}$ and mineralized bone nodule, and the expression levels of OB marker genes (ALP, osteocalcin, Runx2) are measured. $GFP^{+}$ cells during OB differentiation are observed as in OCs. In a parallel experiment, human MSCs (from Lonza) are treated with BP-Btz, Btz, or BP in OB-inducing medium and their effects examined on OB differentiation as show in FIGS. 5C and 5D.

4. Western blot/Ub assays. OCPs or MPCs are treated with a preferred dose of leading BP-Btz, Btz and BP. OCP lysates are subjected to Western blot using α-NF-κB members and TRAF6 Abs. OB lysates are subjected to Western blot with α-ubiquitin, Runx2, or JunB Abs, and Ub assays using UbiQapture matrix (Biomol) to pull down Ub-proteins followed by α-Runx2 and JunB Abs using previously described methods (Zhao et al., 2010, J. Bone Min. Res. 25:1246-1256; Zhao et al., 2011, Stem cells 29:1601-1610).

Although not wishing to be bound by any particular theory, preliminary data suggest that BP-Btz1 binds to bone and maintains its bioactivity on inhibition of OCs and proteasome function (FIG. 5). The purpose of OB assays is to determine if BP-Btz conjugates are still bioactive, rather than to test the difference between bone-targeting vs non bone-targeting Btz. It is hypothesized that BP-Btz conjugates may have a similar increased ALP staining and nodule formation, and Runx2&JunB levels similar to those of Btz because MPCs are cultured in large plastic dishes and BP-Btz and Btz will be directly added to culture medium.

Examine Bone-Targeted Bortezomib Conjugates on Bone Volume and Regeneration In Vivo BP-Btz is expected to have a higher efficacy on 1) reducing OVX-induced bone loss and 2) promoting fracture healing in aged mice with lesser adverse systemic effects than those of Btz. A critical difference between BP-Btz and Btz is that in vivo BP-Btz brings Btz to bone, thereby exerting its bioactivity locally, while Btz can exert its bioactivity systemically. It is hypothesized that BP-Btz conjugates should have similar or better positive bioactivities than Btz on bone volume, but with a significant reduction in side effects. In humans, the toxicities of Btz include peripheral neuropathy and thrombocytopenis (Weathington and Mallampalli, 2014, J. Clin. Invest. 124:6-12). Little is known the toxicity of Btz in mice. A mouse study reported that Btz injection markedly decreases total and $CD4^+$ and $CD8^+$ thymocyte, but not splenocytes numbers (Maseda et al., 2008, Cell Death Differ. 15:600-612). Low survival rate was observed in aged mice treated with Btz (53% vs. 91% in vehicle), while Btz was not found to influence survival in young mice (94% vs. 100% in vehicle). Although not wishing to be bound by any particular theory, these adverse effects are thought to be due to the systemic distribution of the drug. Thus, the generation of bone-targeted Btz could meet a critical clinical need, by and increasing the local drug concentration to capitalize on the efficacy of BTz while reducing systemic side effects. Because proteasome inhibitors could increase bone volume in normal and OVX mice, and promote fracture healing in adult mice (Khedgikar et al., 2013, Cell Death Dis. 4:e778; Maseda et al., 2008, Cell Death Differ. 15:600-612), OVX and fracture models are used to examine the efficacy of the leading BP-Btz conjugates on bone. Aged mice are used in fracture experiments because they often show delayed or fracture nonunion (Naik et al., 2008, J. Bone Min. Res.). Thymocyte number and death are used as outcome measures for systemic adverse effects of Btz. The effect of BP-Btz conjugates and Btz is examined on bone volume, bone formation/resorption markers, OCs and OBs in 3-m-old WT C57/B6 female mice received OVX by μCT, histology and ELISA assays. The effect of the BP-Btz conjugates on tibial fracture healing of 20-m-old (aged) mice by μCT, histology, and biomechanical testing is examined. The systemic effects of the compounds on mouse survival is examined by a survival curve and on immune cells in thymus, while bone marrow and spleen will be examined by flow cytometry.

Experimental Design and Methods

Examination of the Efficacy of BP-Btz for the Prevention of OVX-Induced Bone Loss 1. Animals and groups: 3-m-old female WT C57/B6 mice receive OVX or sham surgery. Mice are treated with Saline as Vel, two BP-Btz conjugates at 0.2 & 0.6 mg/kg, or Btz via i.p. injection, 2/w×4 wks. It has been observed that 3-m-old mice received Btz (0.6 mg/kg/i.p.) at day 1, 3, 5 have increased bone volume at day 10. N=10 mice/group×7×2=140 mice.

2. Outcome measures: μCT and biomechanical testing is carried out at the Biomechanics and Multimodal Tissue Imaging Core in the Center for Musculoskeletal Research.

a) Body weight is measured weekly. Serum is collected at-baseline and before killing. Mice are double injected with calcein before killing to evaluate bone formation rates (BFRs) and mineral appositional rates (MARs).

b) Biomechanical testing is performed on left femora and L5 vertebrae. Maximum compressive load at failure, maximum deformation at maximum force, stiffness, and energy to failure is measured.

c) μ-CT and BFRs are examined using left tibiae and T12 to L1 vertebrae. Bone mineral density, bone volume fraction, bone surface, trabecular number, separation, and thickness, connectivity density, structural model index, degree of anisotropy, porosity and cortical parameters re-examined (Zhang and Xing, 2013, Stem Cells 31:1574-1583; Zhang et al., 2014, J. Clin. Invest. 124:3200-3214; Xiu et al., 2014, J. Clin. Invest. 124:297-310). These bones are then plastic-embedded and BFRs are evaluated using OsteoMeasure software.

d) Histomorphometry in paraffin sections of right tibiae and LV2 to LV4 to evaluate bone parameters (BV/TV, Tb.Th, Tb.N and Tb.Sp, OC numbers and surface as well as OB surfaces) using OsteoMeasure image analysis software using previously reported methods Zhang and Xing, 2013, Stem Cells 31:1574-1583; Zhang et al., 2014, J. Clin. Invest. 124:3200-3214; Xiu et al., 2014, J. Clin. Invest. 124:297-310).

e) Cortical bone is used to test Ub-protein by Western blot as depicted in FIG. 6.

f) Systemic markers of bone resorption and formation, osteocalcin and TRAP5b, are measured in serum by ELISA using previously reported methods (Xiu et al., 2014, J. Clin. Invest. 124:297-310; Yao et al., 2009, J. Clin. Invest. 119:3024-3034).

g) Thymus, spleen and right femora are harvested and single cell suspensions are stained with fluorescein-labeled α-CD4 and CD8 (T cells), and B220 (B cells) Abs for flow cytometry. The total number of thymus, spleen and femoral BM, and the total number and percent of T cells or B cells is determined. Samples of brain, heart, lung, liver, and kidney are examined histologically for any side effects.

Examination of the Efficacy of BP-Btz Conjugates on Bone Fracture Repair in Aged Mice 1. Animals and groups: 20-m-old WT C57/B6 male mice (purchase from NIA) receive open tibial fracture surgery on the left leg (FIGS. 7-9). Mice are randomly divided into 2 sets. A preferred dose of BP-Btz is given by i.p. at 1, 3, 5, 7 days post-fracture as in FIG. 8.

2. Outcome measures: Survival of mice is then recorded.

a) μCT and Histology: Mice in set 1 are randomly divided into 4 groups: 1) Saline; 2&3) 2 leading BP-Btz conjugates; 4) Btz, and sacrificed at 28, and 35 days post-fracture. Left tibiae (fractured) are subjected to μCT and then to paraffin embedding for histology. The volume of callus and mineralized tissue is quantified as shown in FIG. 8. Histomorphometric analysis is performed using paraffin sections. Sections are stained with Alcian blue/orange G and for TRAP activity. Individual tissue areas within the fracture callus: new formed woven bone, total cartilage and fibrous tissue, and OC parameters are measured using WSI and Visiopharm software using previously described methods (Shi et al., 2013, Biotech. Histochem. 88:3024-3034) and in FIG. 8. N=10 mice/group×4×2=80 total mice b) Flow cytometry: Thymus, spleen and femora BM from the mice in set 1 are subjected to flow cytometry for measuring CD4 and CD8 (T cells), and B220 (B cells) as described above.

c) Biomechanical testing: Mice in set 2 are treated with the optimal dose of BP-Btz, Btz or saline and sacrificed at 28 post-fracture for biomechanical testing as in FIG. 8. N=10 mice/group×4=40 mice These experiments examine whether in comparison to Btz, if BP-Btz conjugates are 1) better at preventing bone loss and promoting fracture healing; and 2) have less or no systemic side effects.

It is hypothesized that BP-Btz conjugates bind the calcified surfaces of bone and act locally. Thus, it is hypothesized that they have higher efficacy to prevent OVX-mediated bone loss and promote fracture healing, either faster or at a lower dose, in comparison to Btz. Although not wishing to be bound by any particular theory, this may be due to a higher local concentration in bone than Btz.

It is hypothesized that Btz will decrease $CD4^+$ and $CD8^+$ thymocytes, while BP-Btz conjugates will have no such effect. Although not wishing to be bound by any particular theory, this suggests that unlike Btz, bone targeting strategy may indeed prevent systemic effects. Common side-effects of Btz in the clinic include peripheral neuropathy and thrombocytopenia, which is due to the drug's systemic distribution. It can be difficult to examine these side-effects in mice. Therefore, reduction of thymocytes and survival are good outcome measures to test potential systemic effect of Btz in mice. Histologic assessment of sections of thymus and other internal organs may also be examined for side-effects.

Statistical Plan and Data Analysis

The sample size of in vivo experiments is based on the unpaired t-test power analysis results carried out using SigmaStat Statistical Software and previously described methods (Brown et al., 2014, PLoS One 9:e99656). Ten mice are needed in each group where callus volume in fracture mice is assessed to detect significant differences from un-fractured controls with an alpha error of 5%. The power is 0.98, i.e. there is 98% chance of detecting a specific effect with a 95% confidence when alpha=0.05. An unpaired t-test is used for comparisons between 2 groups. ANOVA followed by Bonferroni/Dunnet test is used for comparisons among more than 2 groups. Mean values and the standard error of the mean is calculated for each variable. A value of $p<0.05$ is designated as statistically significant.

Example 5: Bone-Targeted Bortezomib Prevents OVX- and Myeloma-Induced Bone Loss with Less Systemic Adverse Effects More Effectively than Bortezomib The results described herein demonstrate that BP-Btz1 should deliver Btz to bone locally at higher concentrations than Btz alone to prevent OVX- and MM-associated bone loss with fewer systemic adverse effects. The effects of Btz linked to a bisphosphonate (BP) moiety lacking anti-resorptive activity to generate bone-targeted Btz (BP-Btz1) were examined in OVX- and MM-induced bone loss and tumor burden in mice. It was hypothesized that BP-Btz1 will more effectively prevent OVX- and MM-induced bone loss with less systemic adverse effects than Btz.

Materials and Methods:

Ovariectomy was carried out in 10-week-old female C57/B6 mice.

A MM model was generated using tail vein injection of 5TGM1-GFP myeloma cells into 6-week-old female NIH-III nude mice. Tumor burden and bone volume were examined.

Figure 15:
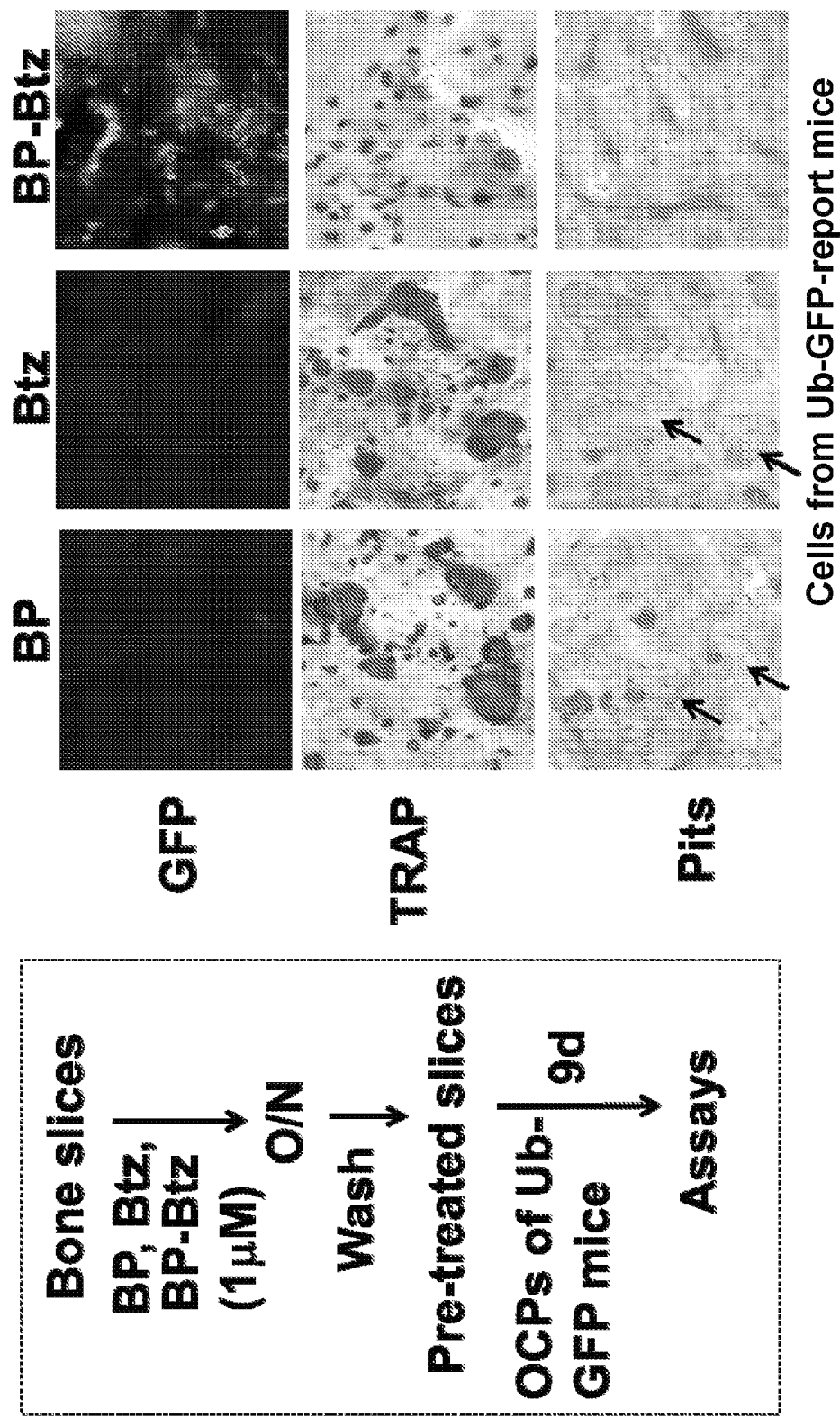
FIG. 15 is a series of images of experimental data demonstrating that BP-Btz1 binds to bone matrix, even after the surfaces is washed to displace any unbound drug, and inhibits osteoclast function and osteoblast differentiation.

BP-Btz1 Binds to Bone Matrix, Inhibits Osteoclast Function, and Osteoblast Differentiation The experiments presented herein demonstrate that BP-Btz1 binds to bone matrix, and inhibits osteoclast function and osteoblast differentiation (FIG. 15).

BP-Btz Stimulates Osteoblast Differentiation

Figure 16:
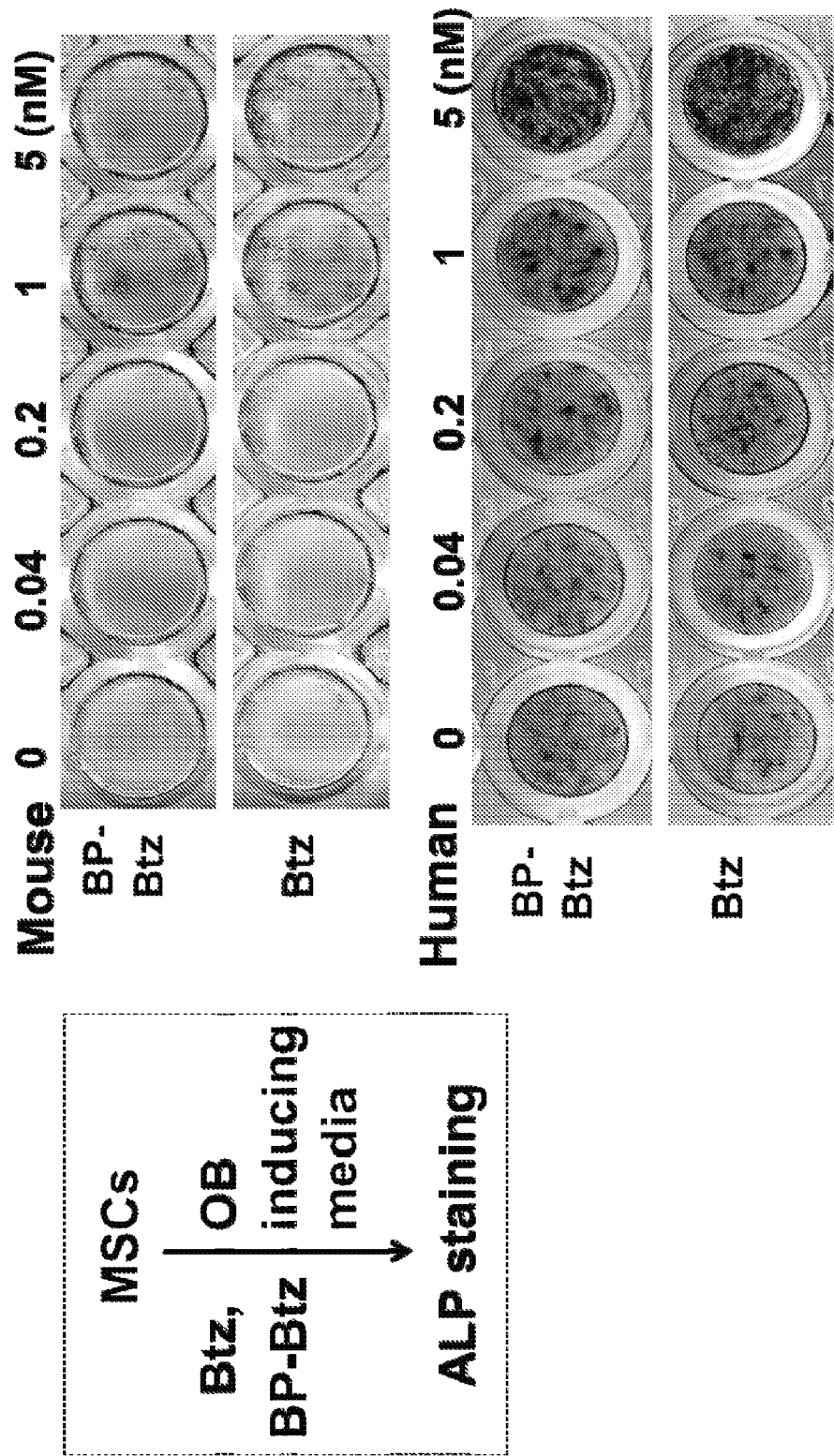
FIG. 16 is a series of images of experimental data demonstrating that that BP-Btz1 stimulates osteoblast differentiation.

The experiments presented herein demonstrate that BP-Btz1 stimulates osteoblast differentiation (FIG. 16).

BP-Btz1 Increases Bone Volume and Osteoblast Differentiation in WT Mice

Figure 17:
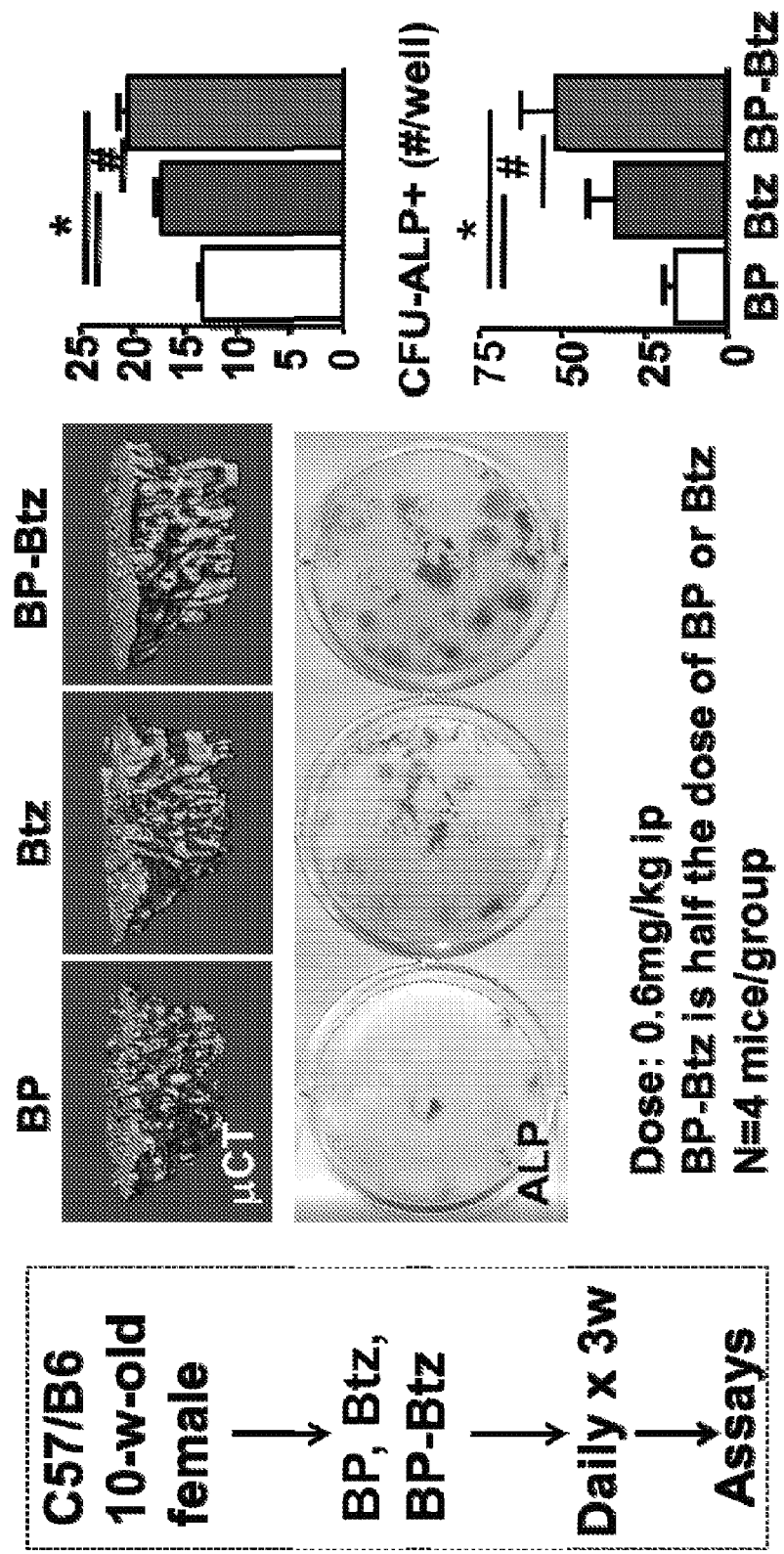
FIG. 17 is an image of experimental data demonstrating that BP-Btz1 increases bone volume and osteoblast differentiation in WT mice.

The experiments presented herein demonstrate that BP-Btz1 increases bone volume and osteoblast differentiation in WT mice (FIG. 17).

BP-Btz1 has a More Sustained Ubiquitinization Effect than Btz

Figure 18:
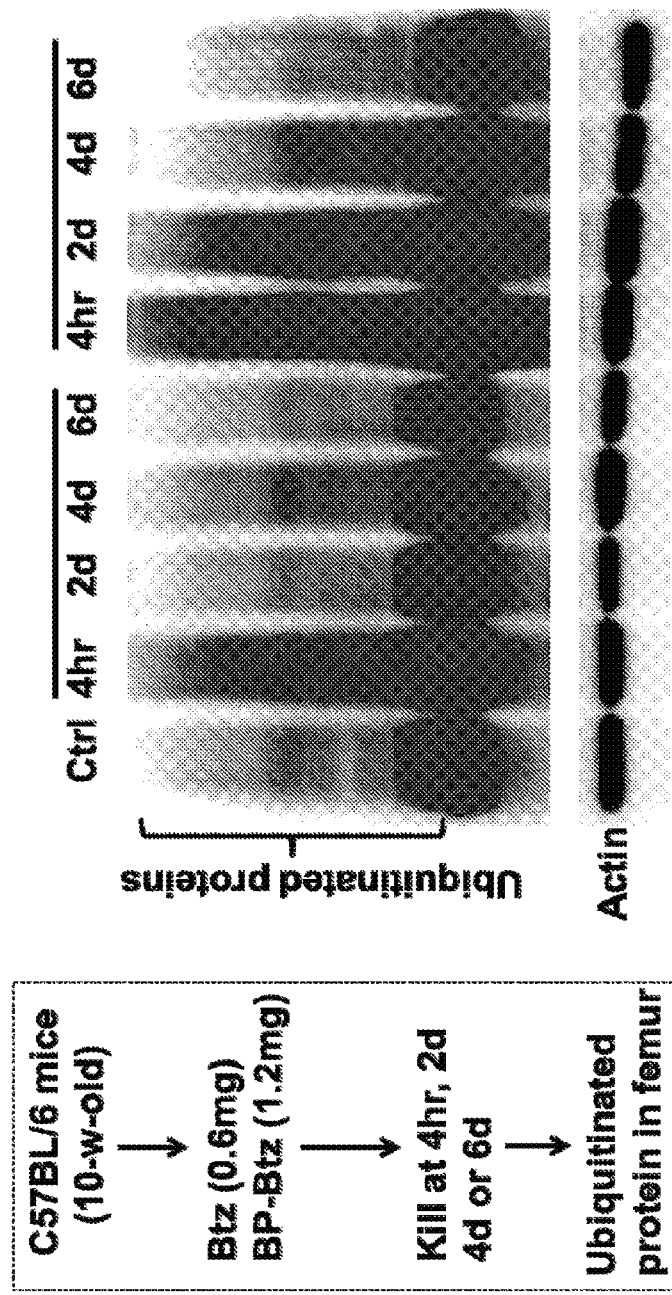
FIG. 18 is an image of experimental data demonstrating that BP-Btz1 has a more sustained ubiquitinization effect than Btz.

The experiments presented herein demonstrate that BP-Btz1 has more sustained ubiquitinization effect than Btz (FIG. 18).

BP-Btz1 Increases Bone Mass and Strength in OVX Mice as Effectively as Btz

Figure 19:
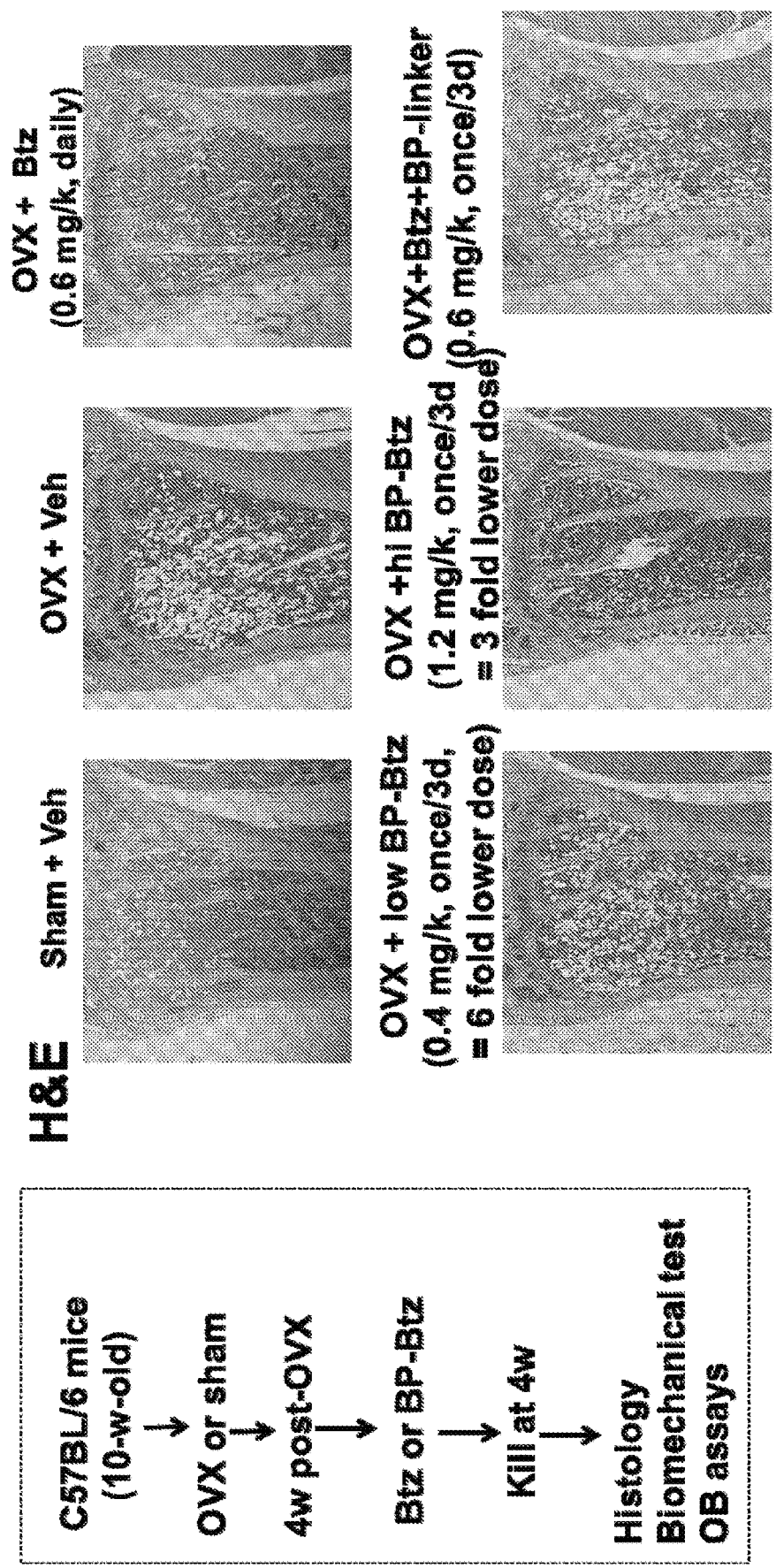
FIG. 19 is a series of images of experimental data demonstrating that BP-Btz1 reduces OVX-induced bone loss, and increases bone mass and strength in OVX mice as effectively as Btz.
Figures 20A, 20B:
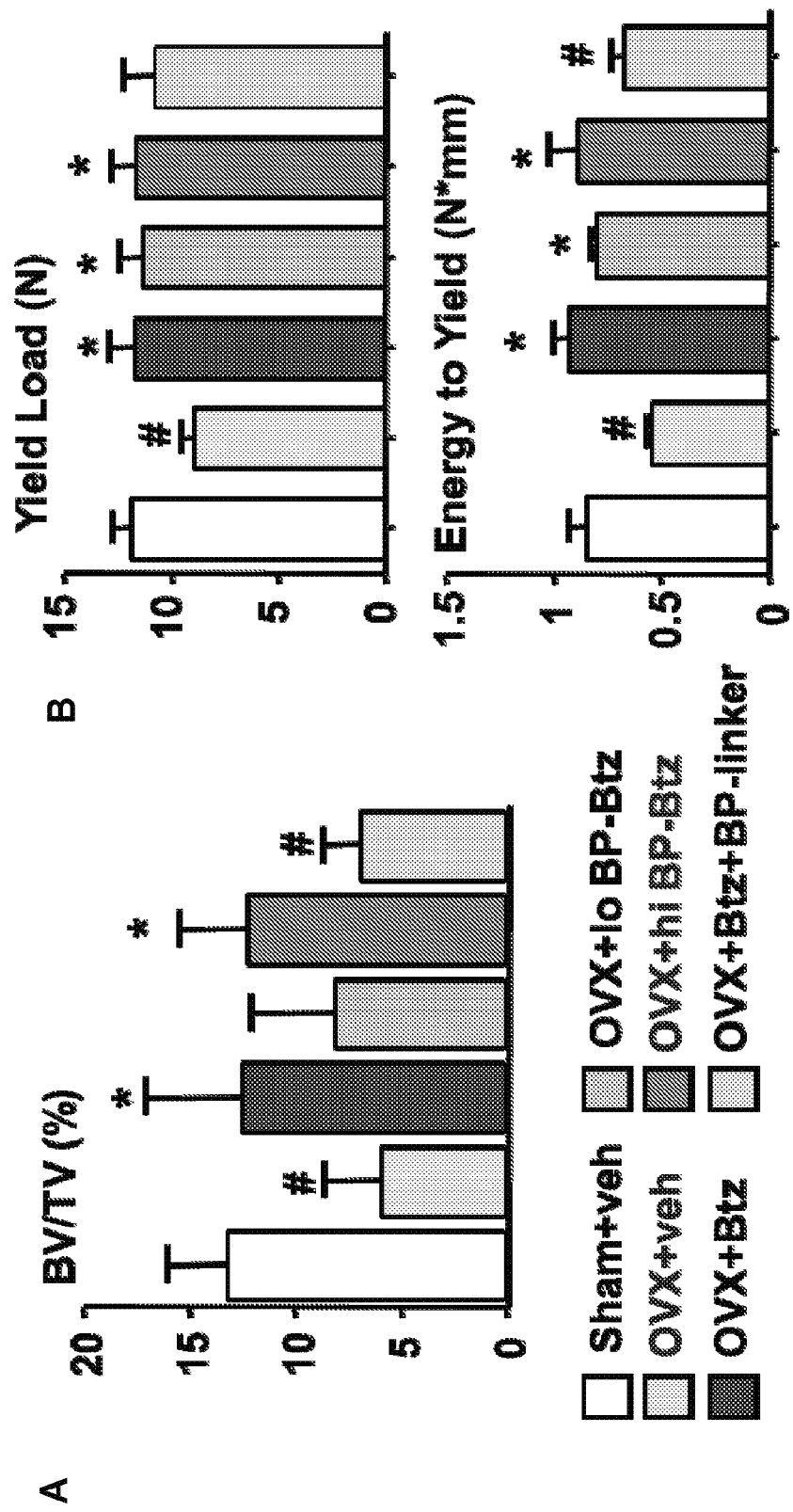
FIGS. 20A-20B, are a series of tables of experimental data demonstrating that BP-Btz1 increases bone mass and strength in OVX mice.

The experiments presented herein demonstrate that BP-Btz1 increases bone mass and strength in OVX mice as effectively as Btz (FIG. 19). Histomorphometry (FIG. 20A) and biomechanical testing (FIG. 20B) were also done. These experiments were done using C57/B6 mice, 10 w, treatment at 4 w post-OVX for 4 w.

BP-Btz1 More Potently Promotes Osteoblast Differentiation in OVX Mice

Figure 21:
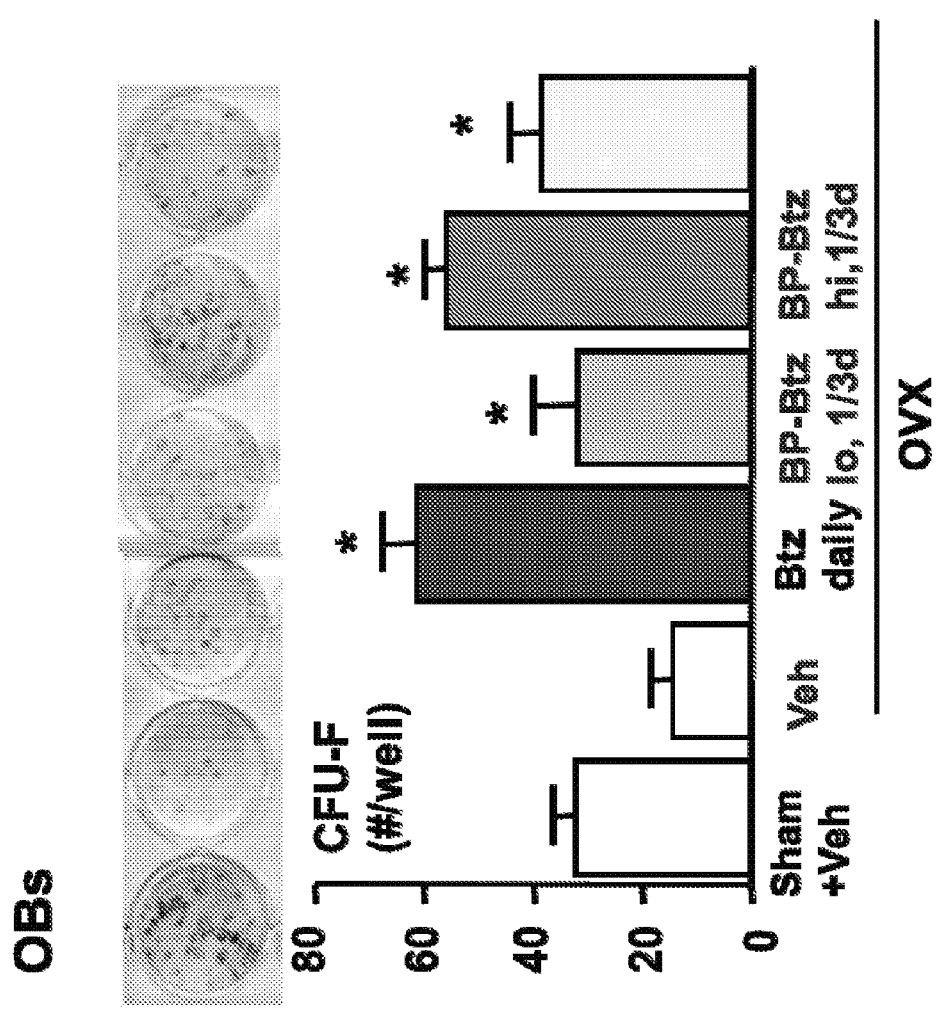
FIG. 21 depicts experimental data demonstrating that BP-Btz1 increases CFU-F colony formation from cells from OVX mice.
Figure 22:
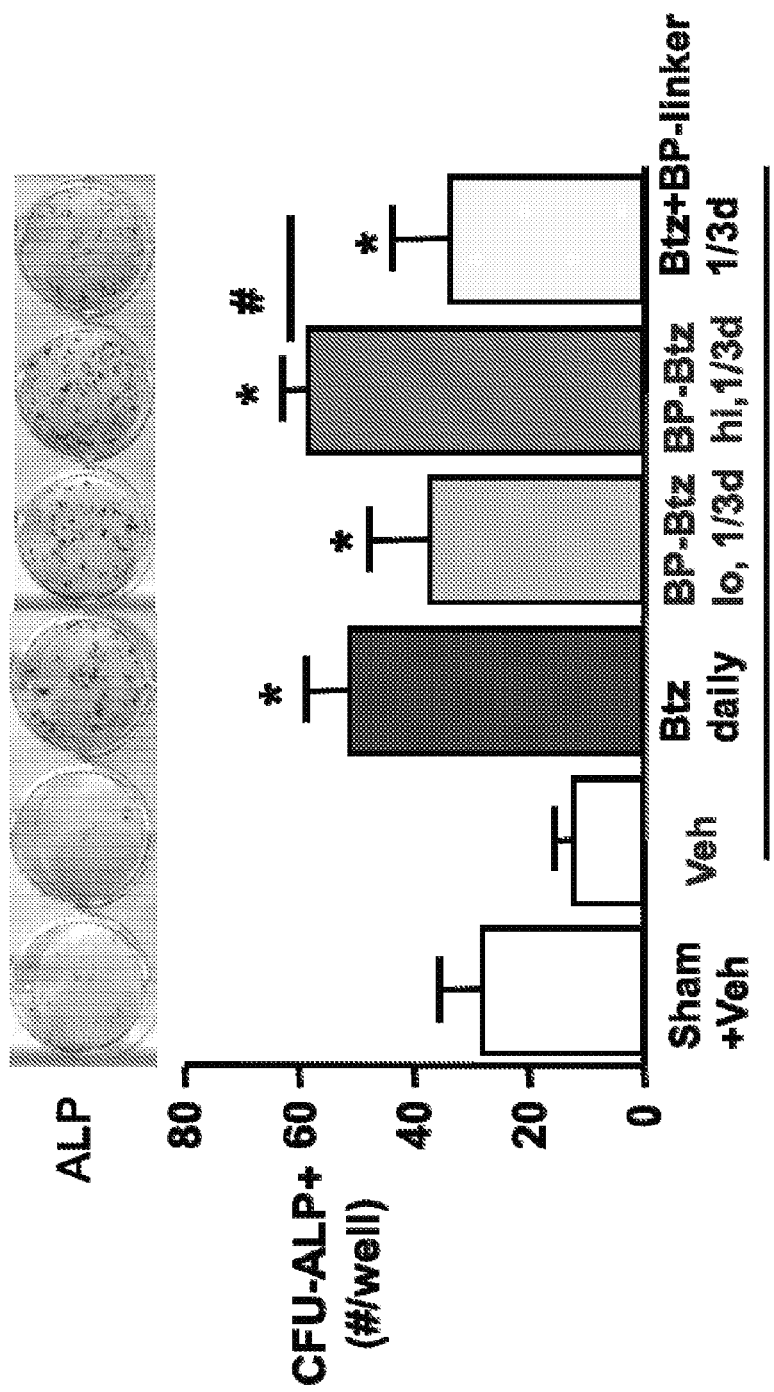
FIG. 22 depicts experimental data demonstrating that BP-Btz1 increases CFU-ALP colony formation from cells from OVX mice.

The experiments presented herein demonstrate that BP-Btz1 more potently promotes osteoblast differentiation in OVX mice. CFU-F (FIG. 21) and CFU-ALP (FIG. 22) colony formation were examined.

BP-Btz1 Inhibits Myeloma Cell Growth In Vitro

Figure 23:
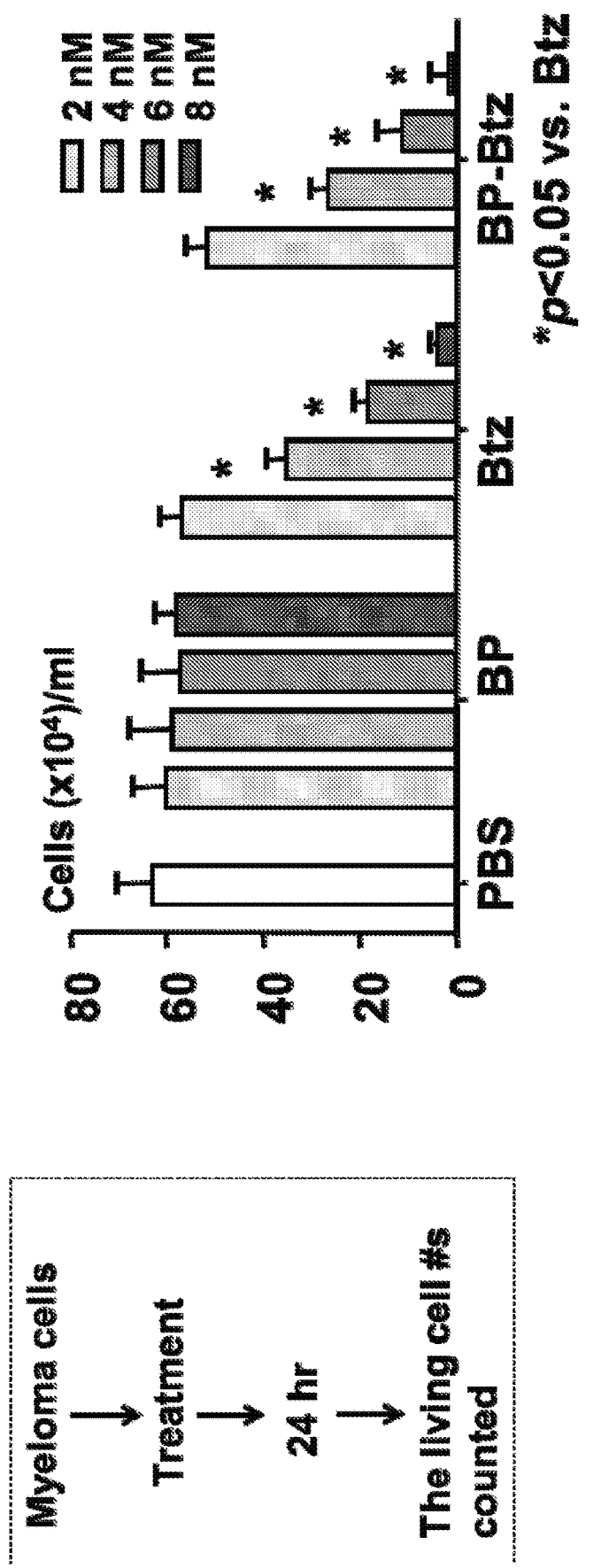
FIG. 23 depicts a table of experimental data demonstrating that BP-Btz1 inhibits myeloma cell growth in vitro
Figure 24:
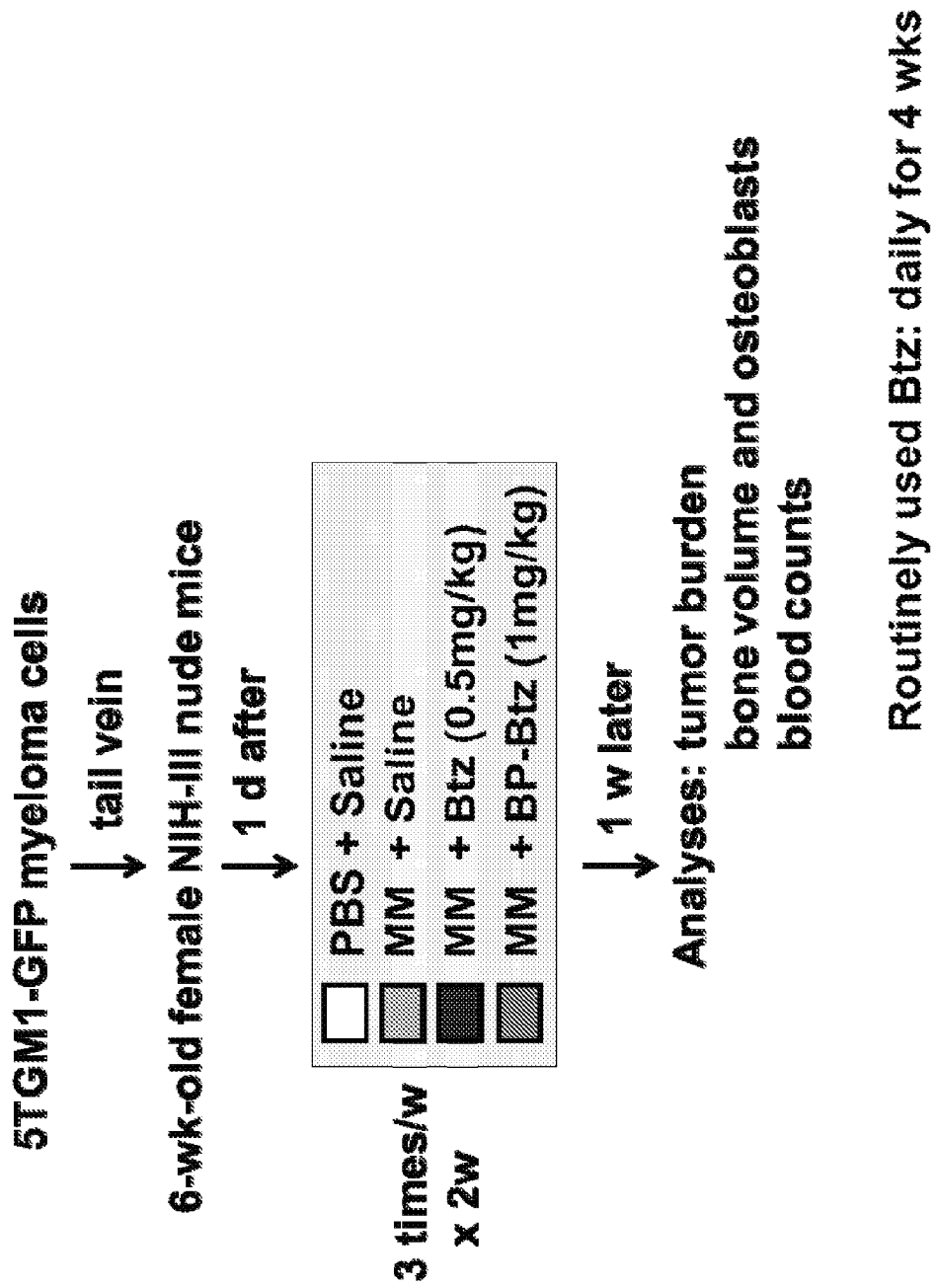
FIG. 24 is an exemplary schematic of a mouse model of multiple myeloma to test BP-Btz1.

The experiments presented herein demonstrate that BP-Btz1 inhibits myeloma cell growth in vitro (FIG. 23). Myeloma cells were treated with different concentrations of testing compounds for 24 hrs. The living cell numbers were counted. *$p<0.05$ vs. Btz. FIG. 24 shows an exemplary mouse model of multiple myeloma that can be used to test BP-Btz1.

Figure 25C:
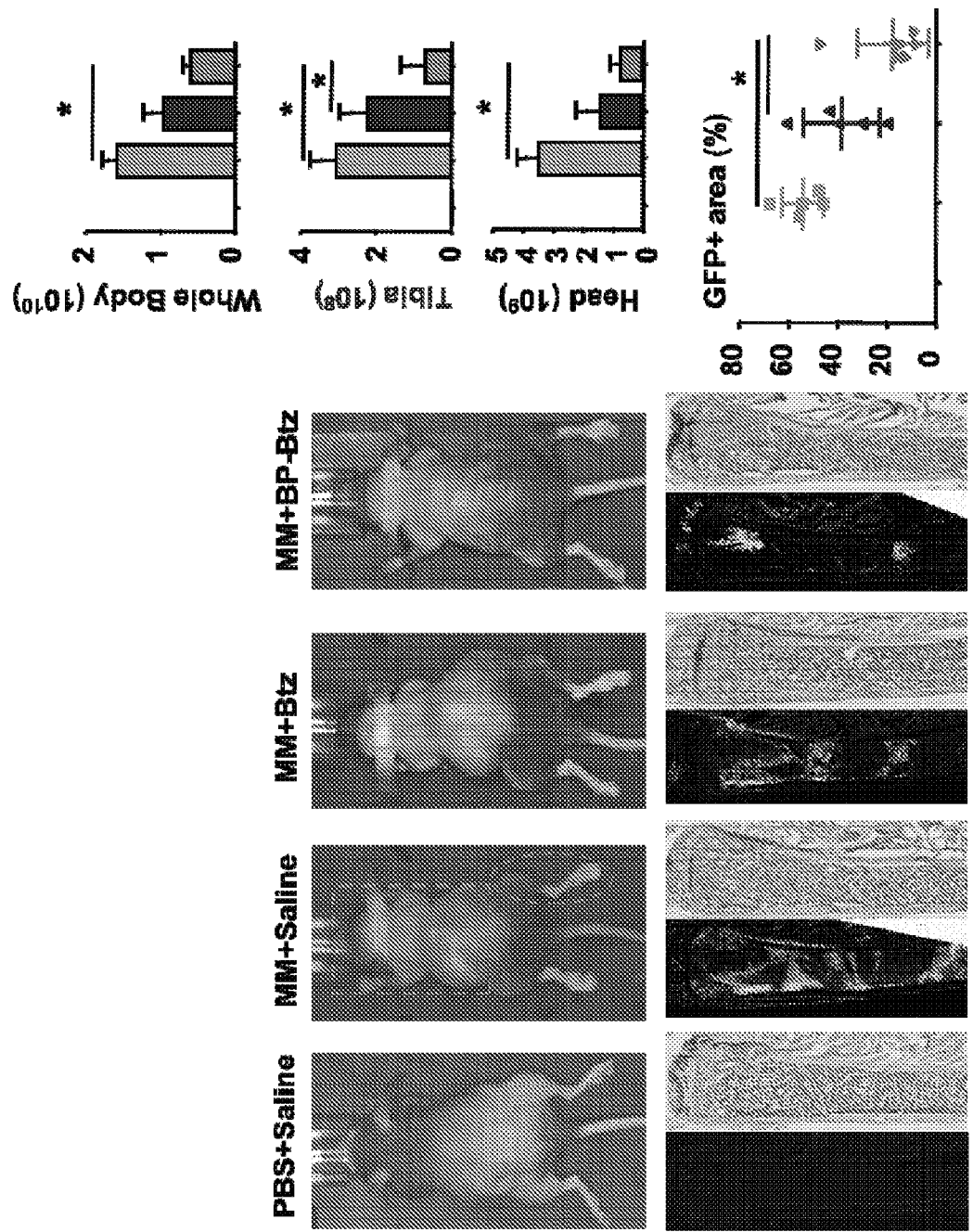
Figures 25D, 25E:
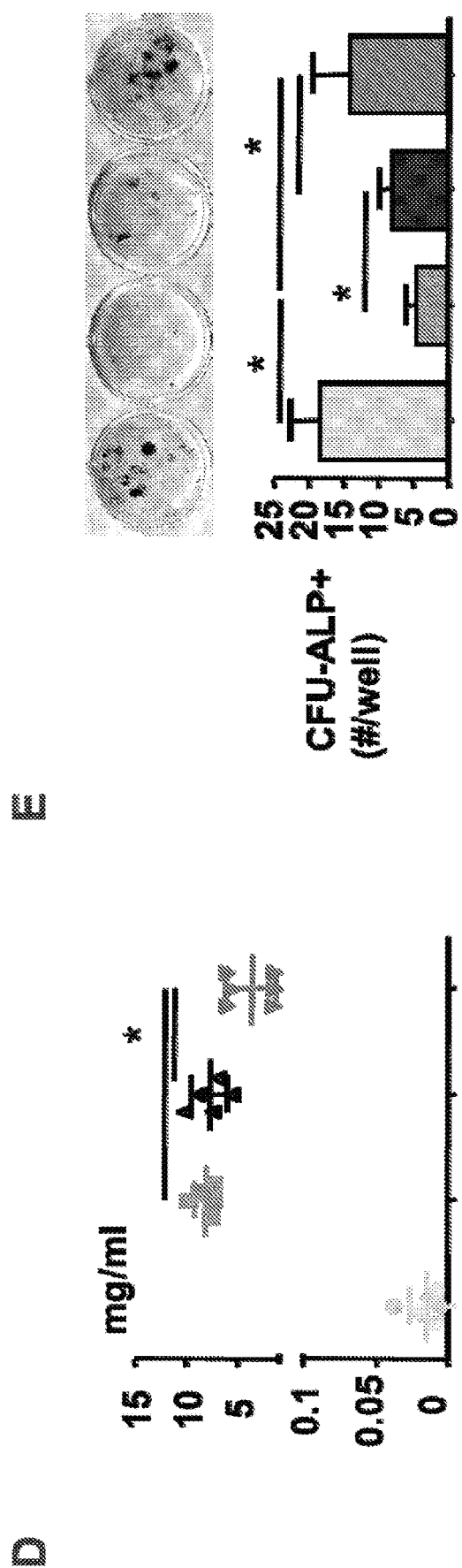

BP-Btz1 Reduces Tumor Burden and Myeloma-Induced Bone Loss More Effectively than Btz The experiments presented herein demonstrate that BP-Btz1 reduces tumor burden and myeloma-induced bone loss more effectively than Btz (FIG. 25).

BP-Btz1 Prevents Myeloma-Induced Bone Loss More Effectively than Btz

Figure 26:
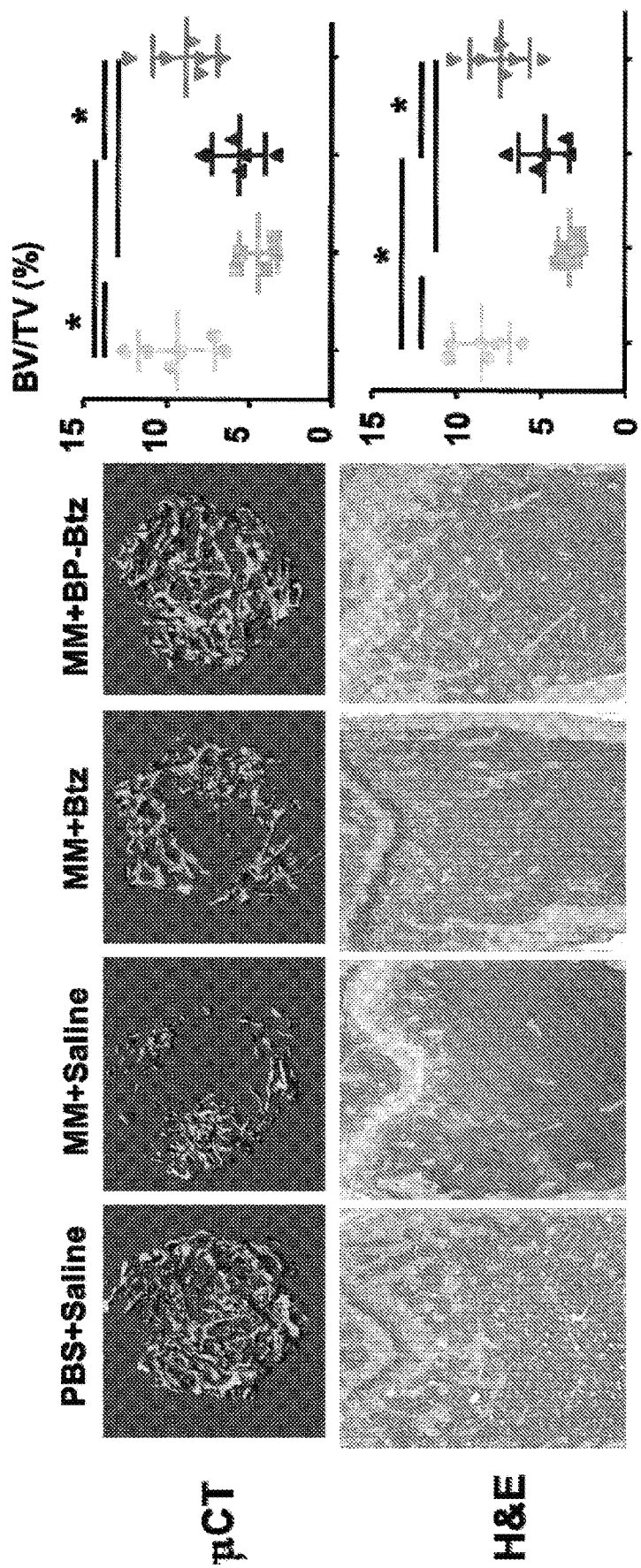
FIG. 26 is a series of images of experimental data demonstrating that BP-Btz1 prevents myeloma-induced bone loss more effectively than Btz. Femur bone volume was examined.
Figure 27:
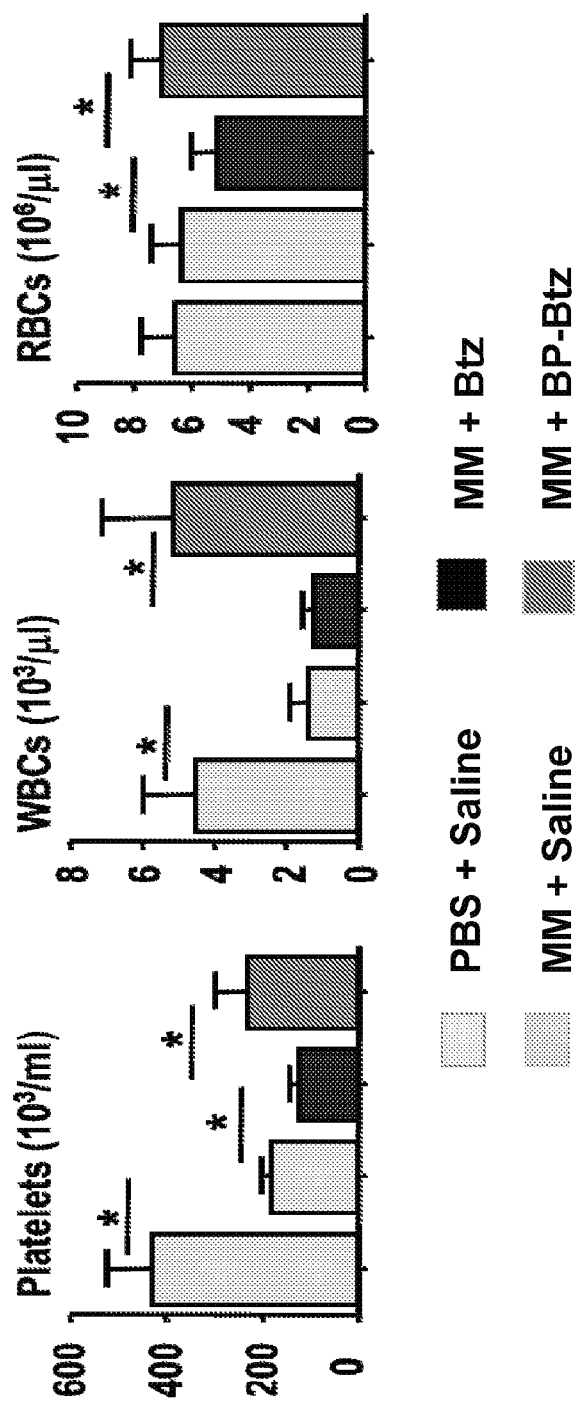
FIG. 27 depicts experimental data demonstrating that BP-Btz1 has less deleterious effects than Btz on peripheral blood platelet and cell numbers.

The experiments presented herein demonstrate that BP-Btz1 prevents myeloma-induced bone loss more effectively than Btz (FIGS. 26-27).

Figure 28:
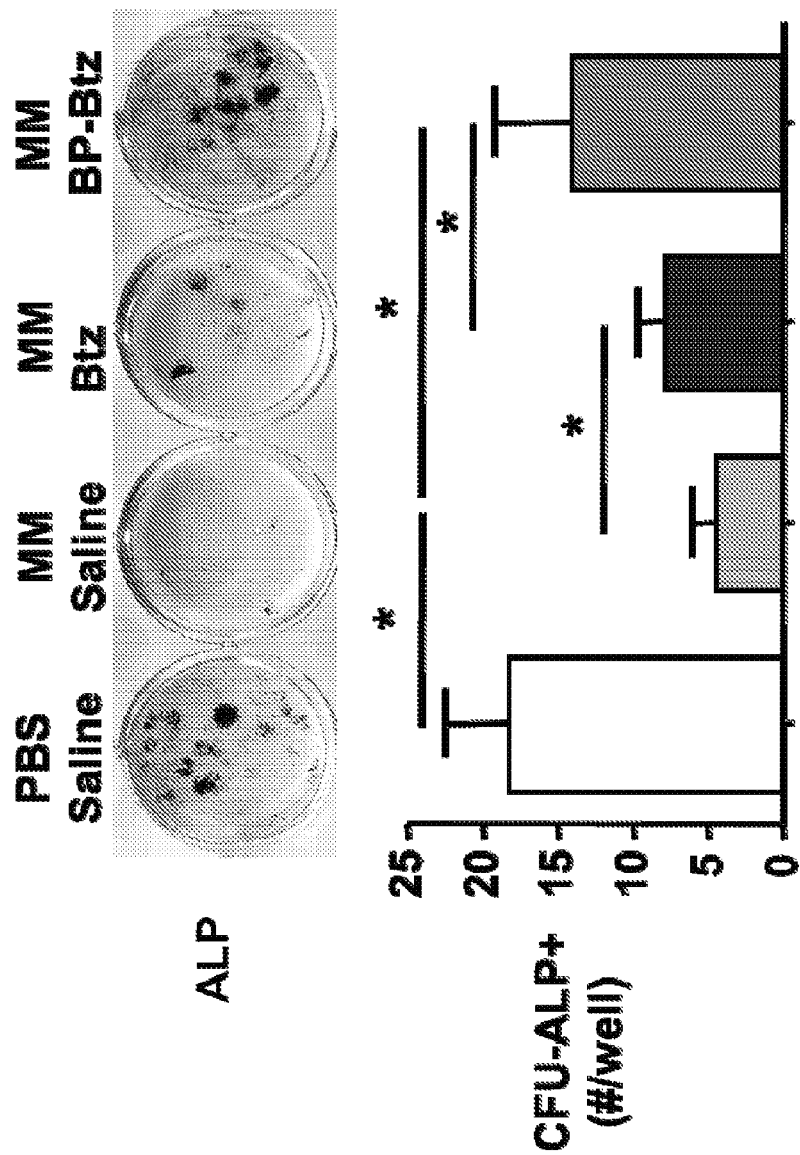
FIG. 28 depicts experimental data demonstrating that bone marrow cells from BP-Btz1-treated myeloma mice form more osteoblast colonies.

Bone Marrow Cells from BP-Btz1-Treated Myeloma Mice Form More Osteoblast Colonies The experiments presented herein demonstrate that bone marrow cells from BP-Btz1-treated myeloma mice form more osteoblast colonies (FIG. 28).

BP-Btz1 Reduces Side Effects on Blood Counts Compared with Btz

The experiments presented herein demonstrate that BP-Btz1 reduces side effects on blood counts compared with Btz (FIG. 27).

BP-Btz1 Reduces B Cell Numbers in Bone Marrow

Figures 29A, 29B, 29C:
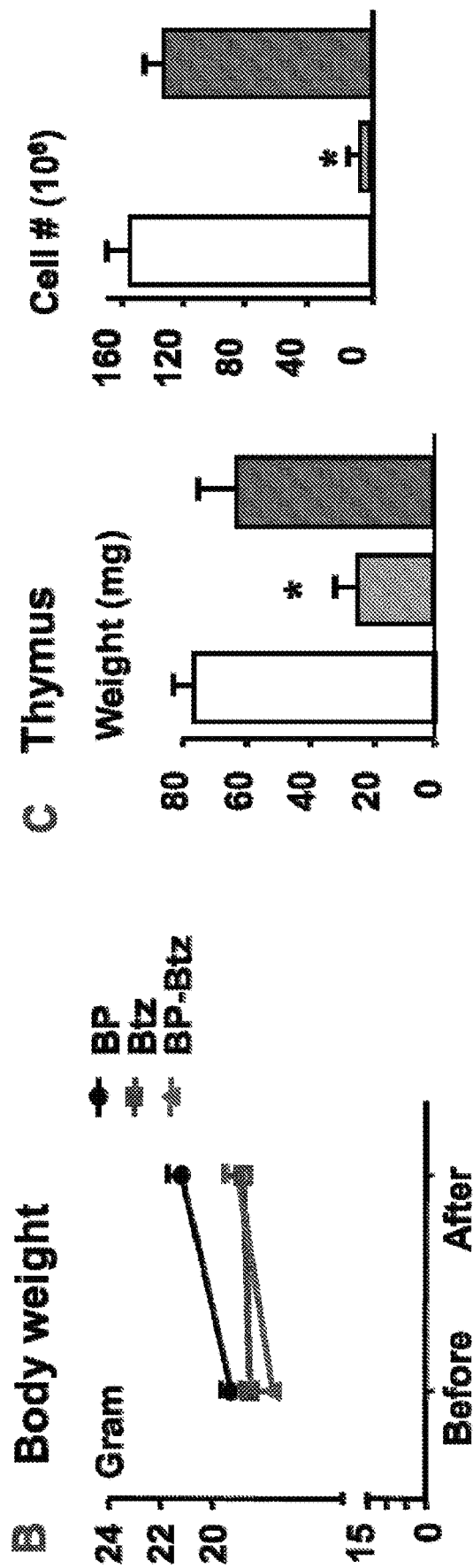
FIGS. 29A-29E, depicts experimental data demonstrating that BP-Btz1 reduces B cell numbers in bone marrow, and has less systemic toxicity than Btz. C57/B6 mice, 7 w, BP or Btz (0.6 mg/kg), BP-Btz (1.2 mg/k), daily for 3 weeks.
Figures 29D, 29E:
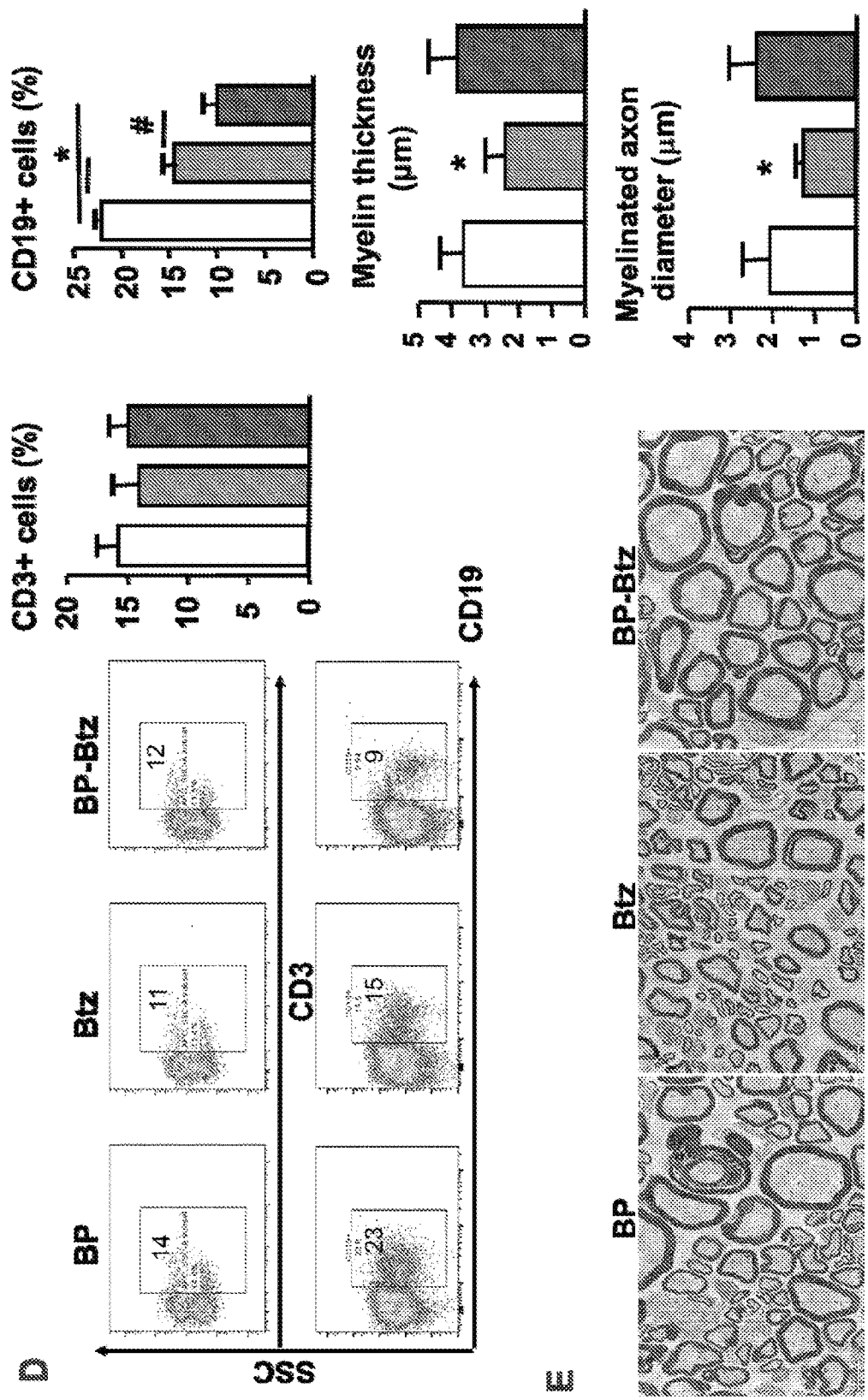

The experiments presented herein demonstrate that BP-Btz1 reduces B cell numbers in bone marrow, has less systemic toxicity than Btz, and prevents toxic effect on neurons (FIG. 29).

Example 6: Synthetic Examples

Synthesis of ((((2-(2-((R)-3-methyl-1-((S)-3-phenyl-2-(pyrazine-2-carboxamido)propanamido)-butyl)-1,3,7,2-dioxazaborecan-7-yl)ethoxy)carbonyl)amino)methylene)diphosphonic acid An exemplary synthesis of ((((2-(2-((R)-3-methyl-1-((S)-3-phenyl-2-(pyrazine-2-carboxamido)propanamido)-butyl)-

Figure 30:
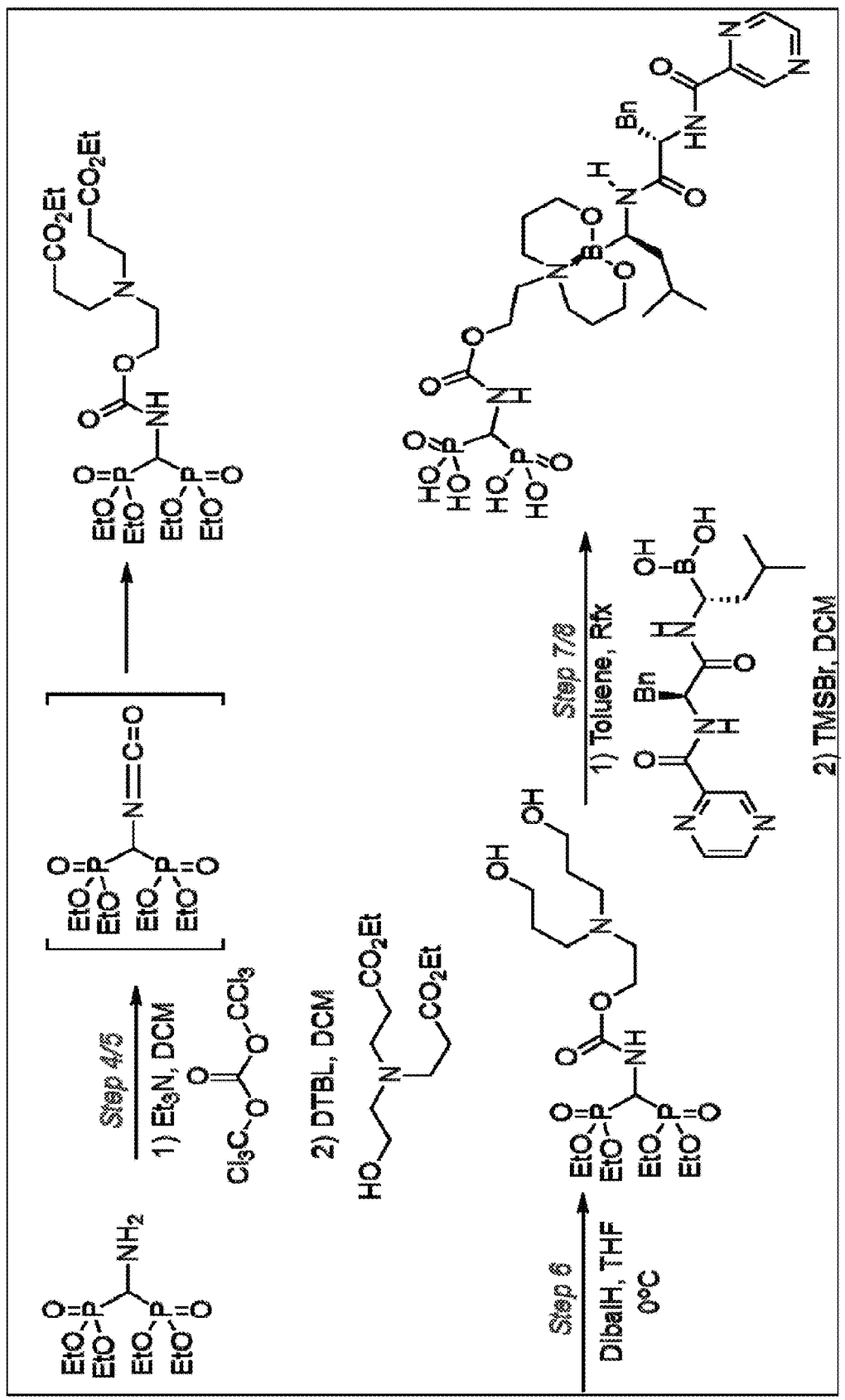
FIG. 30 is a scheme of an exemplary synthesis of ((((2-(2-((R)-3-methyl-1-((S)-3-phenyl-2-(pyrazine-2-carbox-amido)propanamido)-butyl)-1,3,7,2-dioxazaborecan-7-yl) ethoxy)carbonyl)amino)methylene)diphosphonic acid.

1,3,7,2-dioxazaborecan-7-yl)ethoxy)carbonyl)amino)methylene)diphosphonic acid is depicted in FIG. 30.

Step 4/5: Synthesis of diethyl 3,3'-((2-(((bis(diethoxyphosphoryl)methyl)carbamoyl)oxy)-ethyl)azanediyl)dipropanoate

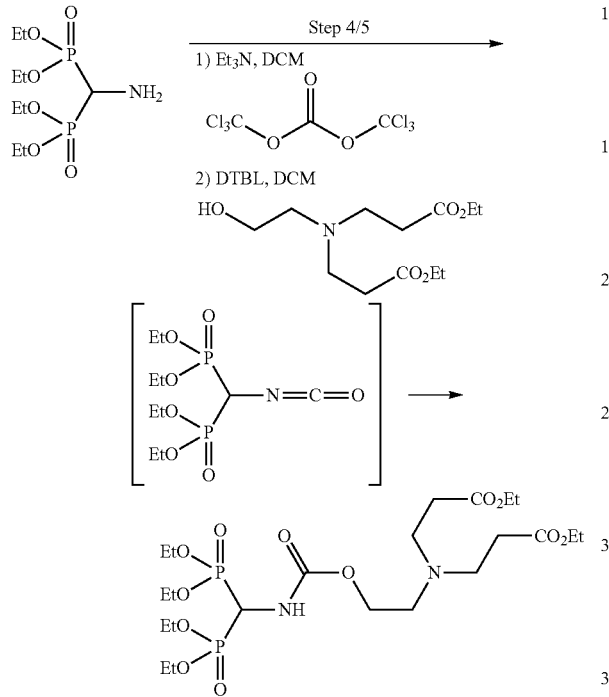

Tetraethyl (aminomethylene)bis(phosphonate) was synthesized as described in Example 1. An oven dried round bottom flask was charged with a solution of tetraethyl (aminomethylene)bis(phosphonate) in anhydrous dichloromethane (2 g, 6.59 mmol in 35 mL). After cooling to 0° C., triphosgene (0.782 g, 2.63 mmol) was added, followed by drop wise addition of triethylamine (1 mL, 7.18 mmol). The reaction mixture was gradually warmed to room temperature and stirred for 14 h. After concentrating under reduced pressure, the crude mixture was re-dissolved in anhydrous dichloromethane (16 mL). Neat dibutyltin dilaurate (0.416 g, 0.659 mmol) and diethyl 3,3'-((2-hydroxyethyl)azanediyl)dipropanoate were added sequentially and the contents were stirred at room temperature for 3 days. After concentrating under reduced pressure, the crude mixture was purified by column chromatography on silica (0%-3% of methanol in dichloromethane) to yield diethyl 3,3'-((2-hydroxyethyl)azanediyl)dipropanoate (2.66 g, 68%) as yellow viscous oil.

| | |
|---|---|
| $R_f$ | 0.2 (100% ethyl acetate, double elution, KMnO$_4$ active) |
| Thermo-MS (ESI) | m/z (M + H) Cald for C$_{22}$H$_{44}$N$_2$O$_{12}$P$_2$: 591.54, found: 591.5 |
| $^1$H-NMR (500 MHz, CDCl$_3$) | δ 5.37 (d, J = 8 Hz, 1H), 4.65-4.45 (m, 1H), 4.25-4.14 (m, 8 H), 4.13-3.96 (m, 6H), 2.79 (t, J = 5.6 Hz, 4H), 2.66 (t, J = 2.8 Hz, 2H), 2.39 (t, J = 5.6 Hz, 4H), 1.39-1.22 (m, 12H), 1.21 (t, J = 6 Hz, 6H). |
| $^{13}$C-NMR (100 MHz, CDCl$_3$) | δ 172.29, 155.68, 63.89, 63.49, 60.33, 42.30, 49.84, 45.94 (t, J = 588 Hz), 32.83, 16.26, 14.10. |
| $^{31}$P-NMR (400 MHz, CDCl$_3$) | δ 17.13. |

Step 6: Synthesis of 2-(bis(3-hydroxypropyl)amino)ethyl (bis(diethoxyphosphoryl)-methyl)carbamate

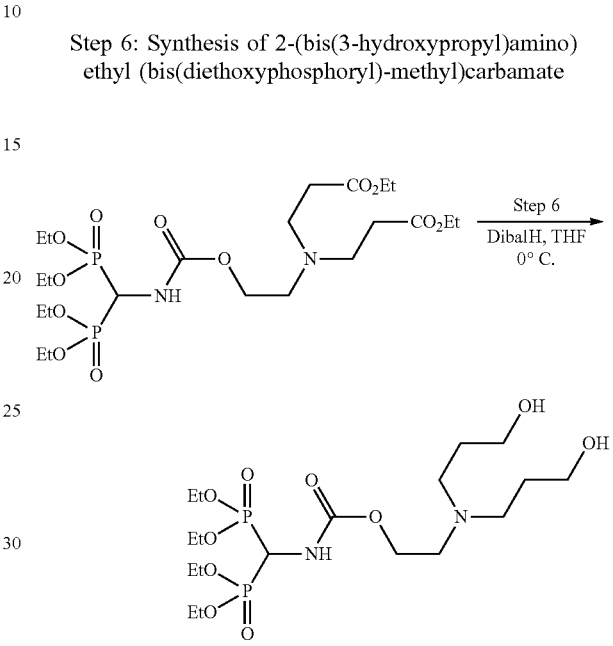

An oven dried round bottom flask was charged with a solution of diethyl 3,3'-((2-(((bis(diethoxyphosphoryl)methyl)carbamoyl)oxy)ethyl)azanediyl)dipropanoate in anhydrous tetrahydrofuran (0.7 g, 1.18 mmol in 7 mL). After cooling to 0° C., neat diisobutylaluminium hydride (0.85 g, 5.92 mmol) was added drop wise and the contents were stirred at 0° C. for 30 min. The reaction mixture was quenched with half saturated sodium sulphate and the contents were stirred at room temperature for an hr. The solids were filtered and the filtrate was concentrated under reduced pressure to yield the crude mixture, which was purified by column chromatography on silica (0%-12% methanol in dichloromethane) to yield 2-(bis(3-hydroxypropyl)amino) ethyl (bis(diethoxyphosphoryl)methyl)carbamate (0.127 g, 22%) as colorless oil.

| | |
|---|---|
| $R_f$ | 0.2 (8% of methanol in dichloromethane, KMnO$_4$ active) |
| Thermo-MS (ESI) | m/z (M + H) Cald for C$_{18}$H$_{40}$N$_2$O$_{10}$P$_2$: 507.47, found: 507.5 |
| $^1$H-NMR (500 MHz, CDCl$_3$) | δ 5.68 (d, J = 12 Hz, 1H), 4.65-4.47 (m, 1H), 4.31-4.07 (m, 10H), 3.69 (t, J = 8 Hz, 4H), 2.75-2.55 (m, 6 H), 1.69 (t, J = 8 Hz, 4H), 1.31 (t, J = 8 Hz, 12H). |
| $^{13}$C-NMR (100 MHz, CDCl$_3$) | δ 155.83, 63.55, 63.37, 61.9, 53.05, 52.38, 46.02 (t, J = 588 Hz), 28.74, 16.28. |
| $^{31}$P-NMR (400 MHz, CDCl$_3$) | δ 17.13. |

Step 7/8: Synthesis of ((((2-(2-((R)-3-methyl-1-((S)-3-phenyl-2-(pyrazine-2-carboxamido)-propanemido)butyl)-1,3,7,2-dioxazaborecan-7-yl)ethoxy)carbonyl)-amino)methylene)diphosphonic acid

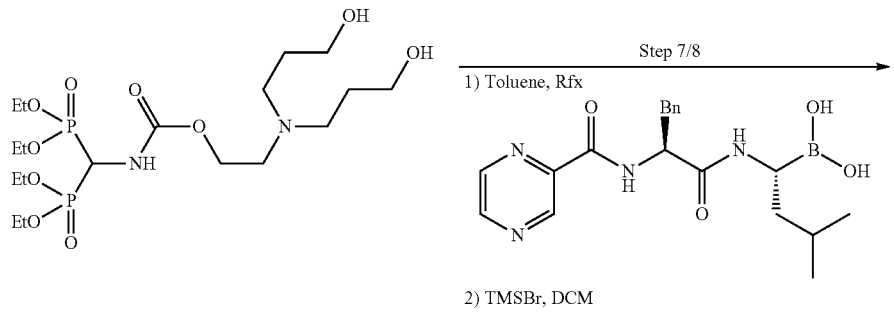

An oven dried round bottom flask was charged with a solution of 2-(bis(3-hydroxypropyl)amino)ethyl (bis(diethoxyphosphoryl)methyl)carbamate in toluene (87 mg, 0.171 mmol in 15 mL). Velcade (84 mg, 0.22 mmol) was added and the contents were refluxed using Dean Stark apparatus for 4 days. Toluene was distilled under reduced pressure and the contents were redissolved in anhydrous dichloromethane (1 mL). After cooling to 0° C., neat trimethylsilyl bromide (1.2 mL) was added and the contents were stirred at room temperature for 16 h. After concentrating under reduced pressure, the crude mixture was dissolved in 10 mL of methanol and the contents were stirred at room temperature for 10 min. The reaction mixture was concentrated under reduced pressure and the above procedure is repeated twice. The crude mixture was then washed with ether (three times) to yield (((2-(2-((R)-3-methyl-1-((S)-3-phenyl-2-(pyrazine-2-carboxamido)-propanemido)butyl)-1,3,7,2-dioxazaborecan-7-yl)ethoxy)carbonyl)-amino)methylene)diphosphonic acid.

| | |
|---|---|
| Thermo-MS (ESI) | m/z (M + H) Cald for $C_{29}H_{45}BN_6O_{12}P_2$: 743.46, found: 743.5. |
| $^1$H-NMR (400 MHz, DMSO-d$_6$ with D$_2$O) | δ 9.02 (s, 1H), 8.76 (s, 1H), 8.64 (s, 1H), 7.29-7.05 (m, 5H), 4.81-4.61 (m, 1H), 4.32-4.21 (m, 1H), 4.12-4.01 (m, 2H), 3.59-3.39 (t, J = 4 Hz, 4H), 3.21-2.89 (m, 3H), 2.53-2.39 (t, J = 4 Hz, 6H), 1.79-1.61 (m, 4H), 1.44-1.36 (m, 1H), 1.35-1.21 (m, 1H), 1.20-1.05 (m, 1H), 0.72 (d, J = 7 Hz, 6H). |
| $^{13}$C-NMR (400 MHz, DMSO-d$_6$ with D$_2$O) | δ 170.61, 162.82, 148.23, 144.32, 144.03, 143.63, 137.59, 129.63, 128.58, 126.95, 58.41, 54.25, 54.02, 52.06, 51.72, 51.53, 48.92, 38.62, 26.22, 25.2, 23.57, 22.30. |
| $^{31}$P-NMR (400 MHz, DMSO-d$_6$ with D$_2$O) | δ −0.913. |

Figure 31:
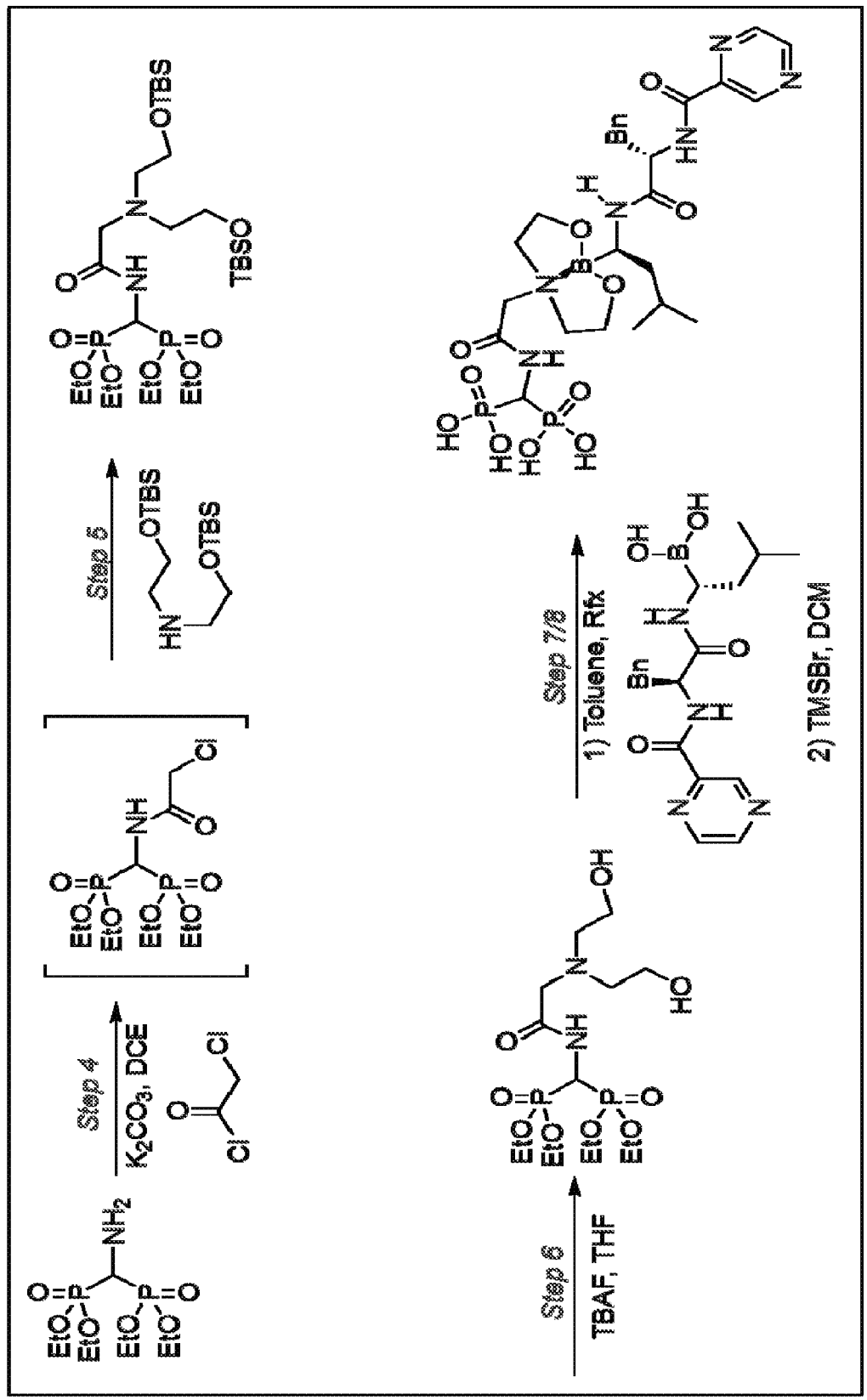
FIG. 31 is a scheme of an exemplary synthesis of ((2-(2-((R)-3-methyl-1-((S)-3-phenyl-2-(pyrazine-2-carbox-amido)-propanamido)butyl)-1,3,6,2-dioxazaborocan-6-yl) acetamido)methylene)diphosphonic acid.

Synthesis of ((2-(2-((R)-3-methyl-1-((S)-3-phenyl-2-(pyrazine-2-carboxamido)-propanamido)butyl)-1,3,6,2-dioxazaborocan-6-yl)acetamido)methylene)diphosphonic acid An exemplary synthesis of ((2-(2-((R)-3-methyl-1-((S)-3-phenyl-2-(pyrazine-2-carboxamido)-propanamido)butyl)-1,3,6,2-dioxazaborocan-6-yl)acetamido)methylene)diphosphonic acid is depicted in FIG. 31.

Step 4/5: Synthesis of tetraethyl (5-(2-((tert-butyldimethylsilyl)oxy)ethyl)-9,9,10,10-tetramethyl-3-oxo-8-oxa-2,5-diaza-9-silaundecane-1,1-diyl)bis(phosphonate)

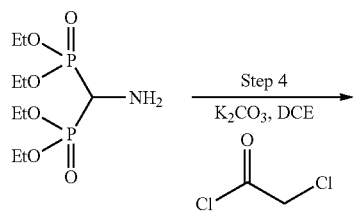

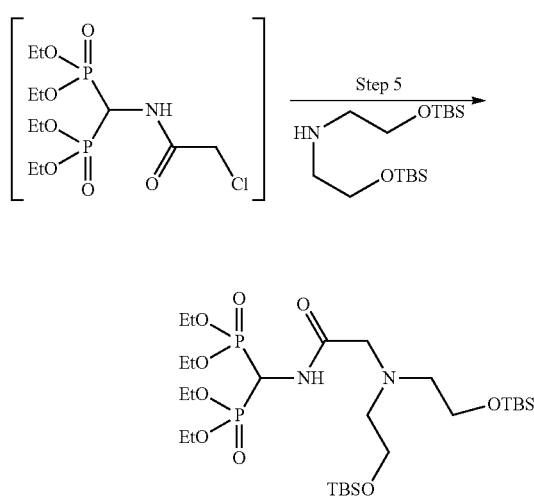

An oven dried round bottom flask was charged with a solution of tetraethyl (aminomethylene)bis(phosphonate) in anhydrous dichloroethane (2 g, 6.6 mmol in 15 mL). Pre-activated potassium carbonate (4.5 g 33 mmol) was added in one portion and the white suspension was cooled to 0° C. Neat 2-chloroacetyl chloride (0.55 mL, 6.93 mmol) was added and the contents were gradually warmed to room temperature and stirred for 14 h. Neat bis(2-((tert-butyldimethylsilyl)oxy)ethyl)amine (2.42 g, 7.26 mmol) and sodium iodide (0.1 g, 0.66 mmol) was added and the contents were stirred at room temperature for 24 h. After diluting with anhydrous dichloromethane (75 mL), the reaction mixture was filtered and the filtrate was concentrated under reduced pressure. The crude mixture was purified by column chromatography on alumina (40%-60% ethyl acetate in n-hexanes) to yield tetraethyl (5-(2-((tert-butyldimethylsilyl)oxy)ethyl)-9,9,10,10-tetramethyl-3-oxo-8-oxa-2,5-diaza-9-silaundecane-1,1-diyl)bis(phosphonate) (1.72 g, 39%) as pale yellow oil.

| | |
|---|---|
| $R_f$ | 0.6 (4% of methanol in dichloromethane, double elution, KMnO$_4$ active) |
| Thermo-MS (ESI) | m/z (M + H) Cald for C$_{27}$H$_{62}$N$_2$O$_9$P$_2$Si$_2$: 677.91, found: 677.9 |
| $^1$H-NMR (500 MHz, CDCl$_3$) | δ 7.63 (d, J = 8 Hz, 1H), 5.03-4.87 (m, 1H), 4.24-4.08 (m, 8 H), 3.68 (t, J = 4.8 Hz, 4H), 3.33 (s, 2H), 2.72 (t, J = 4.8 Hz, 4H), 1.35-1.21 (m, 12 H), 0.84 (s, 18H), 0.01 (s, 12H) |
| $^{13}$C-NMR (100 MHz, CDCl$_3$) | δ 170.71, 63.29 (d, J = 52 Hz), 61.57, 59.45, 56.98, 43.08 (t, J = 584 Hz), 25.75, 18.03, 16.29 (t, J = 12 Hz), −5.52. |
| $^{31}$P-NMR (400 MHz, CDCl$_3$) | δ 17.32 |

Step 6: Synthesis of tetraethyl ((2-(bis(2-hydroxyethyl)amino)acetamido)methylene)-bis(phosphonate)

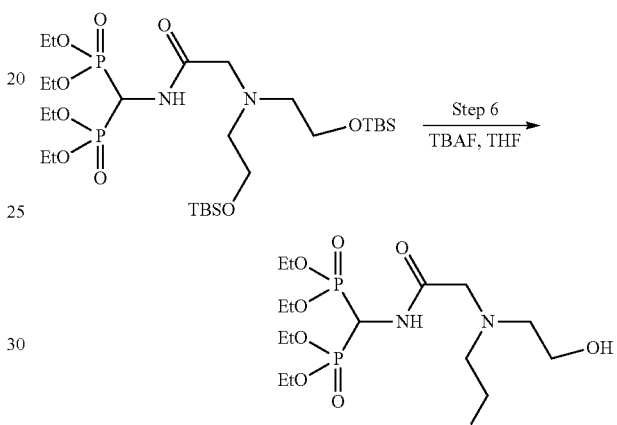

An oven dried round bottom flask was charged with a solution of tetraethyl (5-(2-((tert-butyldimethylsilyl)oxy)ethyl)-9,9,10,10-tetramethyl-3-oxo-8-oxa-2,5-diaza-9-silaundecane-1,1-diyl)bis(phosphonate) in anhydrous tetrahydrofuran (0.39 g, 0.576 mmol in 1 mL). A solution of tetrabutylammonium fluoride (2.3 mL, 2.3 mmol, 1 M) was added and the contents were stirred at room temperature for an hour. After concentrating under reduced pressure, the crude mixture was purified by column chromatography on silica (3%-6% methanol in dichloromethane) to yield tetraethyl ((2-(bis(2-hydroxyethyl)amino)acetamido)methylene)-bis(phosphonate) (0.14 g, 54%) as colorless oil.

| | |
|---|---|
| $R_f$ | 0.3 (5% of methanol in dichloromethane, KMnO$_4$ active) |
| Thermo-MS (ESI) | m/z (M + H) Cald for C$_{15}$H$_{34}$N$_2$O$_9$P$_2$: 449.39, found: 449.4 |
| $^1$H-NMR (500 MHz, CDCl$_3$) | δ 8.70 (d, J = 8 Hz, 1H), 5.01-4.87 (m, 1H), 4.21-4.03 (m, 8 H), 3.93 (bs, 2H), 3.60 (t, J = 3.6 Hz, 4H), 3.29 (s, 2H), 2.75 (t, J = 3.6 Hz, 4H), 1.75-1.57 (bs, 2H), 1.37-1.23 (m, 12 H). |
| $^{13}$C-NMR (100 MHz, CDCl$_3$) | δ 171.26, 63.83 (d, J = 140 Hz), 59.73, 59.6, 58.28, 43.35 (t, J = 588 Hz), 16.23. |
| $^{31}$P-NMR (400 MHz, CDCl$_3$) | δ 17.50 |

Step 7/8: Synthesis of ((2-(2-((R)-3-methyl-1-((S)-3-phenyl-2-(pyrazine-2-carboxamido)-propanamido)butyl)-1,3,6,2-dioxazaborocan-6-yl)acetamido)methylene)diphosphonic acid

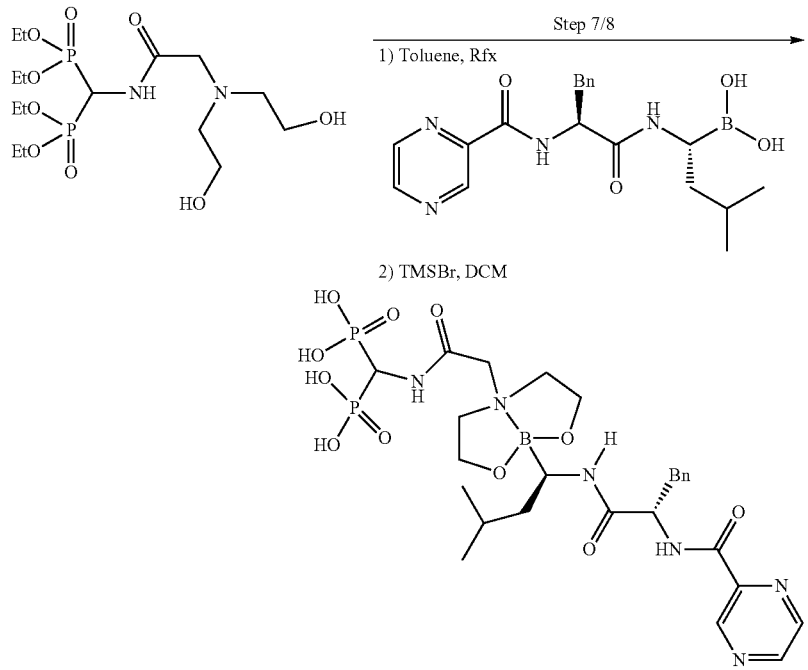

An oven dried round bottom flask was charged with a solution of tetraethyl ((2-(bis(2-hydroxyethyl)amino)acetamido)methylene)-bis(phosphonate) in toluene (0.13 g, 0.29 mmol in 15 mL). Velcade (0.145 g, 0.377 mmol) was added and the contents were refluxed using Dean Stark apparatus for 4 days. Toluene was distilled under reduced pressure and the contents were redissolved in anhydrous dichloromethane (1 mL). After cooling to 0° C., neat trimethylsilyl bromide (1.5 mL) was added and the contents were stirred at room temperature for 16 h. After concentrating under reduced pressure, the crude mixture was dissolved in 10 mL of methanol and the contents were stirred at room temperature for 10 min. The reaction mixture was concentrated under reduced pressure and the above procedure is repeated twice. The crude mixture was then washed with ether (three times) to yield ((2-(2-((R)-3-methyl-1-((S)-3-phenyl-2-(pyrazine-2-carboxamido)-propanamido)butyl)-1,3,6,2-dioxazaborocan-6-yl)acetamido)methylene)-diphosphonic acid.

| | |
|---|---|
| Thermo-MS (ESI) | m/z (M + H) Cald for $C_{26}H_{39}BN_6O_{11}P_2$: 685.38, found: 685.4. |
| $^1$H-NMR (400 MHz, DMSO-$d_6$ with $D_2O$) | δ 9.02 (s, 1H), 8.76 (s, 1H), 8.65 (s, 1H), 7.29-7.03 (m, 5H), 4.81-4.61 (m, 1H), 4.59-4.41 (m, 1H), 3.69-3.57 (m, 4H). 3.33-3.23 (s, 2H), 3.19-2.89 (m, 3H), 2.91-2.78 (m, 4H), 1.48-1.39 (m, 1H), 1.35-1.21(m, 1H), 1.21-1.11 (m, 1H), 0.74 (d, J = 7 Hz, 6H). |
| $^{13}$C-NMR (100 MHz, DMSO-$d_6$ with $D_2O$) | δ 173.75, 163.47, 147.89, 144.10, 143.35, 143.2, 136.81, 129.41, 128.69, 127.13, 56.23, 55.14, 54.95, 54.28, 40.87, 38.63, 25.01, 23.25, 21.91. |
| $^{31}$P-NMR (400 MHz, DMSO-$d_6$ with $D_2O$) | δ −0.787. |

Figure 32:
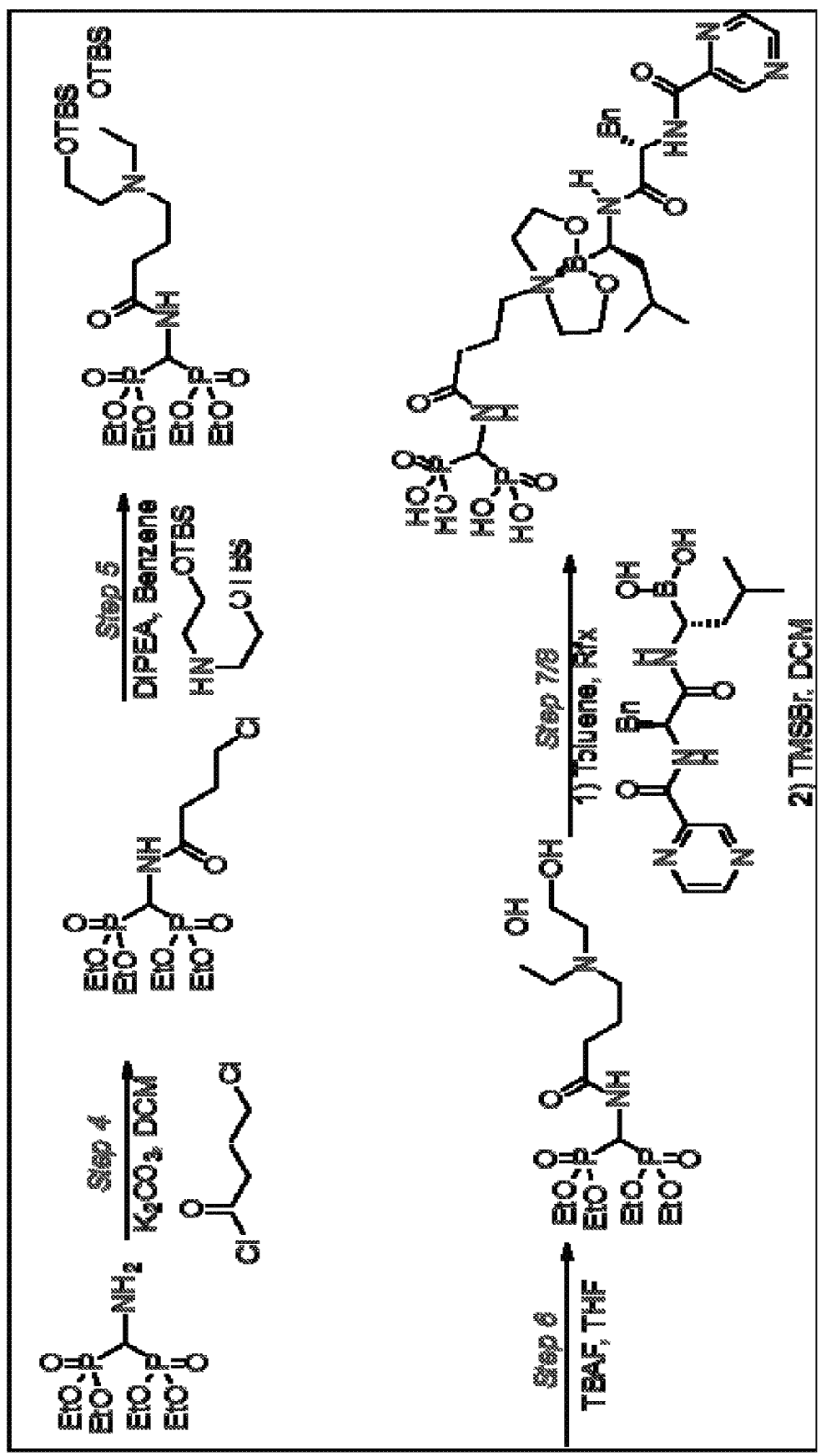
FIG. 32 is a scheme of an exemplary synthesis of ((4-(2-((R)-3-methyl-1-((S)-3-phenyl-2-(pyrazine-2-carboxamido) propan-amido)butyl)-1,3,6,2-dioxazaborocan-6-yl)butana-mido)methylene)diphosphonic acid.

Synthesis of ((4-(2-((R)-3-methyl-1-((S)-3-phenyl-2-(pyrazine-2-carboxamido)propan-amido)butyl)-1,3,6,2-dioxazaborocan-6-yl)butanamido)methylene) diphosphonic acid An exemplary synthesis of ((4-(2-((R)-3-methyl-1-((S)-3-phenyl-2-(pyrazine-2-carboxamido)propan-amido)butyl)-1,3,6,2-dioxazaborocan-6-yl)butanamido)methylene)diphosphonic acid is depicted in FIG. 32.

Step 4: Synthesis of tetraethyl ((4-chlorobutanamido)methylene)bis(phosphonate)

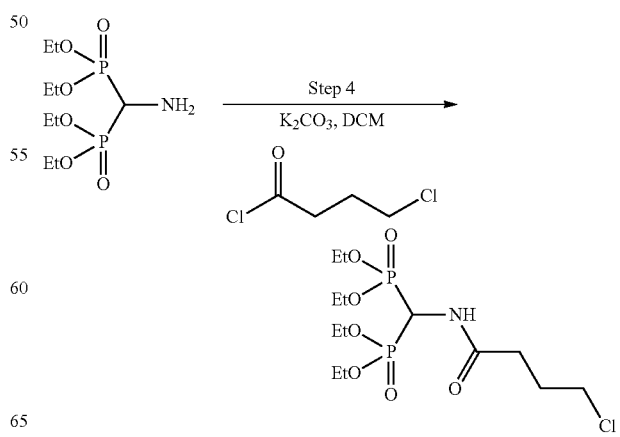

An oven dried round bottom flask was charged with a solution of tetraethyl (aminomethylene)bis(phosphonate) in anhydrous dichloromethane (0.8 g, 2.64 mmol in 6 mL). Preactivated potassium carbonate (1.8 g 13.2 mmol) was added in one portion and the white suspension was cooled to 0° C. Neat 4-chlorobutyrl chloride (0.37 mL, 3.12 mmol) was added and the contents were gradually warmed to room temperature and stirred for 5 h. After diluting with anhydrous dichloromethane (25 mL), the reaction mixture was filtered and the filtrate was treated with methanol (5 mL). The combined organic phase was concentrated under reduced pressure and the crude mixture was purified by column chromatography on silica (0%-4% methanol in dichloromethane) to yield tetraethyl ((4-chlorobutanamido)methylene)bis(phosphonate) (0.79 g, 74%) as pale yellow oil.

| | |
|---|---|
| $R_f$ | 0.5 (5% of methanol in dichloromethane, double elution, KMnO$_4$ active) |
| Thermo-MS (ESI) | m/z (M + H) Cald for $C_{13}H_{28}ClNO_7P_2$: 407.76 and 408.76, found: 407.8 and 408.8 |
| $^1$H-NMR (500 MHz, CDCl$_3$) | δ 6.32 (d, J = 8 Hz, 1H), 5.09-4.91 (m, 1H), 4.29-4.05 (m, 8 H), 3.59 (t, J = 8 Hz, 2 H), 2.42 (t, J = 8 Hz, 2H), 2.13-1.98 (m, 2H), 1.35-1.21 (m, 12H). |
| $^{13}$C-NMR (100 MHz, CDCl$_3$) | δ 171.14, 63.59 (d, J = 64 Hz), 44, 43.34 (t, J = 588 Hz), 32.59, 28.09, 16.23. |
| $^{31}$P-NMR (400 MHz, CDCl$_3$) | δ 16.97. |

Step 5/6: Synthesis of tetraethyl ((4-(bis(2-hydroxyethyl)amino)butanamido)-methylene)bis(phosphonate)

An oven dried round bottom flask was charge with a solution of tetraethyl ((4-chlorobutanamido)methylene)bis (phosphonate) in anhydrous benzene (0.68 g, 1.667 mmol in 2 mL). Neat N-ethyl-N-isopropylpropan-2-amine (0.3 mL) and neat bis(2-((tert-butyldimethyl-silyl)oxy)ethyl)amine (0.528 g, 1.58 mmol) were added sequentially and the contents were refluxed for 16 h. The reaction mixture was concentrated under reduced pressure and the crude mixture was taken to the next step without purification.

An oven dried round bottom flask was charged with a solution of crude mixture from the previous step in anhydrous tetrahydrofuran (1 mL). A solution of tetrabutylammonium fluoride in tetrahydrofuran (5 mL, 5 mmol, 1 M) was added and the contents were stirred at room temperature for 1 h. The reaction mixture was concentrated under reduced pressure and the crude mixture was purified by column chromatography on silica (0-8% methanol in dichloromethane) to yield tetraethyl ((4-(bis(2-hydroxyethyl)amino)butanamido)-methylene)bis(phosphonate) as colorless oil.

| | |
|---|---|
| $R_f$ | 0.3 (5% of methanol in dichloromethane, KMnO$_4$ active) |
| Thermo-MS (ESI) | m/z (M + H) Cald for $C_{17}H_{38}N_2O_9P_2$: 477.44 found: 477.4 |
| $^1$H-NMR (500 MHz, CDCl$_3$) | δ 6.06 (d, J = 8 Hz, 1H), 5.08-4.91 (m, 1H), 4.25-4.11 (m, 8 H), 3.68 (t, J = 8 Hz, 4H), 3.57 (t, J = 8 Hz, 2H), 2.72 (t, J = 8 Hz, 4H), 2.42 (t, J = 5.6 Hz, 2H), 2.14-2.11 (m, 2H), 1.35-1.21 (m, 12H) |
| $^{31}$P-NMR (400 MHz, CDCl$_3$) | δ 17.32 |

Step 7/8: Synthesis of ((4-(2-((R)-3-methyl-1-((S)-3-phenyl-2-(pyrazine-2-carboxamido)propan-amido) butyl)-1,3,6,2-dioxazaborocan-6-yl)butanamido) methylene)diphosphonic acid

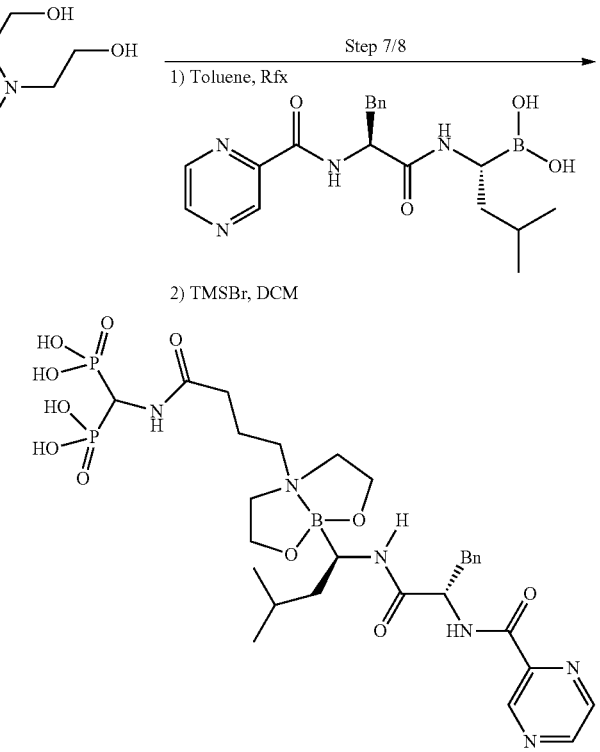

An oven dried round bottom flask was charged with a solution of tetraethyl ((4-(bis(2-hydroxyethyl)amino)butanamido)-methylene)bis(phosphonate) in toluene (0.1 g, 0.21 mmol in 15 mL). Velcade (0.105 g, 0.273 mmol) was added and the contents were refluxed using Dean Stark apparatus for 4 days. Toluene was distilled under reduced pressure and the contents were redissolved in anhydrous dichloromethane (1.5 mL). After cooling to 0° C., neat trimethylsilyl bromide (1.5 mL) was added and the contents were stirred at room temperature for 16 h. After concentrating under reduced pressure, the crude mixture was dissolved in 10 mL of methanol and the contents were stirred at room temperature for 10 min. The reaction mixture was concentrated under reduced pressure and the above procedure is repeated twice. The crude mixture was then washed with ether (three times) to yield ((4-(2-((R)-3-methyl-1-((S)-3-phenyl-2-(pyrazine-2-carboxamido)propan-amido)butyl)-1,3,6,2-dioxazaborocan-6-yl)butanamido)methylene)-diphosphonic acid.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A compound of formula (I):

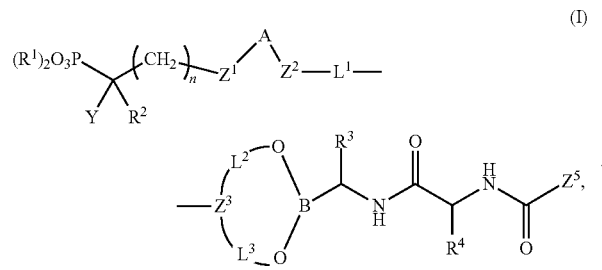

wherein in formula (I):
each occurrence of $R^1$ is independently selected from the group consisting of hydrogen and alkyl;
$R^2$ is selected from the group consisting of hydrogen and —$OR^{13}$;
$R^3$ is selected from the group consisting of hydrogen and alkyl;
$R^4$ is selected from the group consisting of hydrogen, alkyl, aryl, and alkylaryl wherein the alkyl group is optionally substituted with hydroxyl group;
$L^1$ is selected from the group consisting of alkyl, and alkyl-$Z^4C(O)NR^{10}$;
$L^2$ is aryl or an alkyl chain of $C_1$-$C_6$ alkyl, wherein any carbon atom in the alkyl chain is optionally substituted with one to two substituents selected from the group consisting of alkyl, cycloalkyl, and carbonyl;
$L^3$ is aryl or an alkyl chain of $C_1$-$C_6$ alkyl, wherein any carbon atom in the alkyl chain is optionally substituted with one to two substituents selected from the group consisting of alkyl, cycloalkyl, and carbonyl; or
Y is selected from the group consisting of —$PO(OR^8)(OR^9)$, —$PO(R^9)(OR^8)$, and —$CO_2R^8$;

$Z^1$ is selected from the group consisting of $CH_2$ and $NR_6$;
A is $C(=O)$;
$Z^2$ is selected from the group consisting of $CH_2$, $NR^{11}$, S, and O;
$Z^3$ is N;
$Z^4$ is selected from the group consisting of $CH_2$ and O;
$Z^5$ is selected from the group consisting of

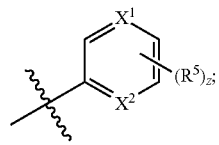

each occurrence of $R^5$ is independently selected from the group consisting of alkyl, aryl, F, Cl, Br, and I;
$X^1$ is selected from the group consisting of $CR^{15}$ and N;
$X^2$ is selected from the group consisting of $CR^{1'}$ and N;
$R^6$ is selected from the group consisting of hydrogen and alkyl;
$R^8$, $R^9$, and $R^{10}$ are each independently selected from the group consisting of hydrogen and alkyl;
$R^{11}$ and $R^{13}$ are each independently selected from the group consisting of hydrogen and alkyl;
$R^{15}$ and $R^{16}$ are each independently selected from the group consisting of hydrogen, alkyl, aryl, F, Cl, Br, and I;
n is an integer from 0 to 10; and
z is an integer from 0 to 2;
or a pharmaceutically acceptable salt thereof.

2. The compound of claim 1, wherein the compound of formula (I) is a compound of formula (II):

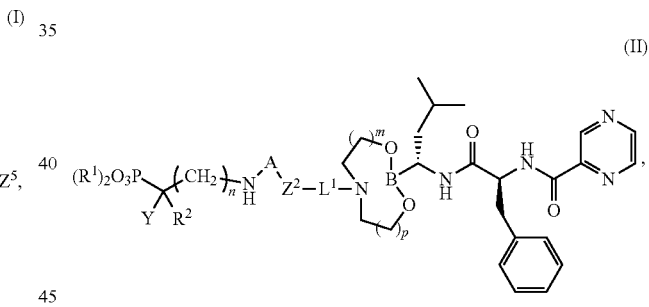

wherein in formula (II):
each occurrence of $R^1$ is independently selected from the group consisting of hydrogen and alkyl;
$R^2$ is selected from the group consisting of hydrogen and —$OR^{13}$;
Y is selected from the group consisting of —$PO(OR^8)(OR^9)$, —$PO(R^9)(OR^8)$, and —$CO_2R^8$;
A is $C(=O)$;
$Z^2$ is selected from the group consisting of $CH_2$, $NR^{11}$, S, and O;
$L^1$ is selected from the group consisting of alkyl, and alkyl-$Z^4C(O)NR^{10}$;
$Z^4$ is selected from the group consisting of $CH_2$ and O;
$R^8$, $R^9$ and $R^{10}$ are each independently selected from the group consisting of hydrogen and alkyl;
$R^{11}$ and $R^{13}$ are each independently selected from the group consisting of hydrogen and alkyl;
m is 1, or 2 or 3;
p is 1, or 2, or 3; and
n is an integer from 0 to 10; or
a pharmaceutically acceptable salt thereof.

3. A compound of formula (III):

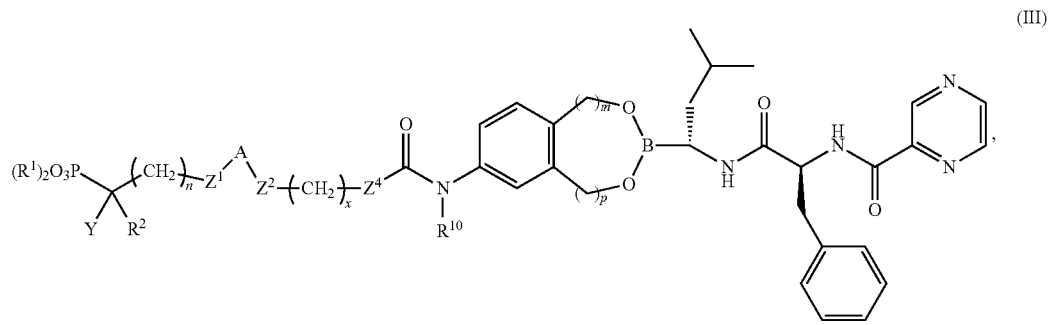

wherein in formula (III):

each occurrence of $R^1$ is independently selected from the group consisting of hydrogen and alkyl;

$R^2$ is selected from the group consisting of hydrogen and —$OR^{13}$;

Y is selected from the group consisting of —$PO(OR^8)(OR^9)$, —$PO(R^9)(OR^8)$, and —$CO_2R^8$;

$Z^1$ is selected from the group consisting of $CH_2$ and $NR^6$;

A is C(=O);

$Z^2$ is selected from the group consisting of $CH_2$, $NR^{11}$, S, and O;

$Z^4$ is selected from the group consisting of $CH_2$ and O;

$R^6$ is selected from the group consisting of hydrogen and alkyl;

$R^8$, $R^9$, and $R^{10}$ are each independently selected from the group consisting of hydrogen and alkyl;

$R^{11}$ and $R^{13}$ are each independently selected from the group consisting of hydrogen and alkyl; and m is an integer from 1 to 5;
n is an integer from 0 to 10;
p is an integer from 1 to 5; and
x is an integer from 0 to 10; or
a pharmaceutically acceptable salt thereof.

4. The compound of claim 1, wherein Y is —$PO_3(R^1)_2$.

5. The compound of claim 1, wherein $L^1$ is alkyl.

6. The compound of claim 1, wherein $L^2$ is selected from the group consisting of phenyl and an alkyl chain of $C_1$-$C_6$ alkyl, wherein one carbon atom in the alkyl chain is optionally substituted with two alkyl groups, a carbonyl group, or a cycloalkyl group.

7. The compound of claim 1, wherein $L^3$ is selected from the group consisting of phenyl and an alkyl chain of $C_1$-$C_6$ alkyl, wherein one carbon atom in the alkyl chain is optionally substituted with two alkyl groups, a carbonyl group, or a cycloalkyl group.

8. The compound of claim 1, wherein $Z^2$ is O.

9. The compound of claim 1, wherein the compound is selected from the group consisting of:

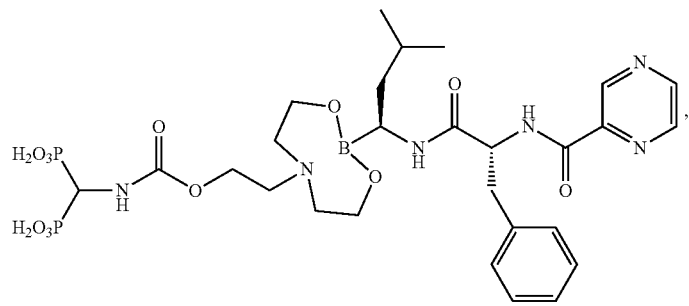

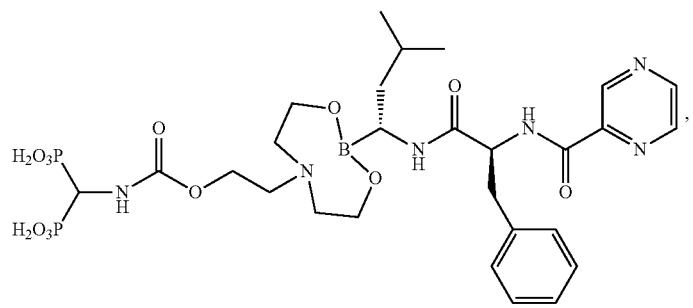

-continued
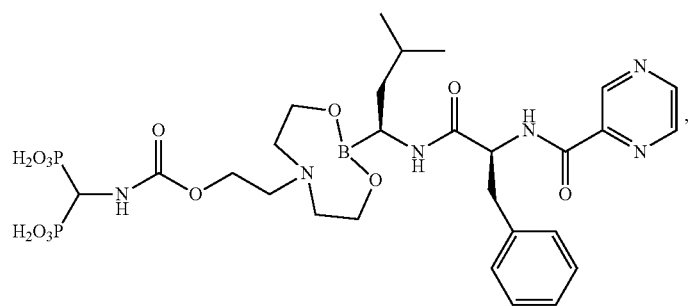
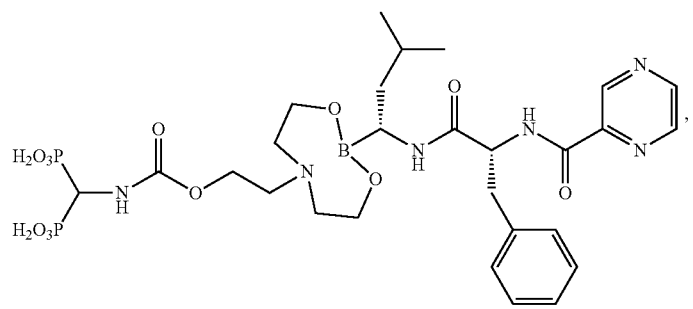
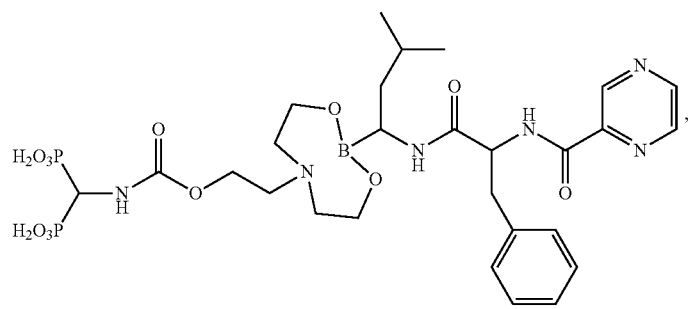
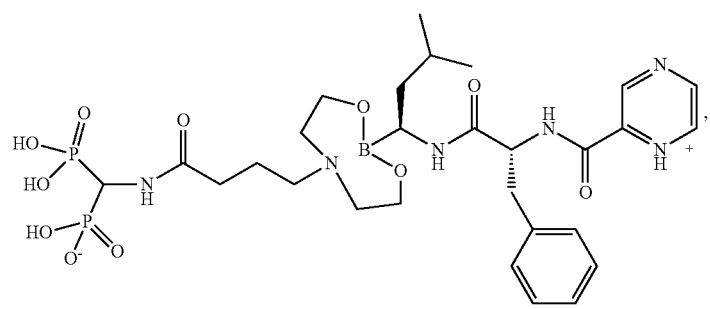
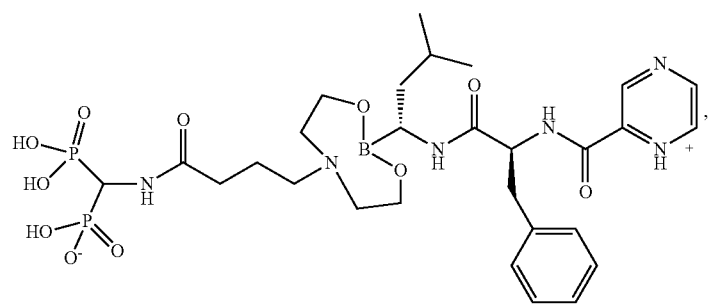

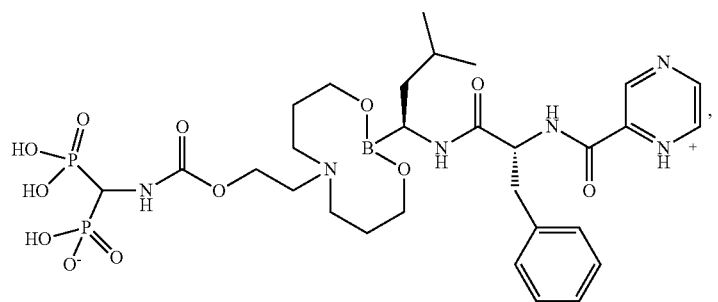
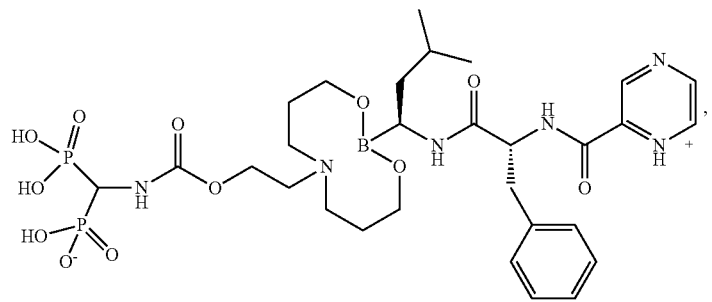
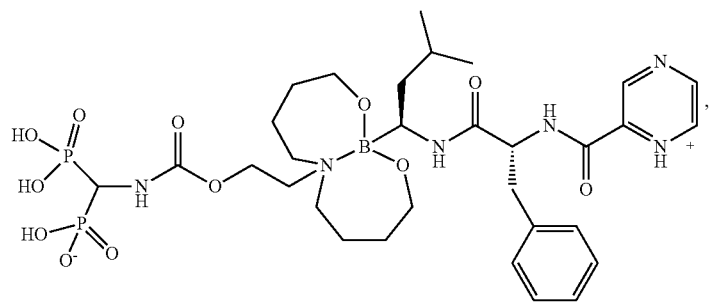
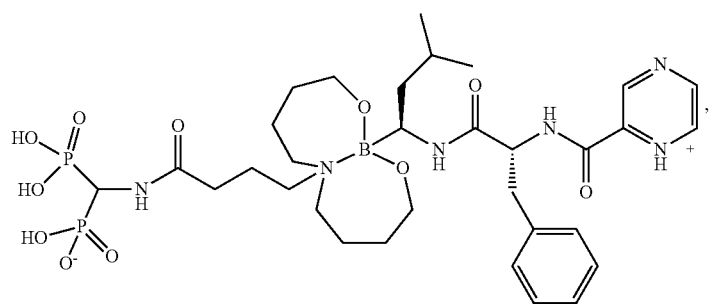
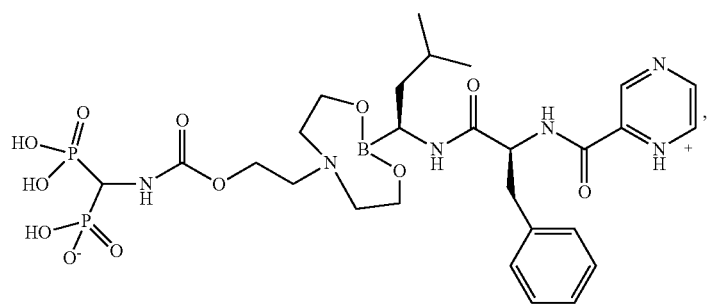

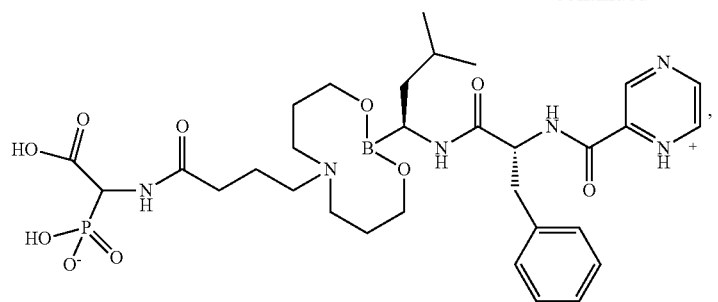
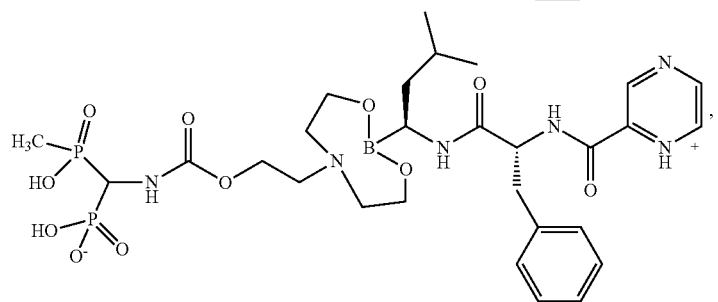
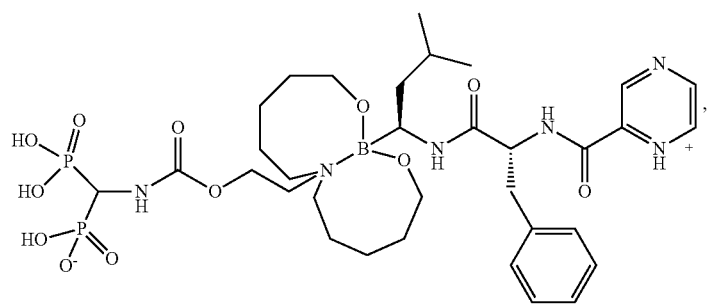
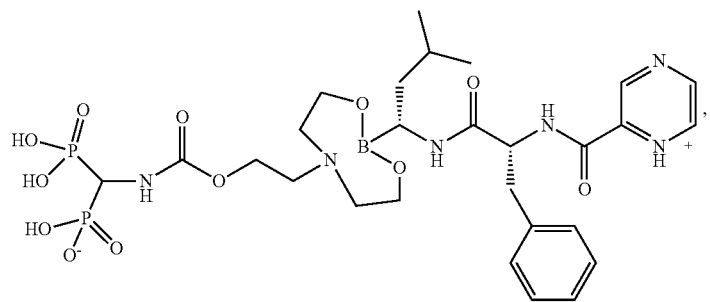
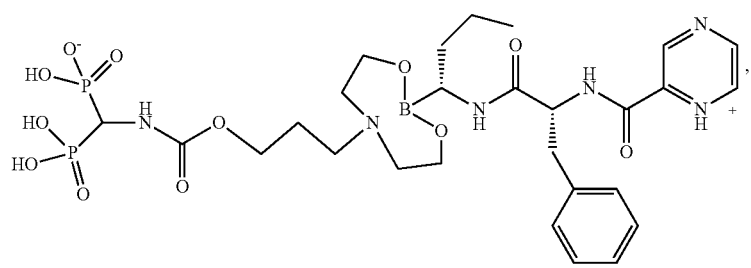

-continued
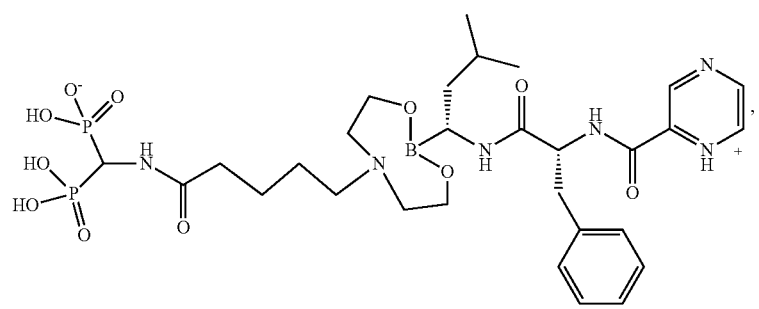
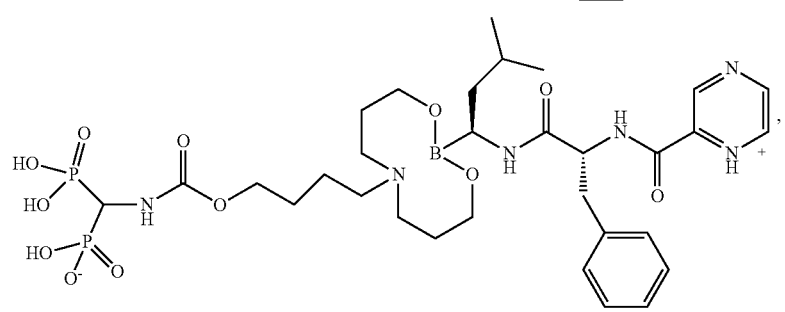
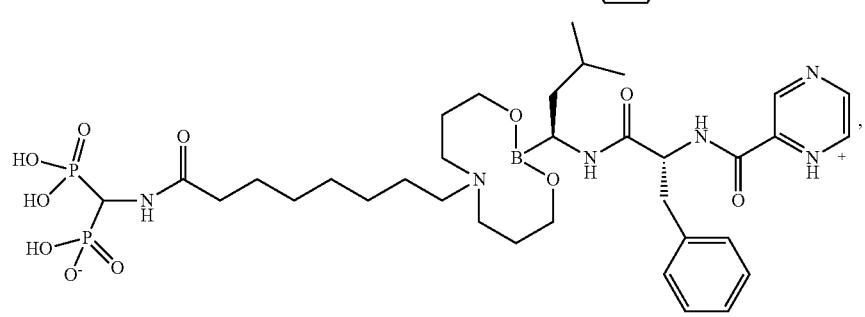
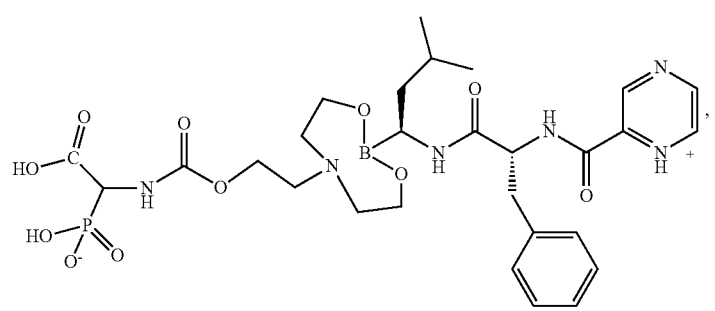
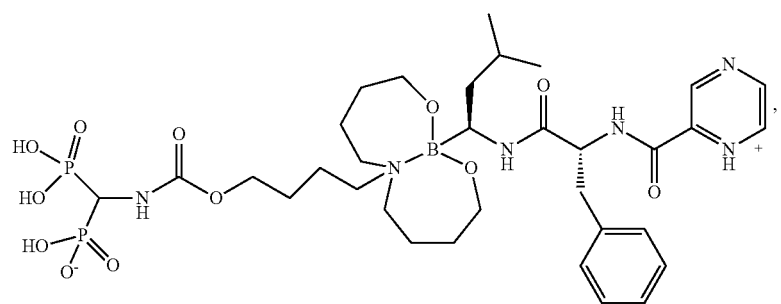

-continued
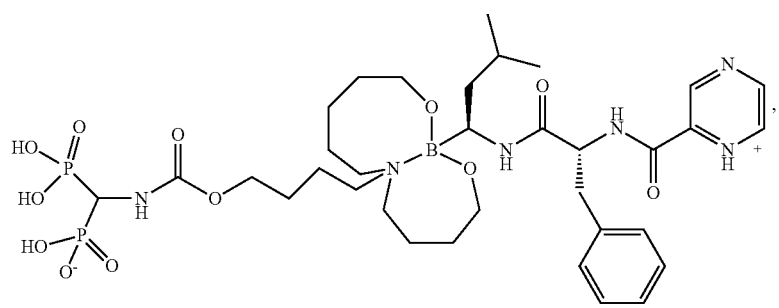
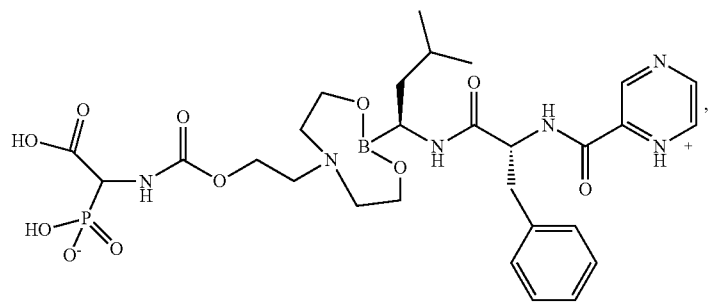
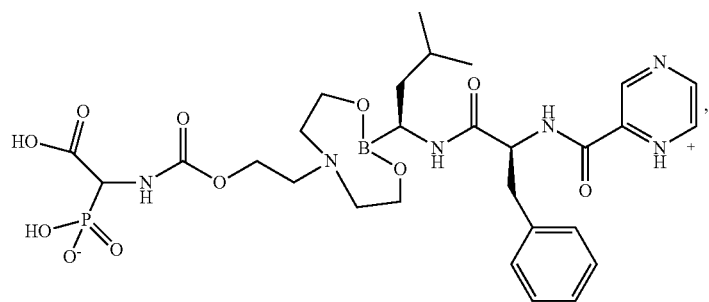
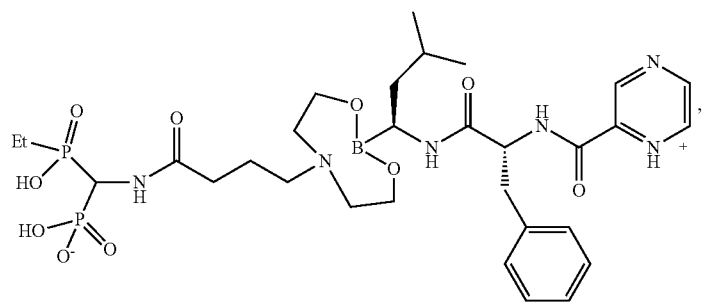
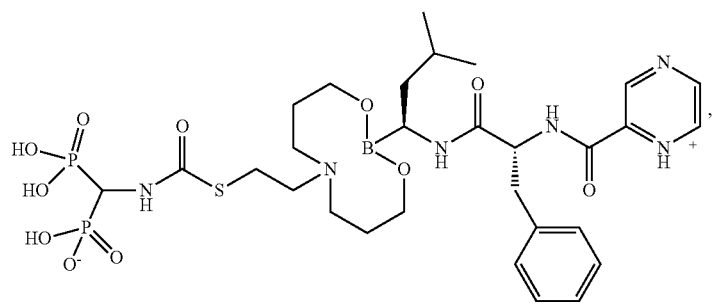

-continued
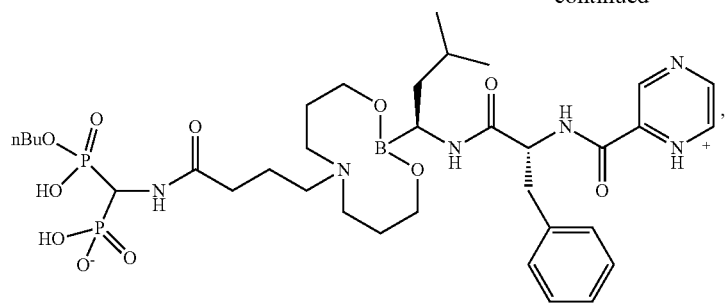
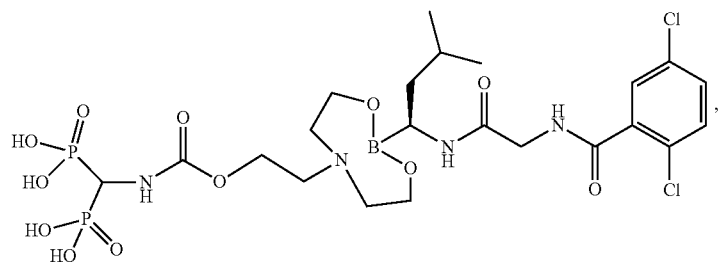
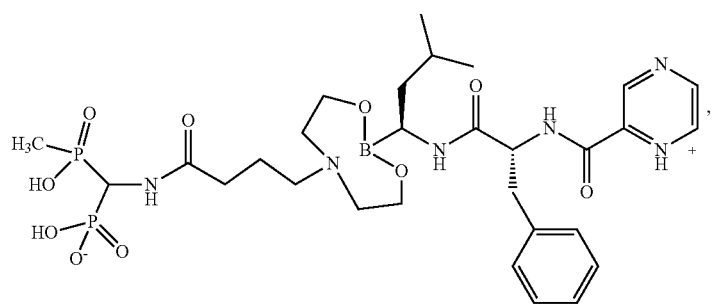
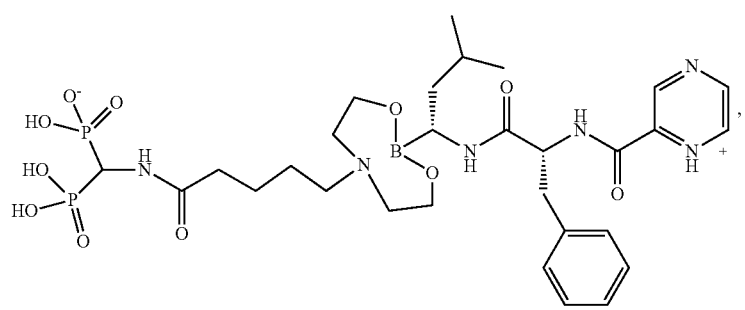
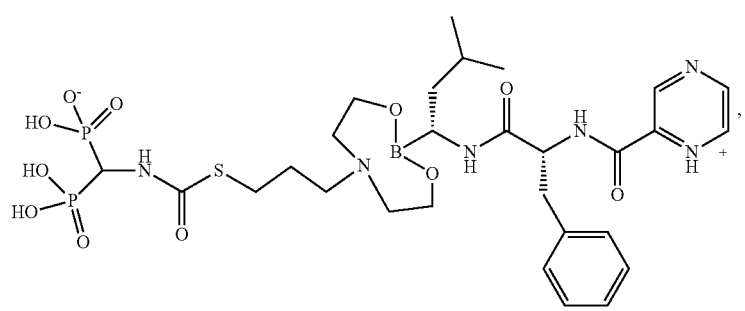

-continued
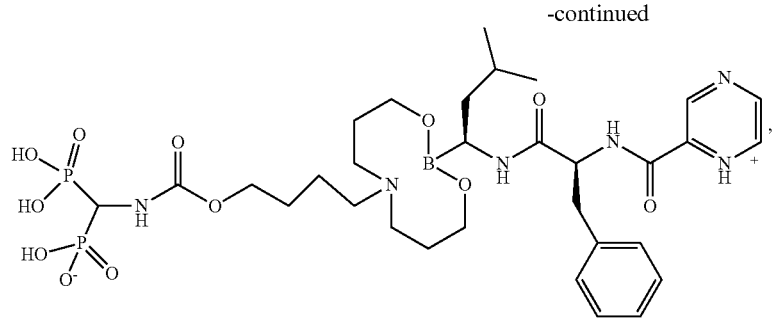
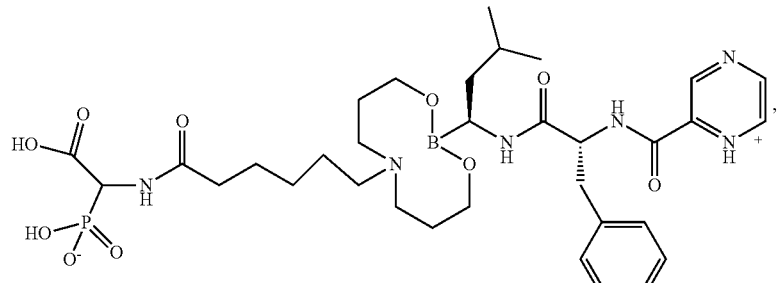
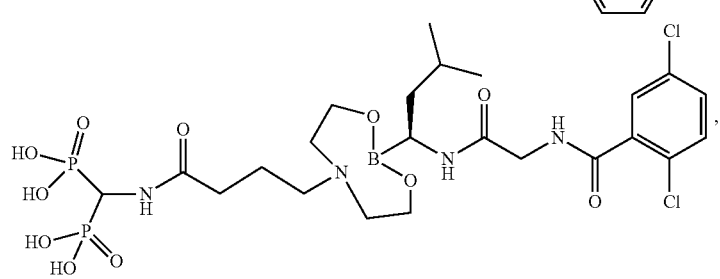
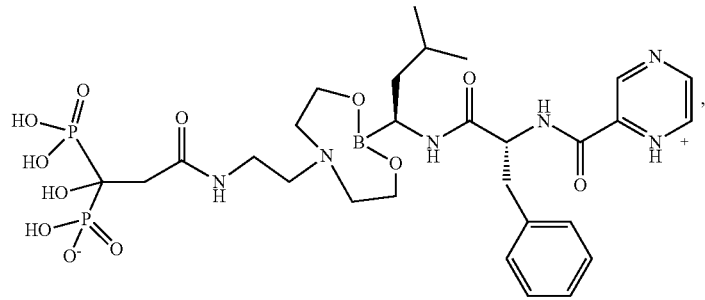
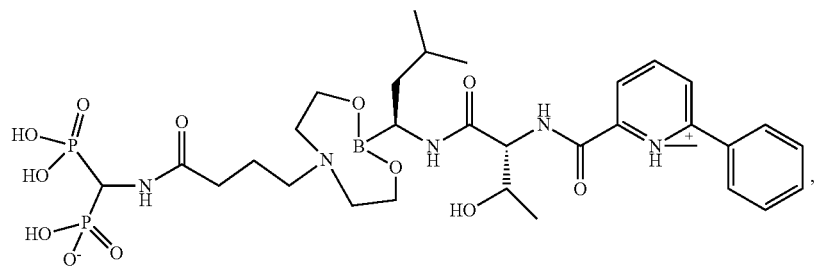
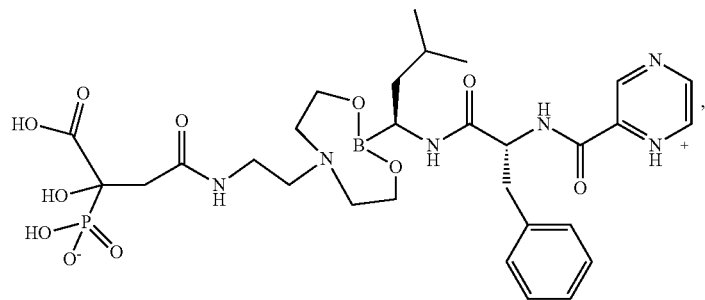

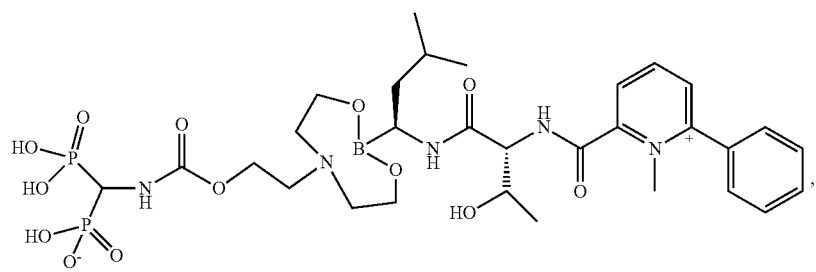
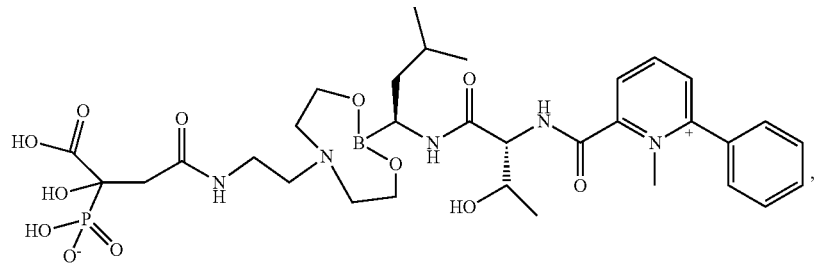
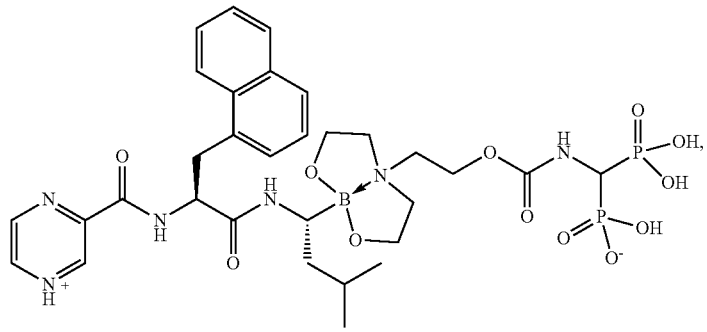
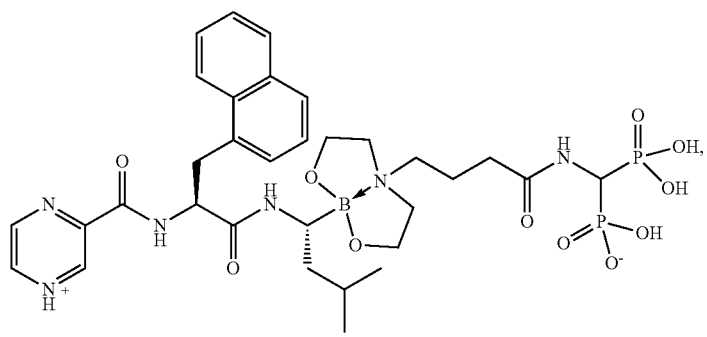
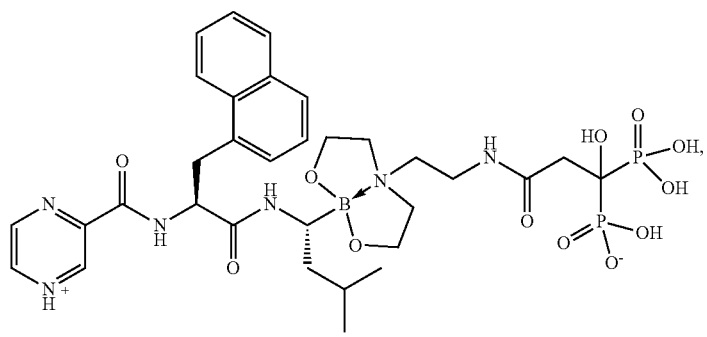

-continued
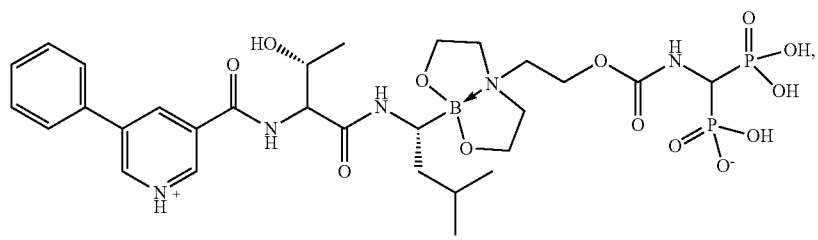
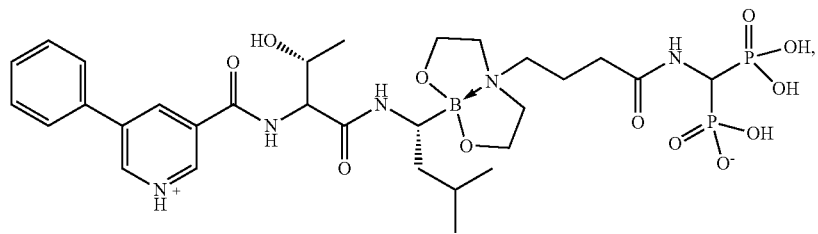
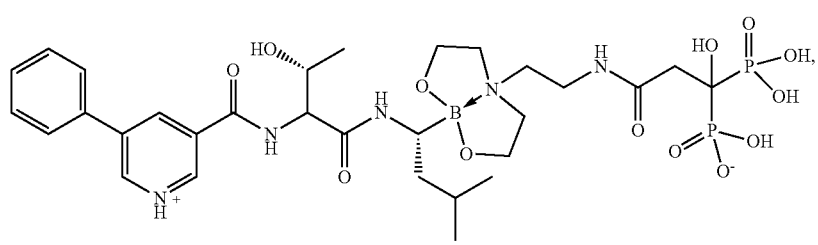
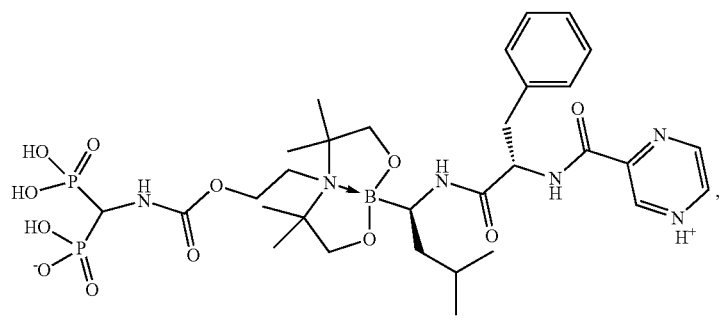
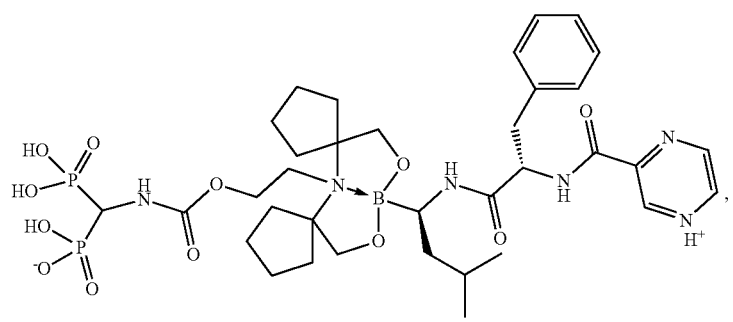
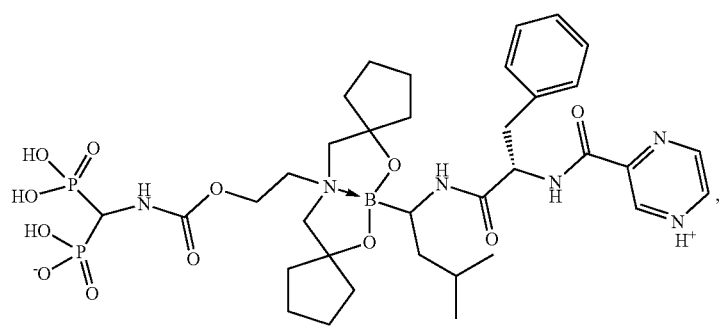

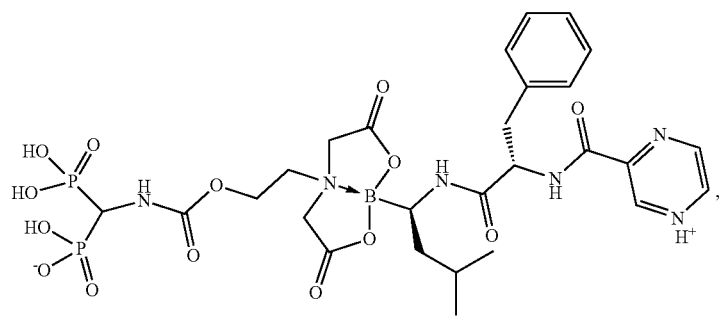,
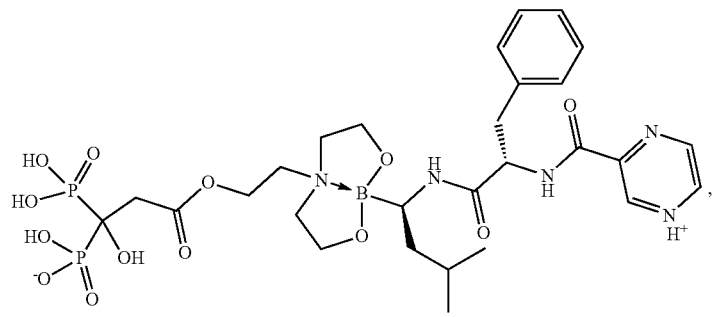,
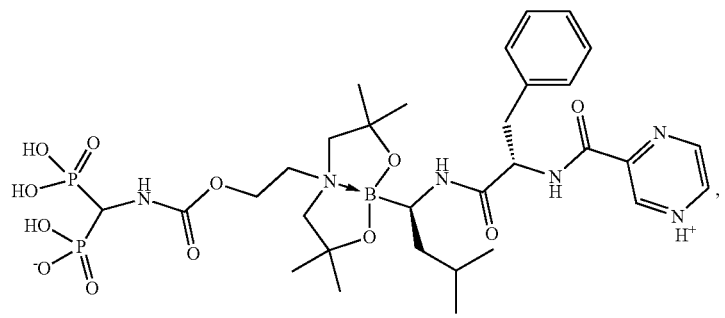,
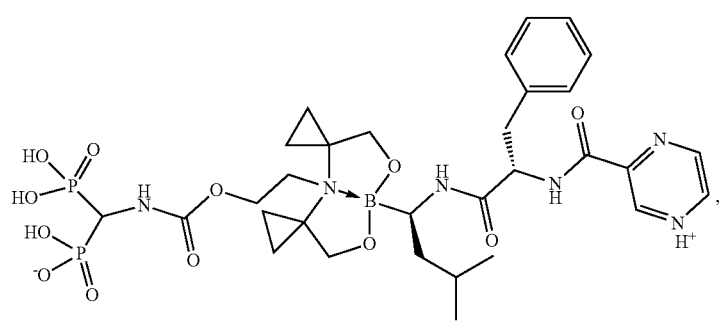,
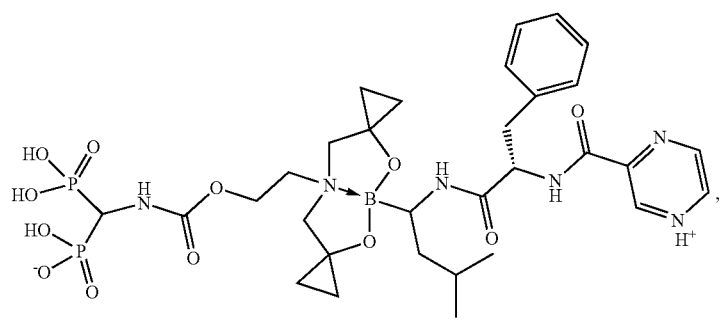,

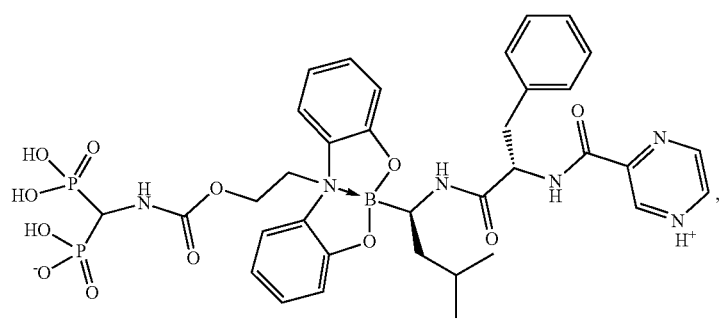
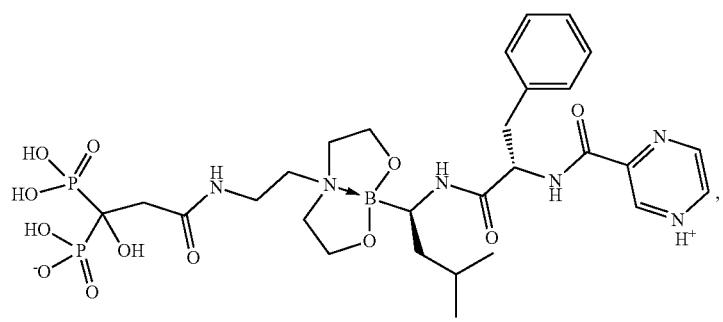
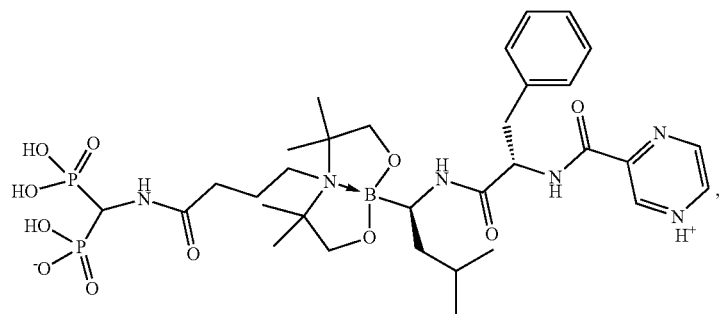
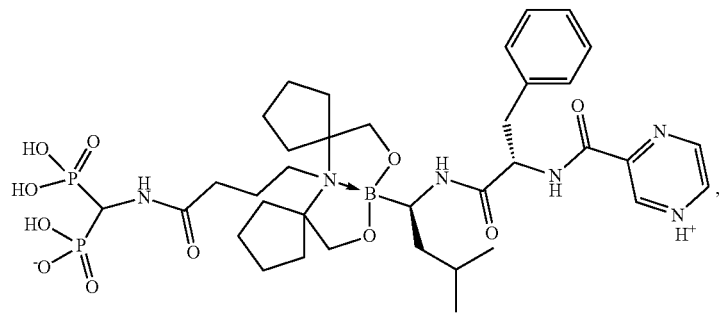
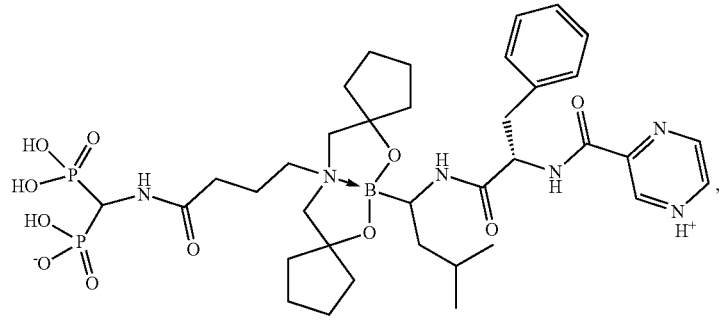

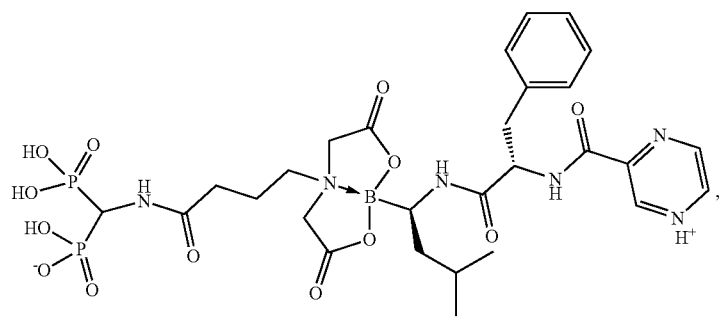
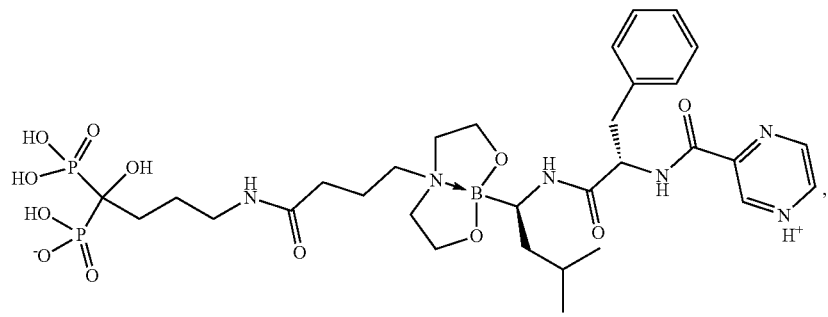
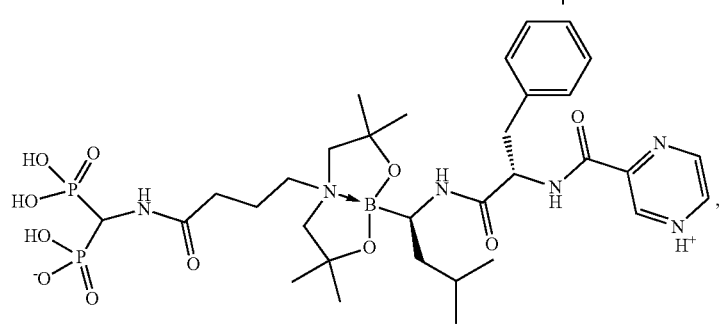
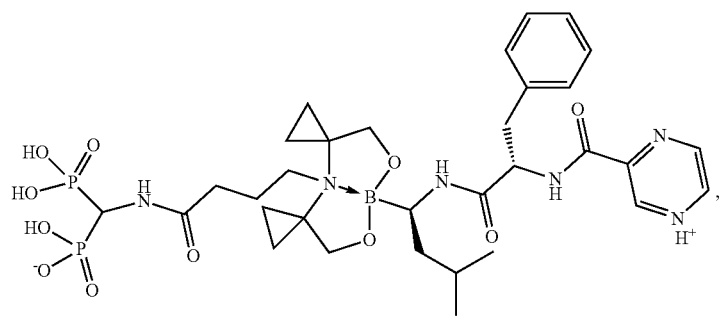
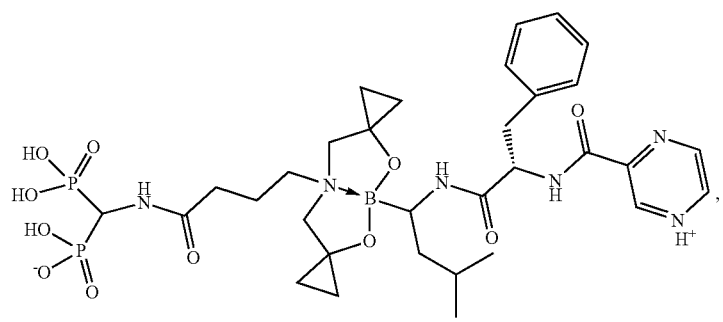

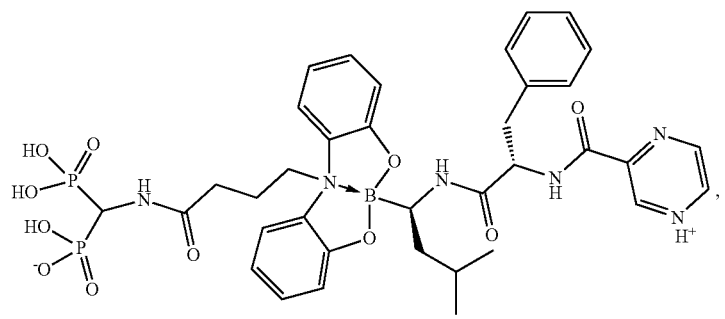
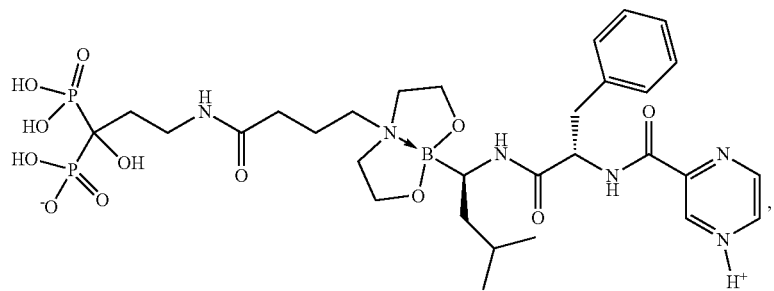
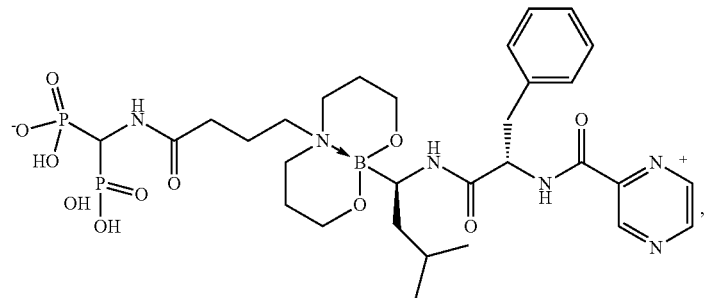
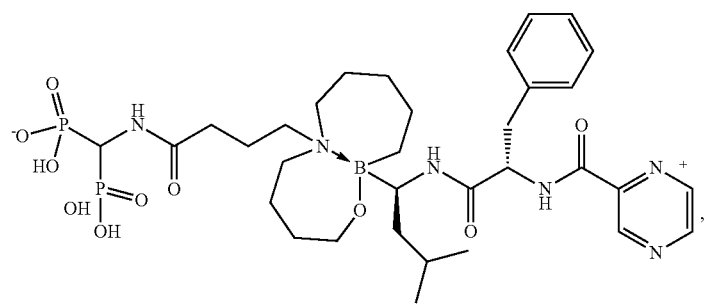
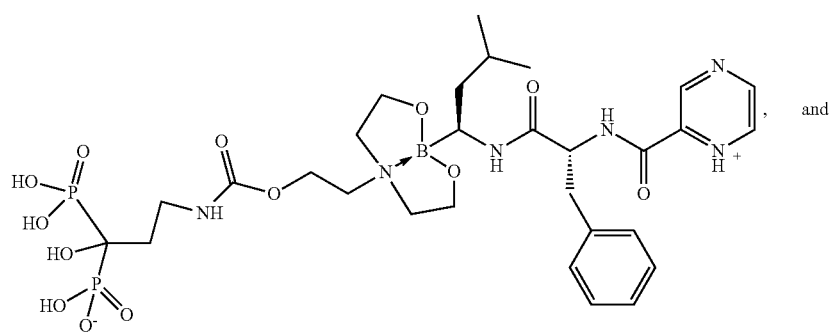

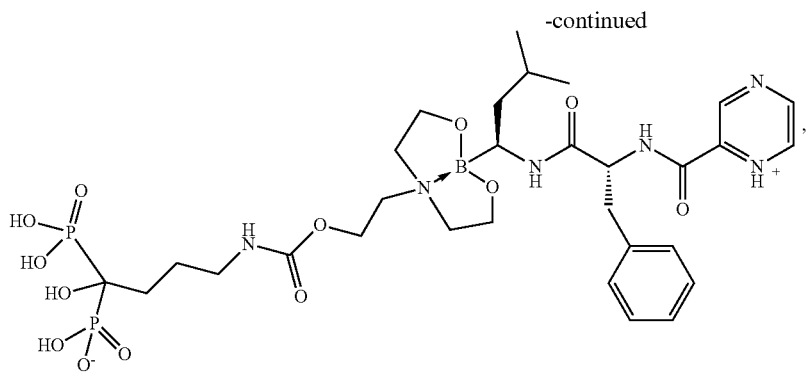

or a pharmaceutically acceptable salt thereof.

10. The compound of claim 9, wherein the compound is

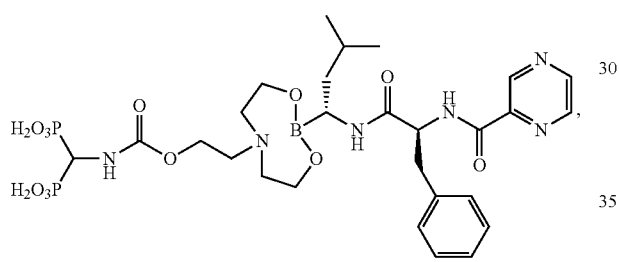

or a pharmaceutically acceptable salt thereof.

11. A composition for controlled local delivery of a therapeutic agent to bone, comprising at least one compound of formula (I) or a pharmaceutically acceptable salt thereof:

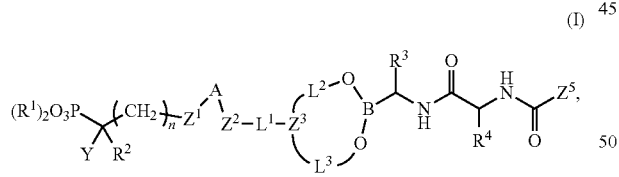

(I)

wherein in formula (I):
each occurrence of $R^1$ is independently selected from the group consisting of hydrogen and alkyl;
$R^2$ is selected from the group consisting of hydrogen and —$OR^{13}$;
$R^3$ is selected from the group consisting of hydrogen and alkyl;
$R^4$ is selected from the group consisting of hydrogen, alkyl, aryl, and alkylaryl wherein the alkyl, group is optionally substituted with hydroxyl group;
$L^1$ is selected from the group consisting of alkyl, and alkyl-$Z^4$C(O)$NR^{10}$;
$L^2$ is aryl or an alkyl chain of $C_1$-$C_6$ alkyl, wherein any carbon atom in the alkyl chain is optionally substituted with one to two substituents selected from the group consisting of alkyl, cycloalkyl, and carbonyl;
$L^3$ is aryl or an alkyl chain of $C_1$-$C_6$ alkyl, wherein any carbon atom in the alkyl chain is optionally substituted with one to two substituents selected from the group consisting of alkyl, cycloalkyl, and carbonyl; or
Y is selected from the group consisting of —PO($OR^8$)($OR^9$), —PO($R^9$)($OR^8$), and —$CO_2R^8$;
$Z^1$ is selected from the group consisting of $CH_2$ and $NR^6$;
A is C(=O);
$Z^2$ is selected from the group consisting of $CH_2$, $NR^{11}$, S, and O;
$Z^3$ is N;
$Z^4$ is selected from the group consisting of $CH_2$ and O;
$Z^5$ is selected from the group consisting of

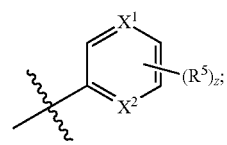

each occurrence of $R^5$ is independently selected from the group consisting of alkyl, aryl, F, Cl, Br, and I;
$X^1$ is selected from the group consisting of $CR^{15}$ and N;
$X^2$ is selected from the group consisting of $CR^{16}$ and N;
$R^6$ is selected from the group consisting of hydrogen and alkyl;
$R^8$, $R^9$, and $R^{10}$ are each independently selected from the group consisting of hydrogen and alkyl;
$R^{11}$ and $R^{13}$ are each independently selected from the group consisting of hydrogen and alkyl;
$R^{15}$ and $R^{16}$ are each independently selected from the group consisting of hydrogen, alkyl, aryl, F, Cl, Br, and I;
n is an integer from 0 to 10; and
z is an integer from 0 to 2;
or a pharmaceutically acceptable salt thereof.

12. The composition of claim 11, wherein the compound is selected from the group consisting of:

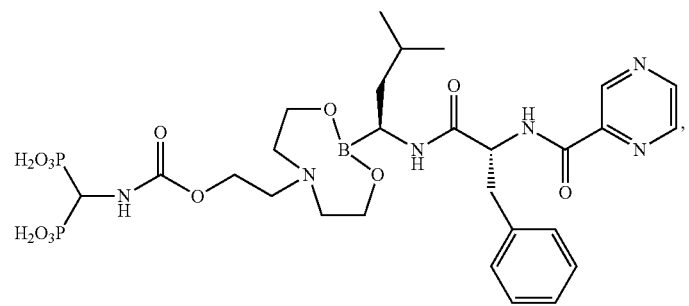
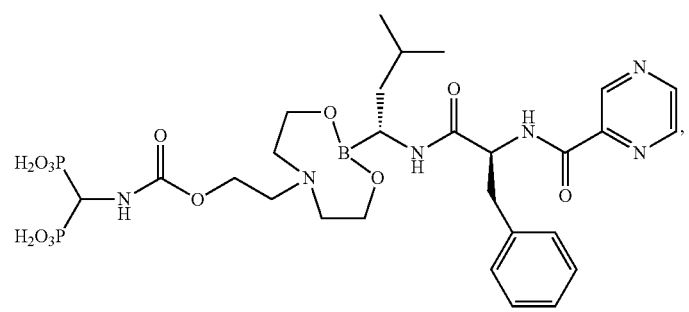
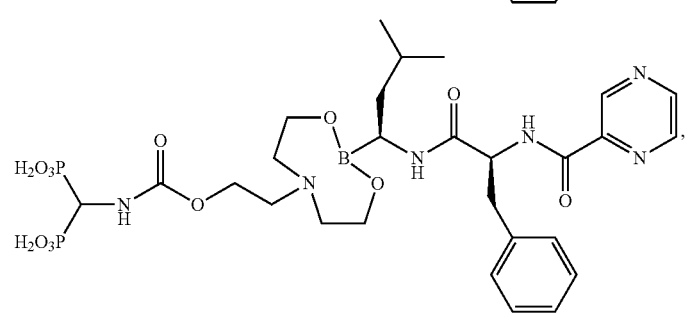
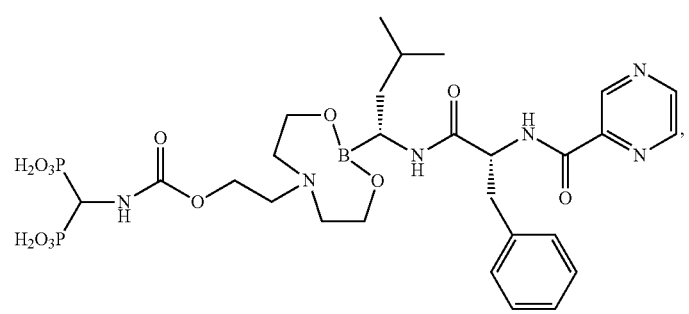
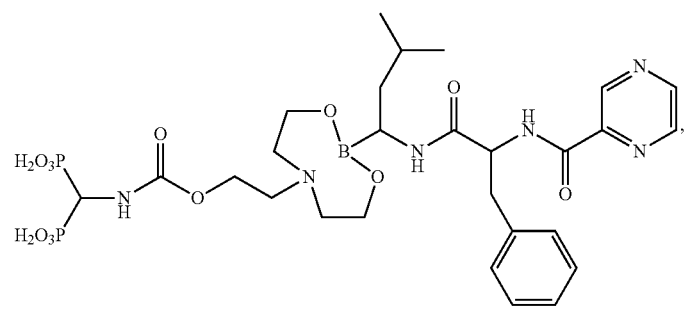

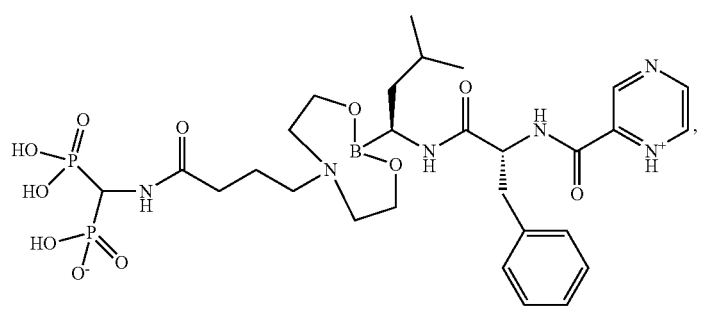
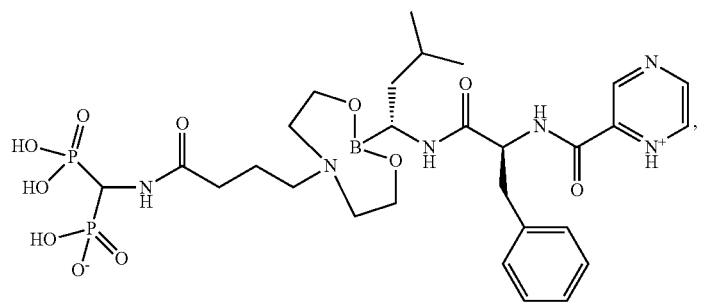
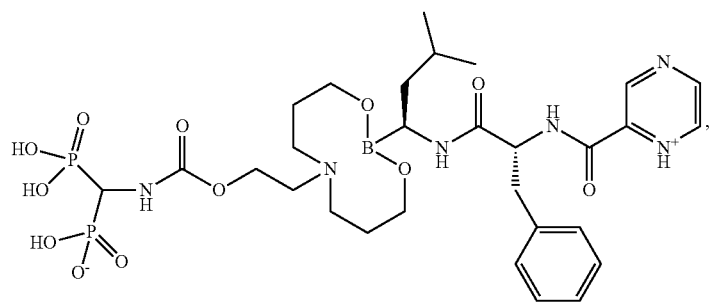
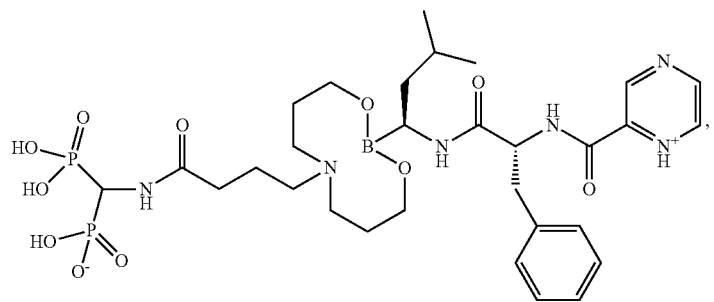
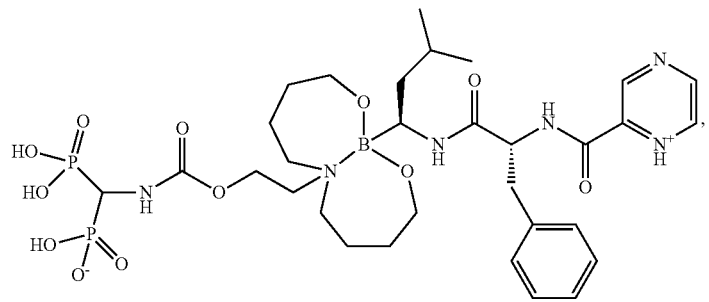

-continued
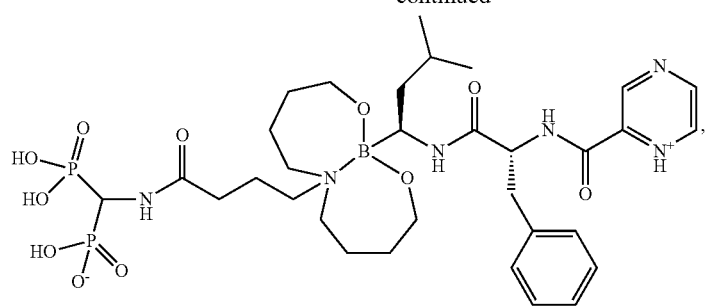
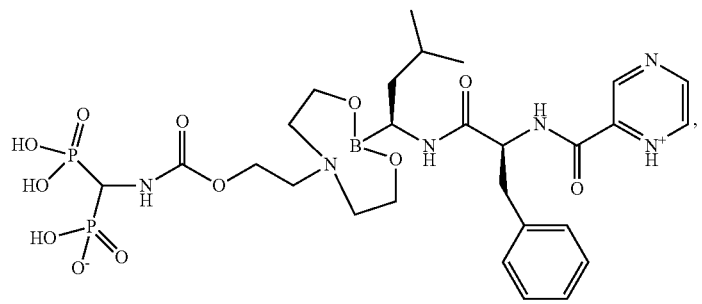
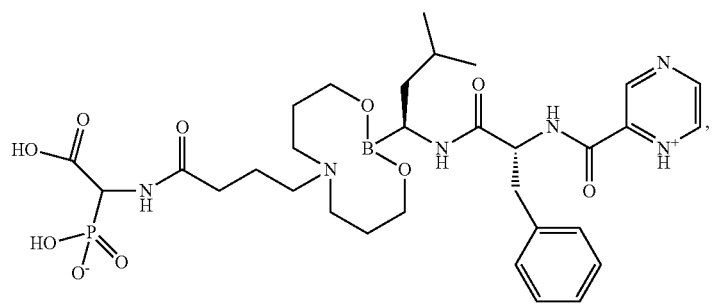
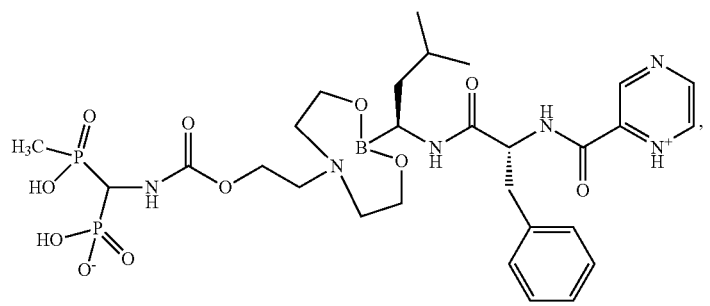
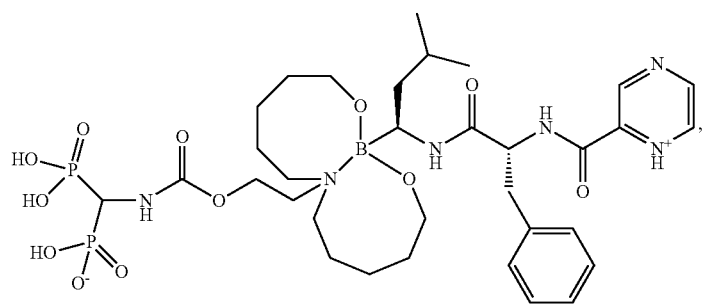

-continued
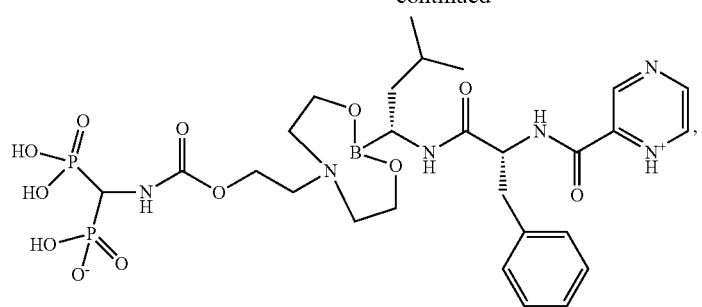
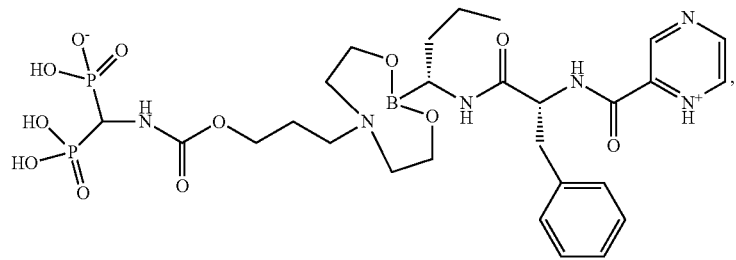
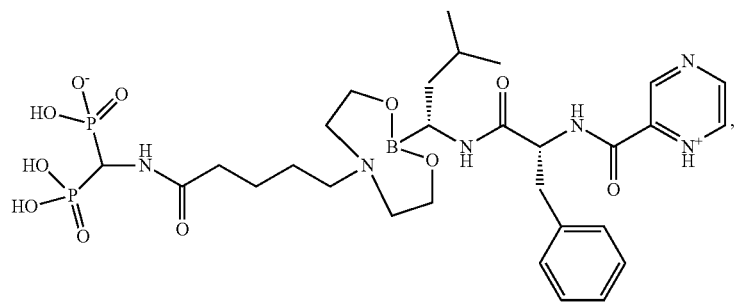
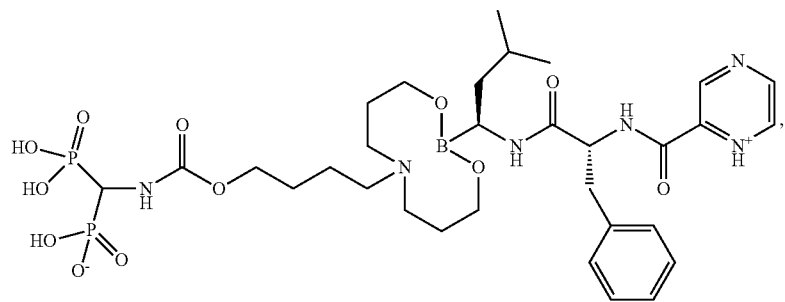
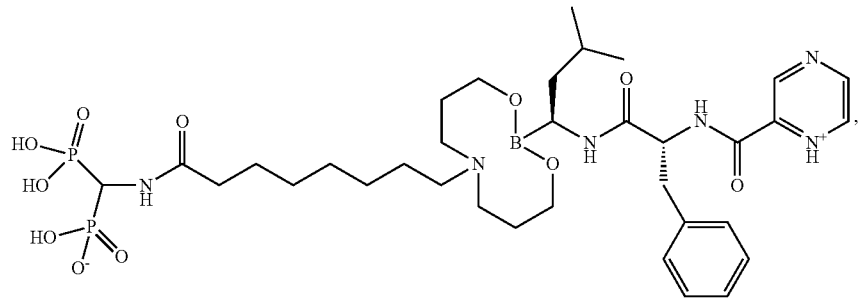

-continued
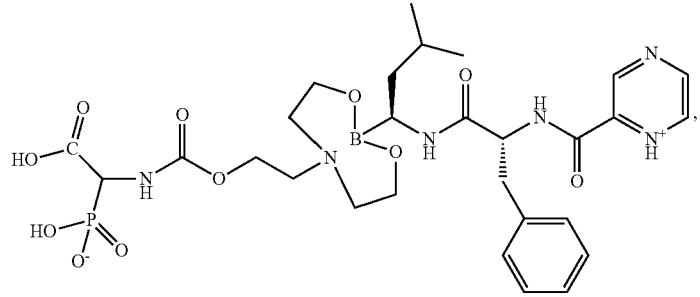
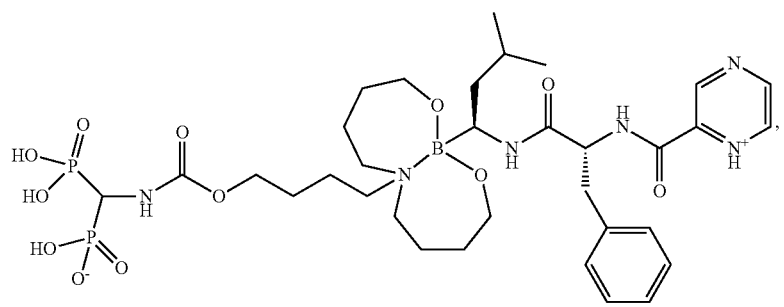
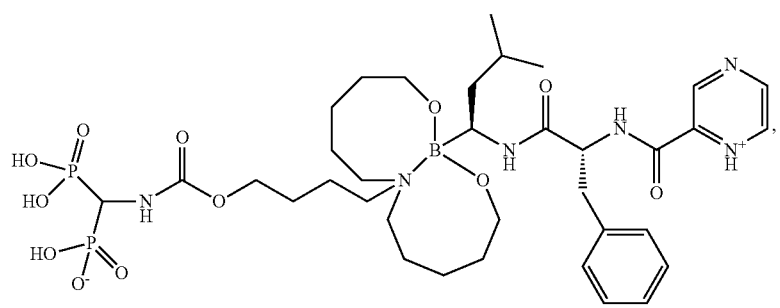
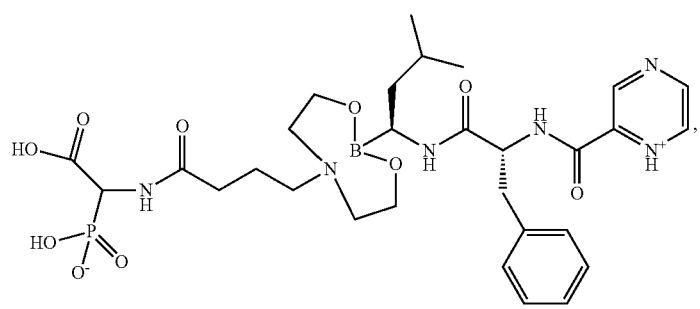
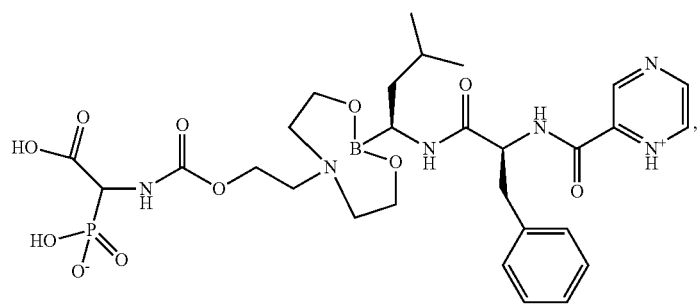

-continued
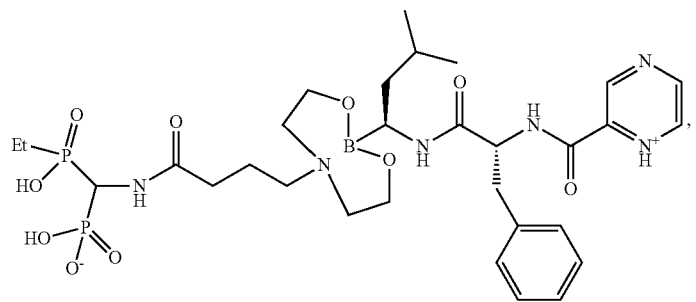
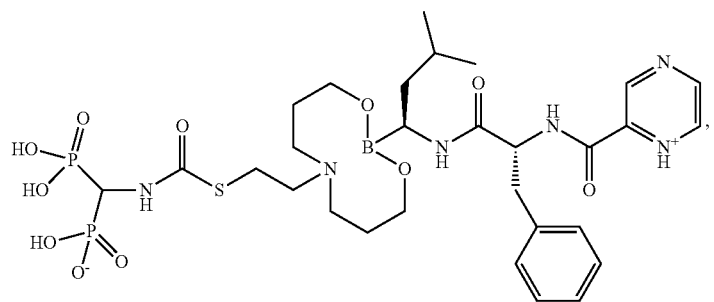
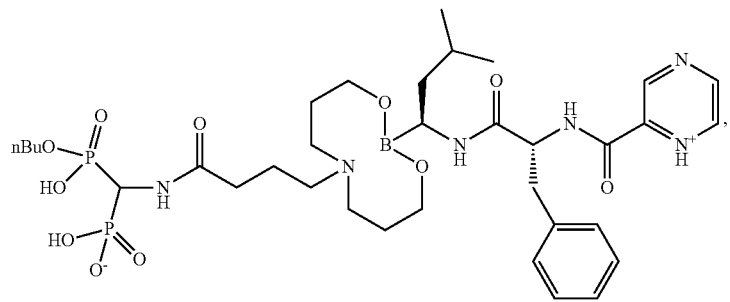
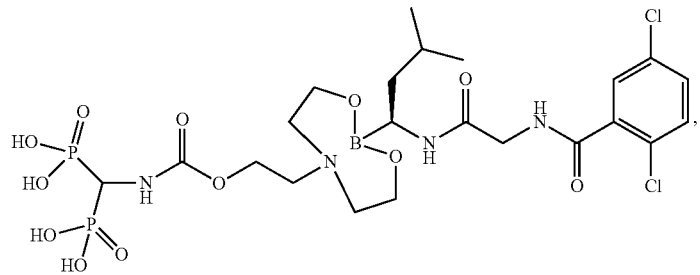
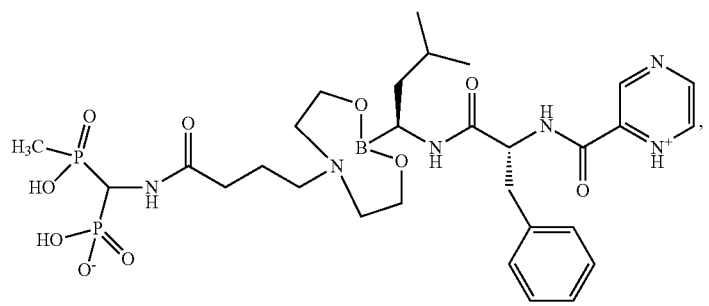

-continued
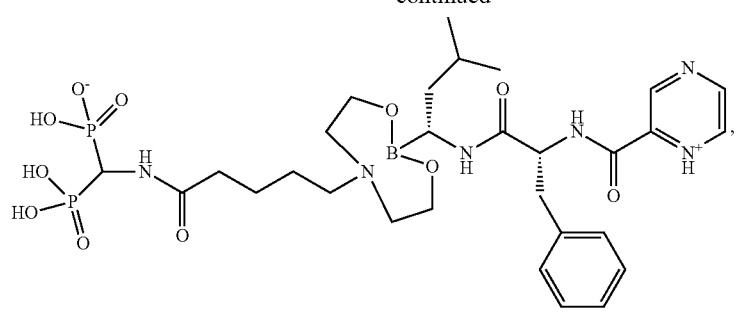
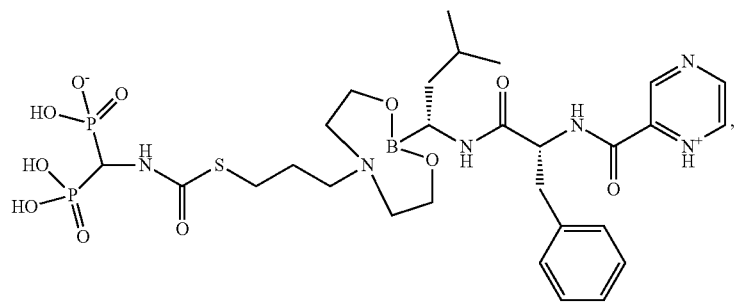
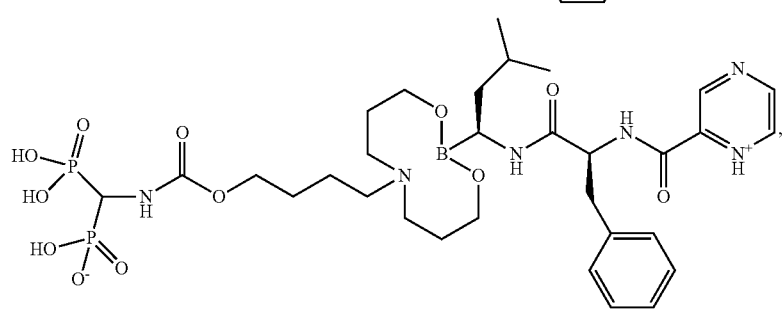
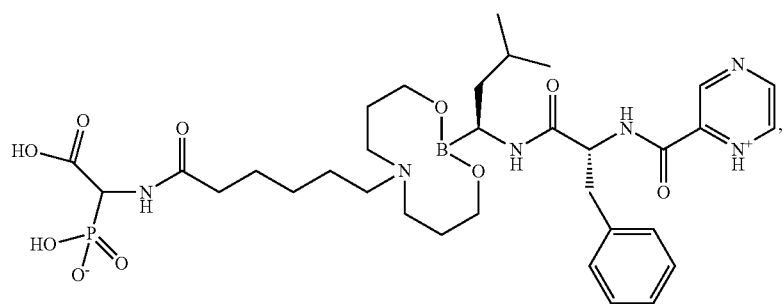
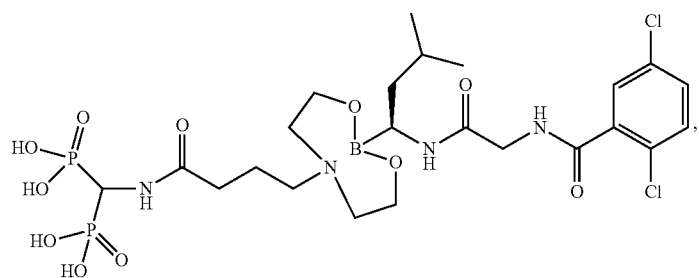

-continued
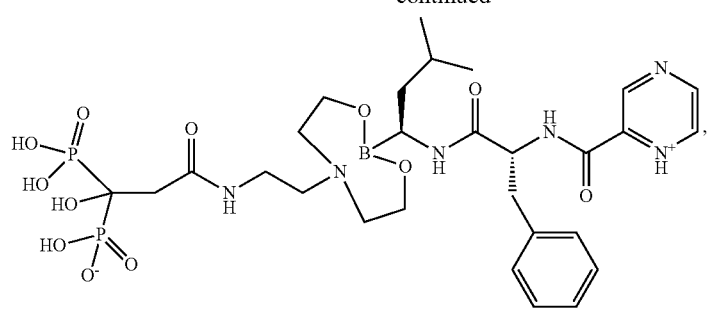
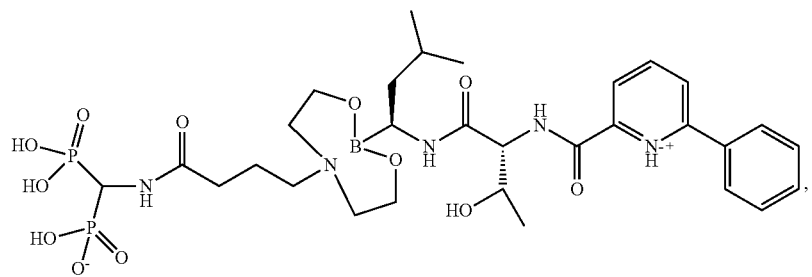
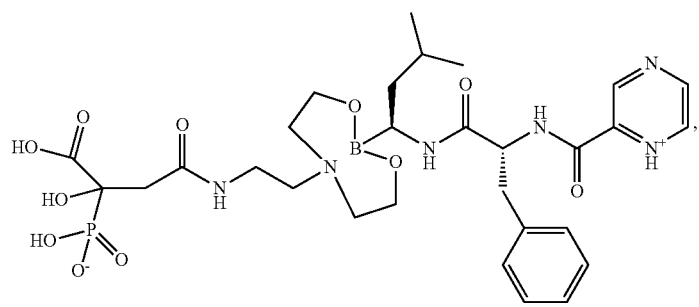
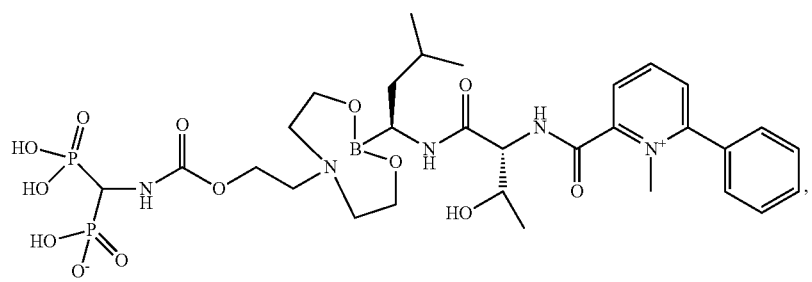
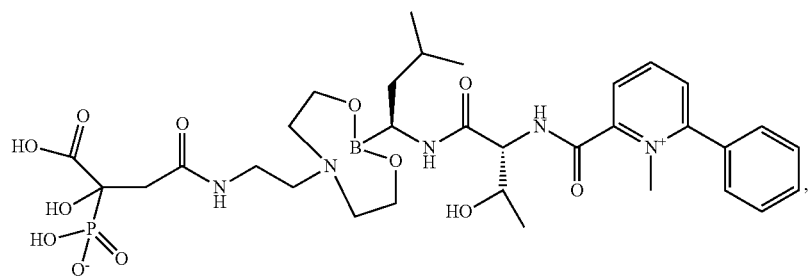

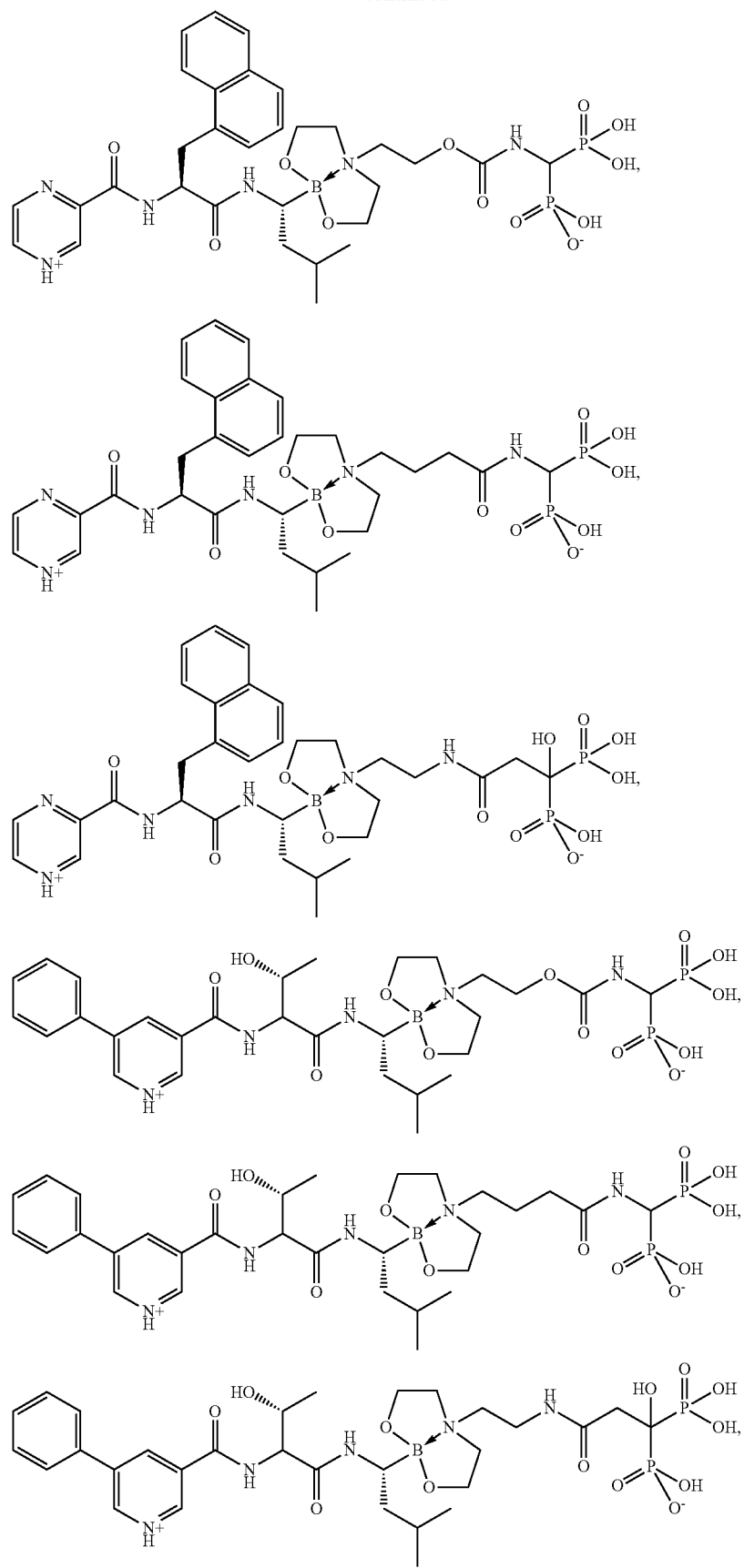

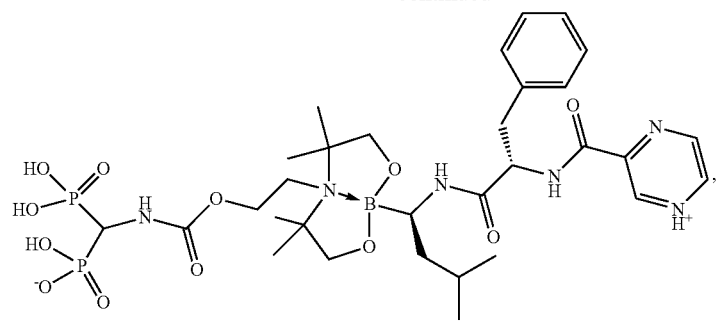
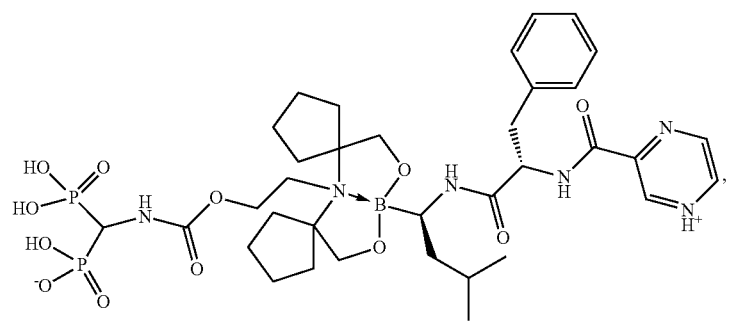
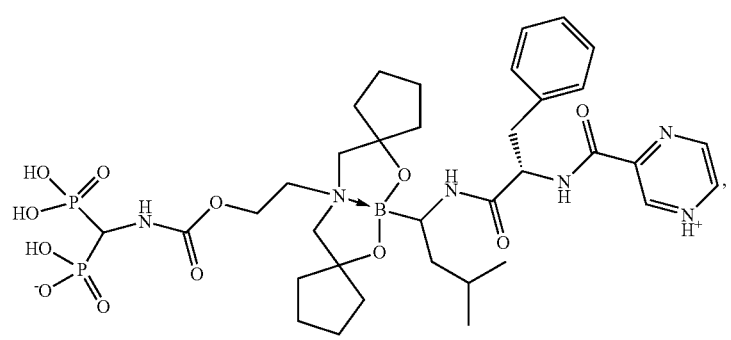
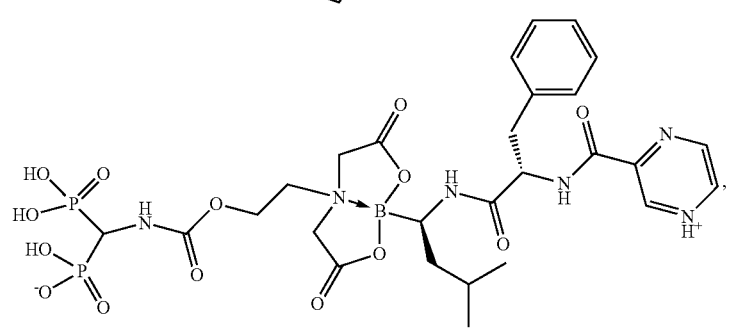
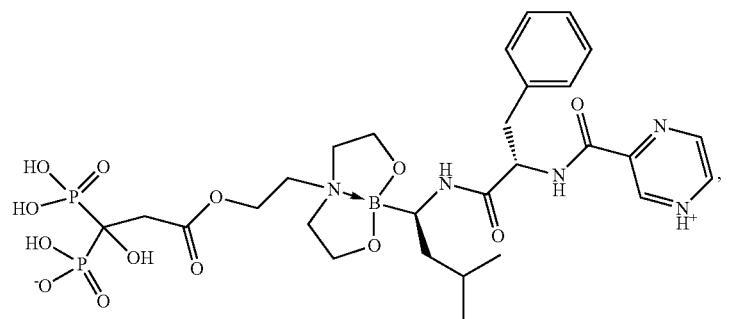

-continued
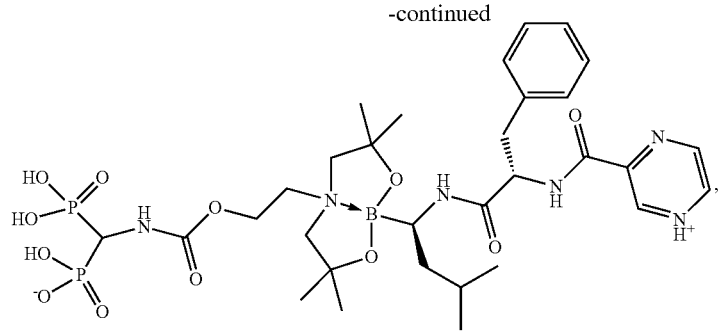
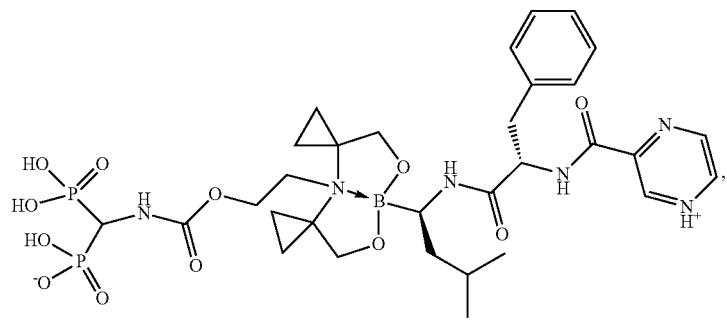
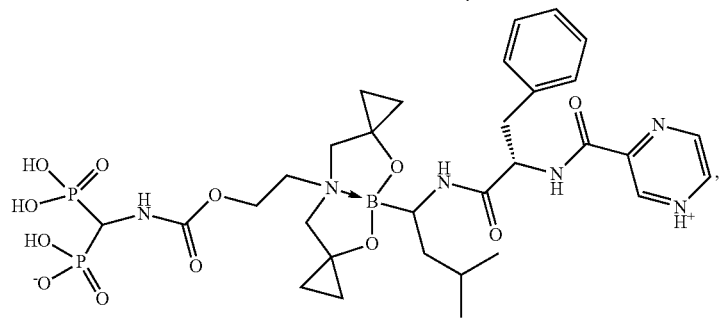
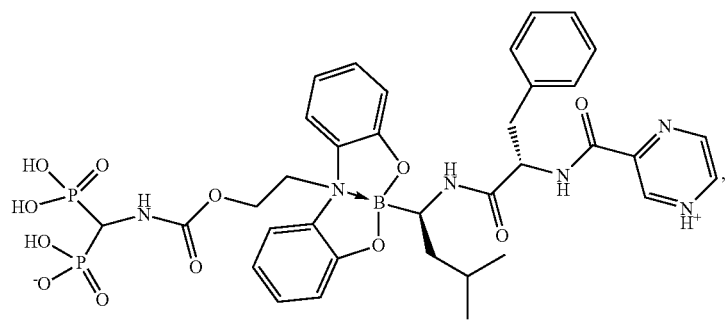
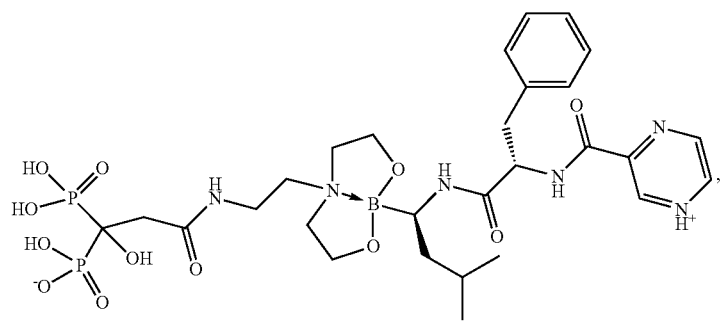

-continued
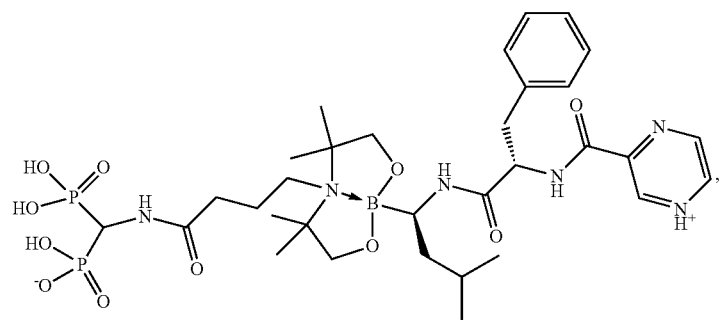
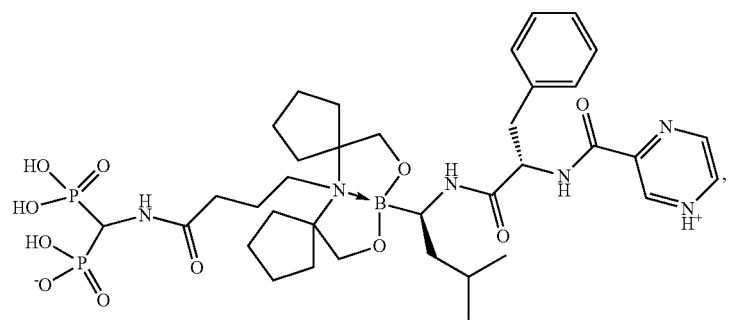
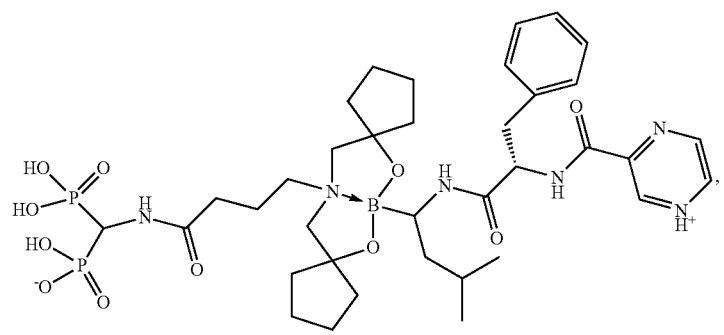
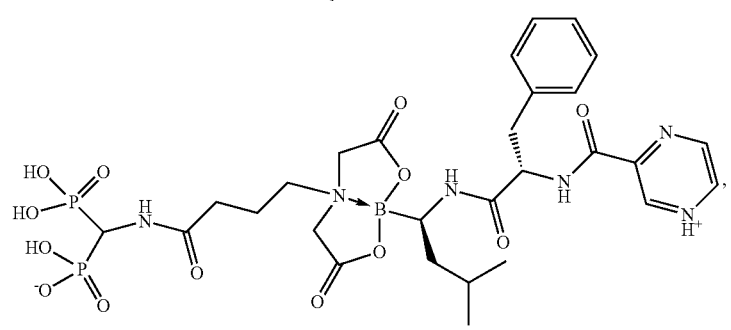
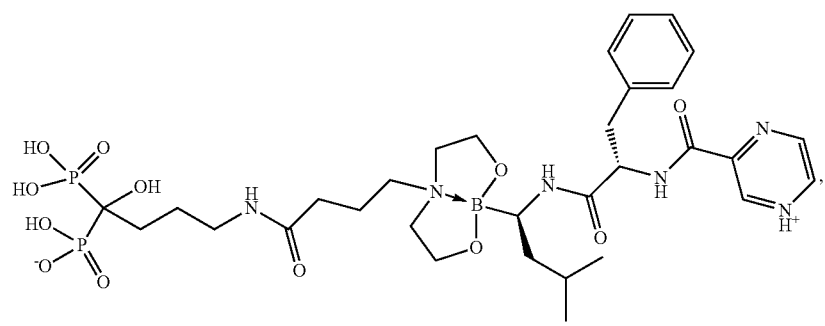

-continued
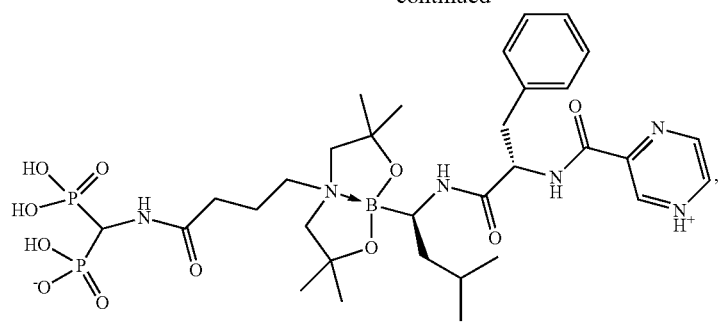
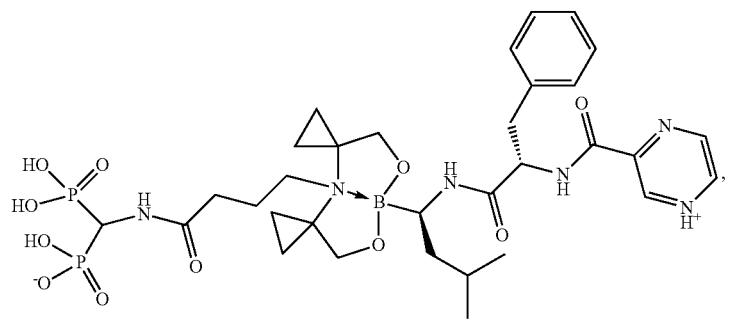
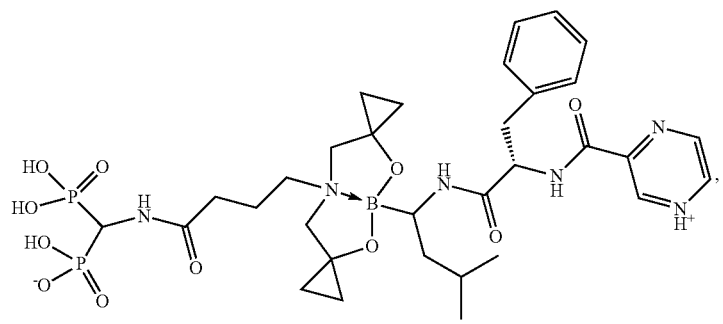
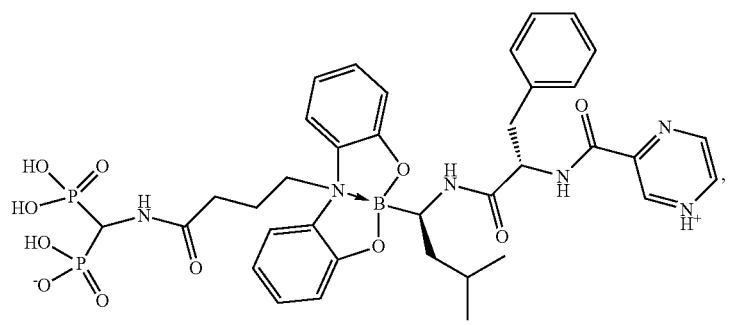
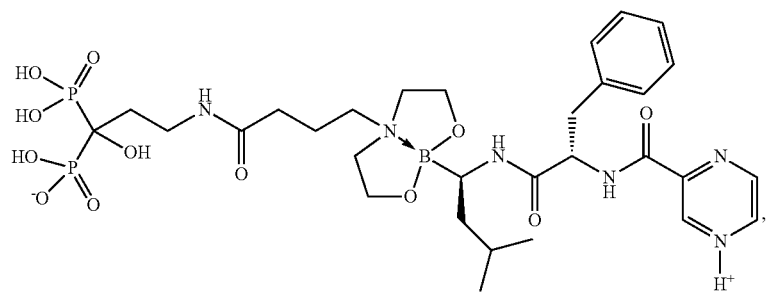

-continued

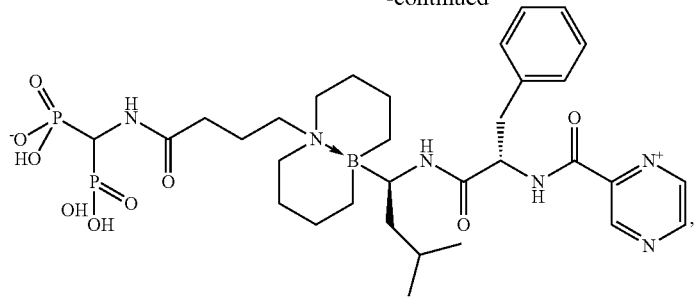

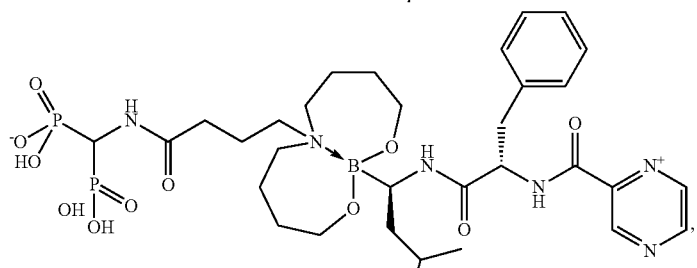

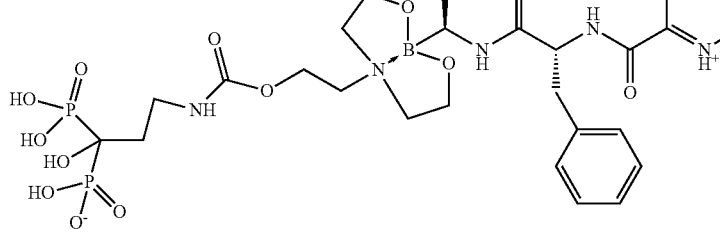

and

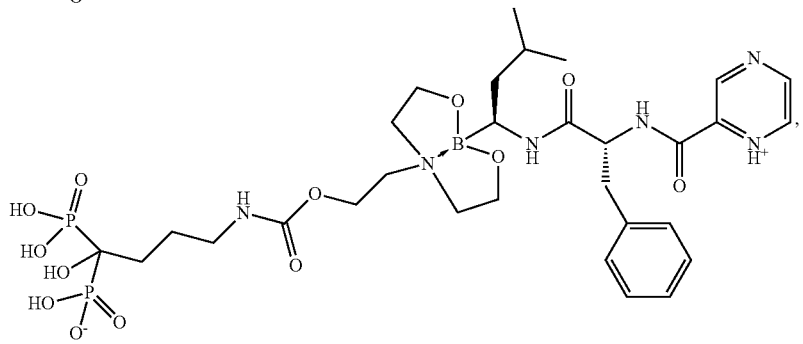

or a pharmaceutically acceptable salt thereof.

13. The composition of claim 12, wherein the compound is

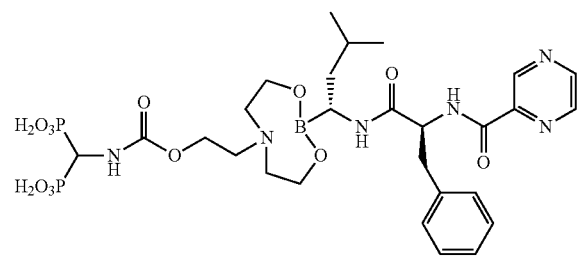

or a pharmaceutically acceptable salt thereof.

14. The composition of claim 11, wherein the composition further comprises at least one pharmaceutically acceptable carrier.

15. The composition of claim 11, wherein the therapeutic agent is controllably released from the compound at a site in need of bone formation.

16. A method of promoting bone formation at a site in need of bone formation in a subject or reducing bone resorption in a subject in need of less bone resorption, or both, the method comprising administering a therapeutically effective amount of a composition comprising at least one compound according to claim 1.

17. A method of treating a disease selected from the group consisting of multiple myeloma and bone cancer in a subject in need thereof, the method comprising administering a therapeutically effective amount of a composition comprising at least one compound according to claim 1.

18. The method of claim 16, wherein the compound is selected from the group consisting of:
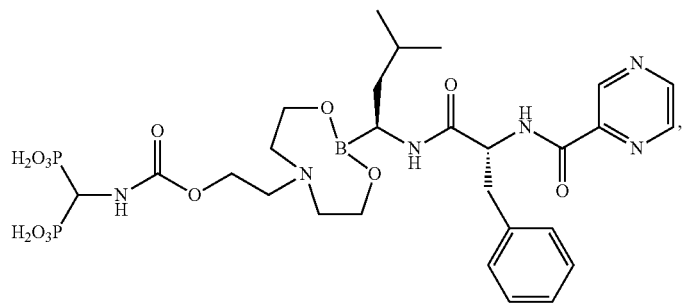
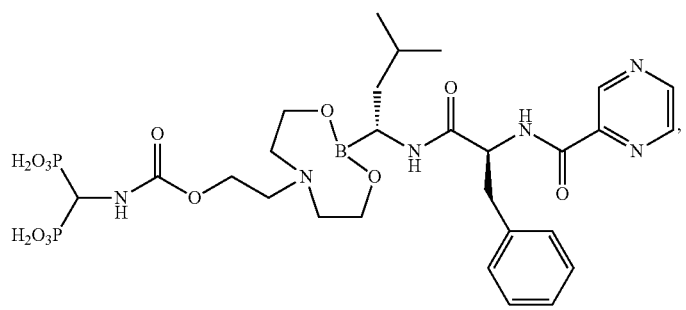
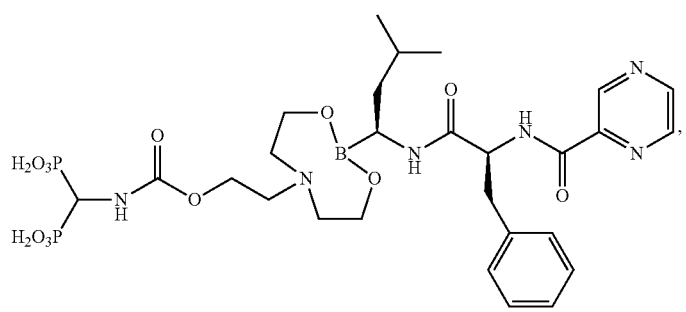
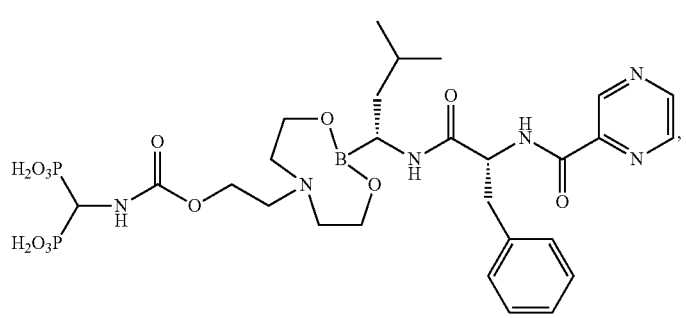
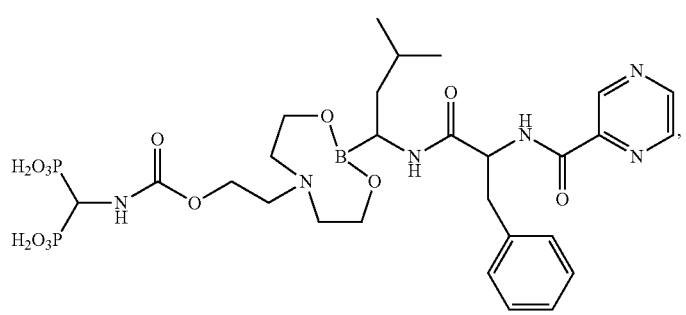

-continued
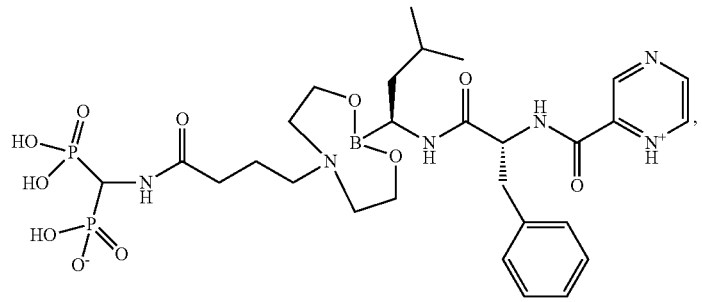
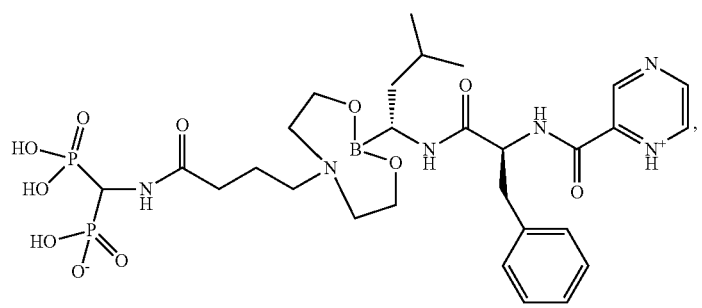
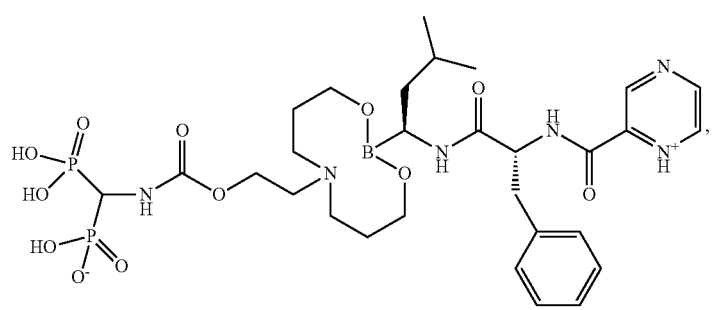
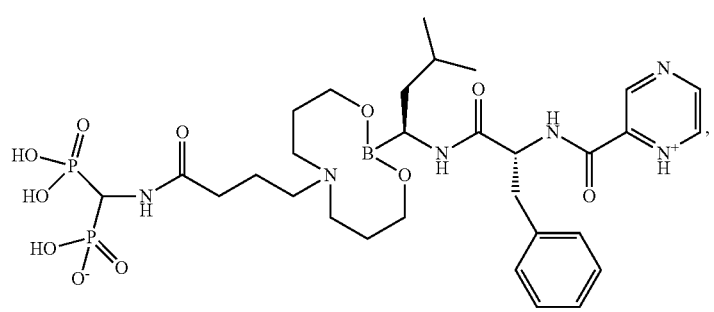
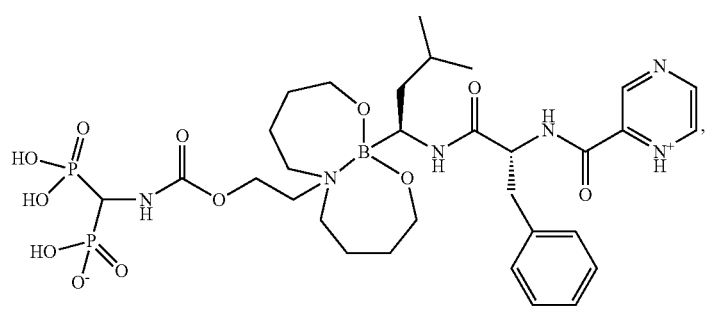

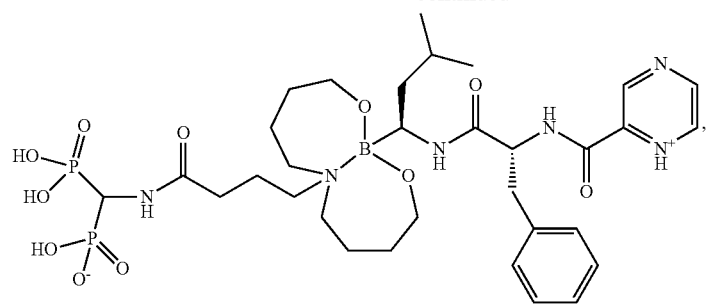
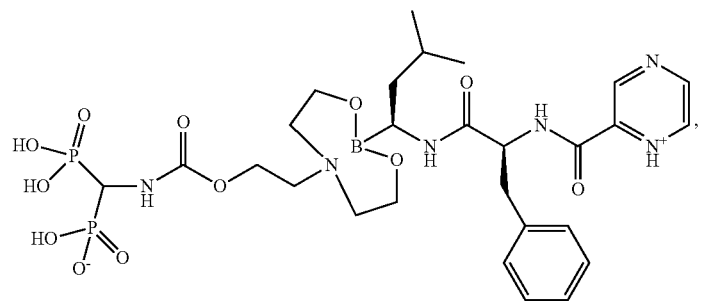
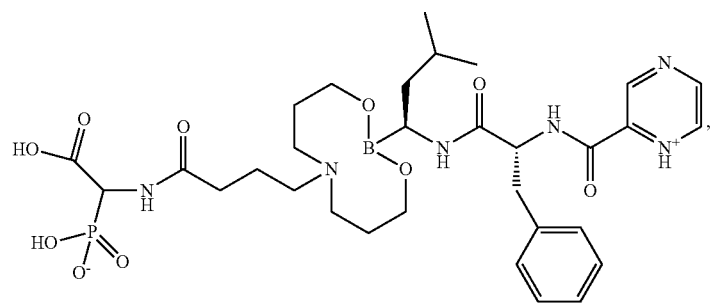
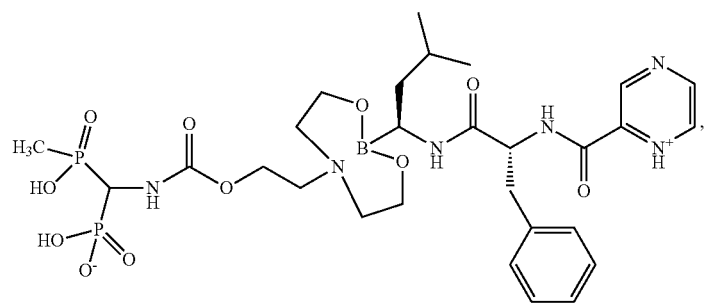
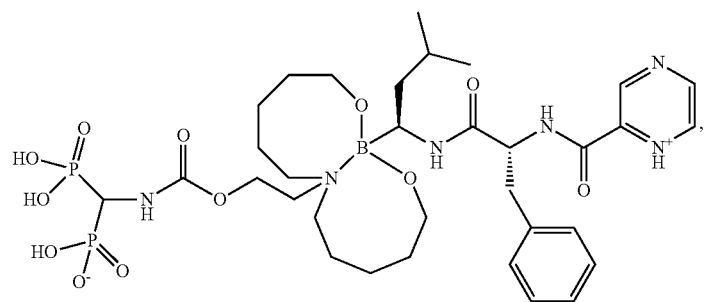

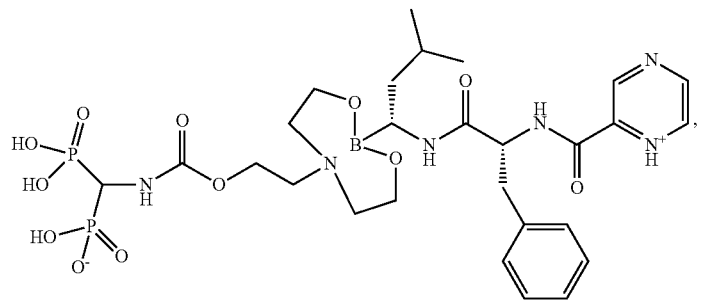
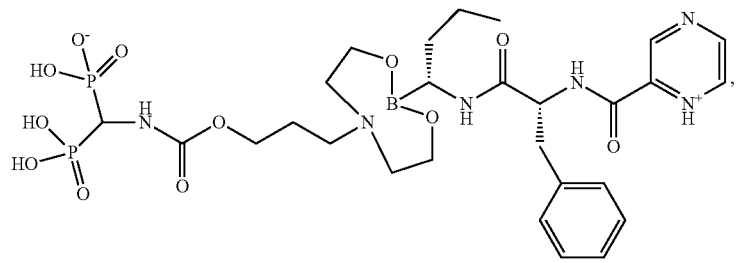
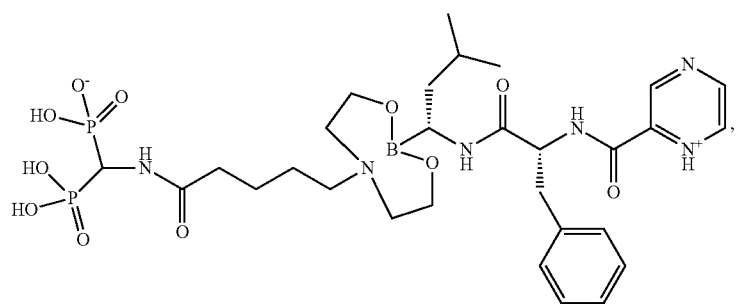
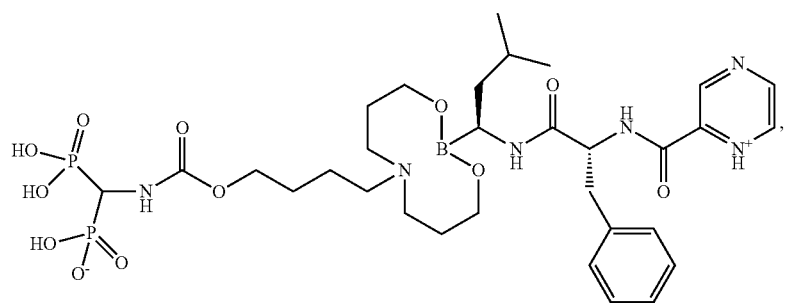
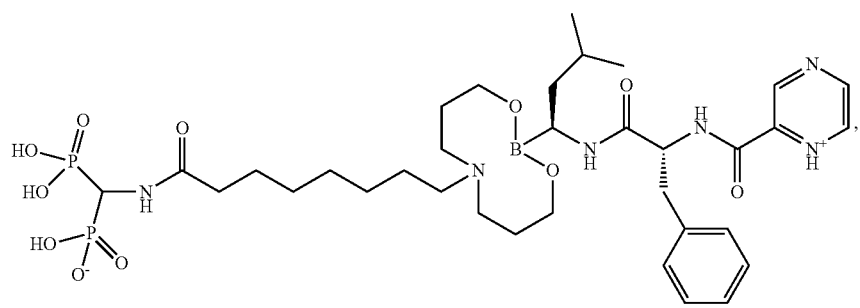

-continued
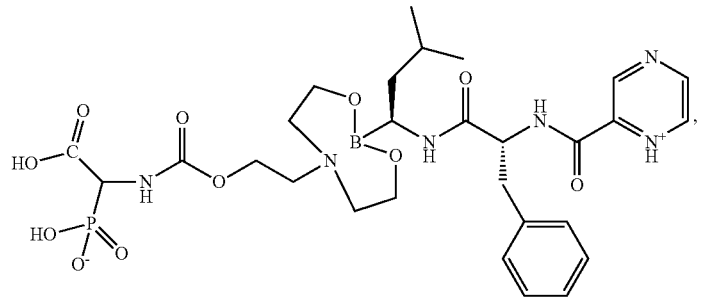
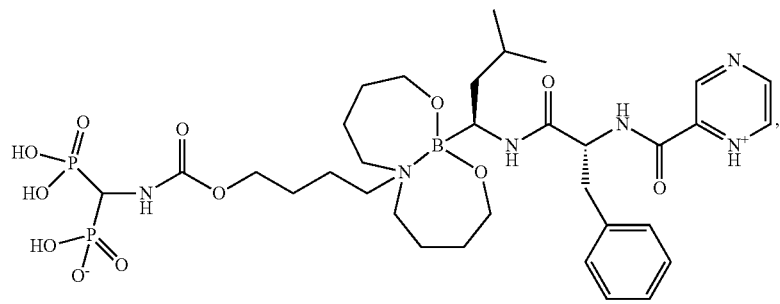
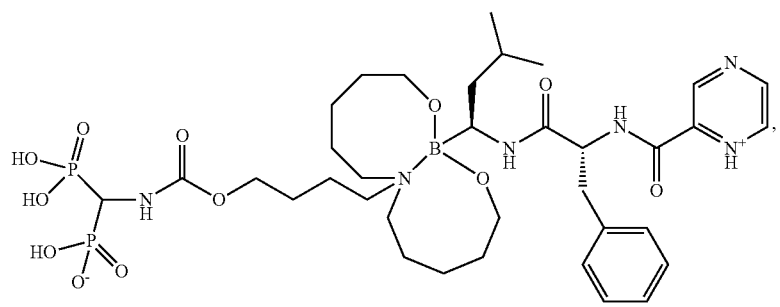
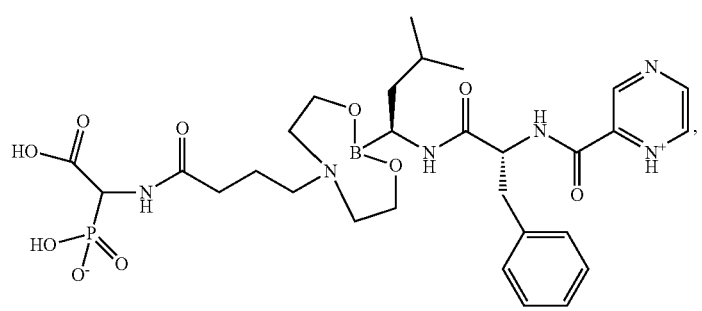
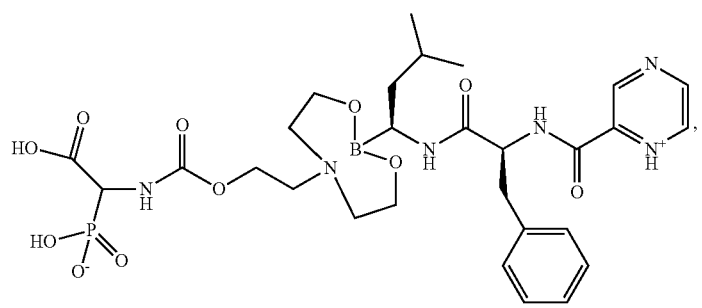

-continued
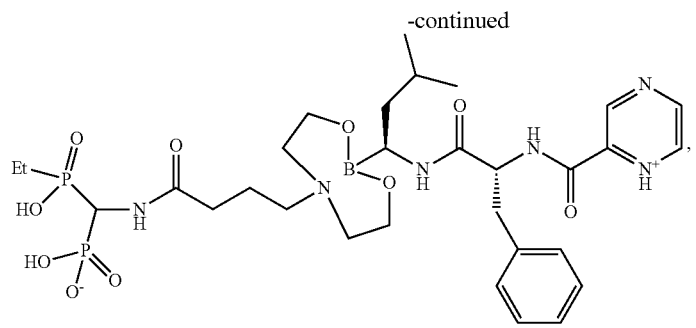
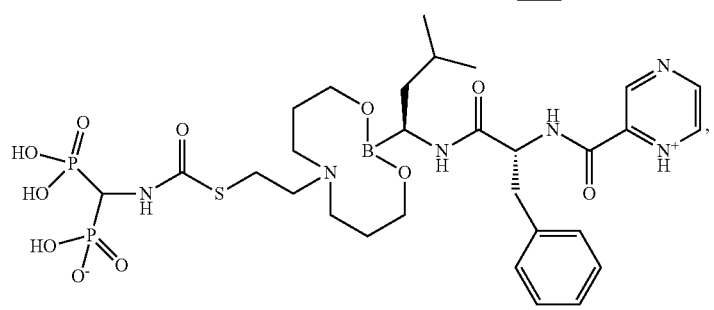
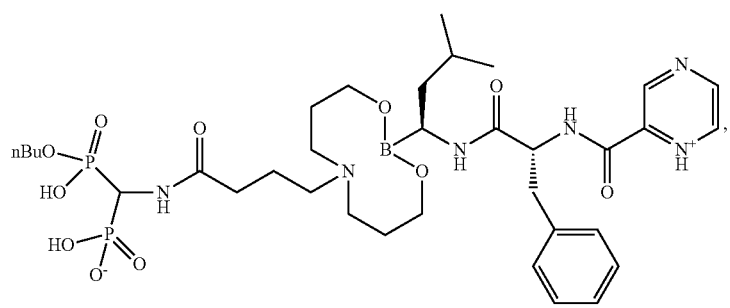
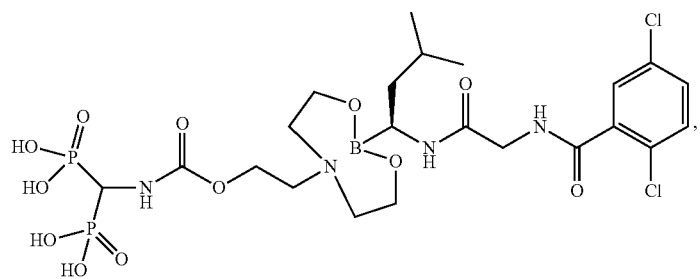
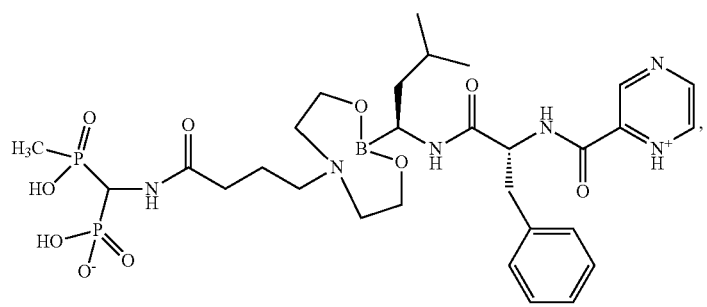

-continued
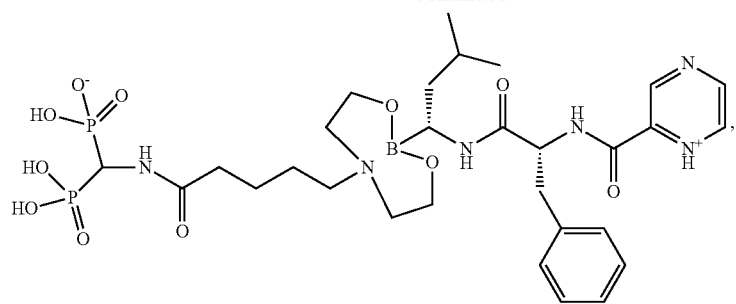
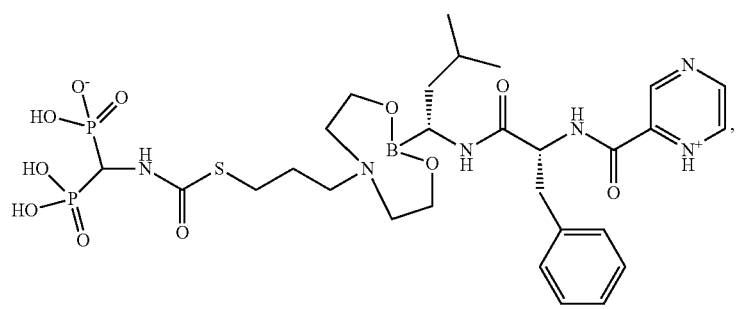
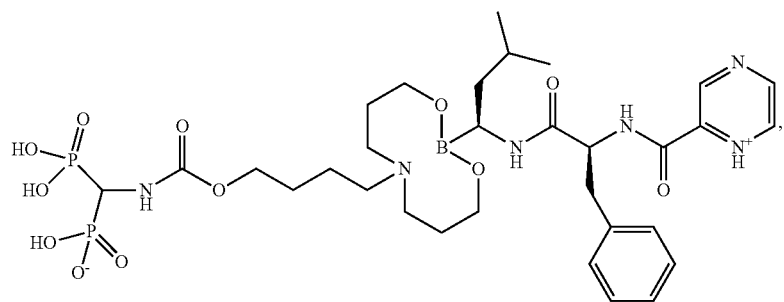
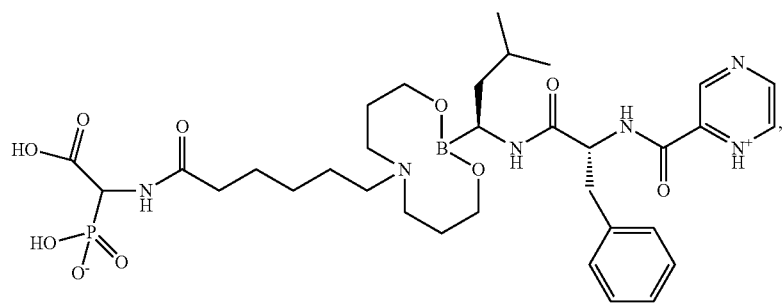
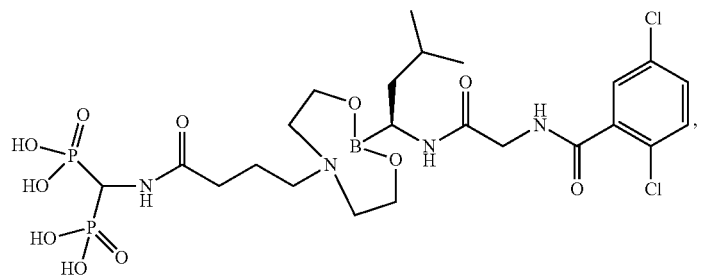

-continued
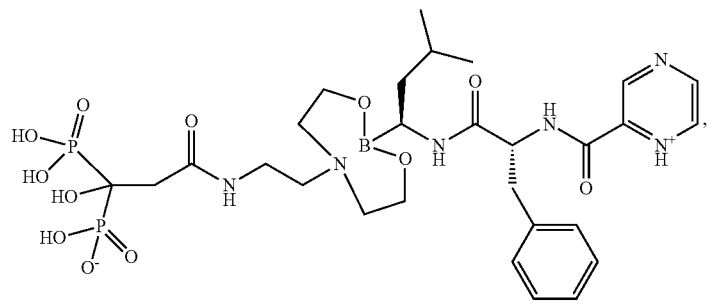,
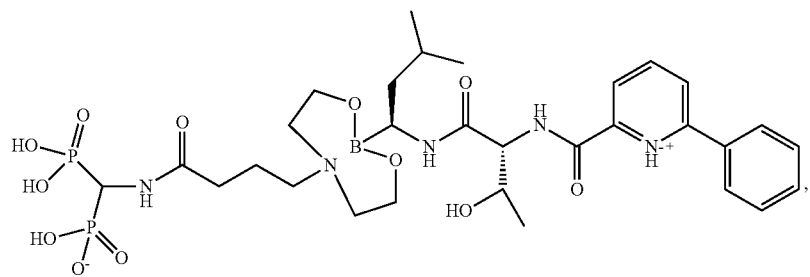,
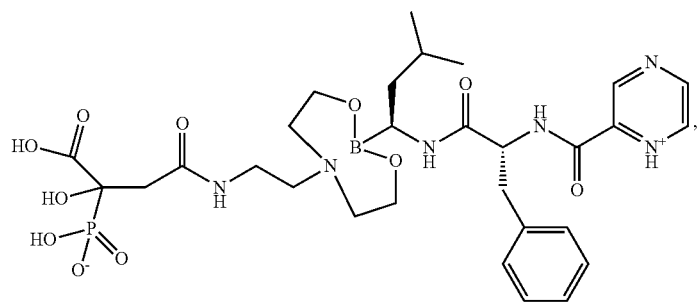,
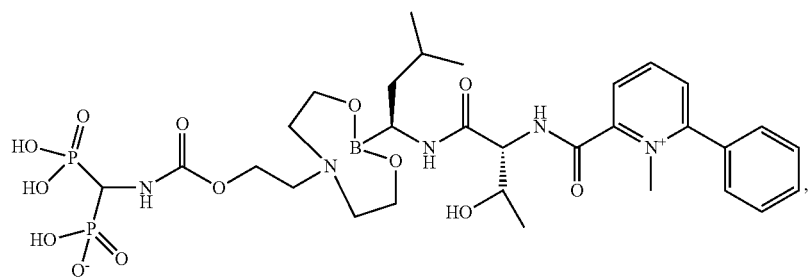,
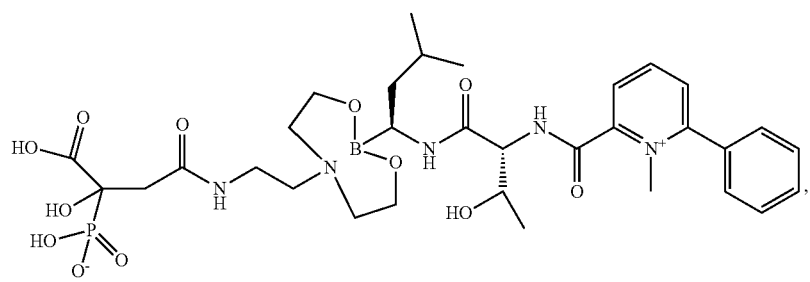,
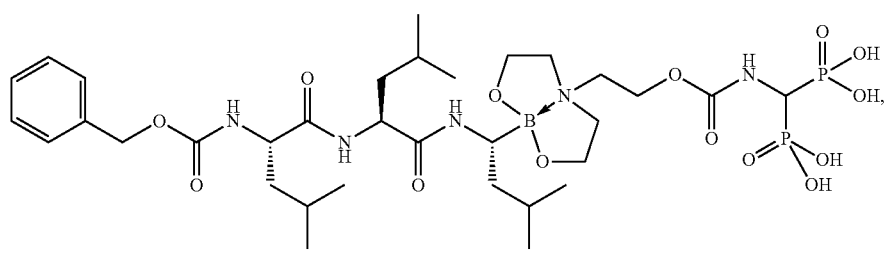, -continued
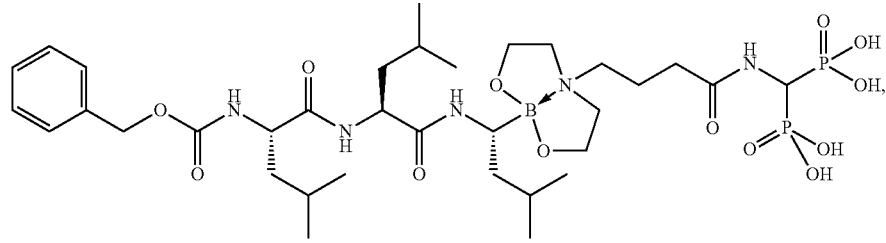
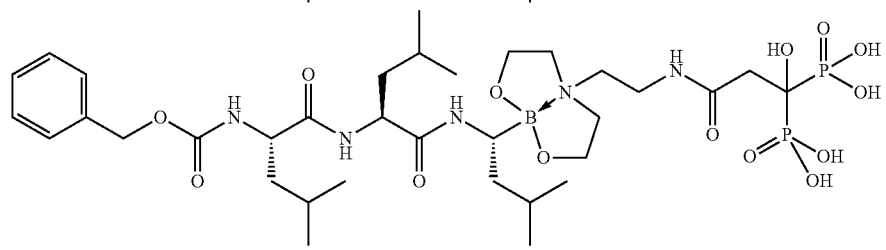
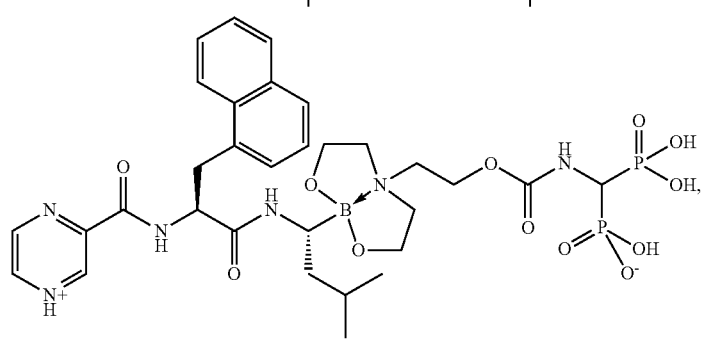
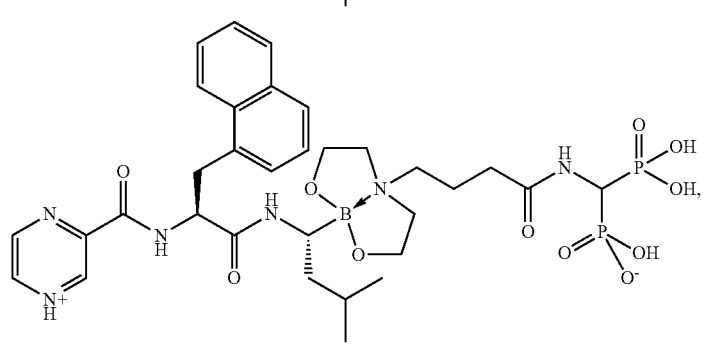
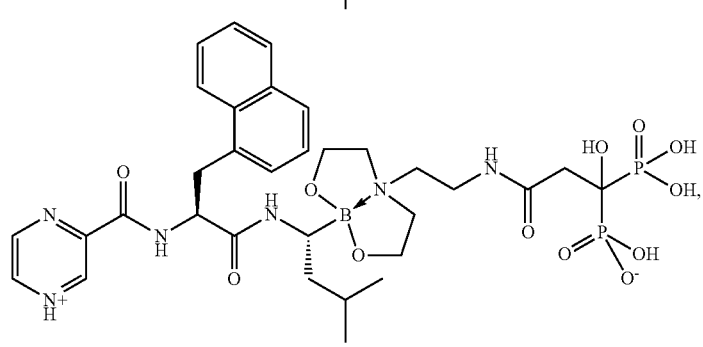
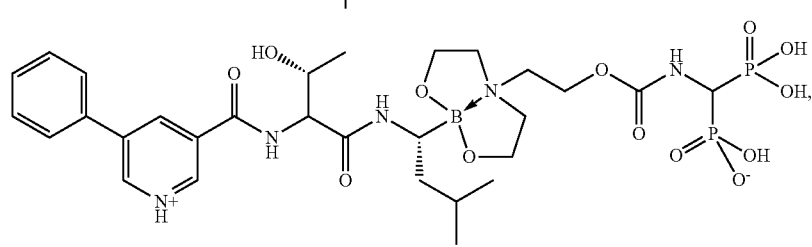

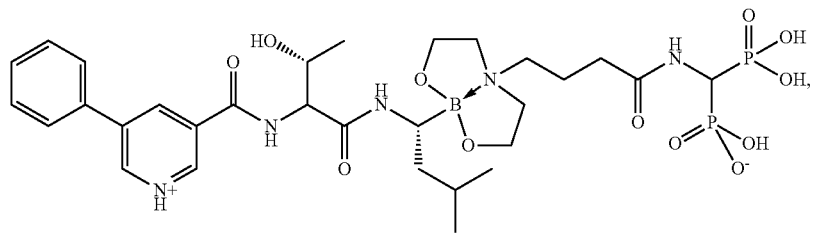
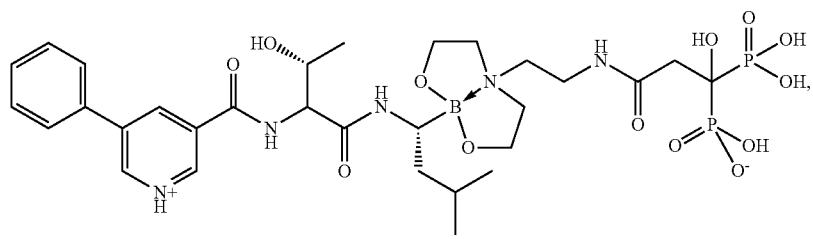
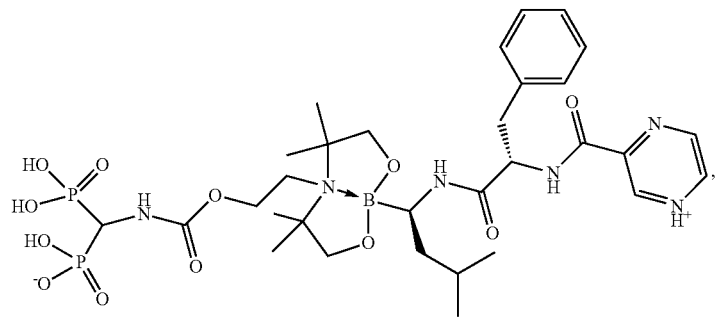
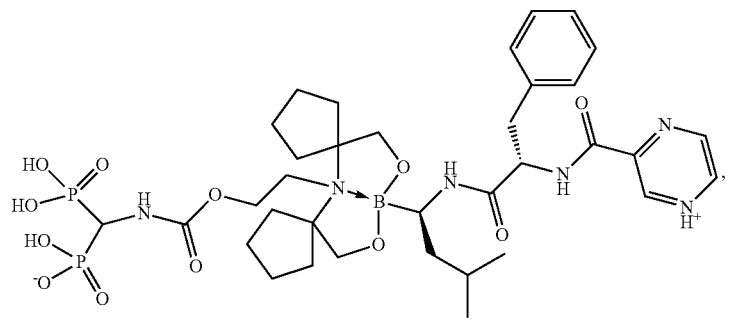
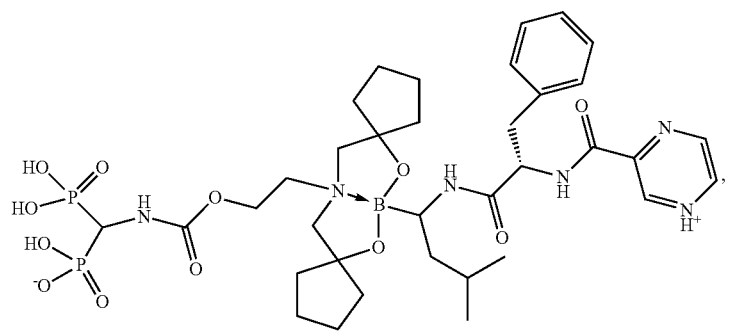

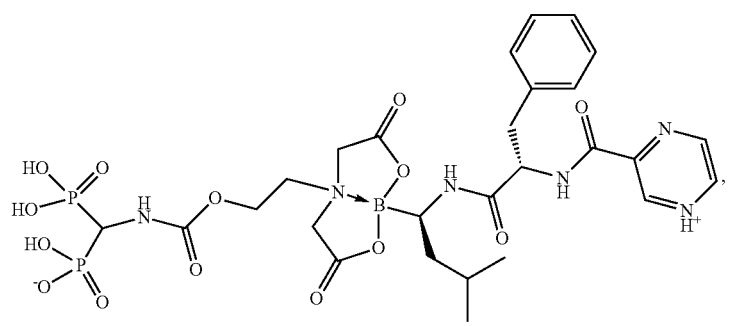
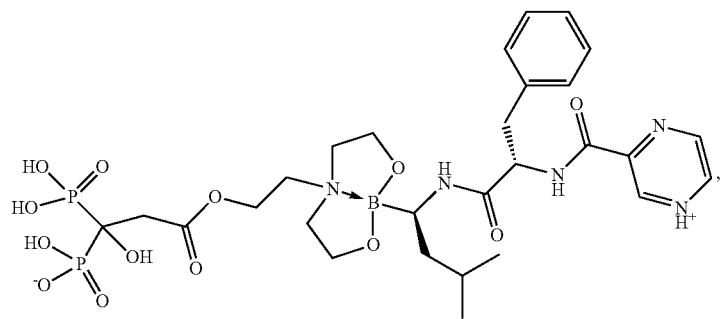
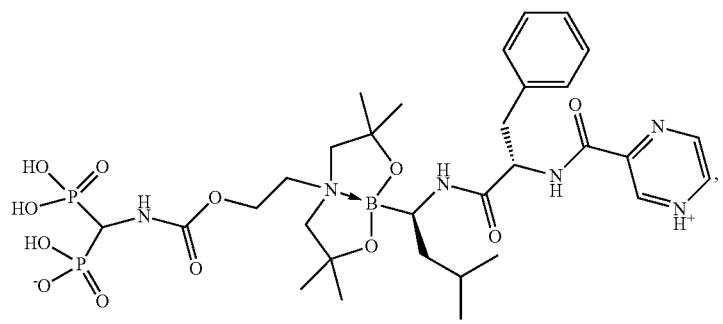
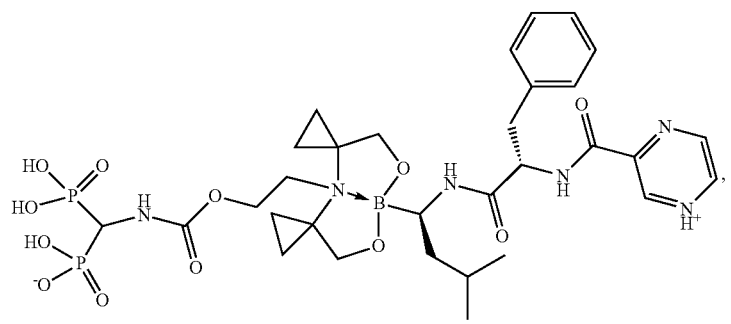
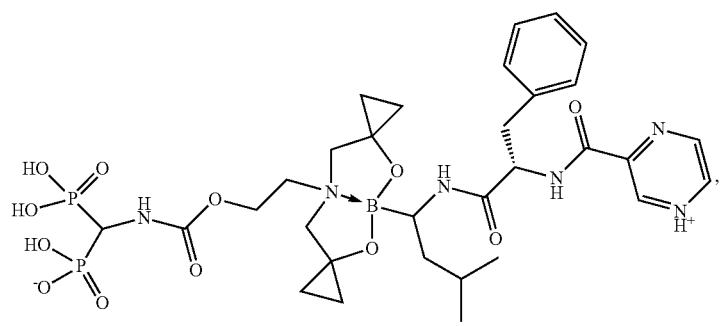

-continued
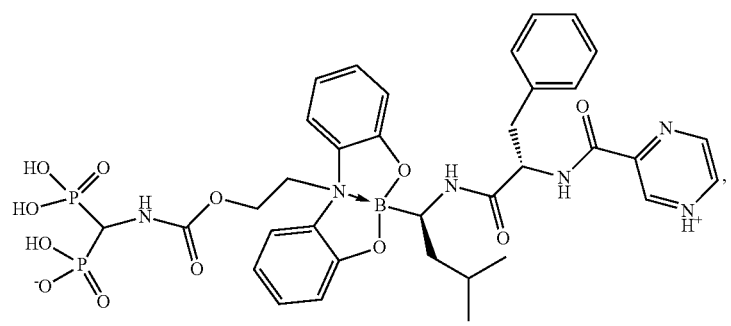
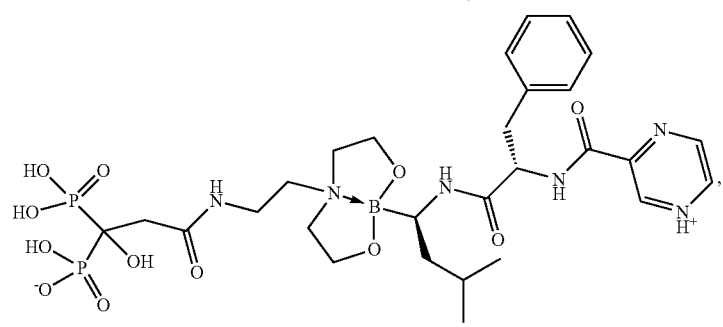
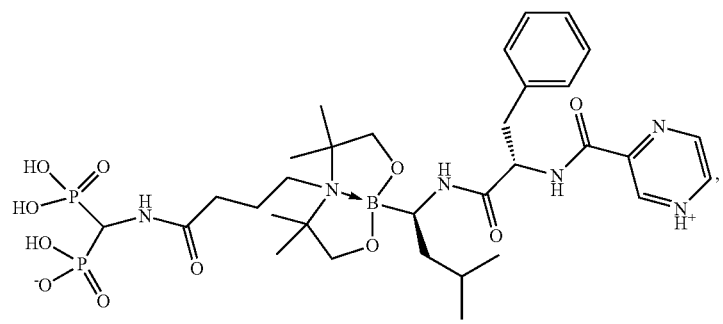
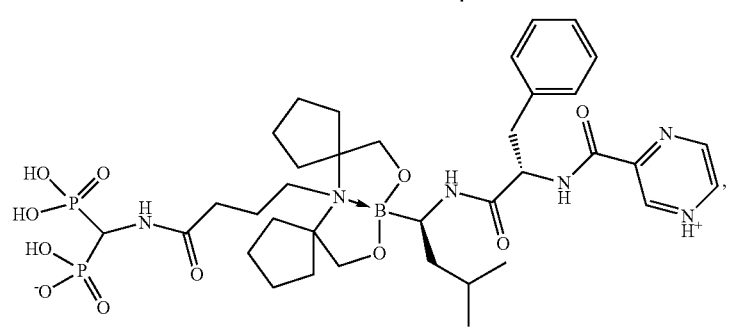
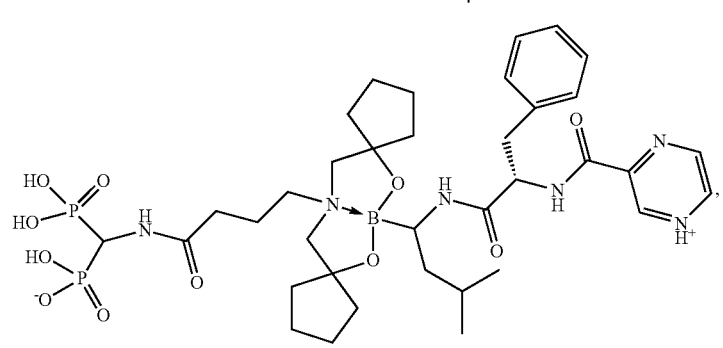

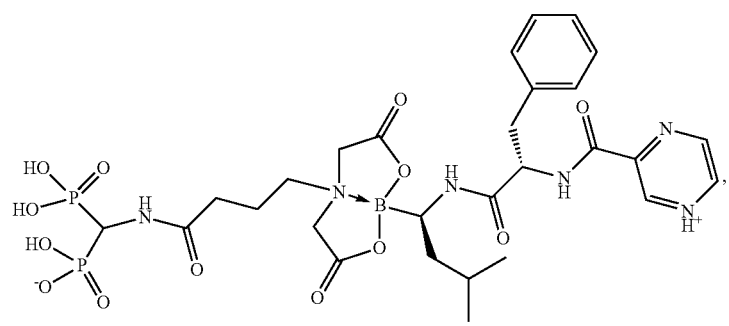
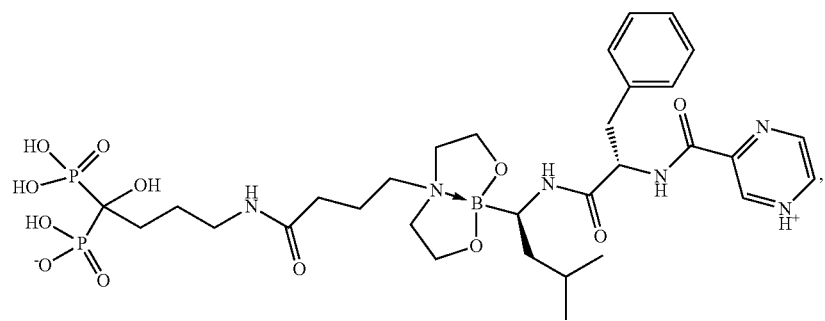
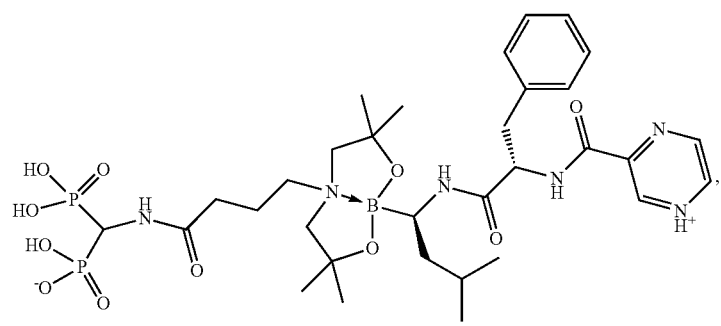
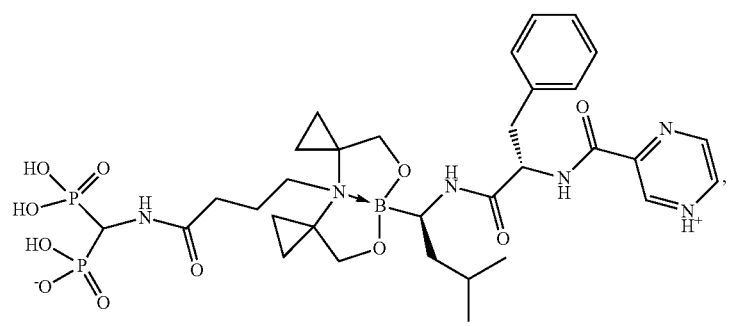
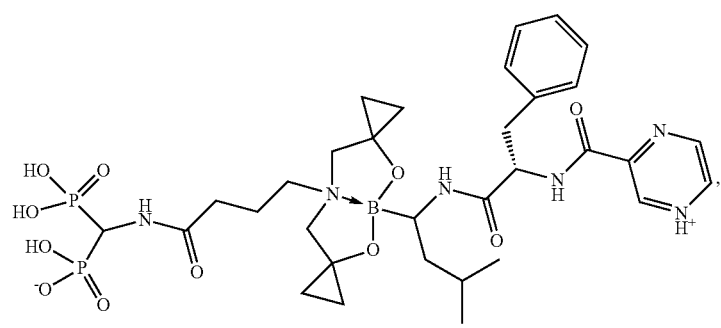

-continued
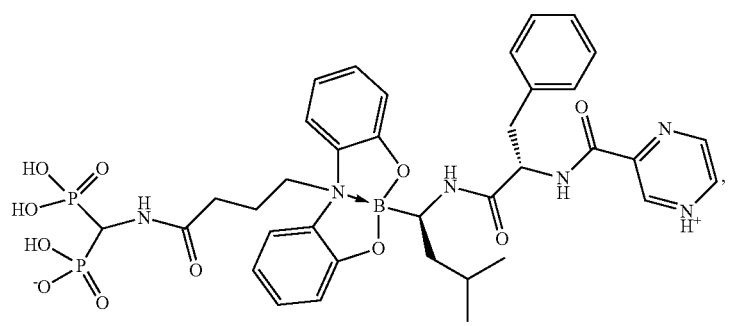
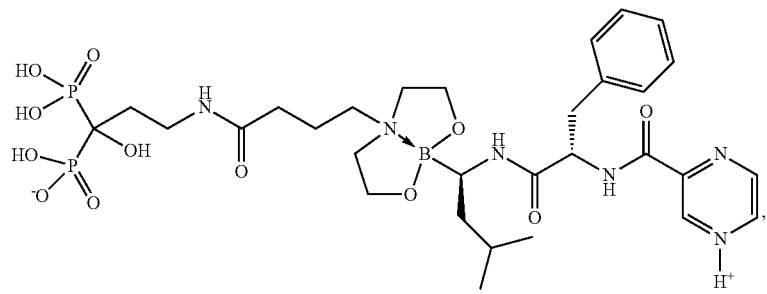
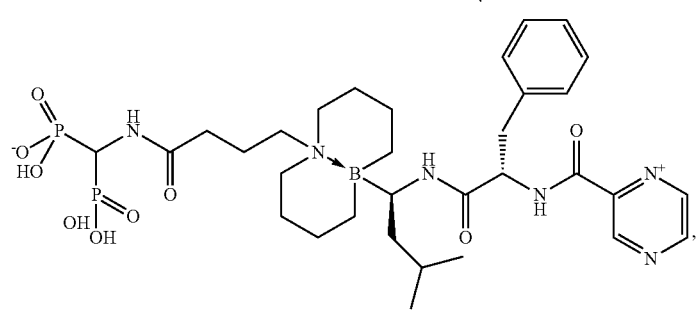
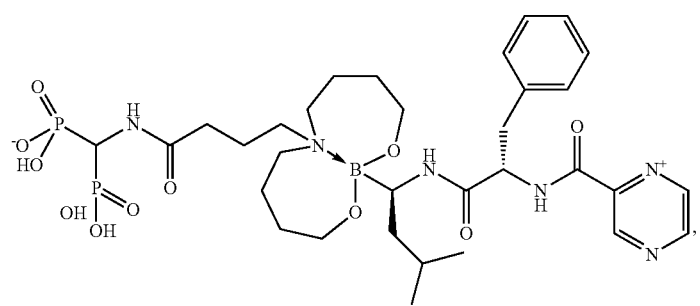
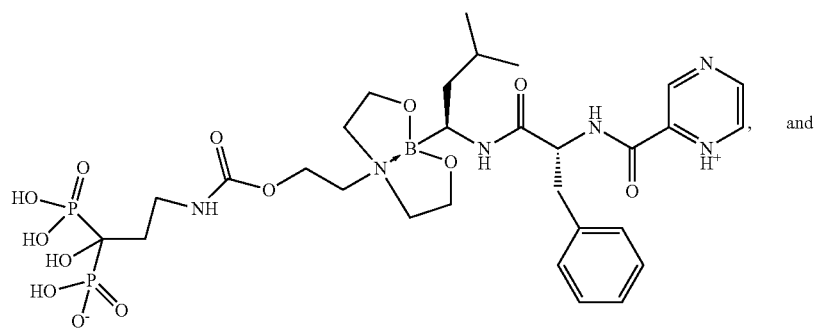
and

-continued

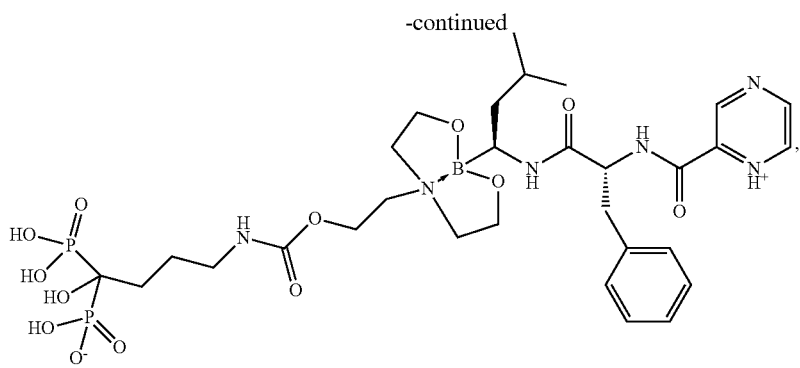

or
a pharmaceutically acceptable salt thereof.

19. The method of claim 18, wherein the compound is

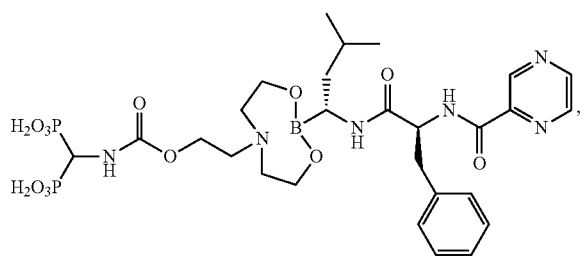

or a pharmaceutically acceptable salt thereof.

20. The method of claim 16, wherein the composition further comprises at least one pharmaceutically acceptable carrier.

21. The method of claim 16 for prevention or treatment of the symptoms of a disease, wherein the subject has a disease or disorder selected from the group consisting of multiple myeloma, osteoporosis, osteonecrosis, osteoarthritis, rheumatoid arthritis, Paget's disease, bone fracture healing, prosthesis loosening, bone cancer, a myeloproliferative disease, radiotherapy-induced osteoporosis, leukemia, and cancers metastasized to bone.

22. The method of claim 16, wherein the therapeutic agent is controllably released from the compound at the site in need of bone formation.

23. A method of killing cancer cells of bone, bone marrow and bone surrounding tissues in a subject, the method comprising administering a therapeutically effective amount of a composition comprising at least one compound according to claim 1.

24. The method of claim 23, wherein the compound is

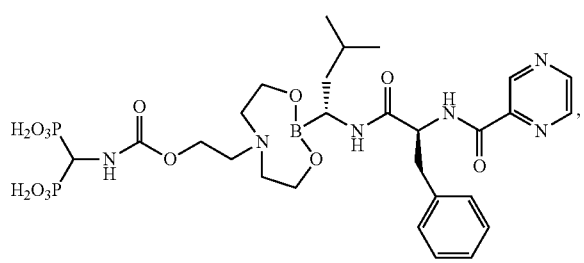

or a pharmaceutically acceptable salt thereof.

25. The method of claim 23, wherein the subject has multiple myeloma.

26. A method of promoting bone formation at a site in need of bone formation in a subject or reducing bone resorption in a subject in need of less bone resorption, or both, the method comprising administering a therapeutically effective amount of a composition comprising at least one compound according to claim 3.

27. A method of treating a disease selected from the group consisting of multiple myeloma and bone cancer in a subject in need thereof, the method comprising administering a therapeutically effective amount of a composition comprising at least one compound according to claim 3.

28. The method of claim 17 for prevention or treatment of the symptoms of a disease, wherein the subject has a disease or disorder selected from the group consisting of multiple myeloma, osteoporosis, osteonecrosis, osteoarthritis, rheumatoid arthritis, Paget's disease, bone fracture healing, prosthesis loosening, bone cancer, a myeloproliferative disease, radiotherapy-induced osteoporosis, leukemia, and cancers metastasized to bone.

29. The method of claim 27 for prevention or treatment of the symptoms of a disease, wherein the subject has a disease or disorder selected from the group consisting of multiple myeloma, osteoporosis, osteonecrosis, osteoarthritis, rheumatoid arthritis, Paget's disease, bone fracture healing, prosthesis loosening, bone cancer, a myeloproliferative disease, radiotherapy-induced osteoporosis, leukemia, and cancers metastasized to bone.

30. The method of claim 17, wherein the therapeutic agent is controllably released from the compound at the site in need of bone formation.

31. The method of claim 27, wherein the therapeutic agent is controllably released from the compound at the site in need of bone formation.

32. A method of killing cancer cells of bone, bone marrow and bone surrounding tissues in a subject, the method comprising administering a therapeutically effective amount of a composition comprising at least one compound according to claim 3.

33. The method of claim 26, wherein the compound is selected from the group consisting of:

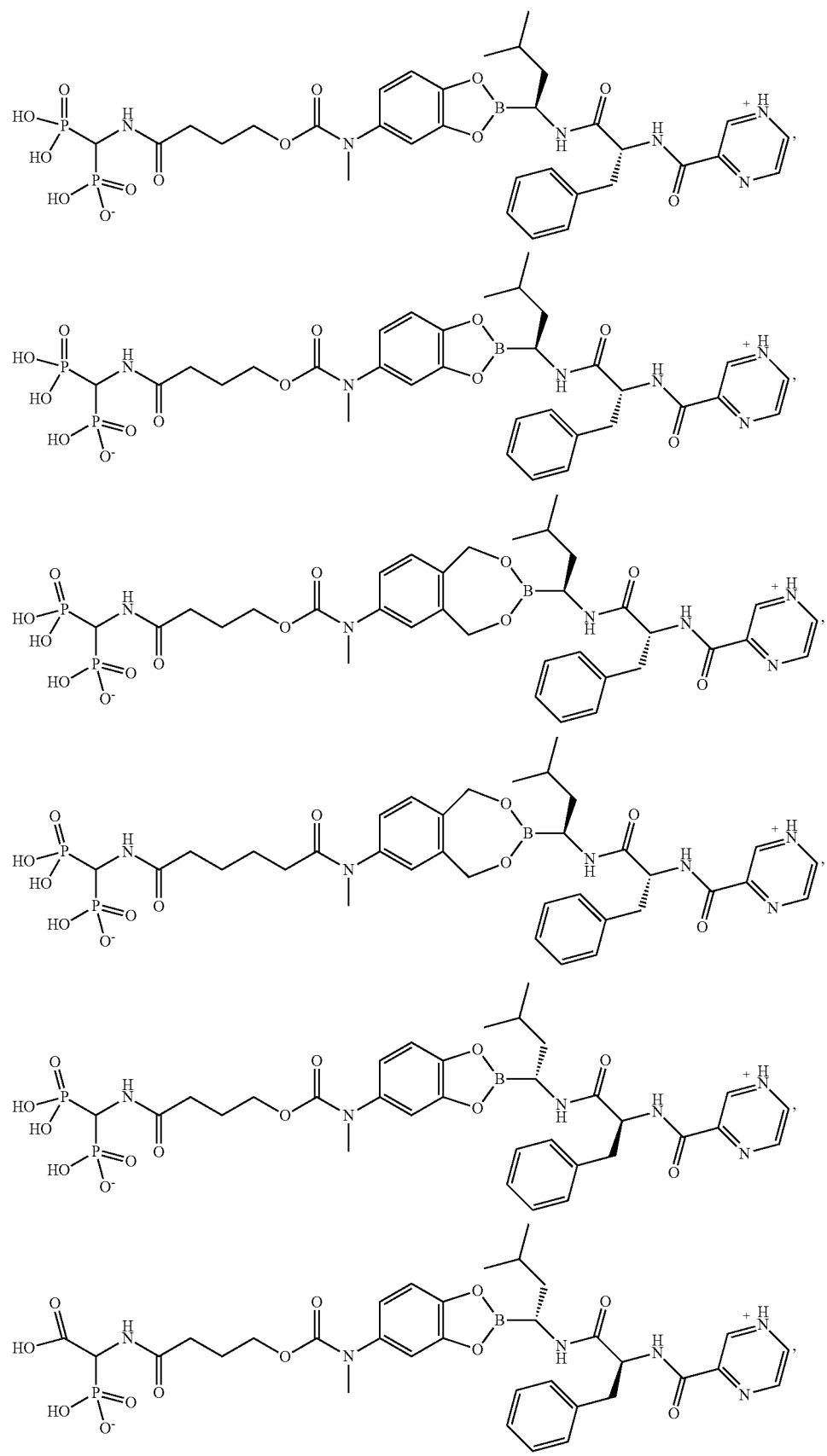

-continued
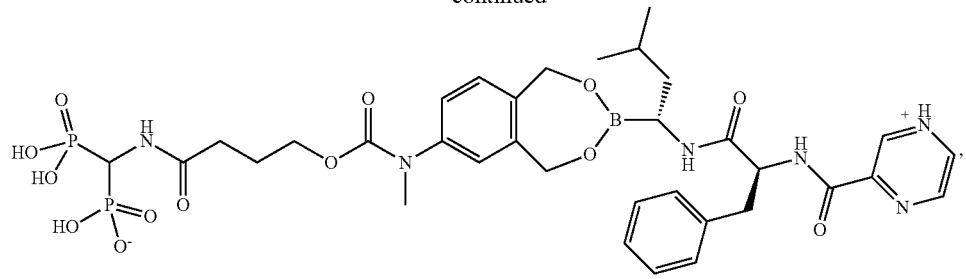
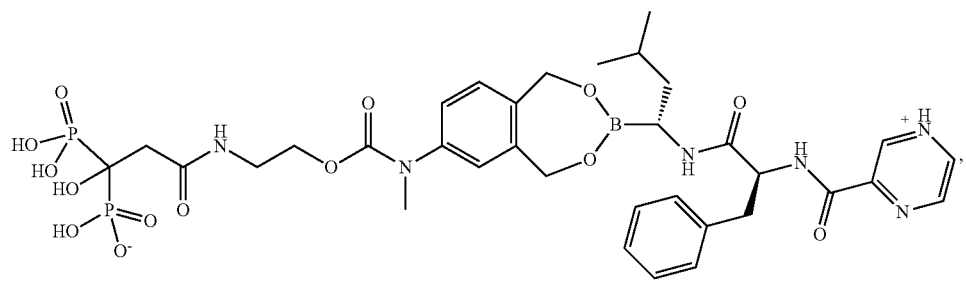
or a pharmaceutically acceptable salt thereof.
34. The method of claim 27, wherein the compound is selected from the group consisting of:
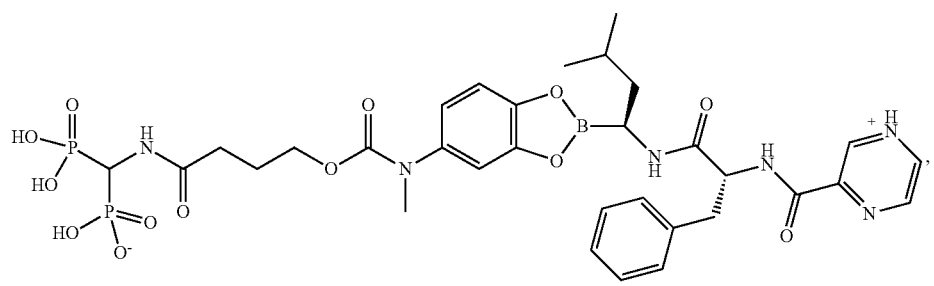
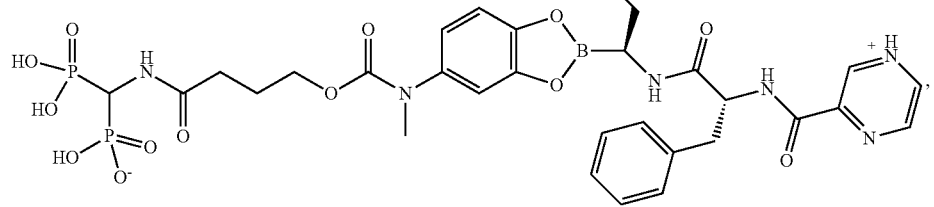
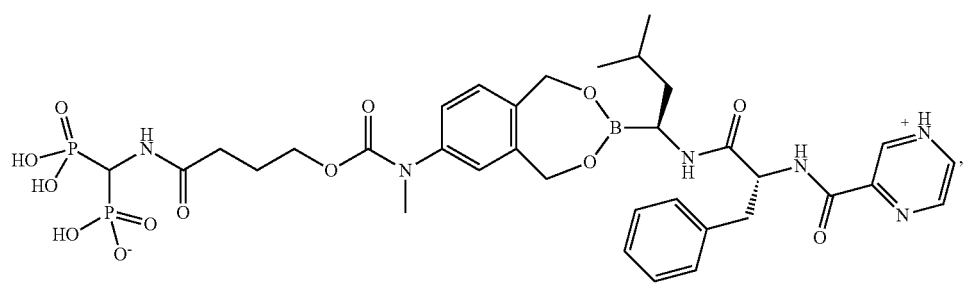

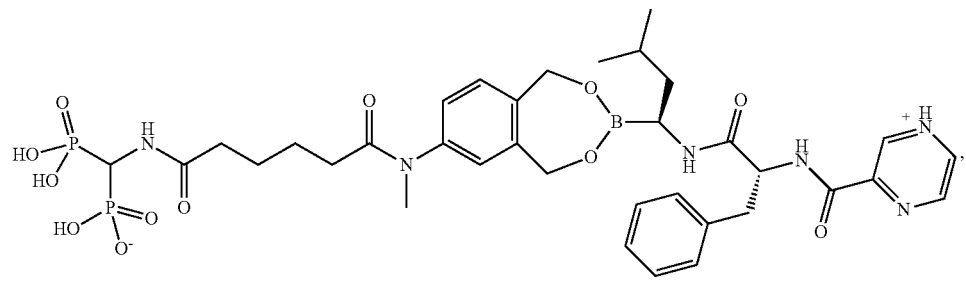
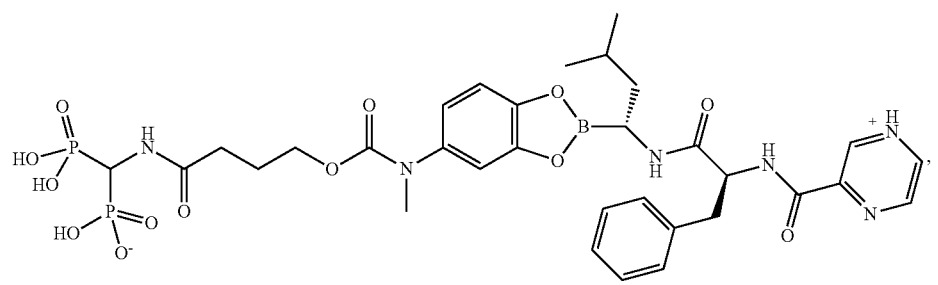
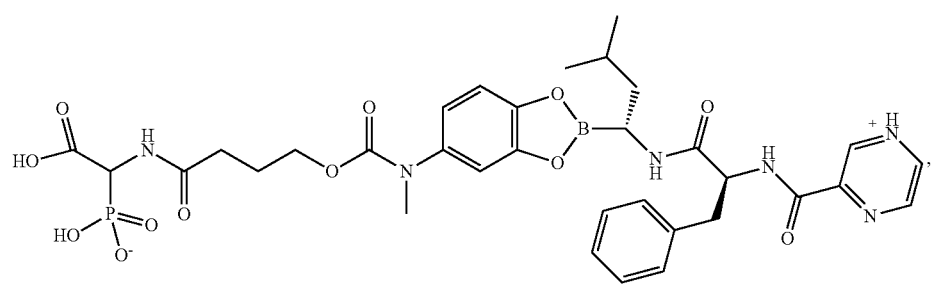
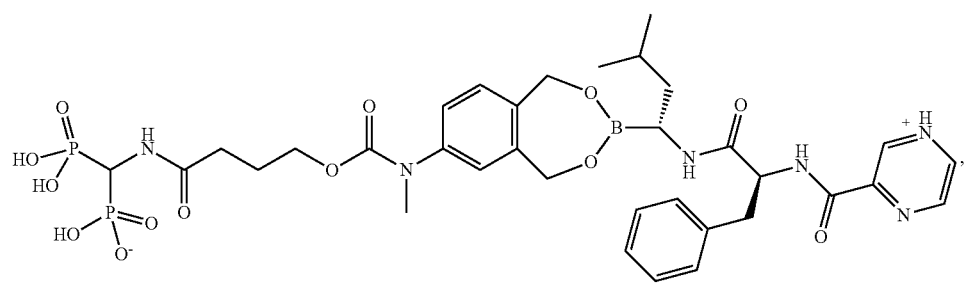

-continued
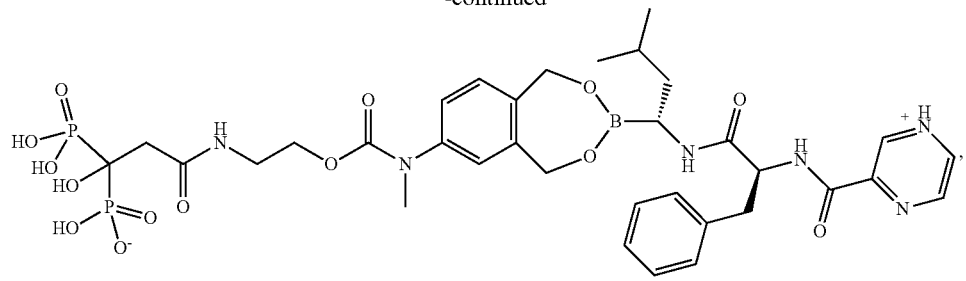
or a pharmaceutically acceptable salt thereof.
35. The method of claim 29, wherein the compound is selected from the group consisting of:
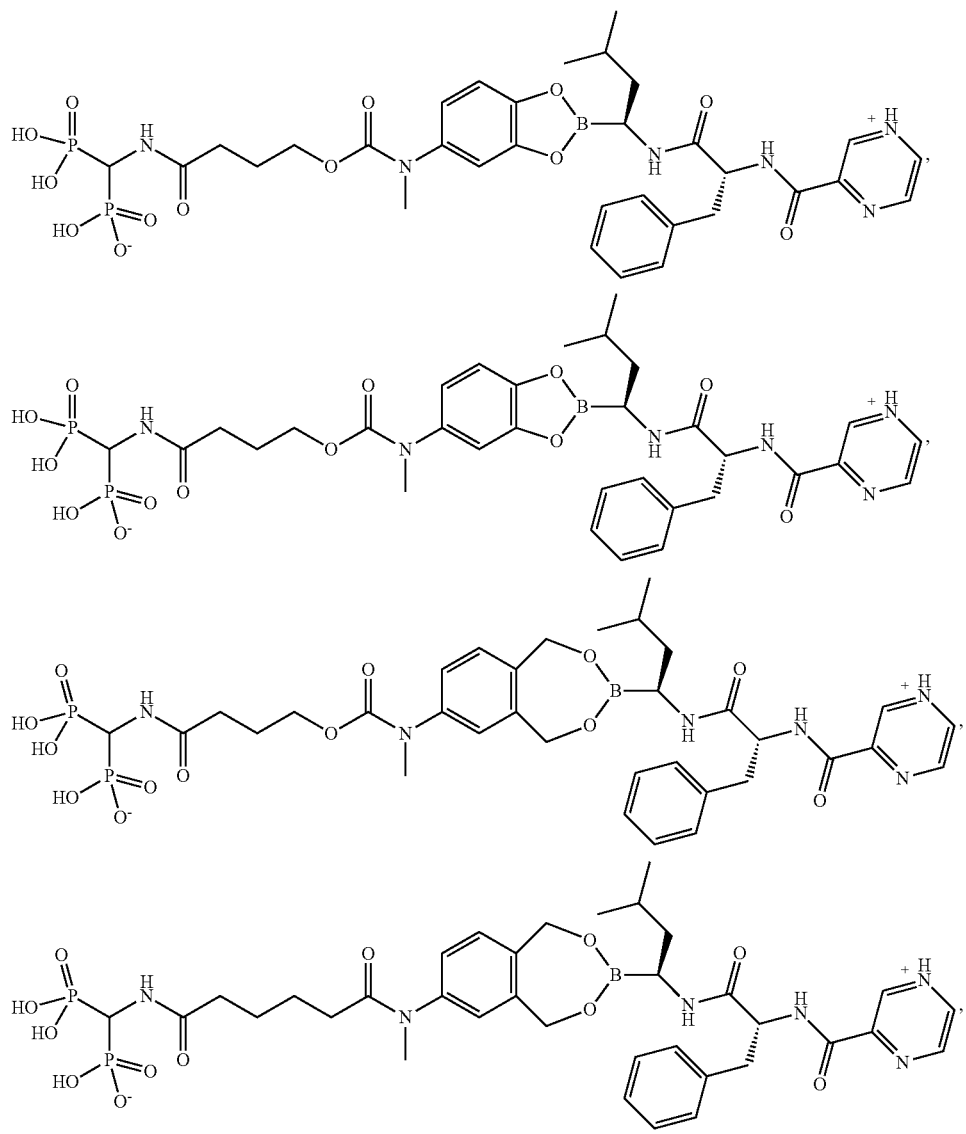

-continued
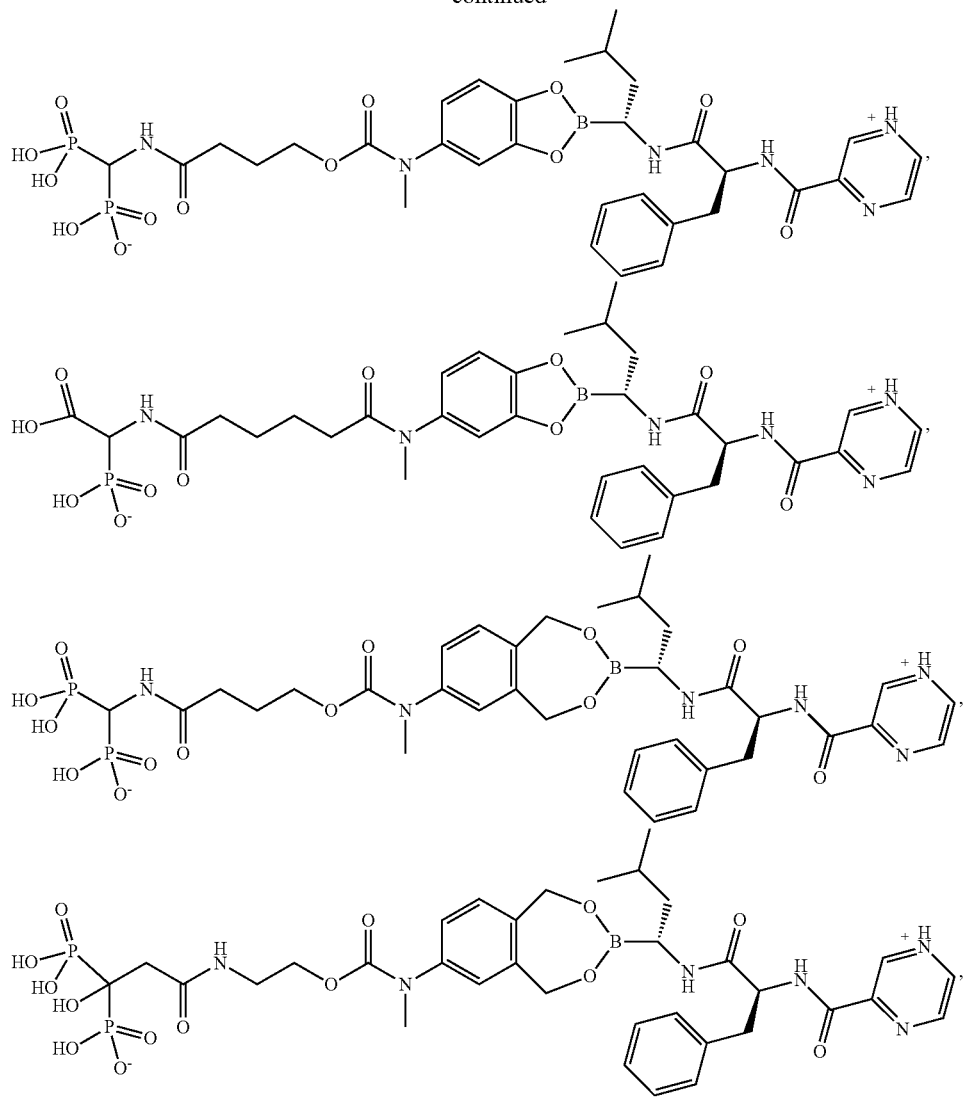
or a pharmaceutically acceptable salt thereof.
36. The method of claim 31, wherein the compound is selected from the group consisting of:
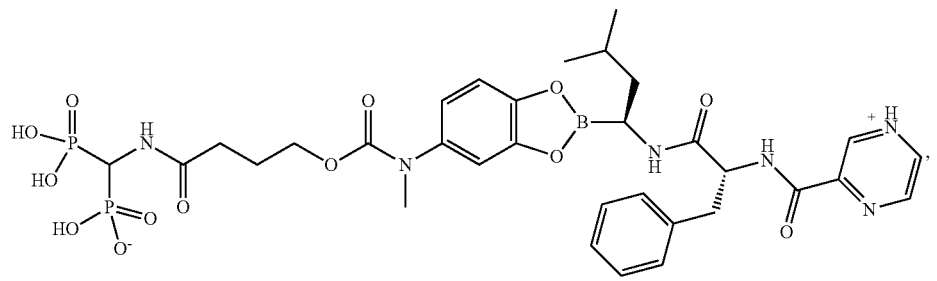

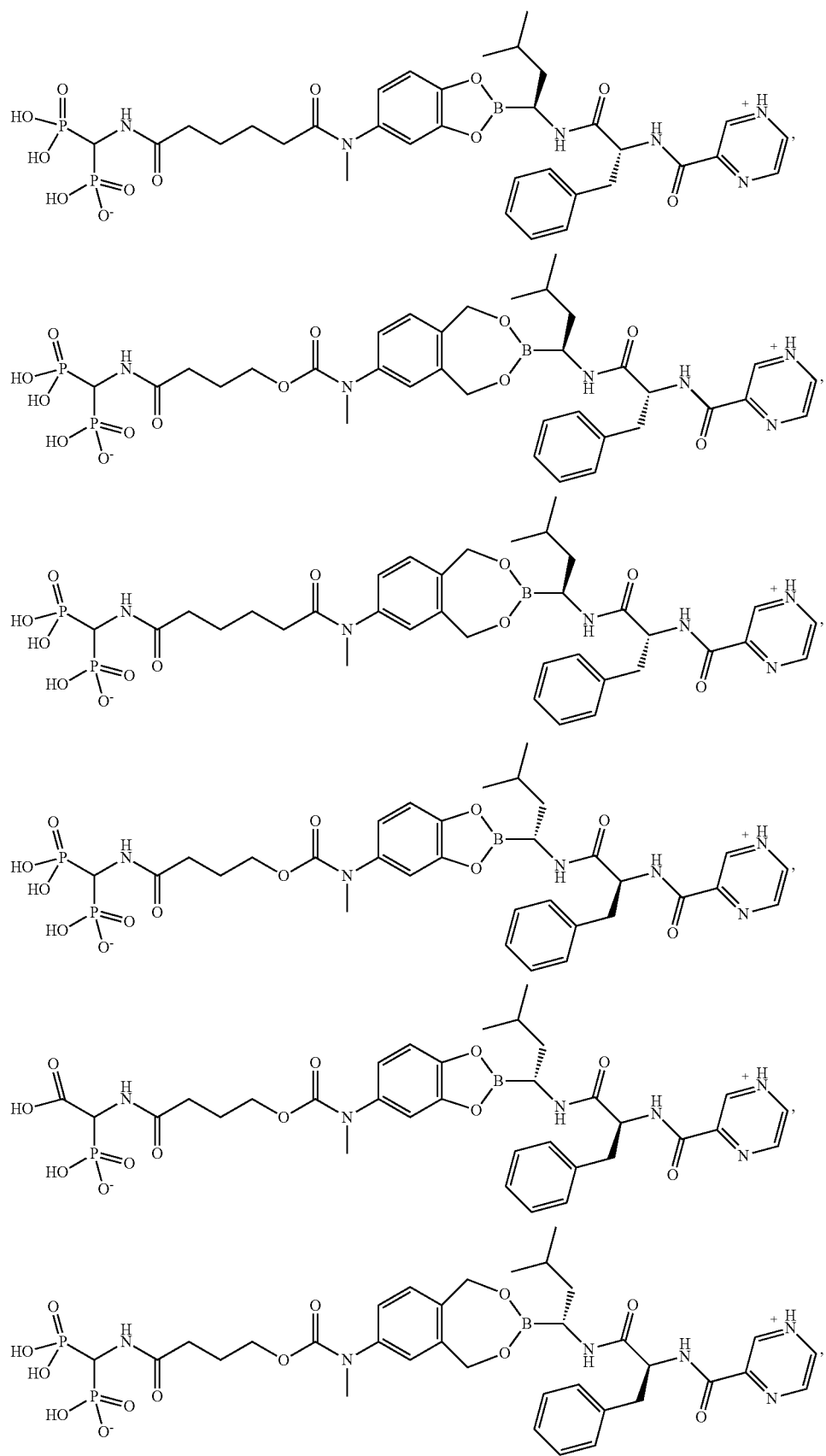

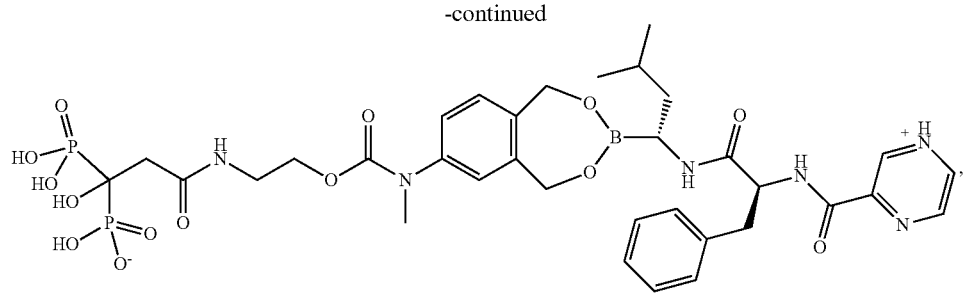
or a pharmaceutically acceptable salt thereof.
* * * * *